(12) United States Patent
Kim et al.

(10) Patent No.: US 10,680,190 B2
(45) Date of Patent: Jun. 9, 2020

(54) ORGANIC COMPOUND, ORGANIC OPTOELECTRONIC ELEMENT, AND DISPLAY DEVICE

(71) Applicant: SAMSUNG SDI CO., LTD., Yongin-si, Gyeonggi-do (KR)

(72) Inventors: Byung-Ku Kim, Suwon-si (KR); Young-Kwon Kim, Suwon-si (KR); Jin-Hyun Lui, Suwon-si (KR); Chang-Ju Shin, Suwon-si (KR); Eun-Sun Yu, Suwon-si (KR); Seung-Jae Lee, Suwon-si (KR); Joo-Hee Seo, Suwon-si (KR)

(73) Assignee: Samsung SDI Co., Ltd., Yongin-si, Gyeonggi-do (KR)

( * ) Notice: Subject to any disclaimer, the term of this patent is extended or adjusted under 35 U.S.C. 154(b) by 0 days.

(21) Appl. No.: 15/312,012

(22) PCT Filed: May 12, 2015

(86) PCT No.: PCT/KR2015/004757
§ 371 (c)(1),
(2) Date: Nov. 17, 2016

(87) PCT Pub. No.: WO2016/021815
PCT Pub. Date: Feb. 11, 2016

(65) Prior Publication Data
US 2017/0141331 A1    May 18, 2017

(30) Foreign Application Priority Data
Aug. 6, 2014 (KR) .................. 10-2014-0101213

(51) Int. Cl.
*H01L 51/00* (2006.01)
*C09K 11/06* (2006.01)
(Continued)

(52) U.S. Cl.
CPC ........ *H01L 51/0094* (2013.01); *C07D 239/70* (2013.01); *C07D 403/04* (2013.01);
(Continued)

(58) Field of Classification Search
None
See application file for complete search history.

(56) References Cited

U.S. PATENT DOCUMENTS 8,518,558 B2    8/2013   Hiyama et al.
2009/0076268 A1  3/2009   Fitzgerald et al.
(Continued)

FOREIGN PATENT DOCUMENTS

CN    106573938 A    4/2017
JP    06-220059      8/1994
(Continued)

OTHER PUBLICATIONS

Tolkunov et al. "Synthesis and Reactions of 2,4-Disubstituted Benzo[b]Furano-", etc, 1990, vol. 26, No. 11, pp. 1310-1312.
(Continued)

*Primary Examiner* — Jay Yang
(74) *Attorney, Agent, or Firm* — Lee IP Law, PC

(57) ABSTRACT

The present invention relates to an organic compound by chemical formula 1, and an organic optoelectronic element and a display device each comprising the organic compound.

7 Claims, 1 Drawing Sheet

(51) Int. Cl.
  *C07D 239/70* (2006.01)
  *C07D 403/04* (2006.01)
  *C07D 403/14* (2006.01)
  *C07D 405/10* (2006.01)
  *C07D 491/048* (2006.01)
  *C07D 495/04* (2006.01)
  *C07F 7/08* (2006.01)
  *H01L 51/50* (2006.01)

(52) U.S. Cl.
  CPC ......... *C07D 403/14* (2013.01); *C07D 405/10* (2013.01); *C07D 491/048* (2013.01); *C07D 495/04* (2013.01); *C07F 7/0814* (2013.01); *C09K 11/06* (2013.01); *H01L 51/006* (2013.01); *H01L 51/0052* (2013.01); *H01L 51/0054* (2013.01); *H01L 51/0071* (2013.01); *H01L 51/0072* (2013.01); *H01L 51/0073* (2013.01); *H01L 51/0074* (2013.01); *H01L 51/0081* (2013.01); *H01L 51/0085* (2013.01); *C09K 2211/1007* (2013.01); *C09K 2211/1011* (2013.01); *C09K 2211/1029* (2013.01); *C09K 2211/1044* (2013.01); *C09K 2211/1088* (2013.01); *C09K 2211/1092* (2013.01); *C09K 2211/1096* (2013.01); *C09K 2211/185* (2013.01); *C09K 2211/186* (2013.01); *H01L 51/5016* (2013.01); *H01L 51/5072* (2013.01); *H01L 51/5092* (2013.01)

(56) References Cited

U.S. PATENT DOCUMENTS

| | | | |
|---|---|---|---|
| 2012/0326135 A1 | 12/2012 | Kim et al. | |
| 2014/0159024 A1 | 6/2014 | Takada et al. | |
| 2017/0200903 A1* | 7/2017 | Park | H01L 51/0071 |

FOREIGN PATENT DOCUMENTS

| | | |
|---|---|---|
| JP | 2004-002703 | 1/2004 |
| JP | 2004-059899 | 2/2004 |
| JP | 2005-048004 | 2/2005 |
| JP | 2005-132829 | 5/2005 |
| JP | 2008-074939 | 4/2008 |
| JP | WO 2008/120611 A | 7/2010 |
| JP | 2013-157634 | 8/2013 |
| KR | 10-2007-0043666 | 4/2007 |
| KR | 10-2008-0092309 | 10/2008 |
| KR | 10-2010-0098714 A | 9/2010 |
| KR | 10-2011-0002156 | 1/2011 |
| KR | 10-2011-0097784 | 8/2011 |
| KR | 10-2011-0129767 | 12/2011 |
| KR | 10-2012-0104067 | 9/2012 |
| KR | 10-2013-0010133 | 1/2013 |
| KR | 10-2013-0042901 | 4/2013 |
| KR | 10-2013-0109837 | 10/2013 |
| KR | 10-2013-0125180 | 11/2013 |
| KR | 10-2013-0135771 | 12/2013 |
| KR | 10-2015-0136942 A | 12/2015 |
| WO | WO 2010/126234 A1 | 11/2010 |
| WO | WO-2015/182872 A1 * | 12/2015 |

OTHER PUBLICATIONS

Arepalli Sateesh Kumar, et al. "Copper- or Palladium-Catalyzed Amidation and Cyclization Route for the Synthesis of Pyrimido[4,5-b]carbazoles", 2013, vol. 45, No. 20, pp. 2893-2903.

R. Alan Aitken et al. "Cascade Synthesis of New Tetracyclic Heteroaromatic Thieno[2,3-b]Pyridine-Containing Ring System", New Journal of Chemistry, 2009, vol. 33, pp. 2402-2404.

Padmashali et al. "Synthesis of Novel Angularly Fused Pentacyclic Heterocycles of Pharmacological Interest", Indian Journal of Chemistry, vol. 44B, Jul. 2005, pp. 1446-1451.

Zhang, et al., Synthesis of pyrimido[4,5-b]indoles and benzo[4,5]furo[2,3-d]pyrimidines via palladium-catalyzed intramolecular arylation, Tetrahedron Letters 43 (2002) 8235-8239.

Taiwanese Search Report dated Mar. 9, 2016, of the corresponding Taiwanese Patent Application No. 104117294.

Franck, et al., Angew. Chem. Internat. Edit. 1966, 5, p. 131.

Chinese Office Action/ Search Report dated Jan. 26, 2018, in connection with the corresponding Chinese Patent Application No. 201580040479.4.

* cited by examiner

【Figure 1】
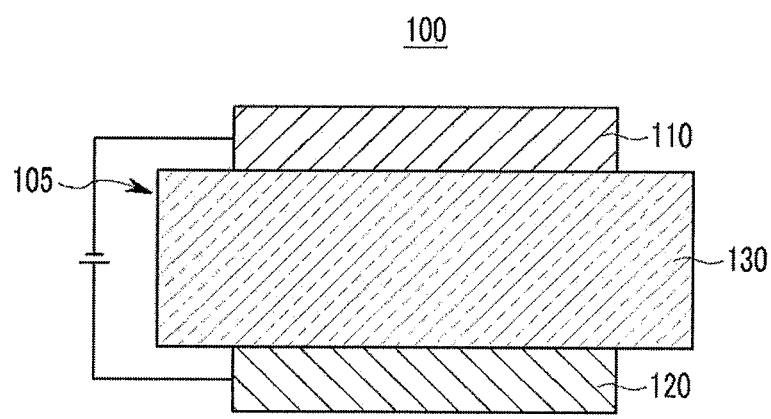
【Figure 2】
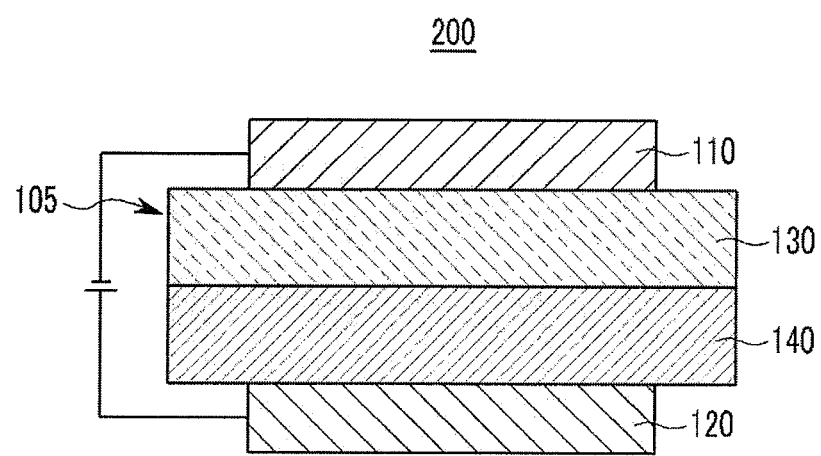

ORGANIC COMPOUND, ORGANIC OPTOELECTRONIC ELEMENT, AND DISPLAY DEVICE

CROSS REFERENCE TO RELATED APPLICATIONS

This is the U.S. national phase application based on PCT Application No. PCT/KR2015/004757, filed May 12, 2015, which is based on Korean Patent Application No. 10-2014-0101213, filed Aug. 6, 2014, the entire contents of all of which are hereby incorporated by reference.

TECHNICAL FIELD

An organic compound, an organic optoelectric device and a display device are disclosed.

BACKGROUND ART

An organic optoelectric device is a device that converts electrical energy into photoenergy, and vice versa.

An organic optoelectric device may be classified as follows in accordance with its driving principles. One is an optoelectric device where excitons are generated by photoenergy, separated into electrons and holes the electrons and holes, and are transferred to different electrodes to generate electrical energy, and the other is a light emitting device where a voltage or a current is supplied to an electrode to generate photoenergy from electrical energy.

Examples of an organic optoelectric device may be an organic photoelectric device, an organic light emitting diode, an organic solar cell and an organic photo conductor drum.

Of these, an organic light emitting diode (OLED) has recently drawn attention due to an increase in demand for flat panel displays. Such an organic light emitting diode converts electrical energy into light by applying current to an organic light emitting material. It has a structure in which an organic layer is interposed between an an anode and a cathode.

Performance of an organic light emitting diode may be affected by characteristics of the organic layer, and among them, may be mainly affected by characteristics of an organic material of the organic layer. Particularly, development for an organic material being capable of increasing hole and electron mobility and simultaneously increasing electrochemical stability is needed so that the organic light emitting diode may be applied to a large-size flat panel display.

DISCLOSURE

Technical Problem

One embodiment provides an organic compound being capable of realizing an organic optoelectric device having high efficiency and long life-span.

Another embodiment provides an organic optoelectric device including the organic compound.

Yet another embodiment provides a display device including the organic optoelectric device.

Technical Solution

According to one embodiment, an organic compound represented by the following Chemical Formula 1 is provided.

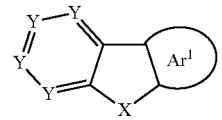

[Chemical Formula 1]

In the Chemical Formula 1,
X is O, S, $CR^aR^b$ or $SiR^cR^d$,
Y is N or $CR^e$,
at least one of Y is N,
$Ar^1$ is a substituted or unsubstituted fused ring,
$R^a$ to $R^d$ are independently hydrogen, deuterium, a substituted or unsubstituted C1 to C10 alkyl group, a substituted or unsubstituted C3 to C12 cycloalkyl group, a substituted or unsubstituted C6 to C12 aryl group, a substituted or unsubstituted C3 to C12 heterocyclic group, or a combination thereof, and
$R^e$ is hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C3 to C30 heterocyclic group or a combination thereof.

According to another embodiment, an organic optoelectric device includes an anode and a cathode facing each other and at least one organic layer positioned between the anode and the cathode, wherein the organic layer includes the organic compound.

According to another embodiment, a display device including the organic optoelectric device is provided.

Advantageous Effects

An organic compound having excellent electrical characteristics and thermal stability is provided, and an organic light emitting diode including the organic compound may have a low driving voltage, high efficiency, high luminance and long life-span characteristics.

DESCRIPTION OF DRAWINGS

FIGS. 1 and 2 are cross-sectional views showing organic light emitting diodes according to each embodiment.

BEST MODE

Hereinafter, embodiments of the present invention are described in detail. However, these embodiments are exemplary, and this disclosure is not limited thereto.

As used herein, when a definition is not otherwise provided, the term "substituted" refers to one substituted with a substituent selected from deuterium, a halogen, a hydroxy group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C3 to C30 cycloalkyl group, a C3 to C30 heterocycloalkyl group, a C6 to C30 aryl group, a C6 to C30 heterocyclic group, a C1 to C20 alkoxy group, a C1 to C10 trifluoroalkyl group such as a trifluoromethyl group and the like, a cyano group, a carboxyl group, or a combination thereof, instead of at least one hydrogen of a substituent or a compound.

In addition, adjacent two substituents selected from the substituted a halogen, a hydroxy group amino group, substituted or unsubstituted C1 to C20 amine group, a nitro group; a substituted or unsubstituted C3 to C40 silyl group, C1 to C30 alkyl group, C1 to C10 alkylsilyl group, C3 to C30 cycloalkyl group, C3 to C30 heterocycloalkyl group, C6 to C30 aryl group, C3 to C30 heterocyclic group, C1 to C20 alkoxy group, C1 to C10 trifluoroalkyl group such as a trifluoromethyl group and the like, cyano group, carboxyl group, or the combination thereof may be fused to each other to form a ring. For example, the substituted C6 to C30 aryl group may be fused to another adjacent substituted C6 to C30 aryl group to form a substituted or unsubstituted fluorene ring.

In the present specification, when specific definition is not otherwise provided, "hetero" refers to one including 1 to 3 hetero atoms selected from N, O, S, P, and Si, and remaining carbons in one functional group.

As used herein, the term "aryl group" refers to a substituent including all element, of the cycle having p-orbitals which form conjugation, and may be monocyclic, polycyclic or fused ring polycyclic (i.e., rings sharing adjacent pairs of carbon atoms) functional group.

As used herein, the term "heterocyclic group" may refer to an aryl group or a cycloalkyl group including 1 to 3 hetero atoms selected from N, O, S, P, and Si and remaining carbons in one functional group. When the heterocyclic group is a fused ring, the entire ring or each ring of the heterocyclic group may include a hetero atom.

More specifically, the substituted or unsubstituted C6 to C30 aryl group and/or the substituted or unsubstituted C2 to C30 heterocyclic group may be a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted quarterphenyl group, a substituted or unsubstituted isoquarterphenyl group, a substituted or unsubstituted chrysenyl group, a substituted or unsubstituted triphenylenyl group, a substituted or unsubstituted perylenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted fluorenyl group, a substituted or unsubstituted dibenzofuranyl group, a substituted or unsubstituted dibenzothiophenyl group, a substituted or unsubstituted carbazole group, a combination thereof, or a combined fused ring of the foregoing groups, but is not limited thereto.

In the specification, hole characteristics refer to characteristics capable of donating an electron to form a hole when electric field is applied, and characteristics that hole formed in the anode is easily injected into the emission layer and transported in the emission layer due to conductive characteristics according to HOMO level.

In addition, electron characteristics refer to characteristics capable of accepting an electron when electric field is applied, and characteristics that electron formed in the cathode is easily injected into the emission layer and transported in the emission layer due to conductive characteristics according to LUMO level.

Hereinafter, an organic compound according to one embodiment is described.

An organic compound according to one embodiment is represented by the following Chemical Formula 1.

[Chemical Formula 1]

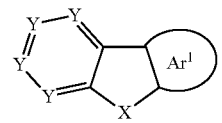

In the Chemical Formula 1,
X is O, S, CR$^a$R$^b$ or SiR$^c$R$^d$,
Y is N or CR$^e$,
at least one of Y is N,
Ar$^1$ is a substituted or unsubstituted fused ring,
R$^a$ to R$^d$ are independently hydrogen, deuterium, a substituted or unsubstituted C1 to C10 alkyl group, a substituted or unsubstituted C3 to C12 cycloalkyl group, a substituted or unsubstituted C6 to C12 aryl group, a substituted or unsubstituted C3 to C12 heterocyclic group, or a combination thereof, and
R$^e$ is hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C3 to C30 heterocyclic group or a combination thereof.

The organic compound represented by the Chemical Formula 1 has a structure that a ring including at least one nitrogen is combined with a substituted or unsubstituted fused ring.

The ring including at least one nitrogen has polarity and thus, may interact with an electrode and thus, facilitate injection of a charge. In addition, the ring including at least one nitrogen may have a structure of easily accepting electrons when an electric field is applied thereto and thus, may decrease the driving voltage of an organic optoelectric device including the organic compound.

Furthermore, the structure that the ring including at least one nitrogen is combined with the substituted or unsubstituted-fused ring may advantageously balance between holes and electrons and thus increase efficiency of an organic optoelectric device including the organic compound.

In addition, the organic compound may have a bipolar structure formed by appropriately disposing substituents and thus, appropriately balance flows of holes and electrons and resultantly, improve efficiency of an organic optoelectric device including the organic compound.

In the Chemical Formula 1, at least one among Y's may be nitrogen (N), and for example, two or three nitrogens (N) may be included.

In the Chemical Formula 1, Ar¹ may be a fused ring that two rings or more than two rings are combined, for example, a substituted or unsubstituted naphthalene a substituted or unsubstituted anthracene group, a substituted or unsubstituted phenanthrene group, a substituted or unsubstituted tetracene group, a substituted or unsubstituted pyrene group or a substituted or unsubstituted triphenylene group, but the present invention is not limited thereto.

For example, Ar¹ of the Chemical Formula 1 may be selected from the groups listed in the following Group 1.

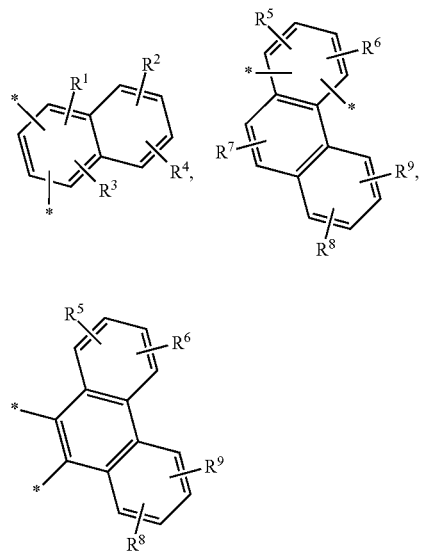

[Group 1]

In the Group 1, $R^1$ to $R^9$ are independently hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C2 to C30 heterocyclic group, a substituted or unsubstituted C4 to C30 arylamine group, wherein the substituted group, for example refers to a group substituted with a halogen, a cyano group, a hydroxyl group, an amino group, a nitro group, a carboxyl group, or a combination thereof, and

* indicates a linking point with the Chemical Formula 1.

For example, at least of $R^e$ in the Chemical Formula 1 may include a substituted or unsubstituted C6 to C30 aryl group, a substituted or unsubstituted C3 to C30 heterocyclic group, or a combination thereof. The aryl group and/or heteroaryl group may be, for example a non-fused ring such as a phenyl group, a biphenyl group, a terphenyl group or a quarterphenyl group, or a fused ring such as a naphthyl group, an anthracenyl group or a phenanthrenyl group.

The organic compound may be represented by for example the following Chemical Formula 2 or 3 depending on the position and the number of nitrogen.

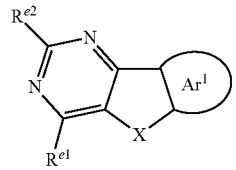

[Chemical Formula 2]

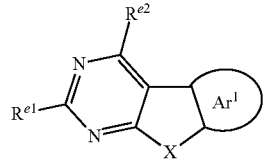

[Chemical Formula 3]

In the Chemical Formula 2 or 3, X, Ar¹ and $R^a$ to $R^d$ are the same as described above, and $R^{e1}$ and $R^{e2}$ are the same as the $R^e$.

In the Chemical Formula 2 or 3, for example at least one of $R^{e1}$ and $R^{e2}$ is a substituted or unsubstituted C6 to C30 aryl group, a substituted or unsubstituted C3 to C30 heterocyclic group, or a combination thereof. The aryl group and/or heteroaryl group may be, for example a non-fused ring such as a phenyl group, a biphenyl group, a terphenyl group or a quarterphenyl group, or a fused ring such as a naphthyl group, an anthracenyl group or a phenanthrenyl group.

For example, at least one of $R^{e1}$ and $R^{e2}$ may be represented by the following Chemical Formula A.

*-L-Ar²  [Chemical Formula A]

In the Chemical Formula A,

* indicates a linking point with the Chemical Formula 2 or 3, the L is a single bond, a substituted or unsubstituted C1 to C30 alkylene group, a substituted or unsubstituted C3 to C30 cycloalkylene group, a substituted or unsubstituted C2 to C30 alkenylene group, a substituted or unsubstituted C2 to C30 alkynylene group, a substituted or unsubstituted C6 to C30 arylene group, a divalent substituted or unsubstituted C2 to C30 heterocyclic group, a combination thereof or a combined fused ring of the foregoing groups, the Ar² may include one of groups listed in the following Group 2.

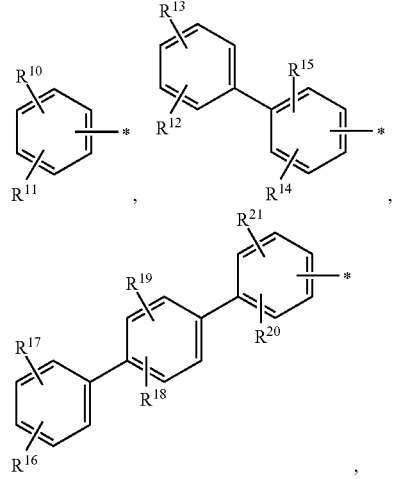

[Group 2]

-continued

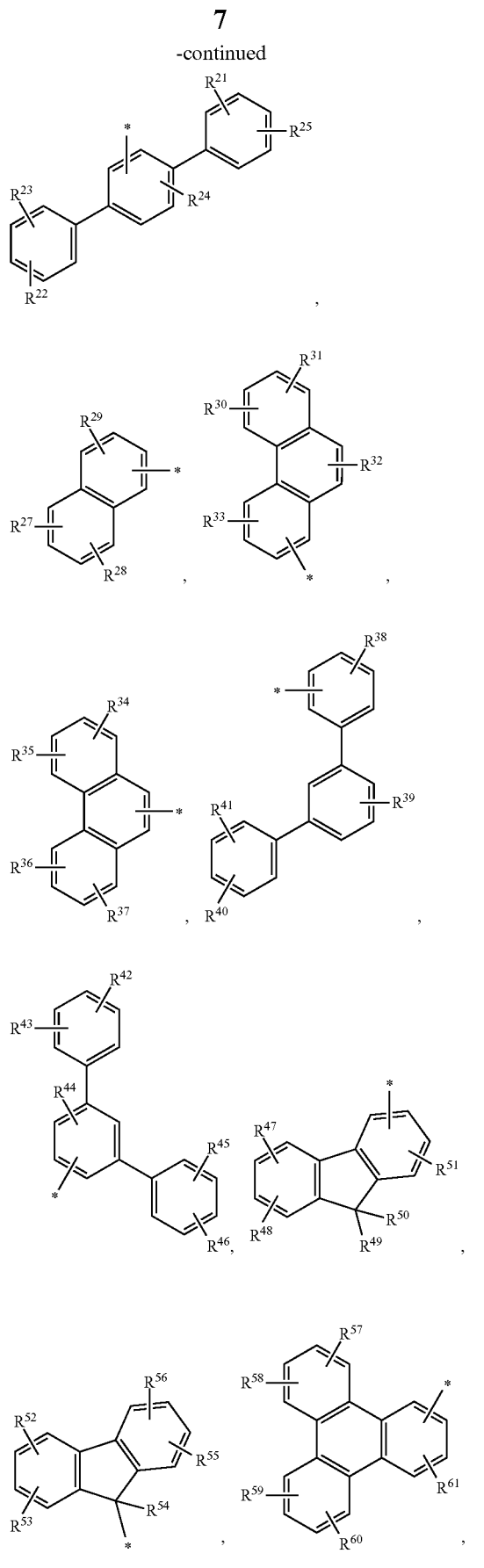

,

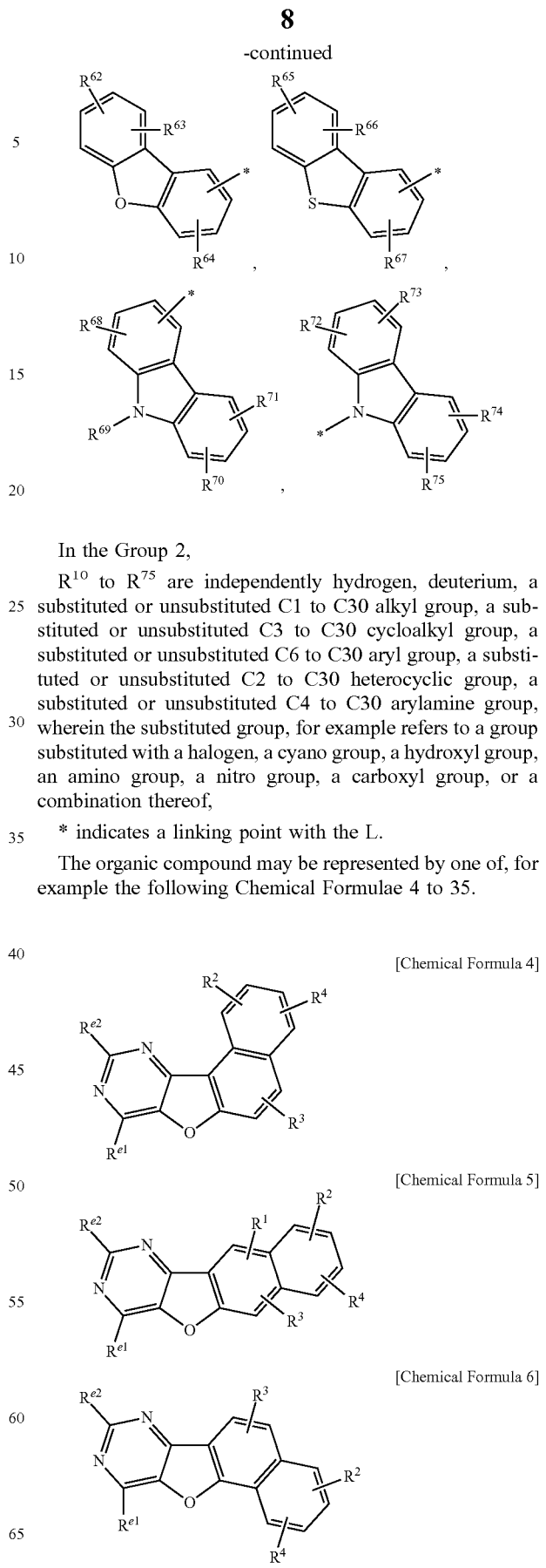

In the Group 2, $R^{10}$ to $R^{75}$ are independently hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C2 to C30 heterocyclic group, a substituted or unsubstituted C4 to C30 arylamine group, wherein the substituted group, for example refers to a group substituted with a halogen, a cyano group, a hydroxyl group, an amino group, a nitro group, a carboxyl group, or a combination thereof,

* indicates a linking point with the L.

The organic compound may be represented by one of, for example the following Chemical Formulae 4 to 35.

[Chemical Formula 7]
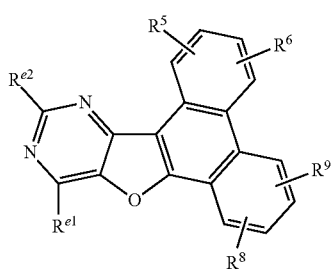
[Chemical Formula 8]
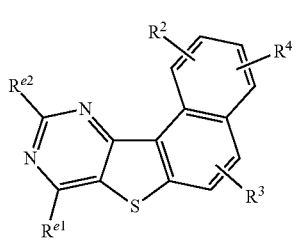
[Chemical Formula 9]
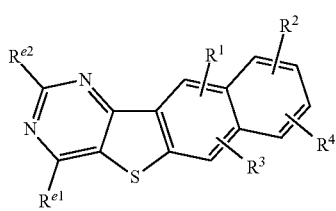
[Chemical Formula 10]
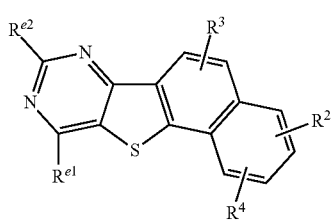
[Chemical Formula 11]
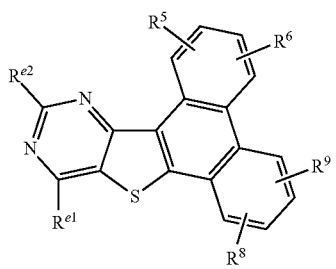
[Chemical Formula 12]
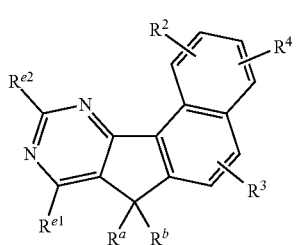
[Chemical Formula 13]
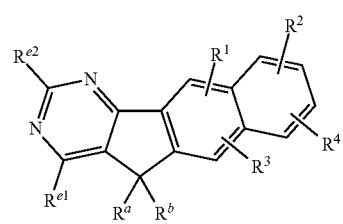
[Chemical Formula 14]
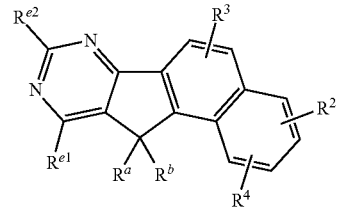
[Chemical Formula 15]
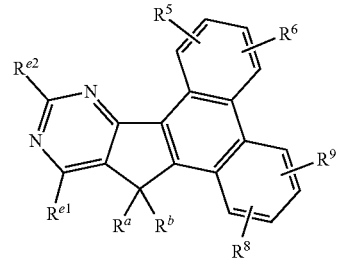
[Chemical Formula 16]
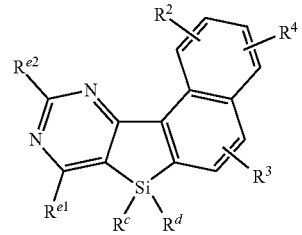
[Chemical Formula 17]
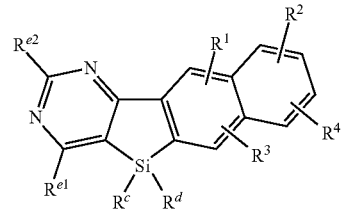
[Chemical Formula 18]
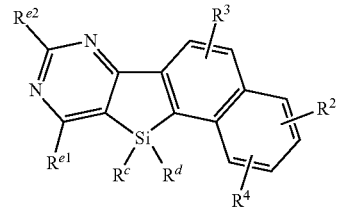

[Chemical Formula 19]
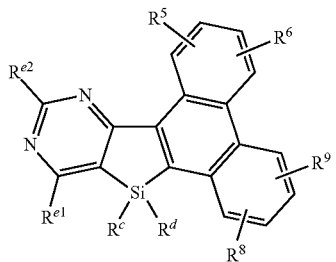
[Chemical Formula 20]
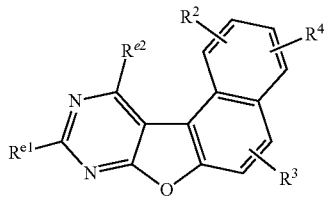
[Chemical Formula 21]
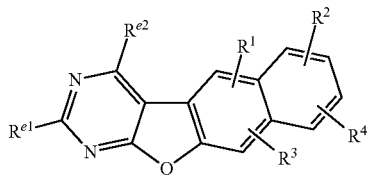
[Chemical Formula 22]
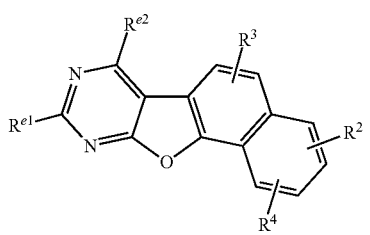
[Chemical Formula 23]
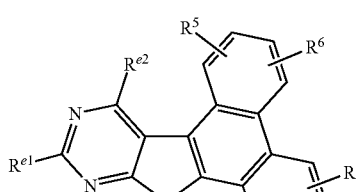
[Chemical Formula 24]
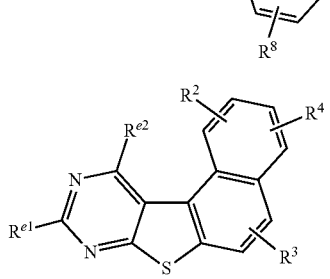
[Chemical Formula 25]
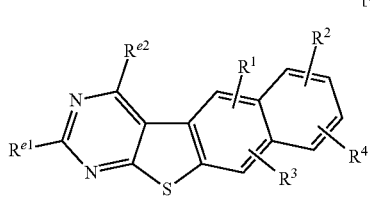
[Chemical Formula 26]
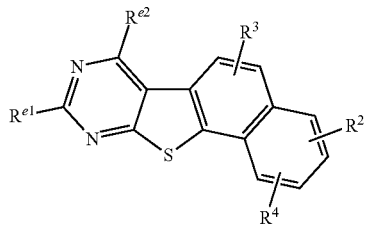
[Chemical Formula 27]
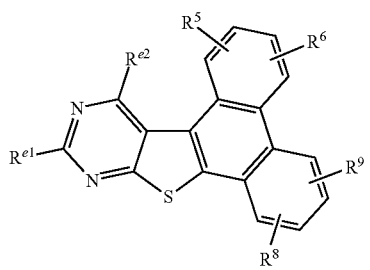
[Chemical Formula 28]
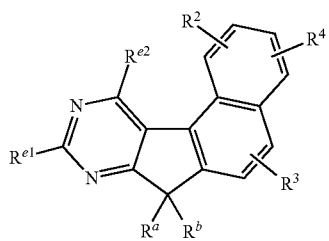
[Chemical Formula 29]
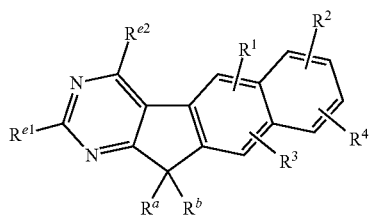
[Chemical Formula 30]
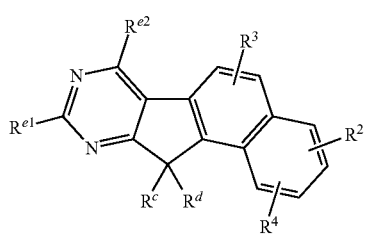

[Chemical Formula 31]
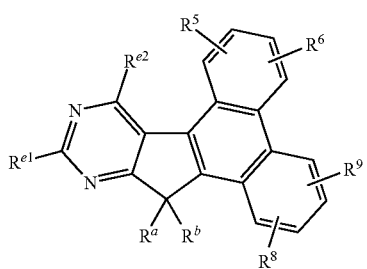
[Chemical Formula 32]
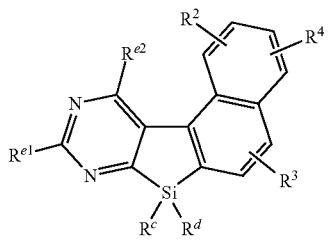
[Chemical Formula 33]
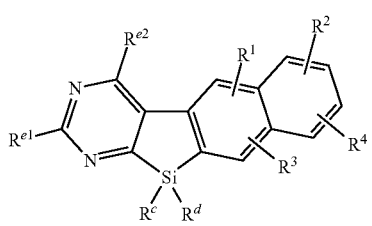
[Chemical Formula 34]
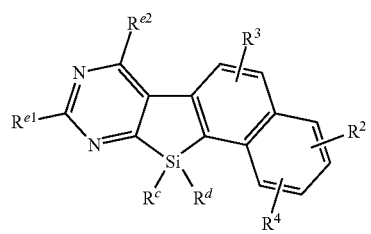
[Chemical Formula 35]
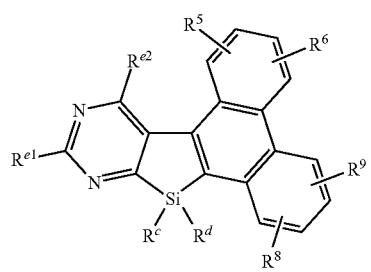
In the Chemical Formulae 4 to 35, $R^1$ to $R^9$, $R^a$ to $R^d$, $R^{e1}$ and $R^{e2}$ are the same as described above.
The organic compound may be, for example one of compounds listed in the following Group 3, but is not limited thereto.
[Group 3]
A-1
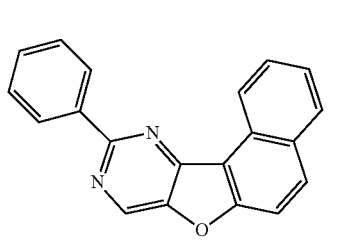
A-2
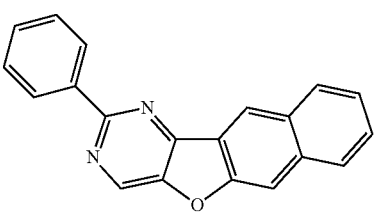
A-3
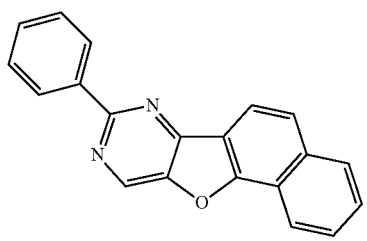
A-4
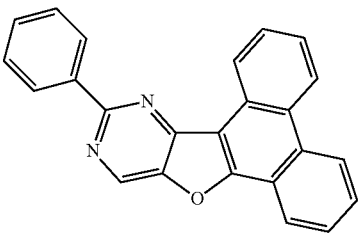
A-5
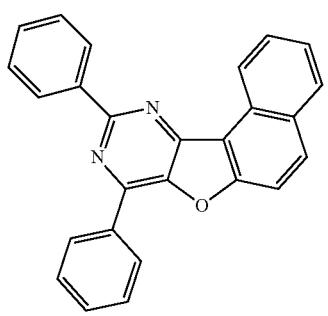
A-6
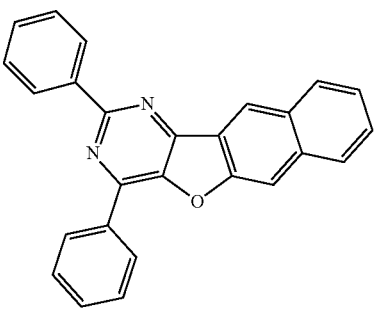

-continued
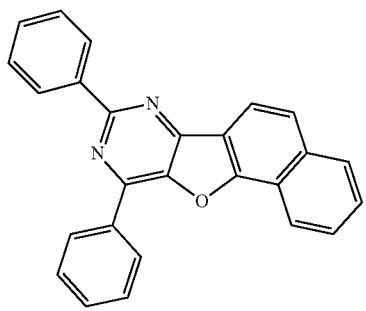
A-7
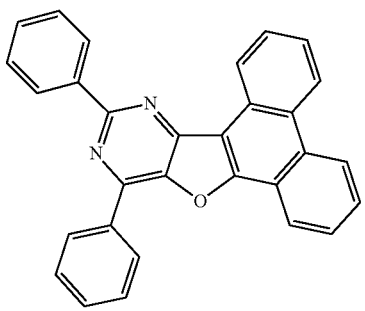
A-8
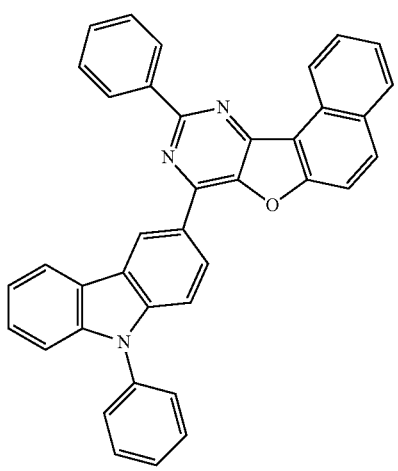
A-9
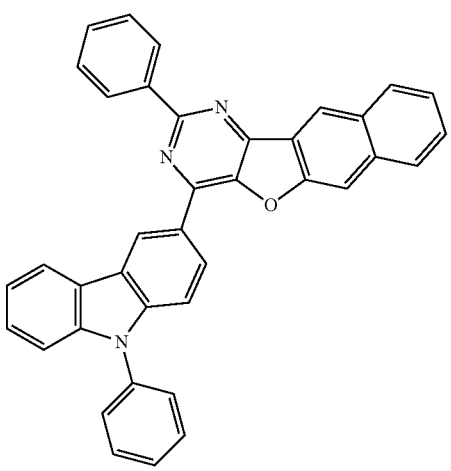
A-10
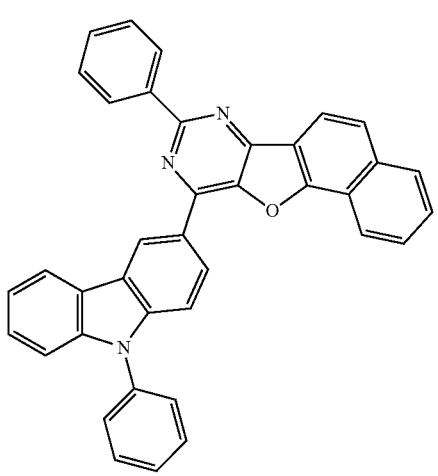
A-11
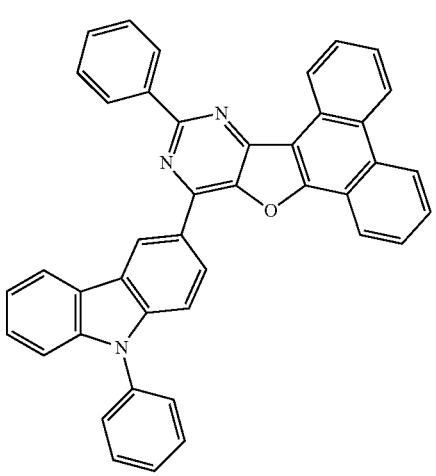
A-12

-continued
A-13
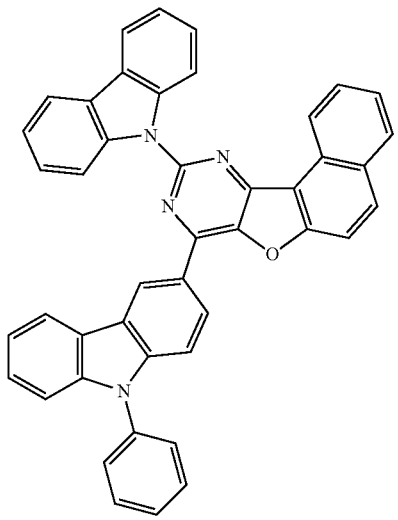
A-14
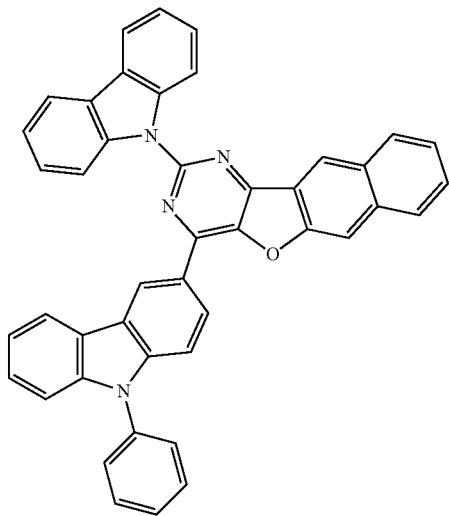
A-15
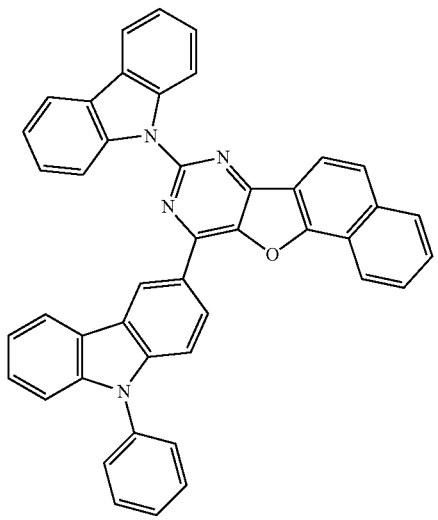
A-16
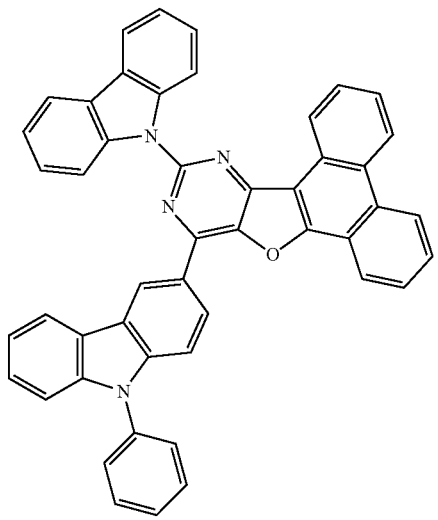
A-17
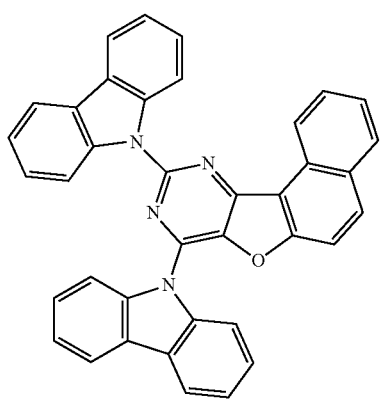
A-18
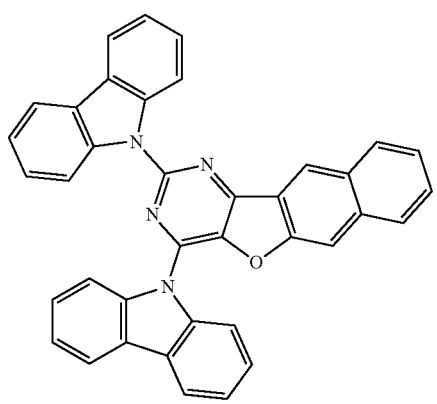

-continued
A-19
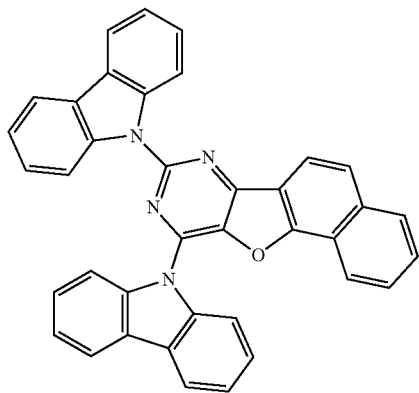
A-20
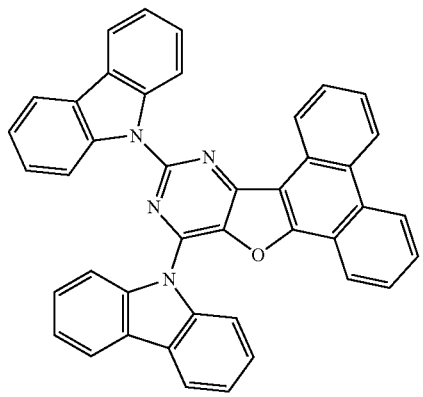
A-21
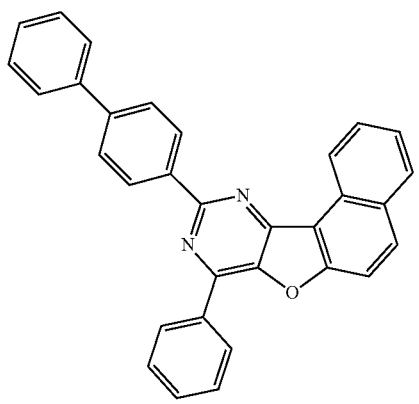
A-22
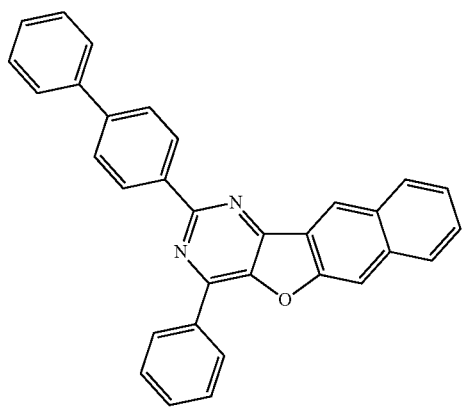
A-23
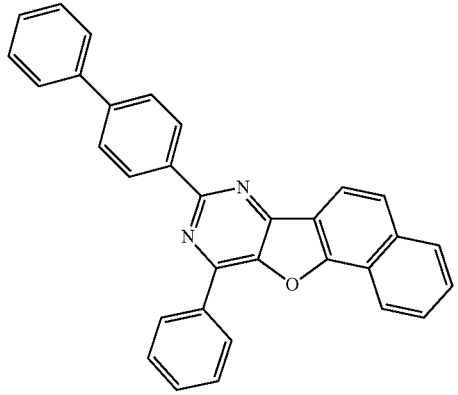
A-24
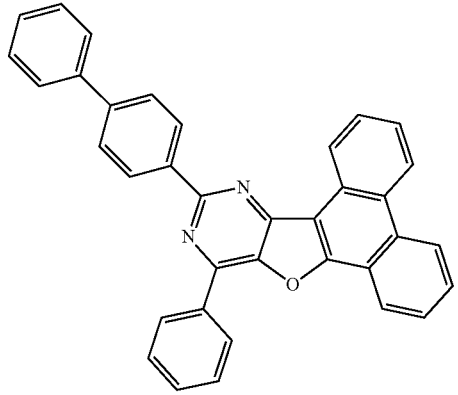
A-25
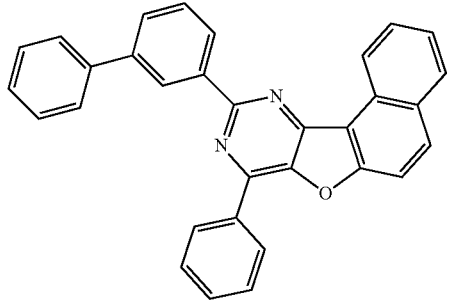
A-26
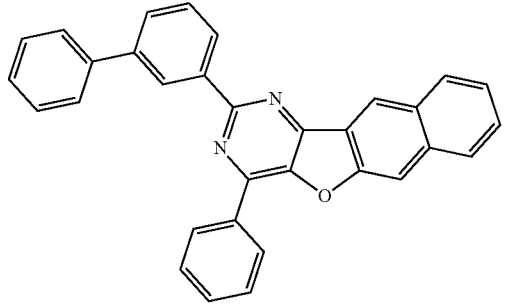

-continued
A-27
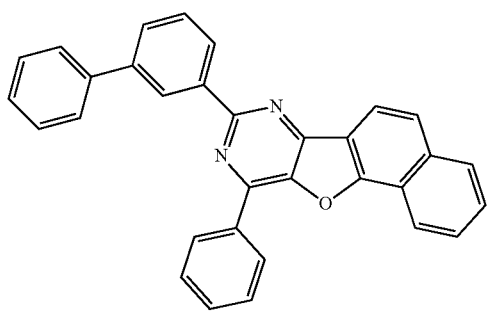
A-28
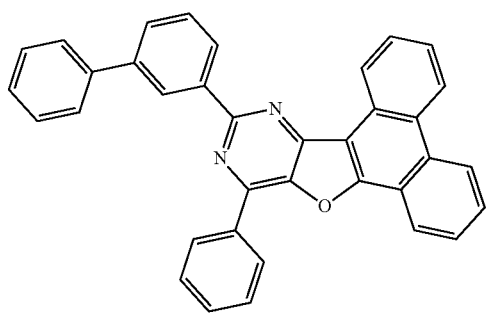
A-29
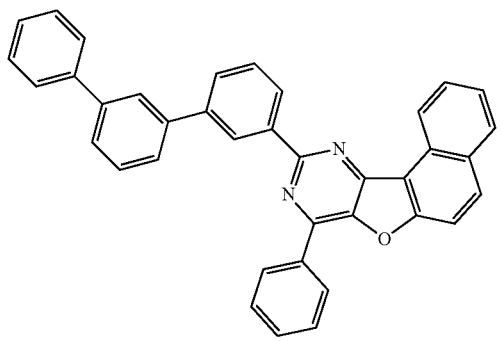
A-30
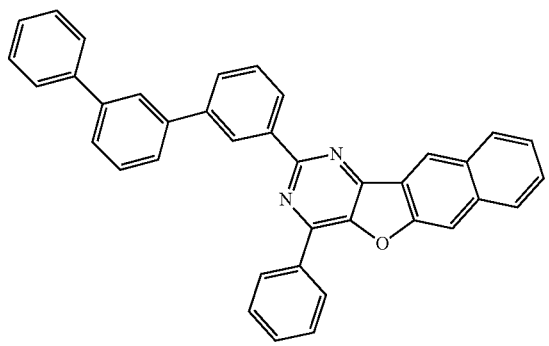
A-31
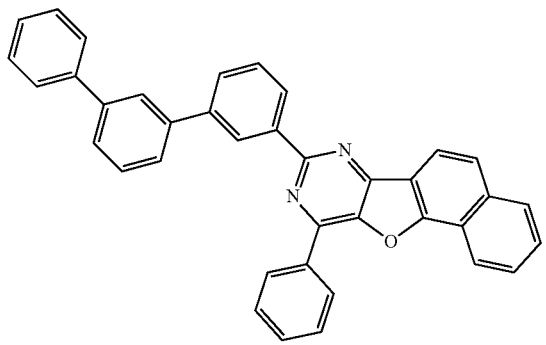
A-32
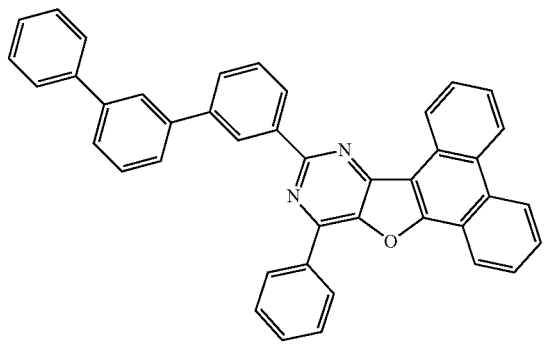
A-33
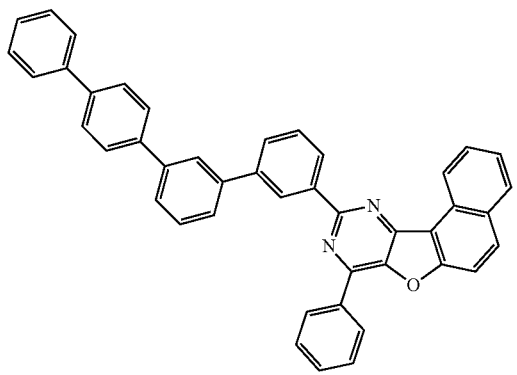
A-34
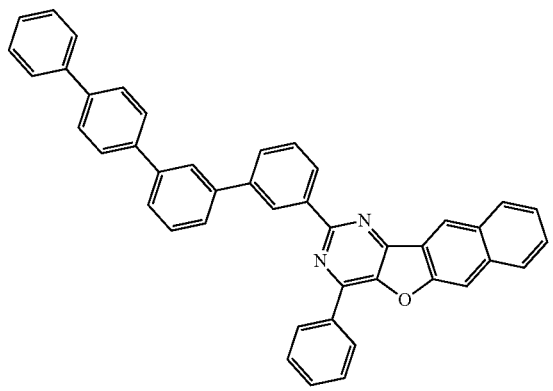

-continued
A-35
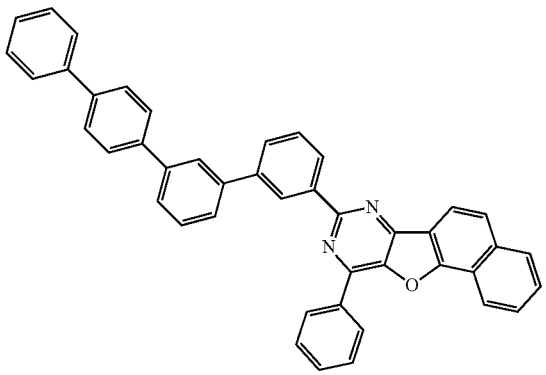
A-36
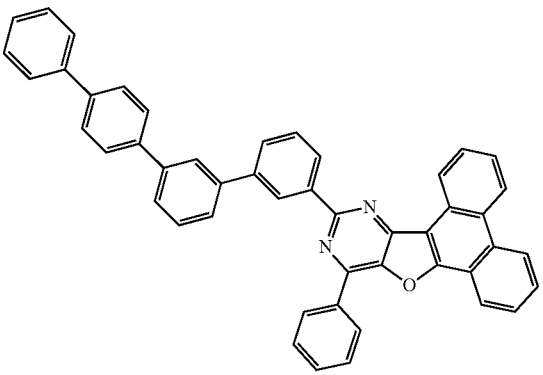
A-37
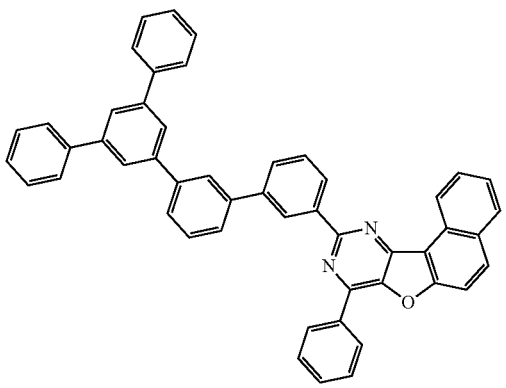
A-38
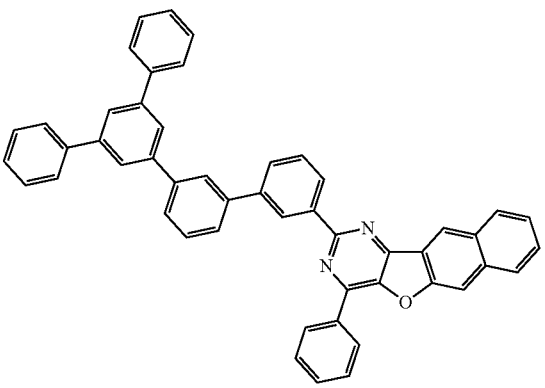
A-39
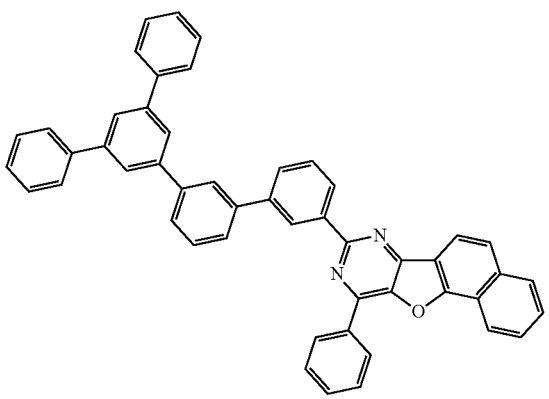
A-40
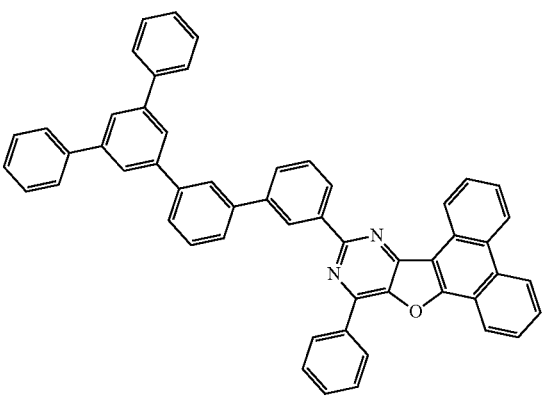
A-41
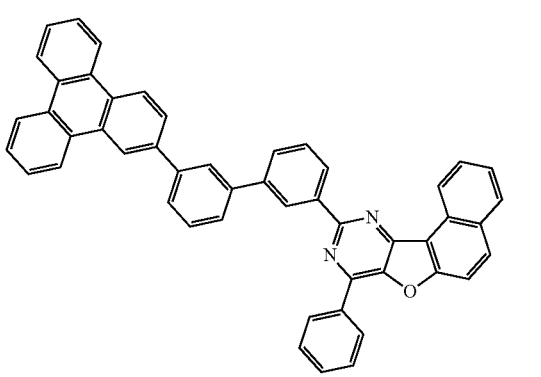
A-42
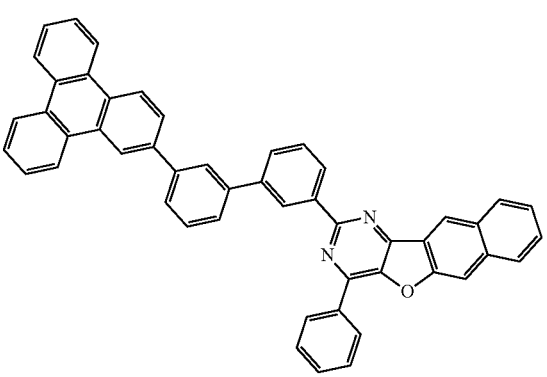

-continued
A-43
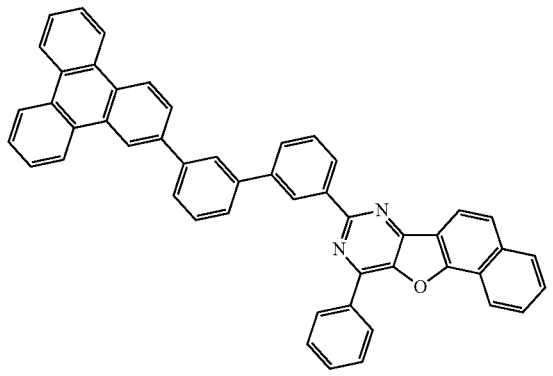
A-44
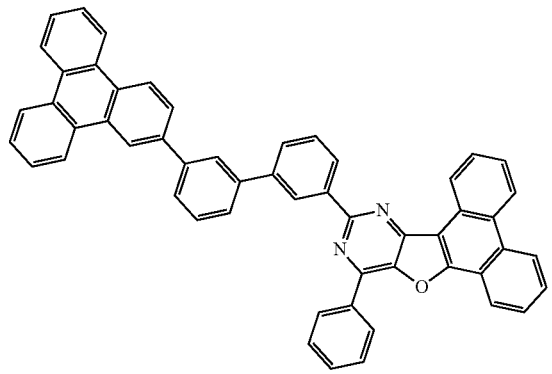
A-45
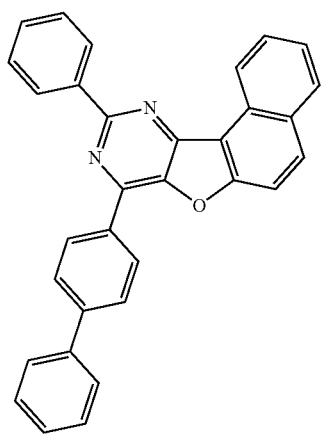
A-46
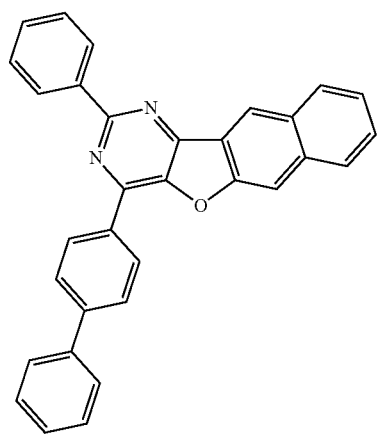
A-47
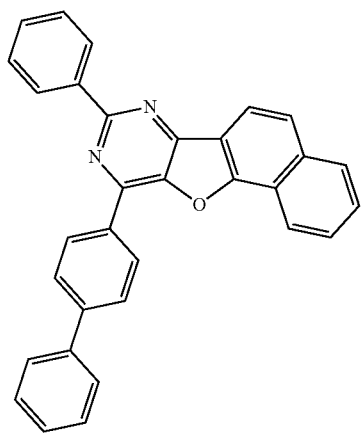
A-48
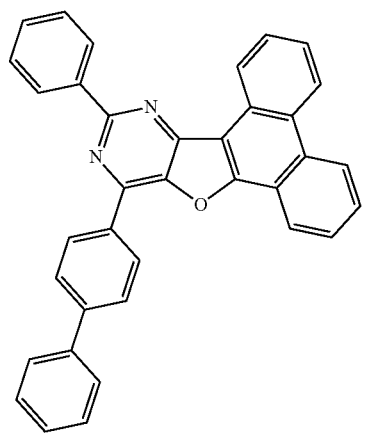

-continued
A-49
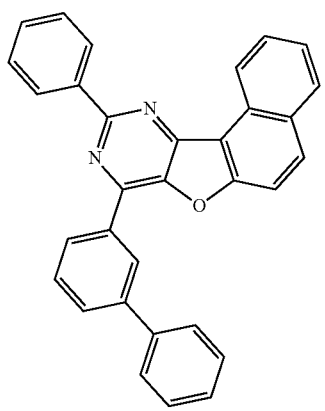
A-50
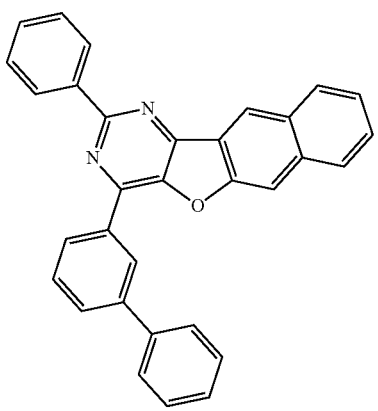
A-51
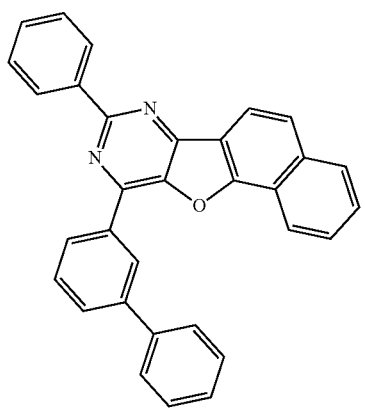
A-52
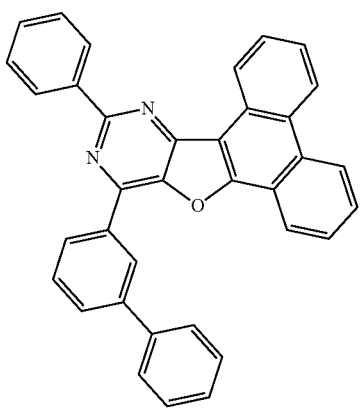
A-53
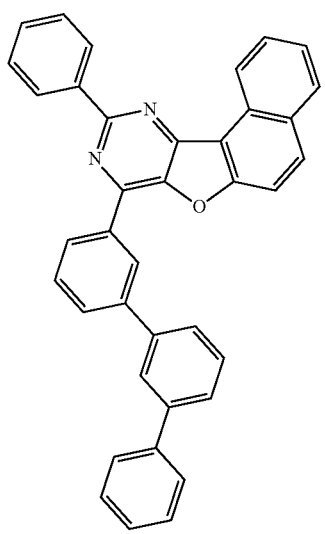
A-54
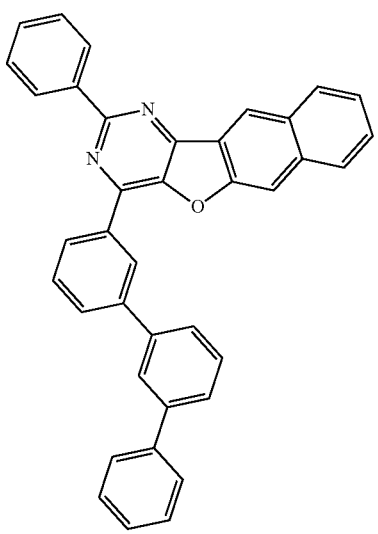

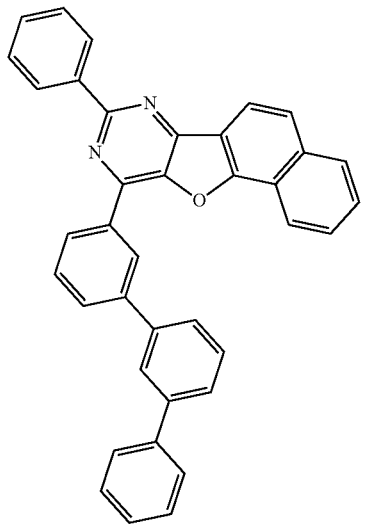
A-55
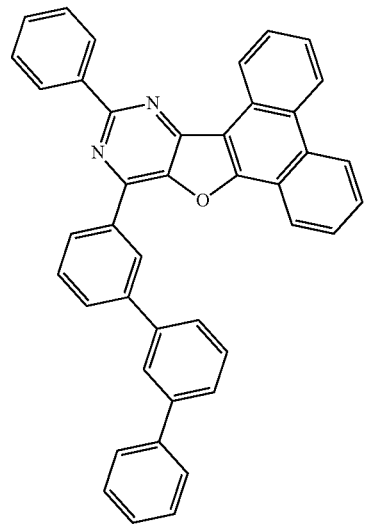
A-56
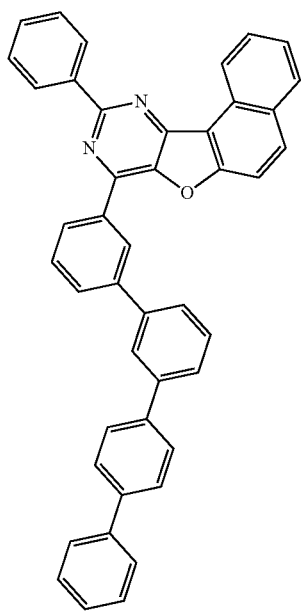
A-57
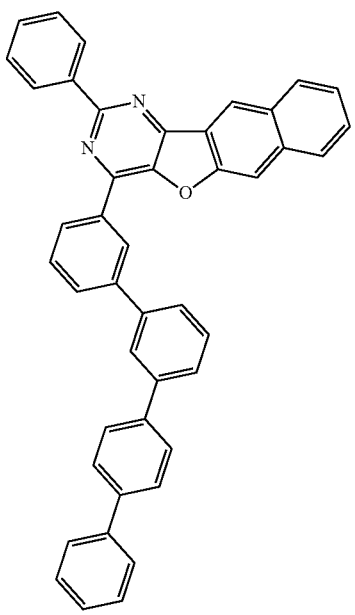
A-58

-continued
A-59
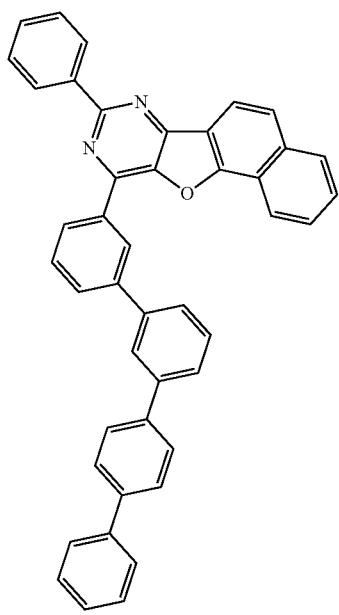
A-60
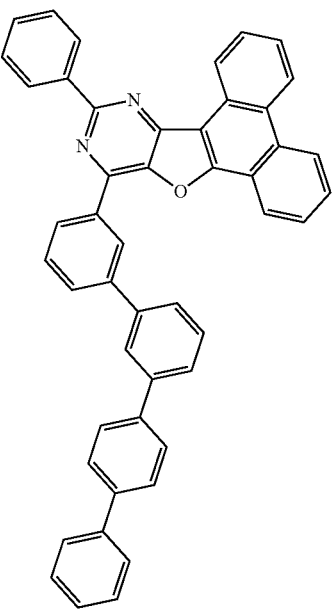
A-61
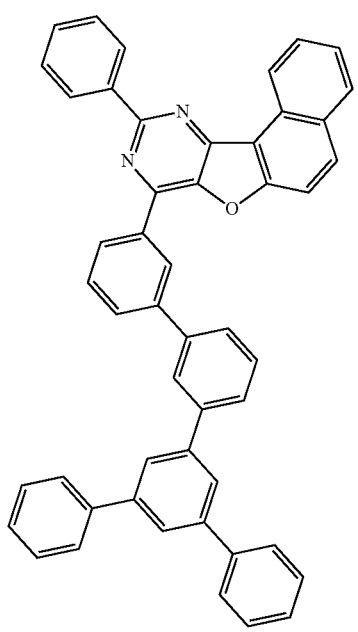
A-62
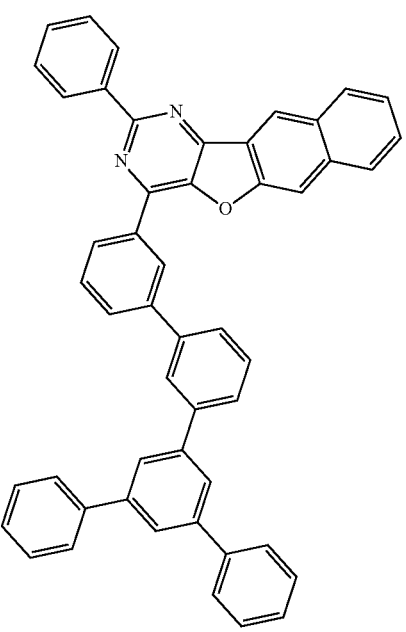

-continued
A-63
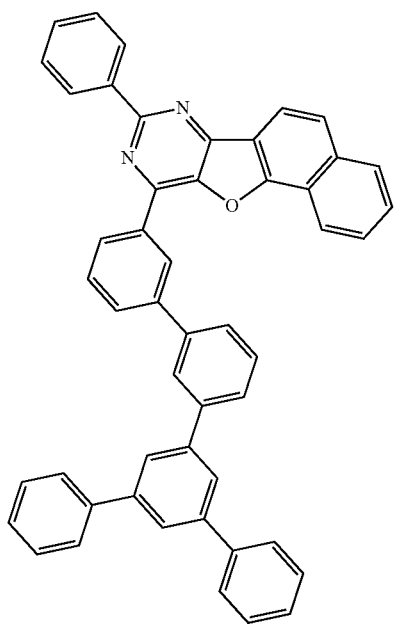
A-64
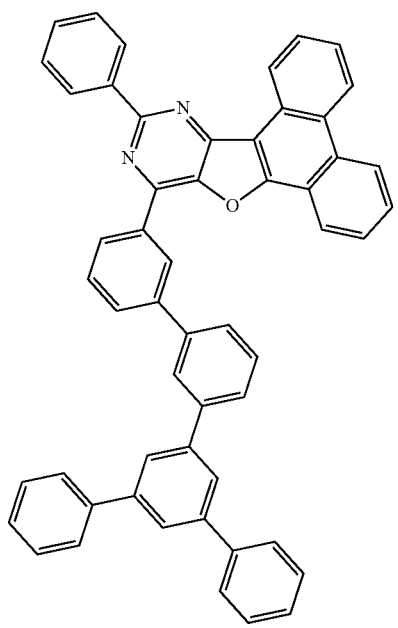
A-65
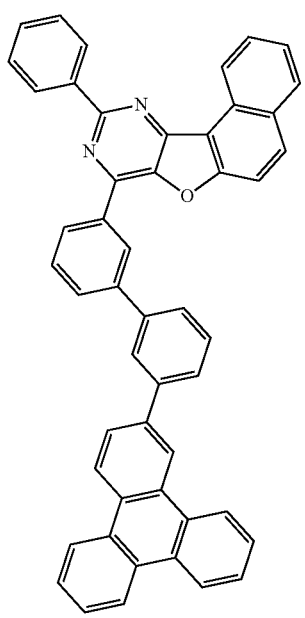
A-66
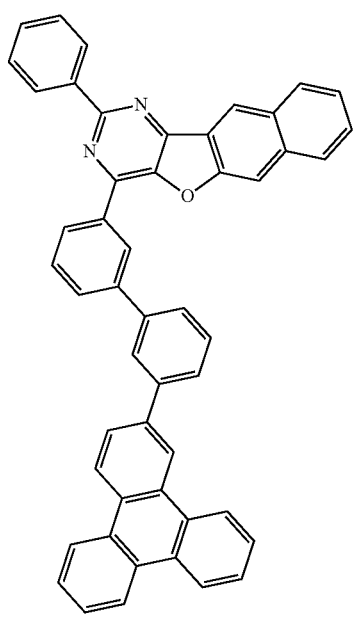

-continued
A-67
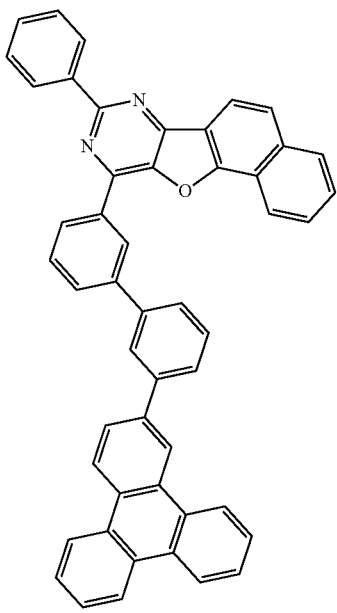
A-68
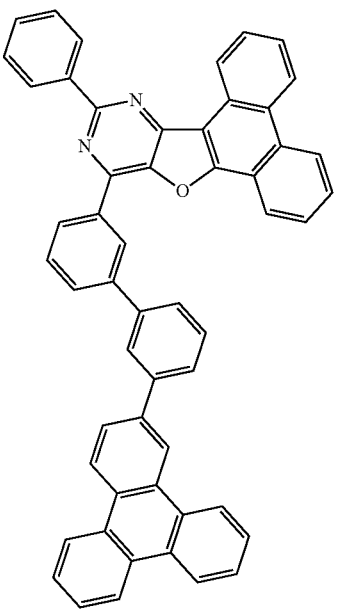
A-69
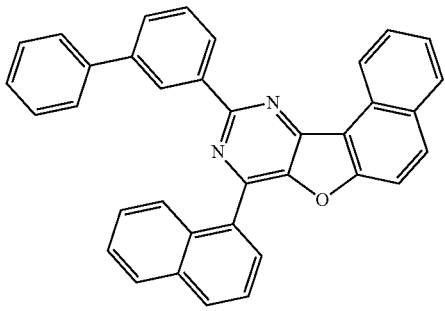
A-70
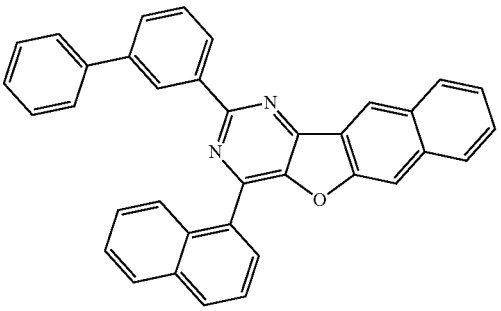
A-71
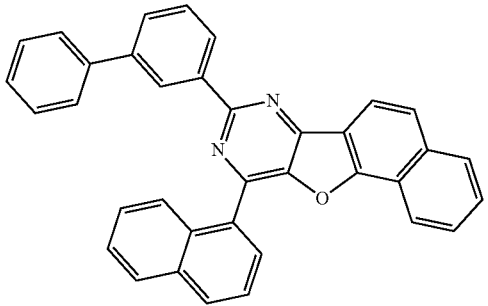
A-72
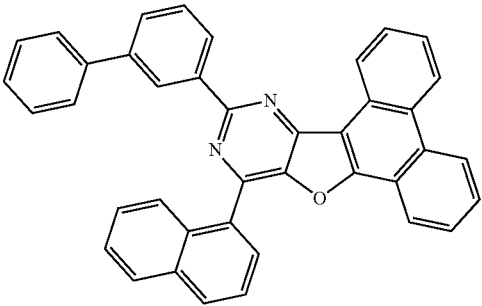
A-73
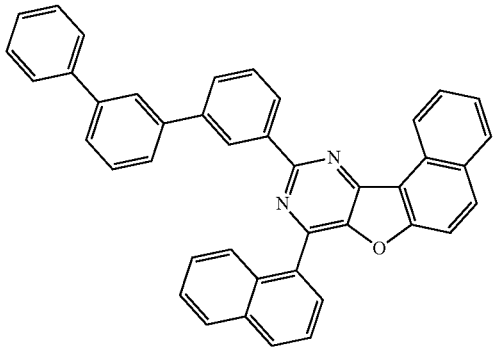
A-74
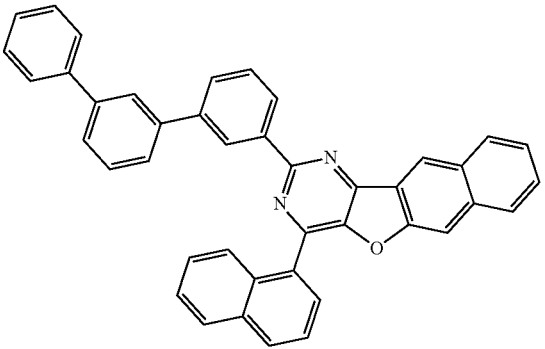

-continued
A-75
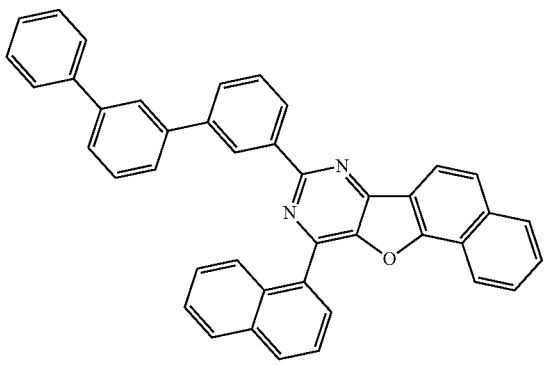
A-76
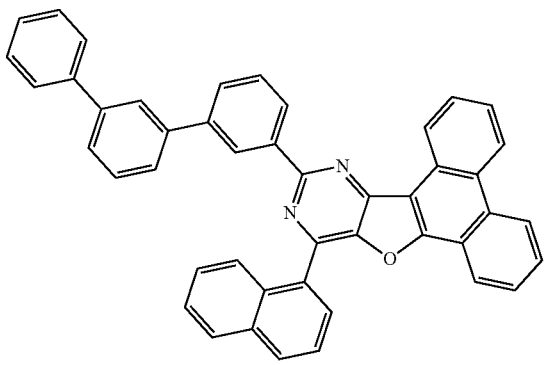
A-77
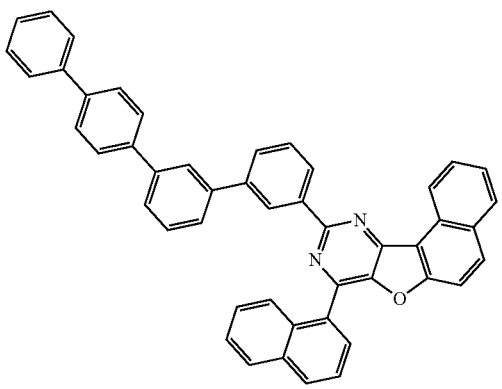
A-78
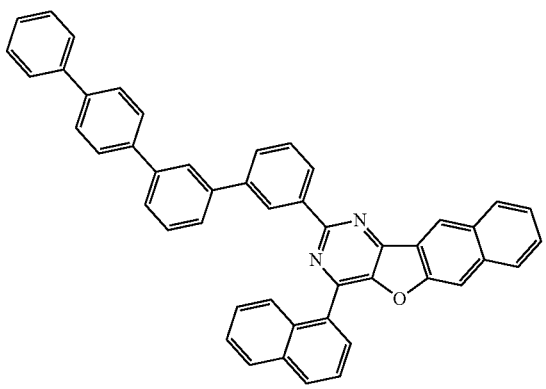
A-79
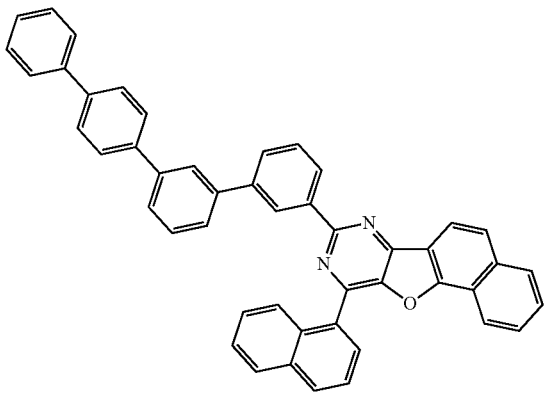
A-80
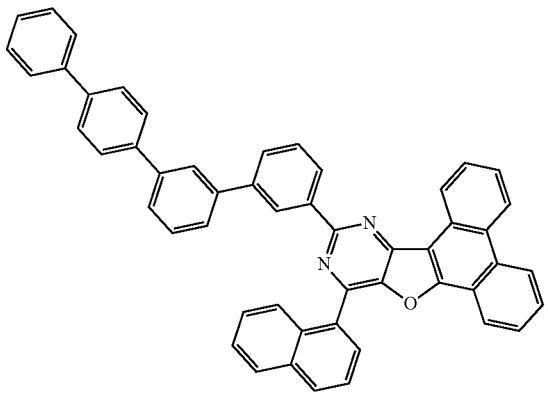
A-81
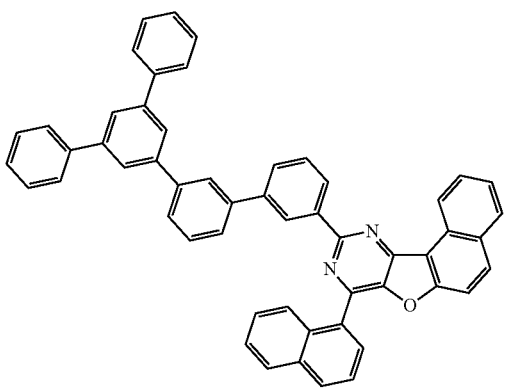
A-82
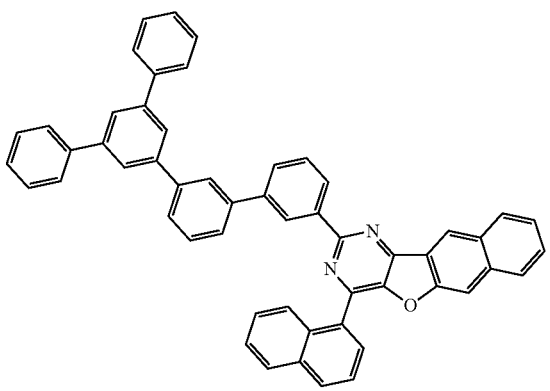

-continued
A-83
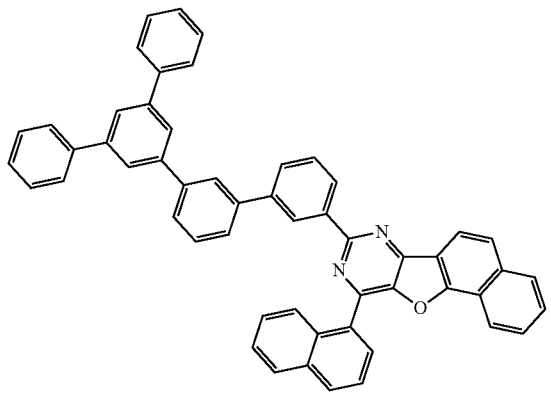
A-84
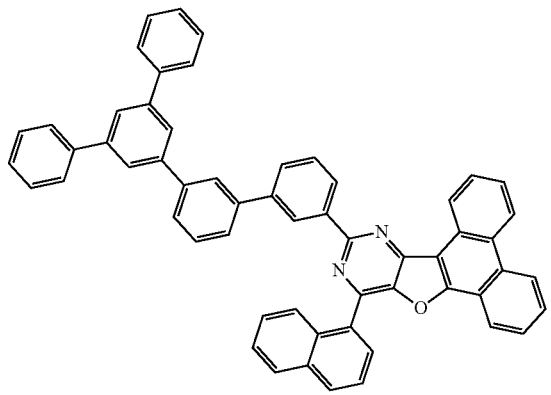
A-85
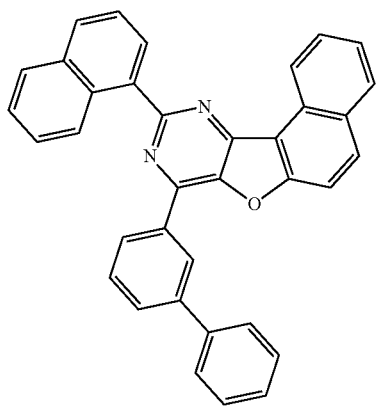
A-86
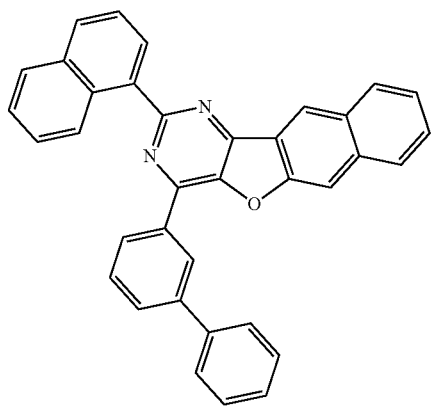
A-87
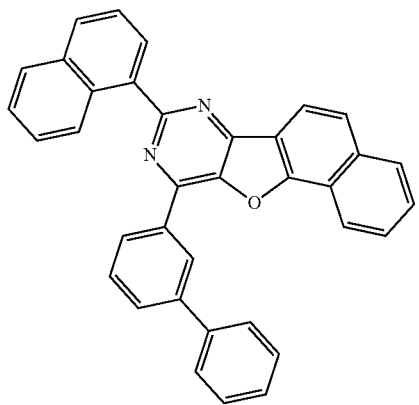
A-88
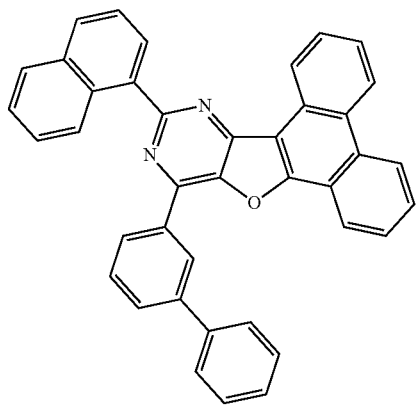

-continued
A-89
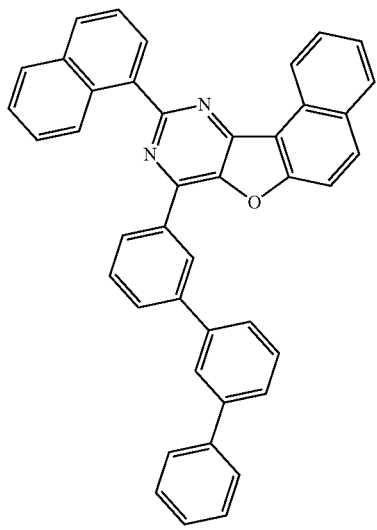
A-90
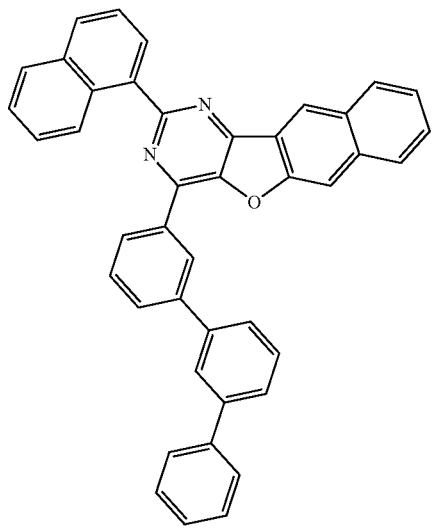
A-91
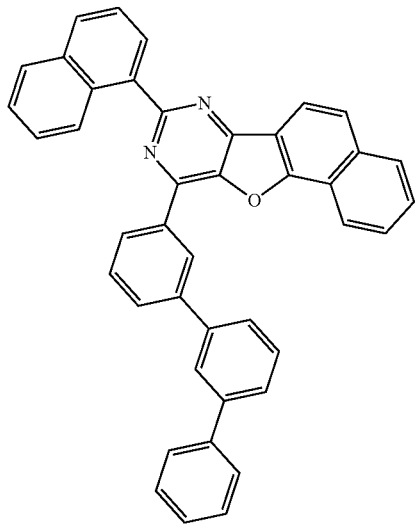
A-92
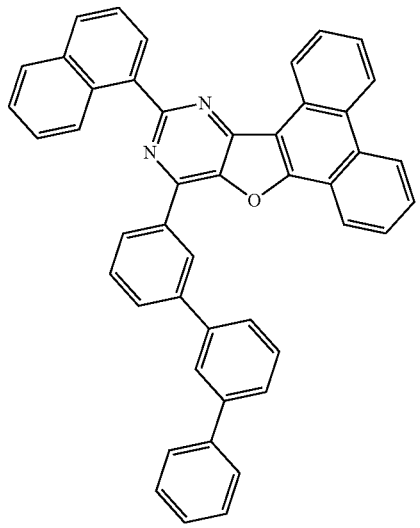
A-93
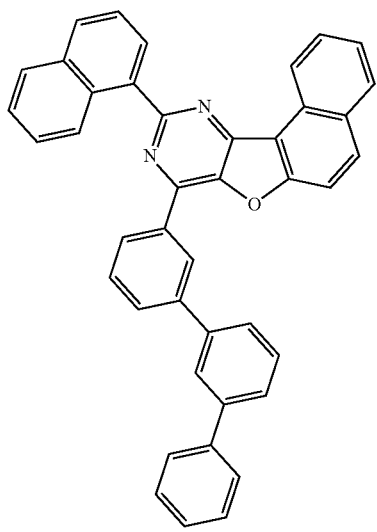
A-94
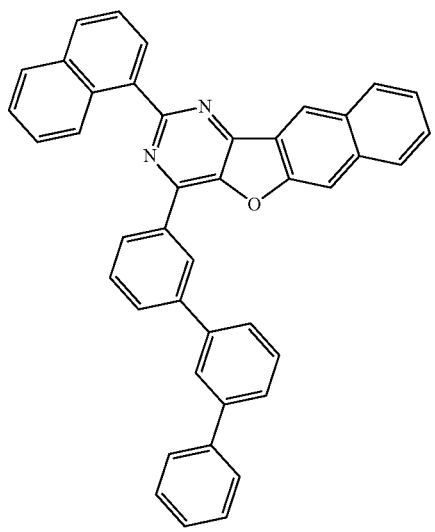

-continued
A-95
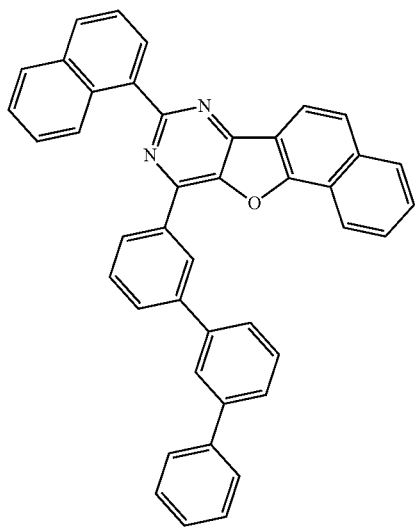
A-96
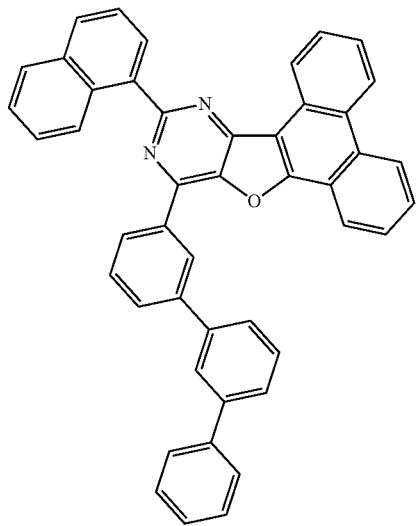
A-97
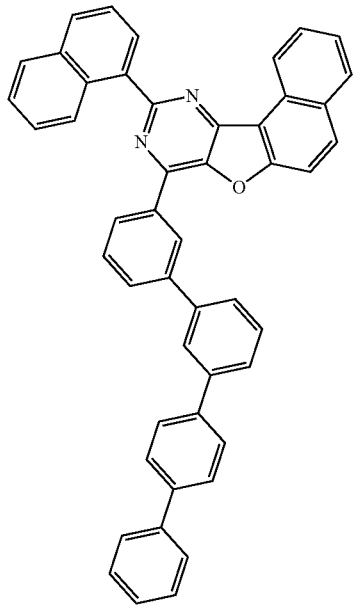
A-98
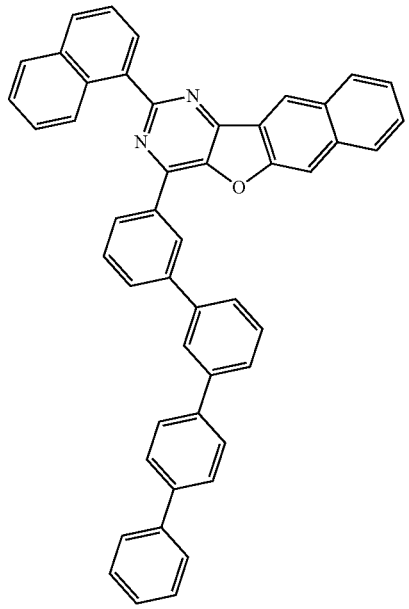

-continued
A-99
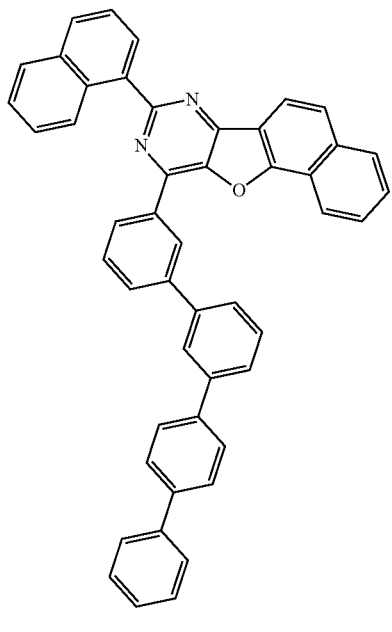
A-100
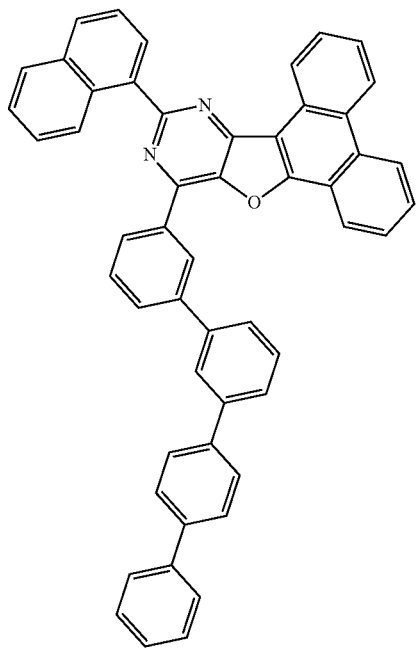
A-101
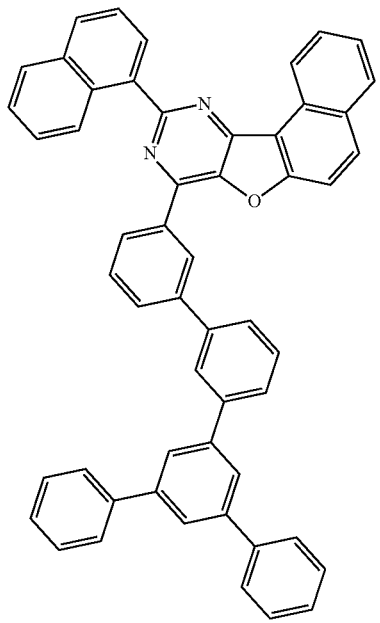
A-102
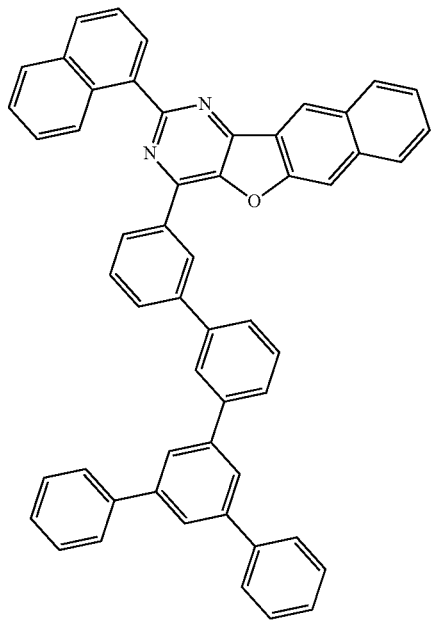

-continued
A-103
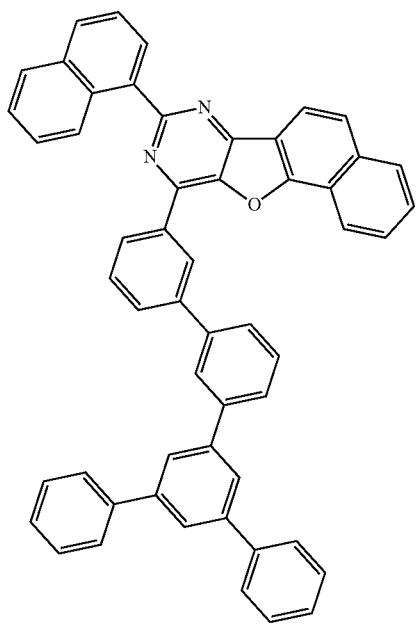
A-104
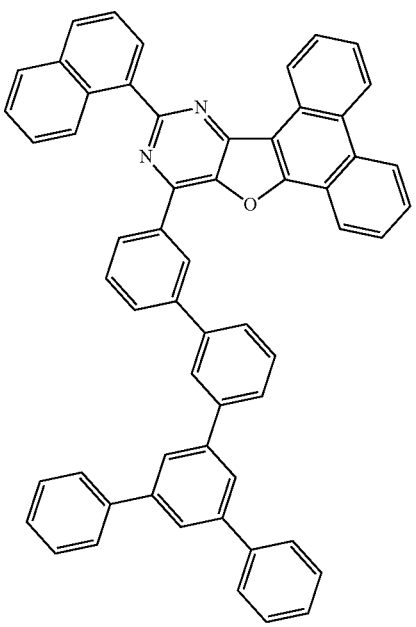
A-105
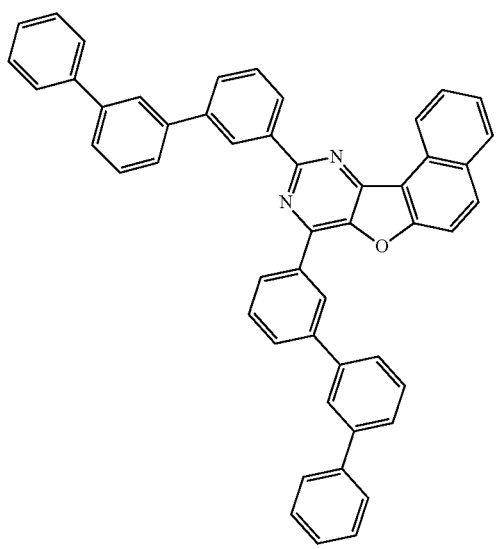
A-106
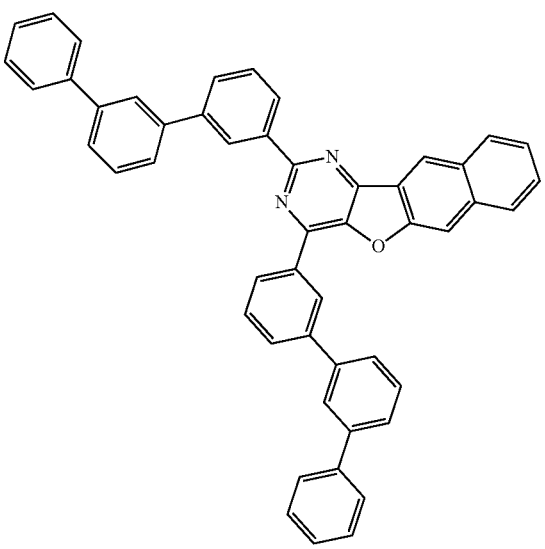

-continued
A-107
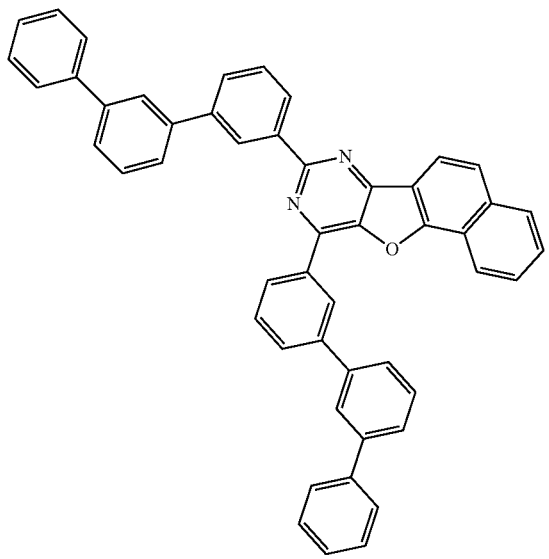
A-108
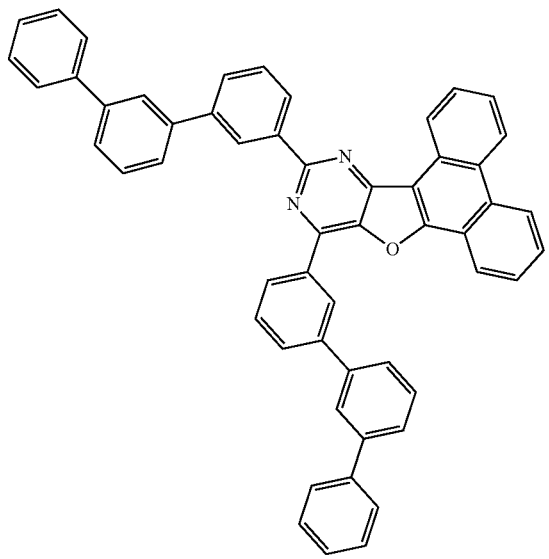
A-109
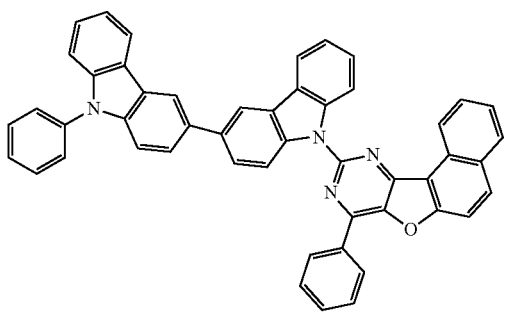
A-110
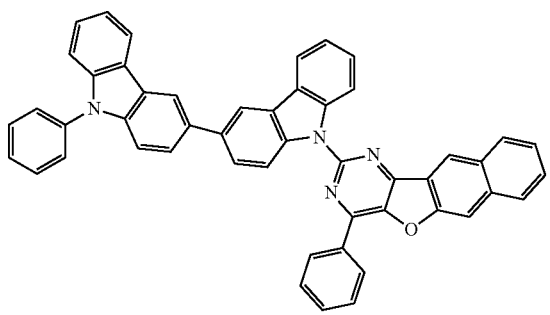
A-111
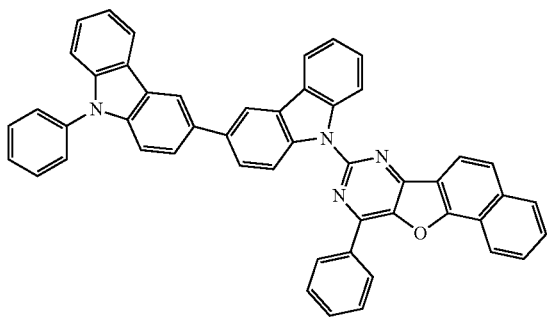
A-112
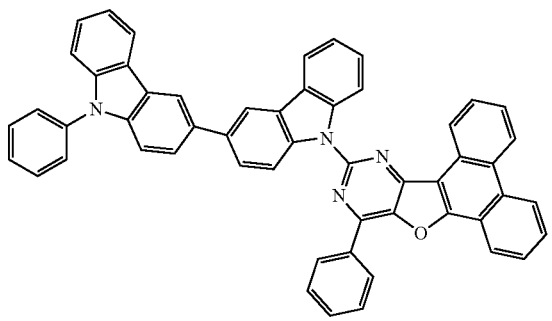
A-113
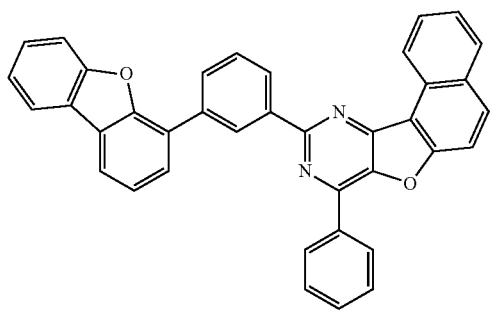
A-114
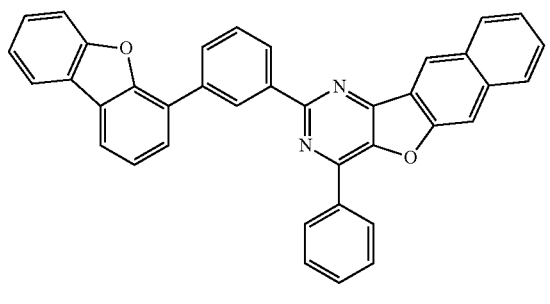

-continued
A-115
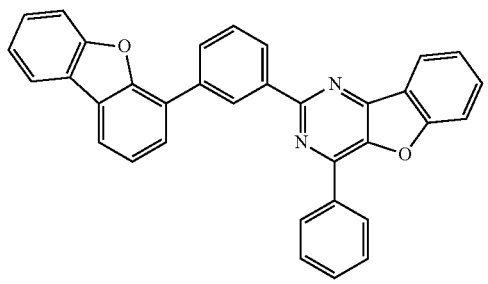
A-116
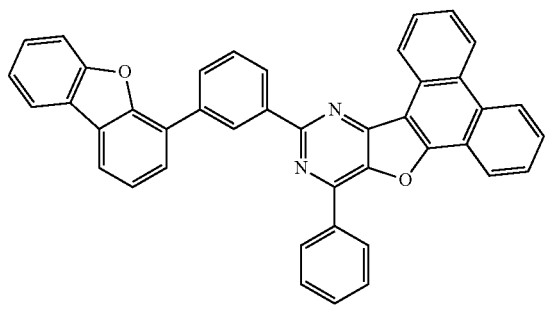
A-117
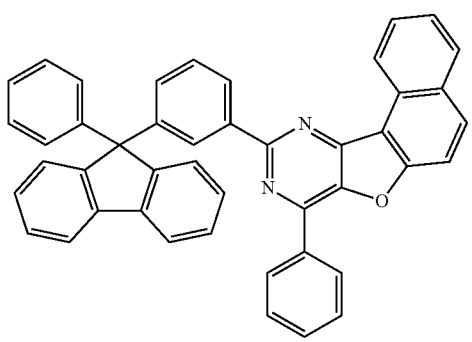
A-118
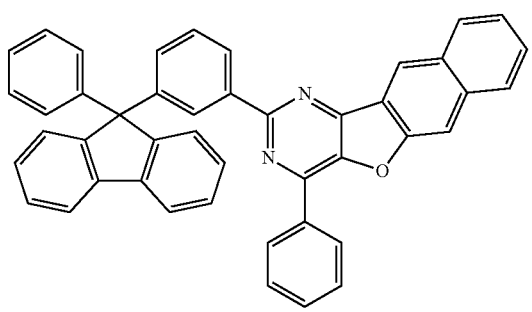
A-119
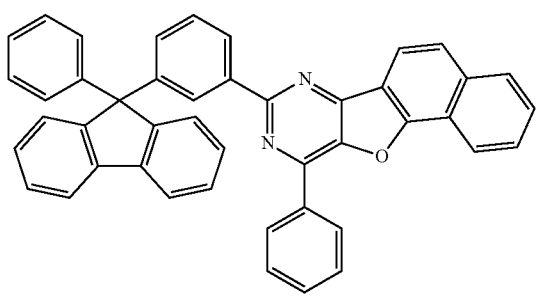
A-120
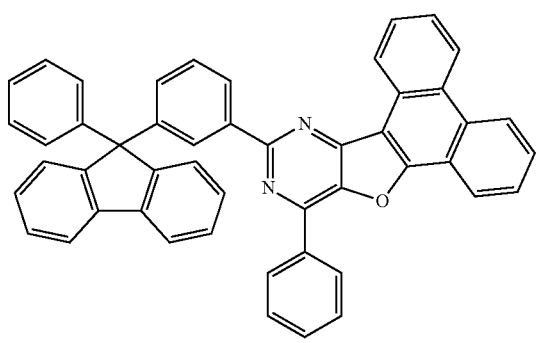
B-1
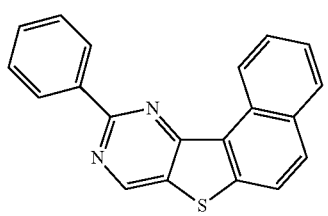
B-2
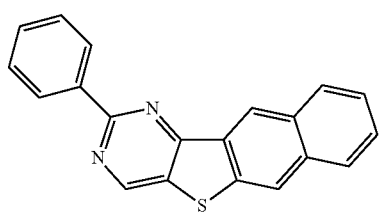
B-3
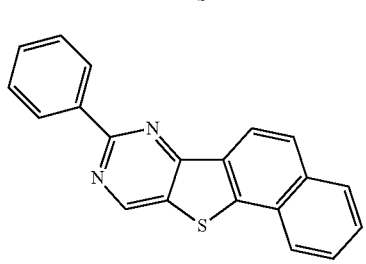
B-4
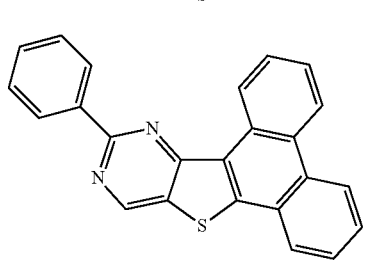

-continued
B-5
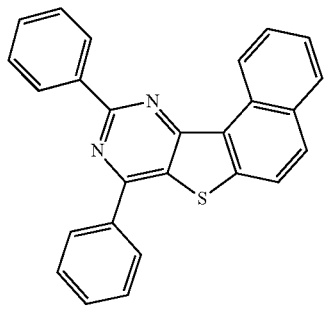
B-6
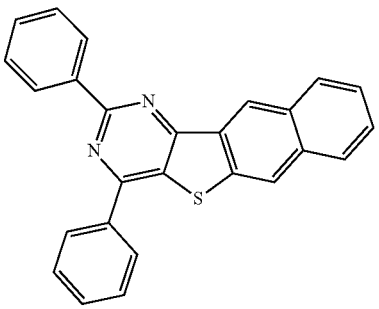
B-7
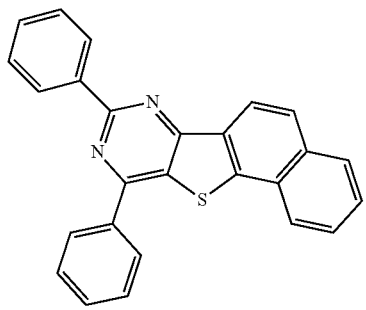
B-8
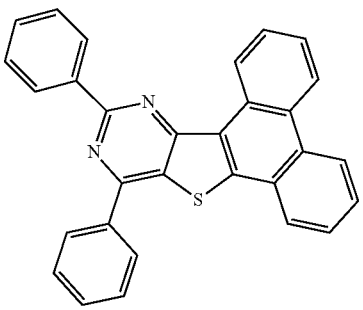
B-9
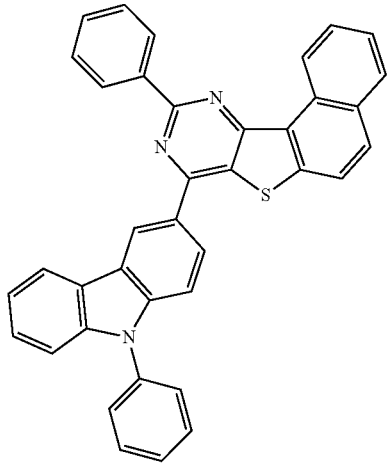
B-10
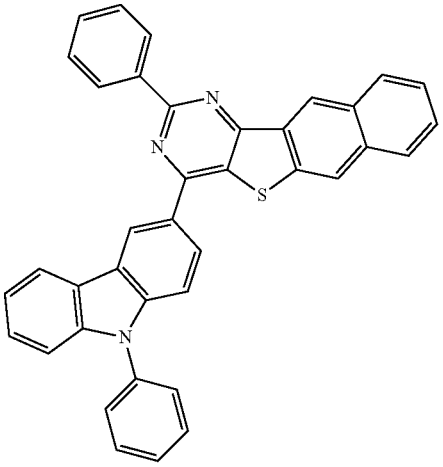
B-11
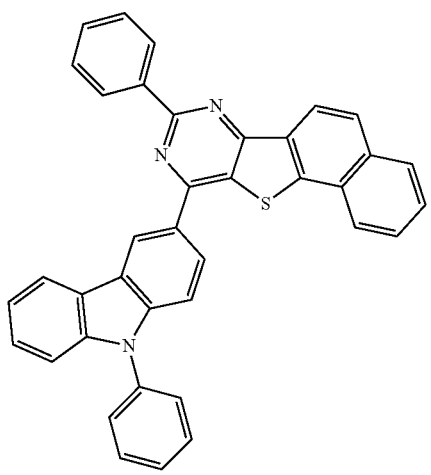
B-12
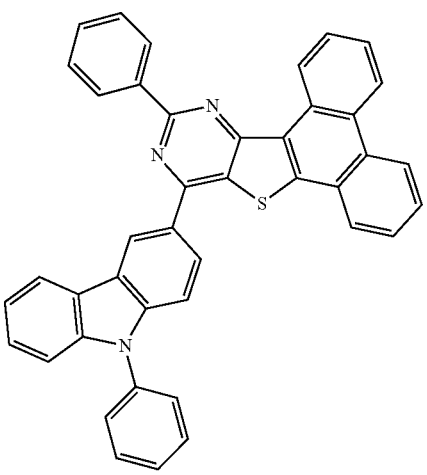

-continued
B-13
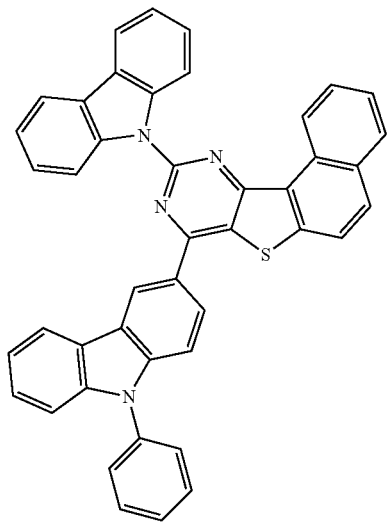
B-14
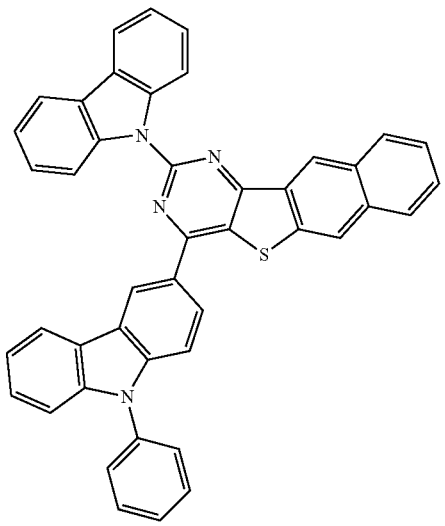
B-15
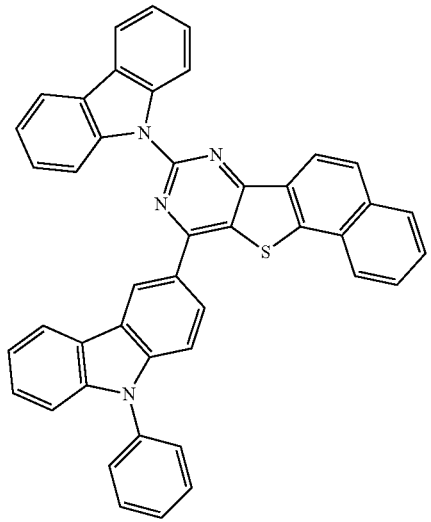
B-16
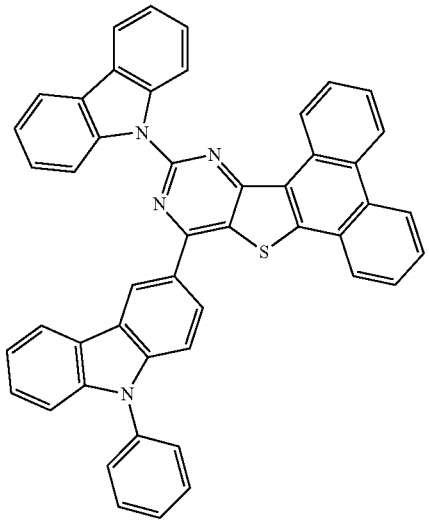
B-17
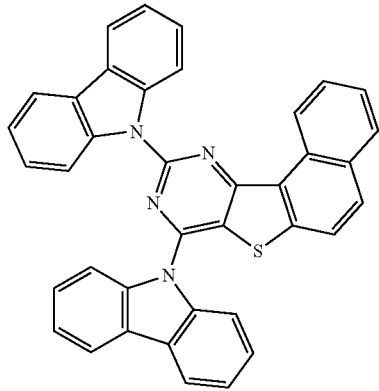
B-18
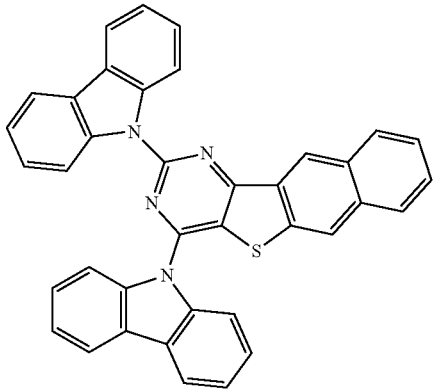

-continued
B-19
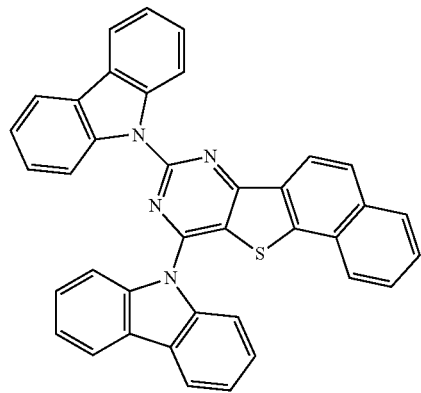
B-20
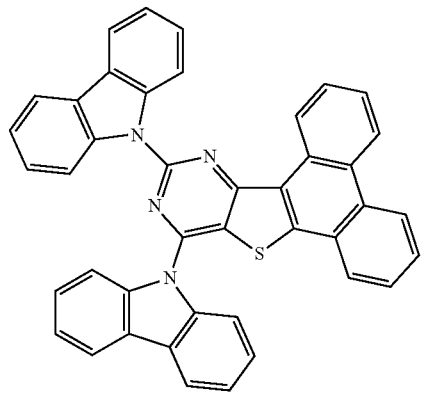
B-21
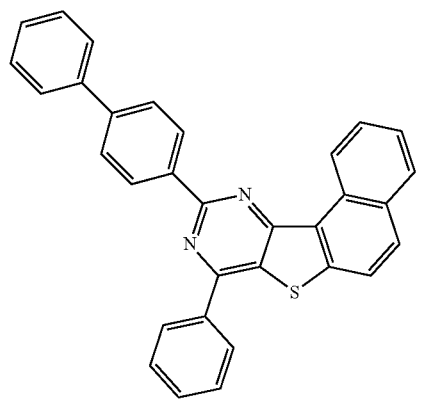
B-22
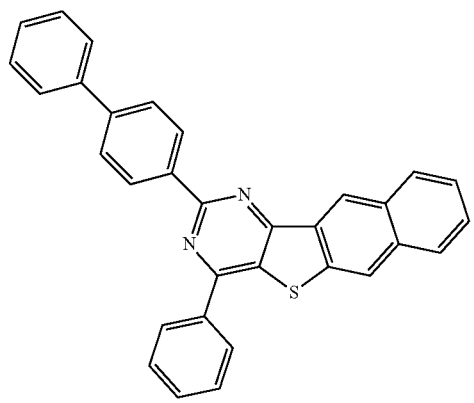
B-23
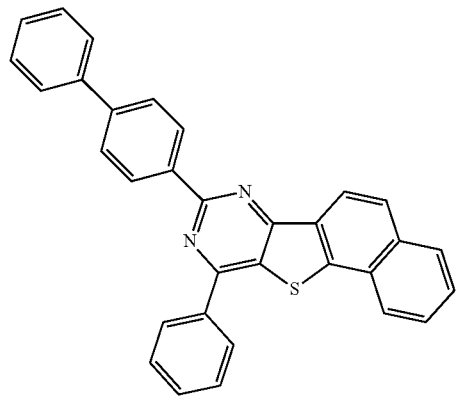
B-24
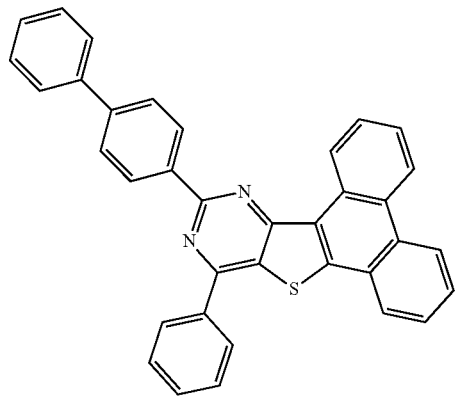
B-25
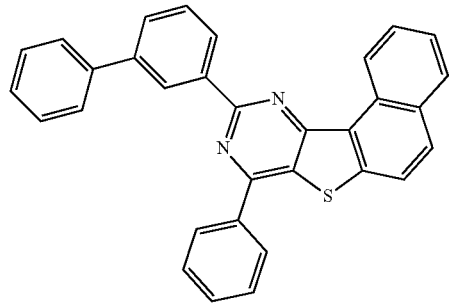
B-26
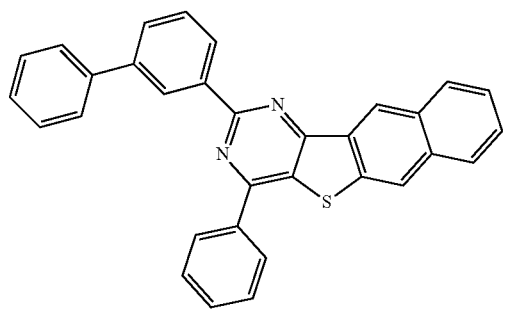

-continued
B-27
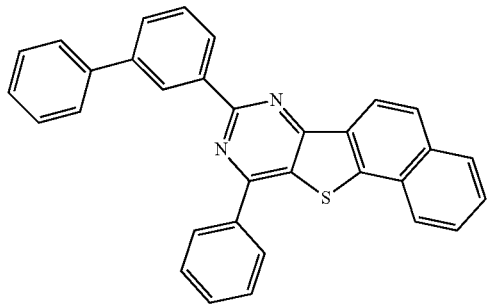
B-28
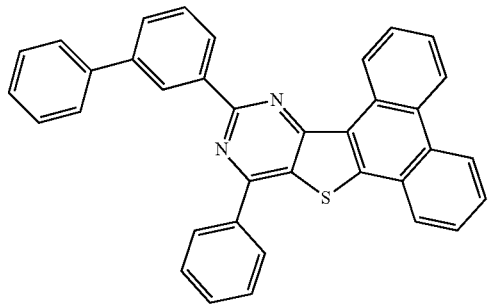
B-29
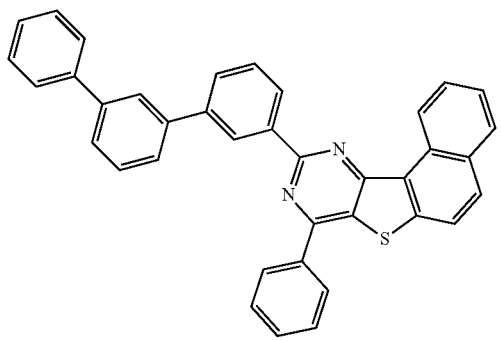
B-30
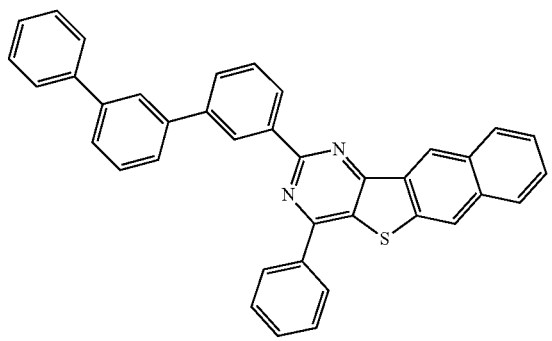
B-31
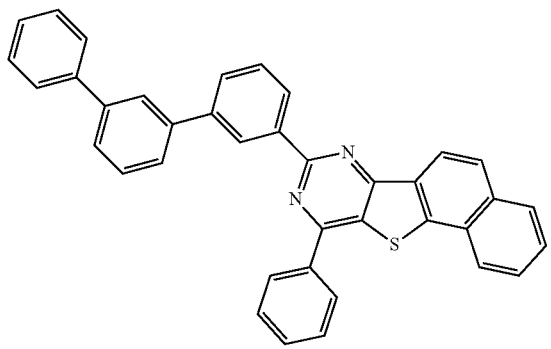
B-32
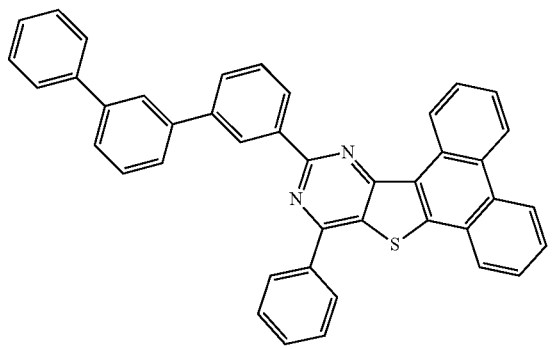
B-33
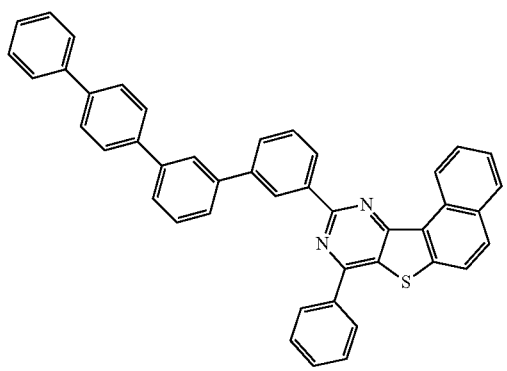
B-34
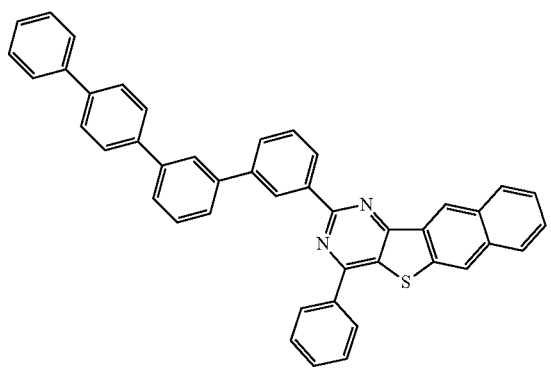

-continued
B-35
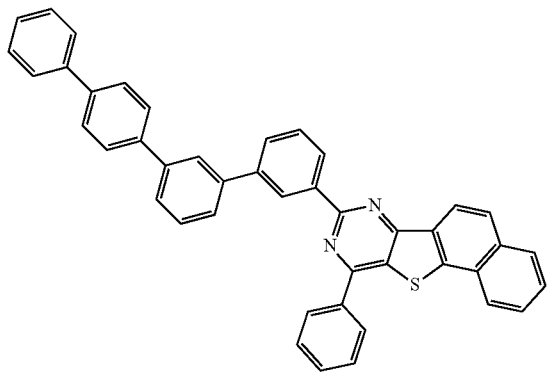
B-36
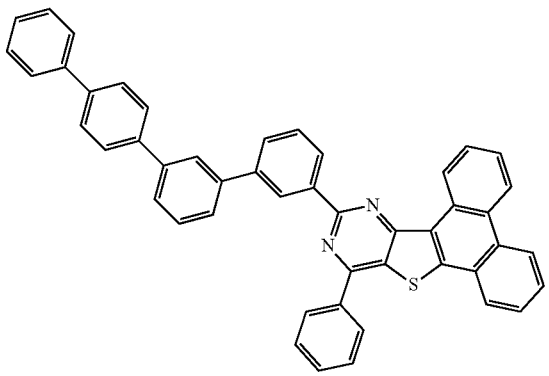
B-37
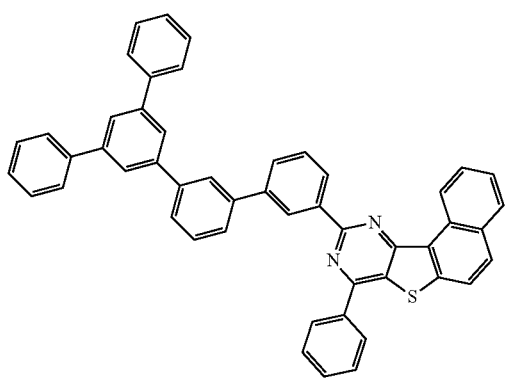
B-38
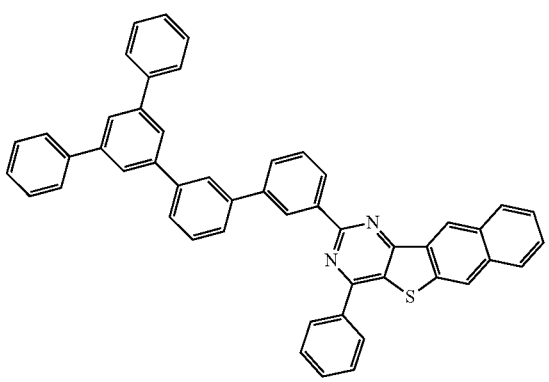
B-39
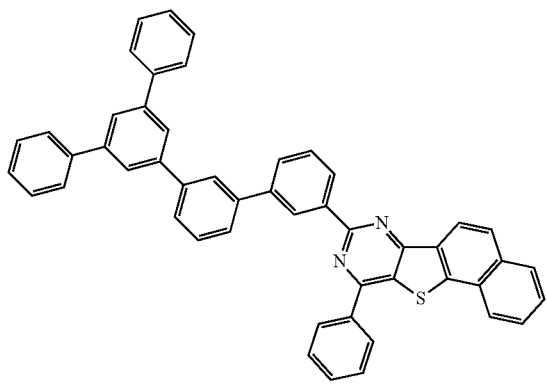
B-40
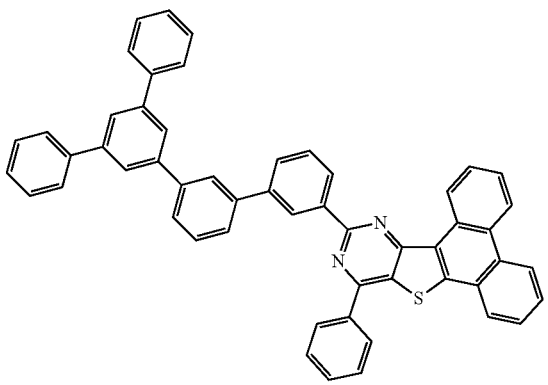
B-41
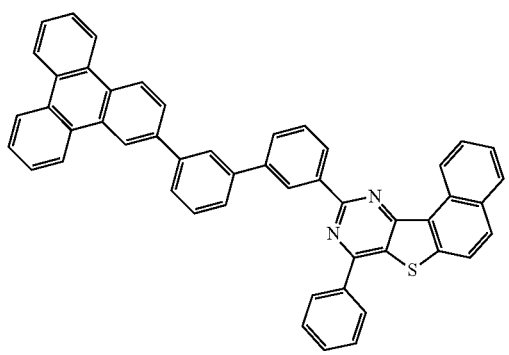
B-42
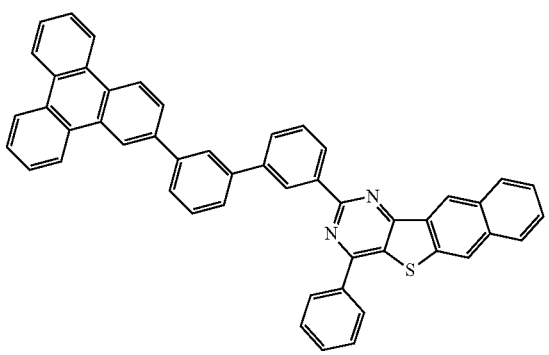

-continued
B-43
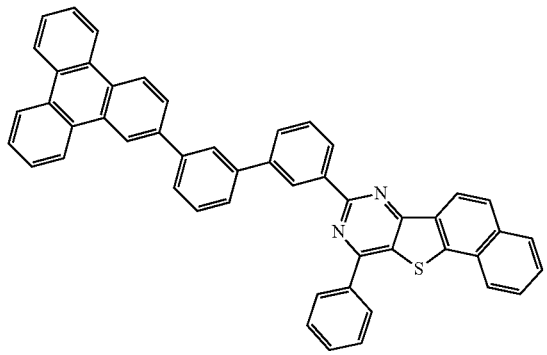
B-44
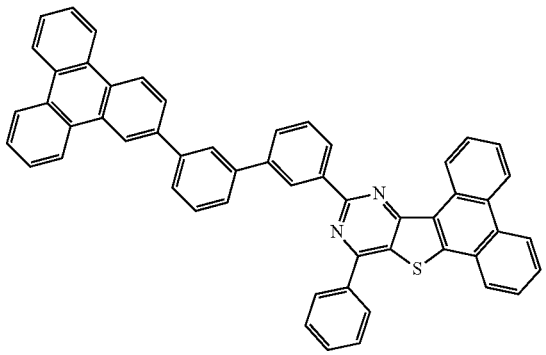
B-45
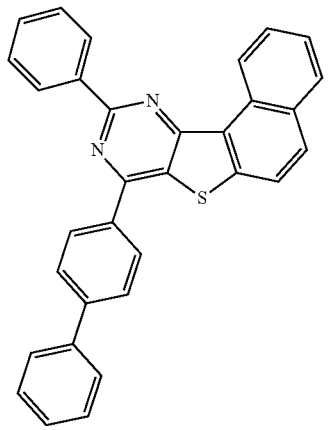
B-46
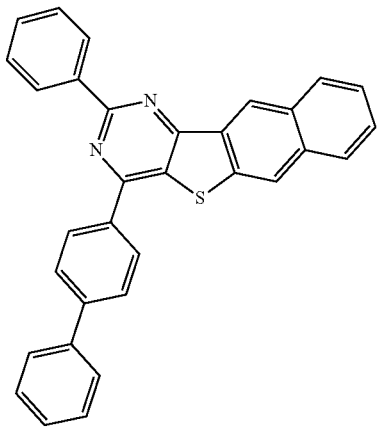
B-47
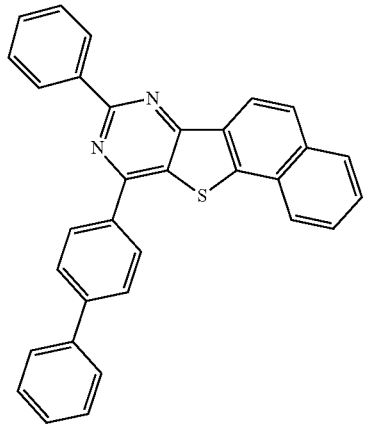
B-48
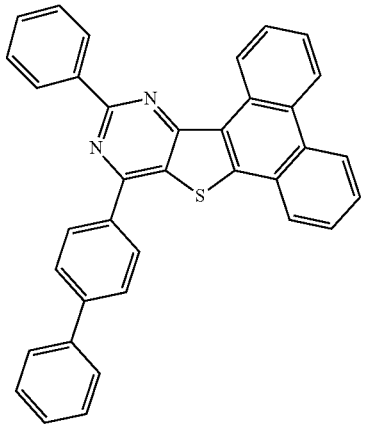
B-49
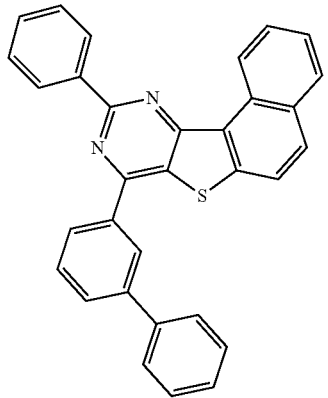
B-50
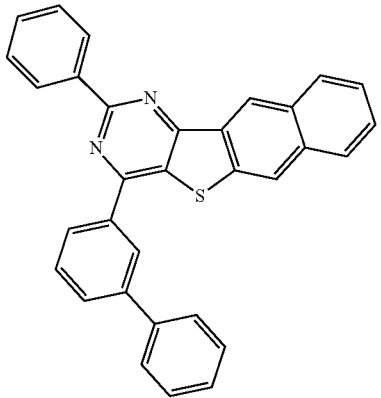

-continued
B-51
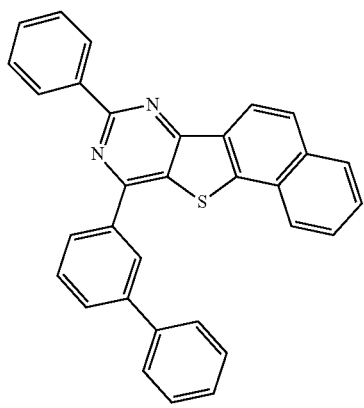
B-52
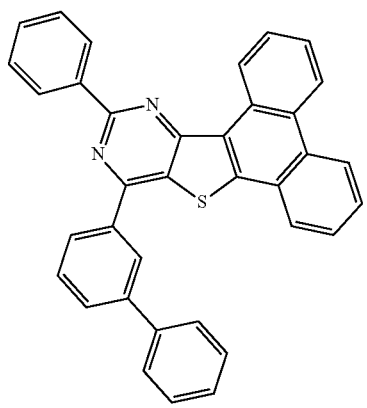
B-53
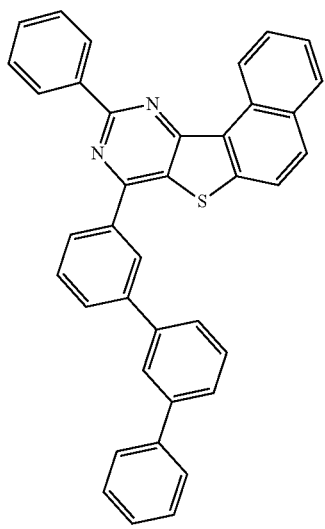
B-54
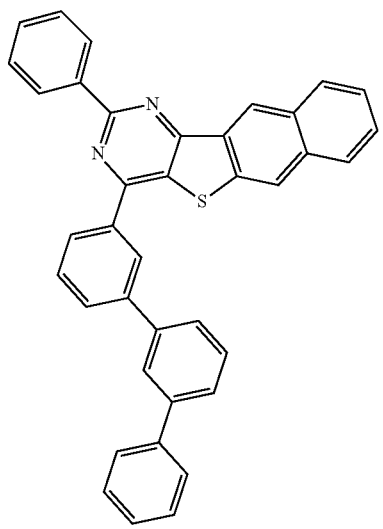
B-55
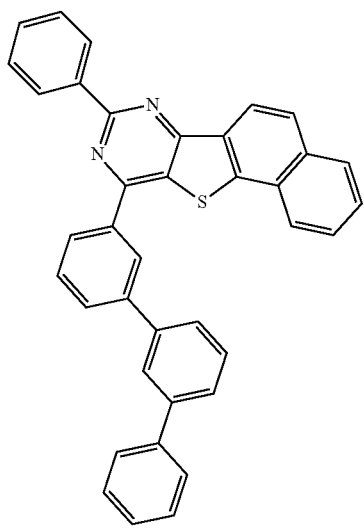
B-56
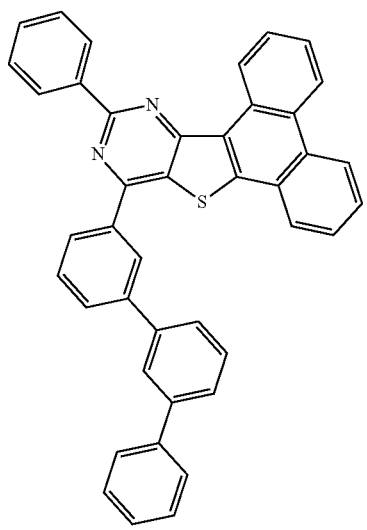

-continued
B-57
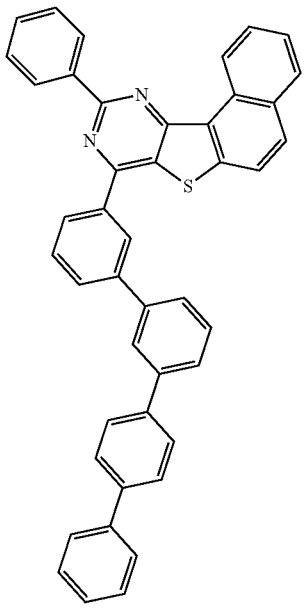
B-58
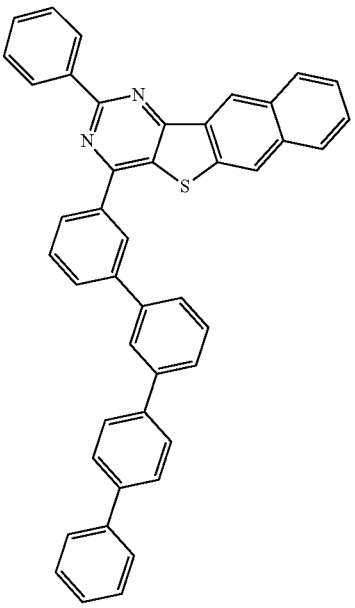
B-59
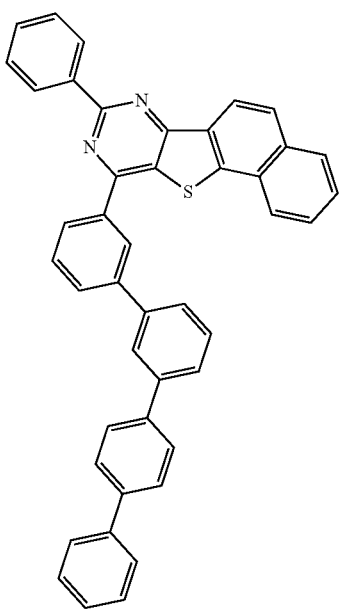
B-60
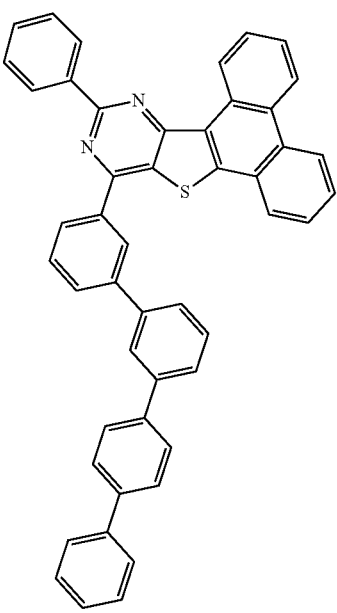

-continued
B-61
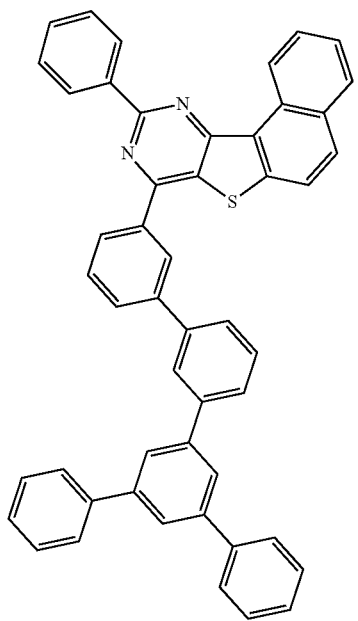
B-62
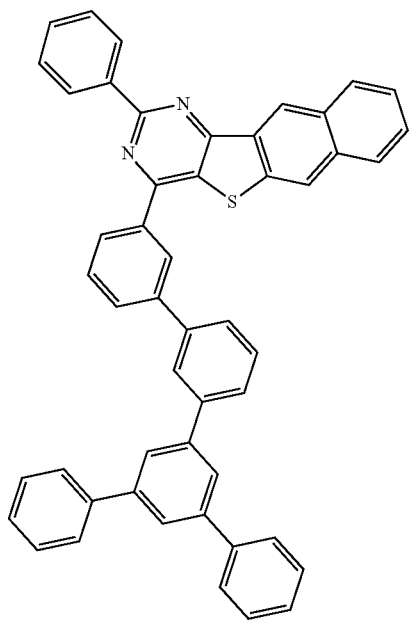
B-63
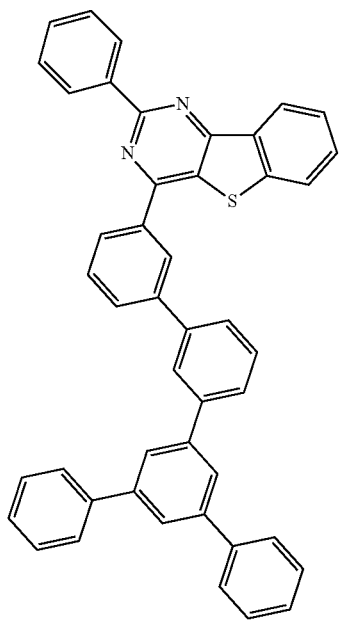
B-64
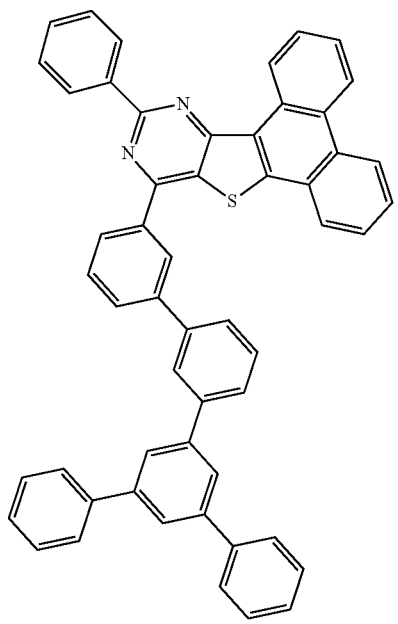

-continued
B-65
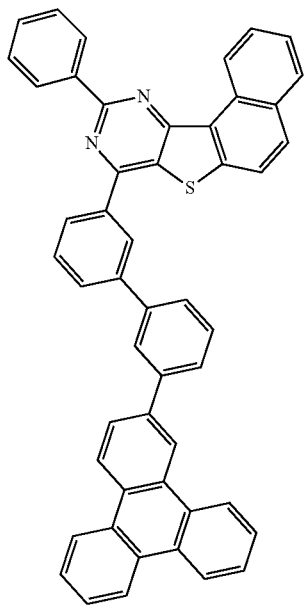
B-66
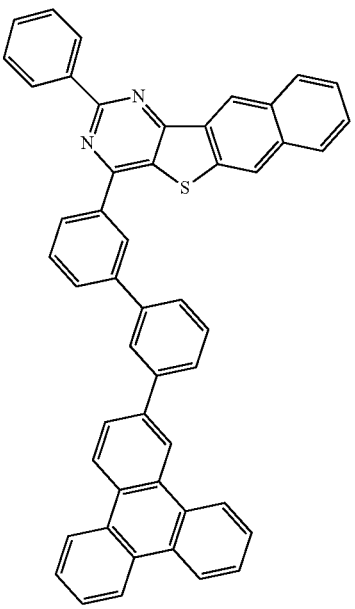
B-67
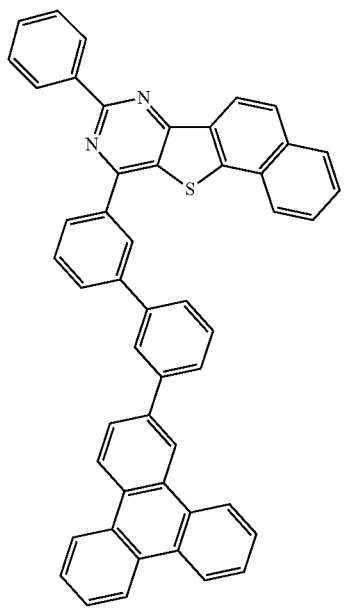
B-68
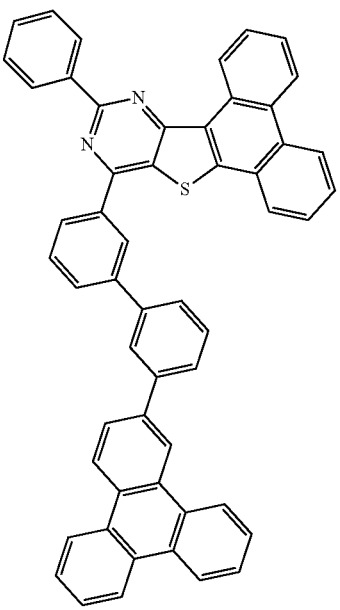
B-69
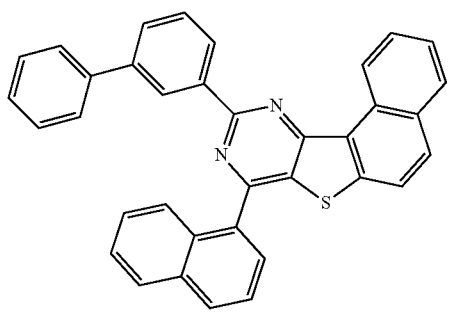
B-70
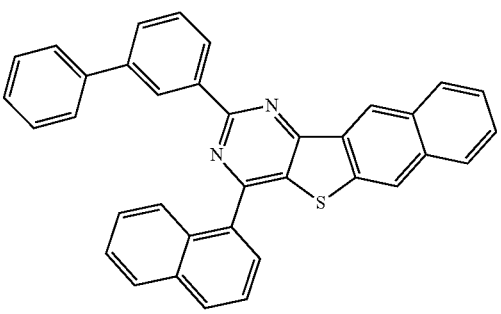

-continued
B-71
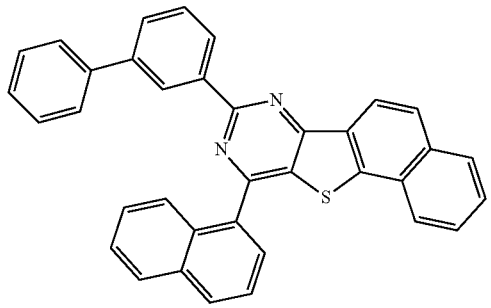
B-72
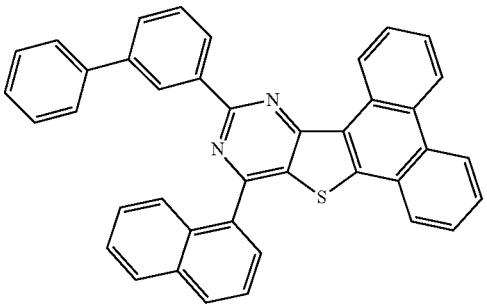
B-73
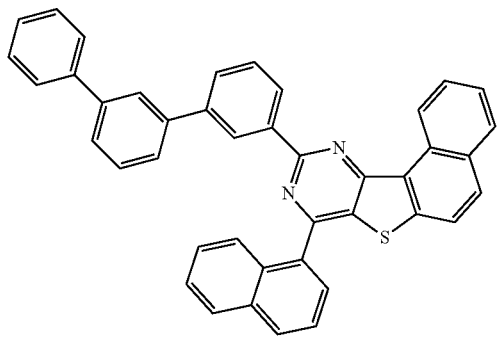
B-74
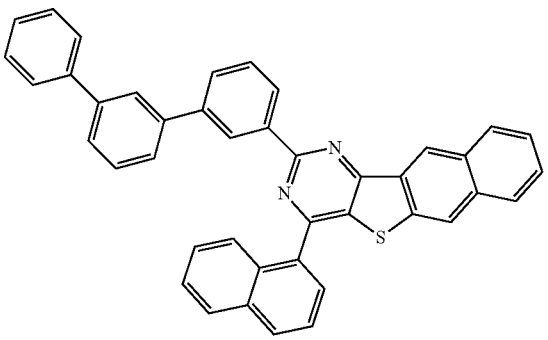
B-75
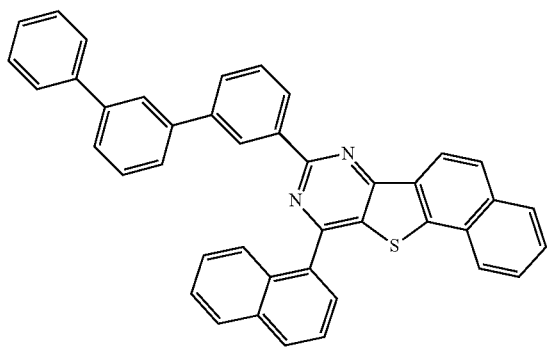
B-76
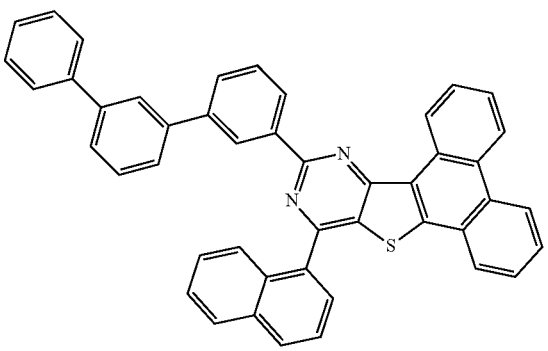
B-77
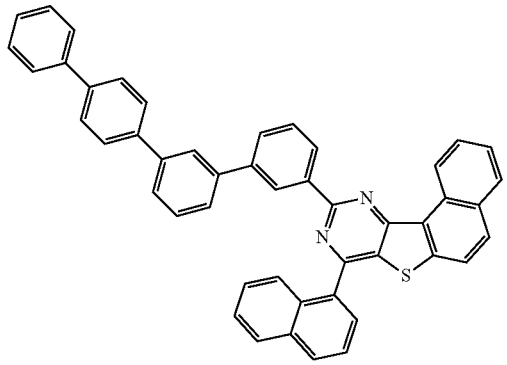
B-78
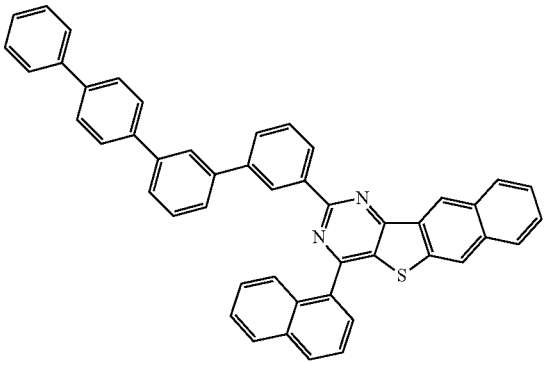

-continued
B-79
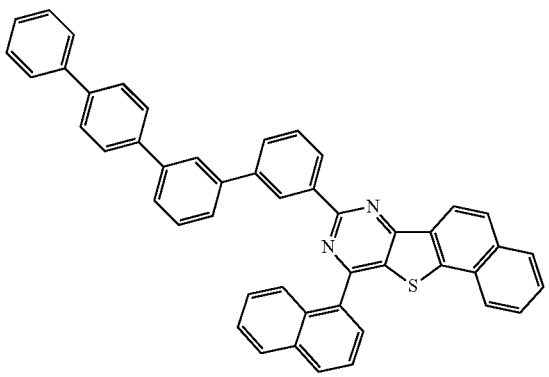
B-80
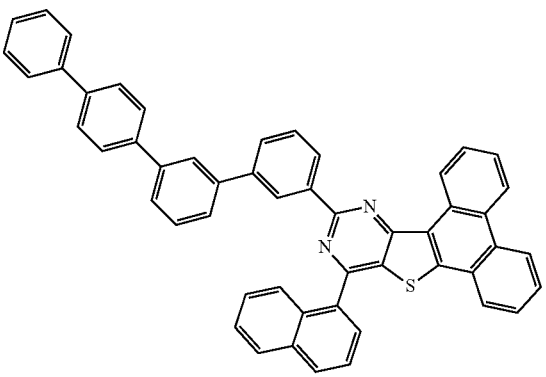
B-81
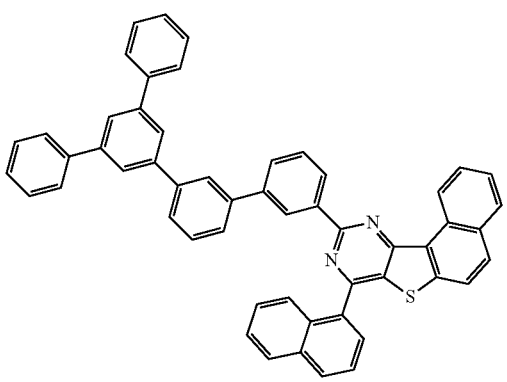
B-82
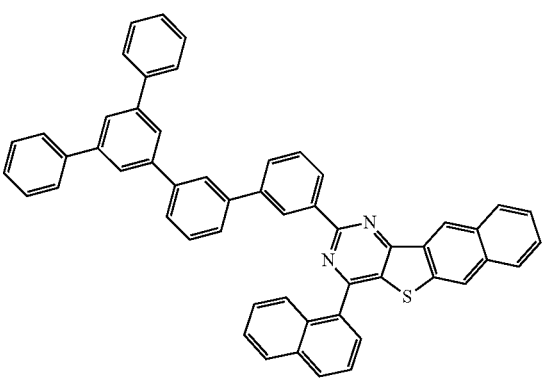
B-83
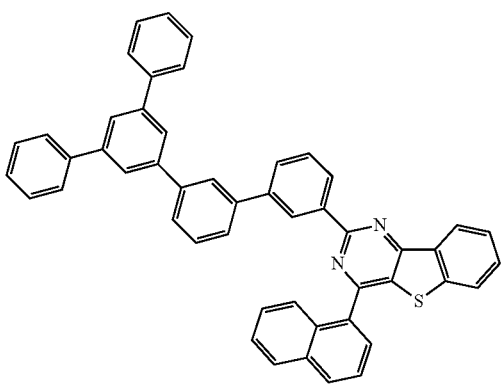
B-84
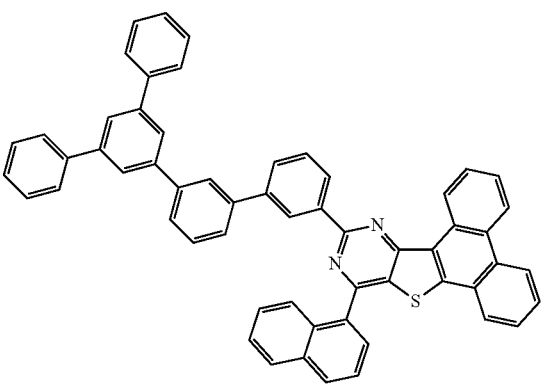
B-85
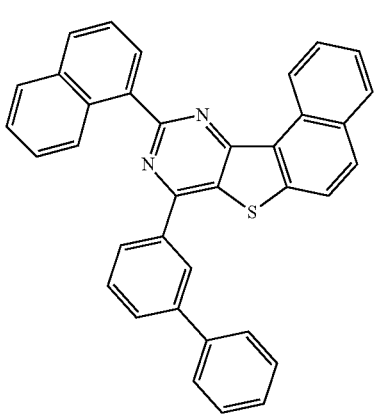
B-86

-continued
B-87
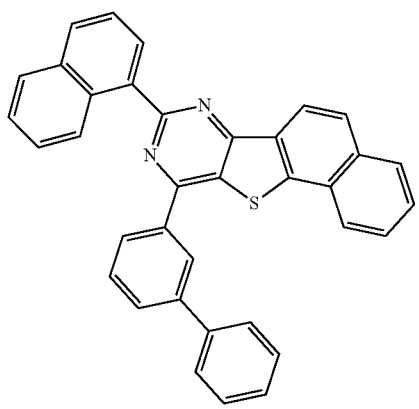
B-88
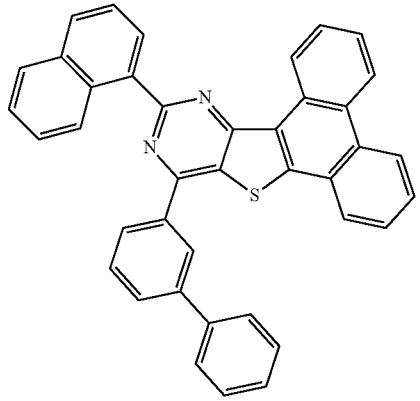
B-89
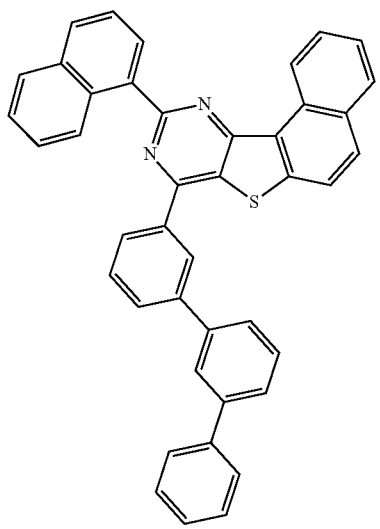
B-90
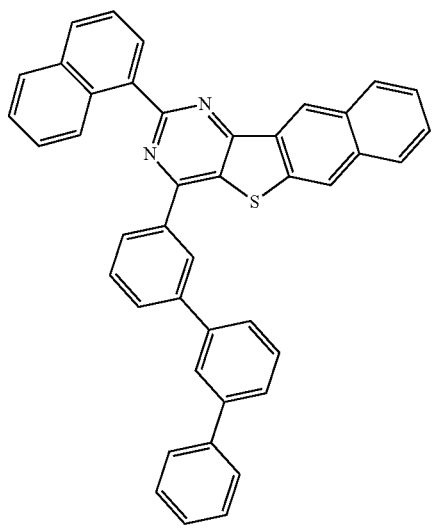
B-91
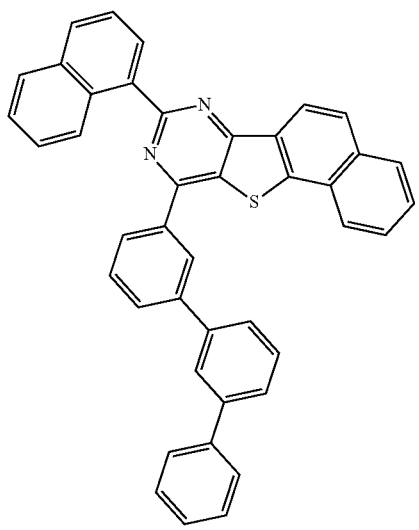
B-92
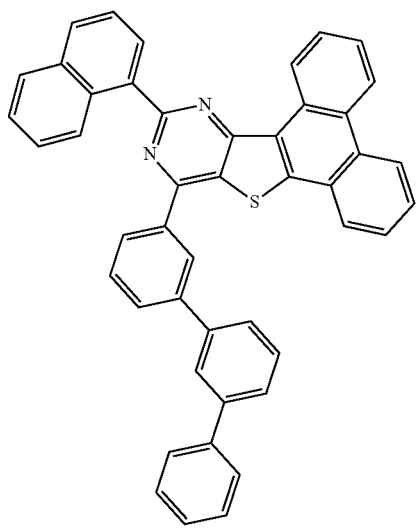

-continued
B-93
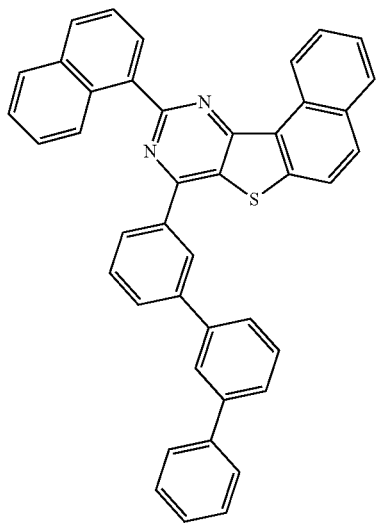
B-94
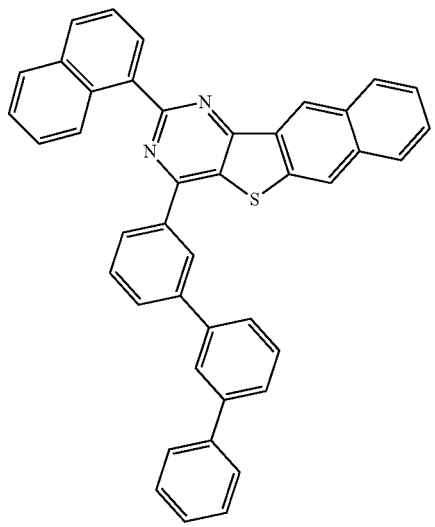
B-95
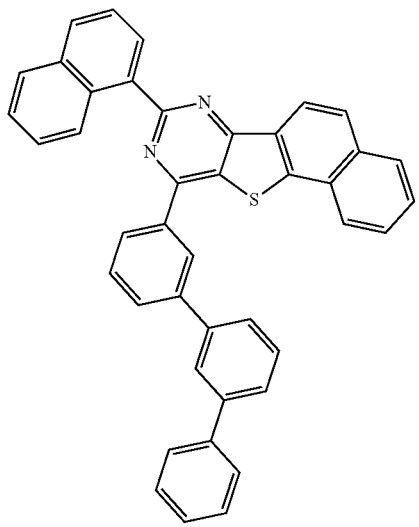
B-96
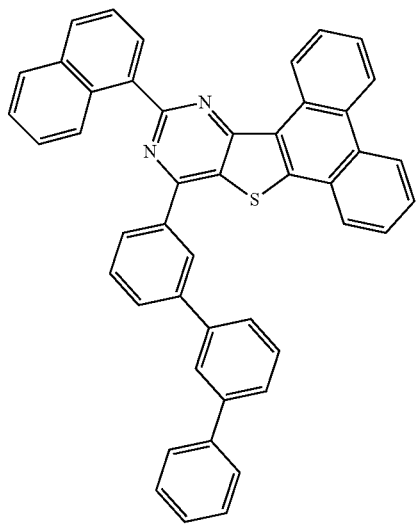
B-97
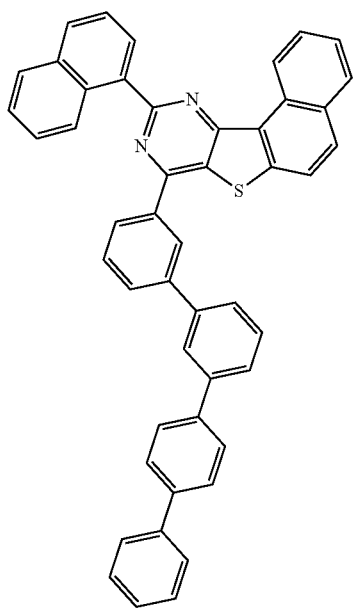
B-98
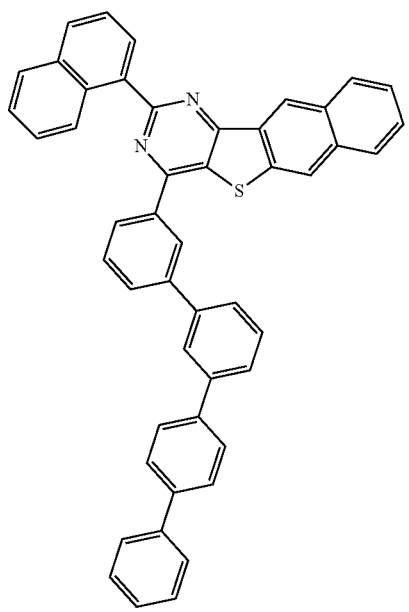

-continued
B-99
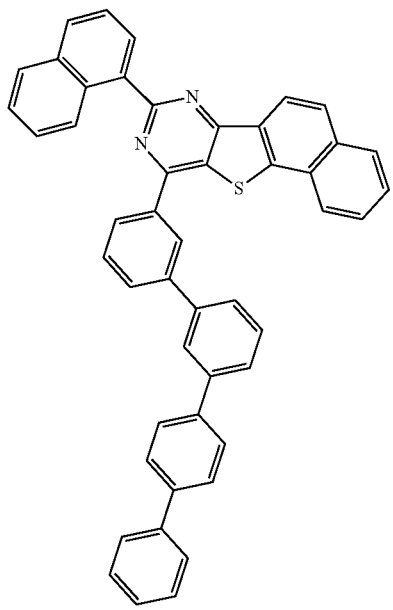
B-100
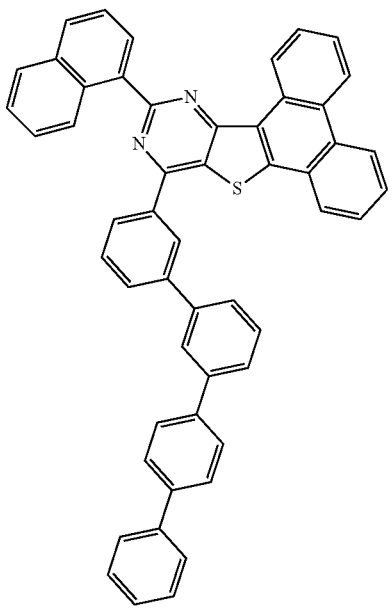
B-101
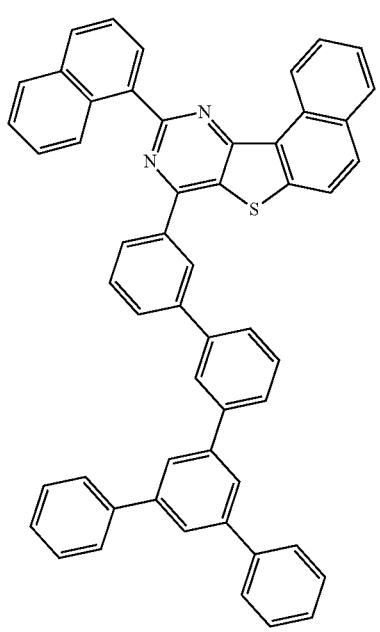
B-102
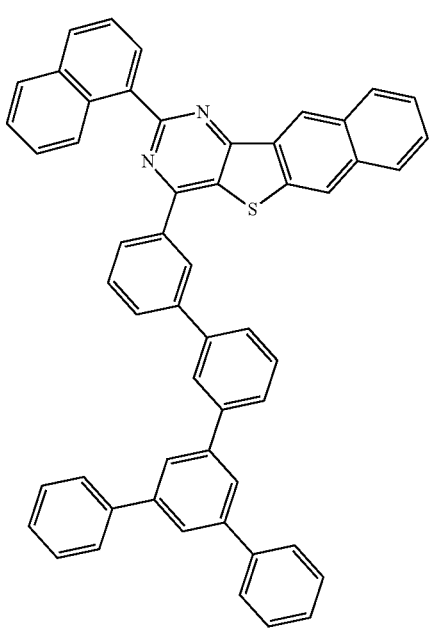

-continued
B-103
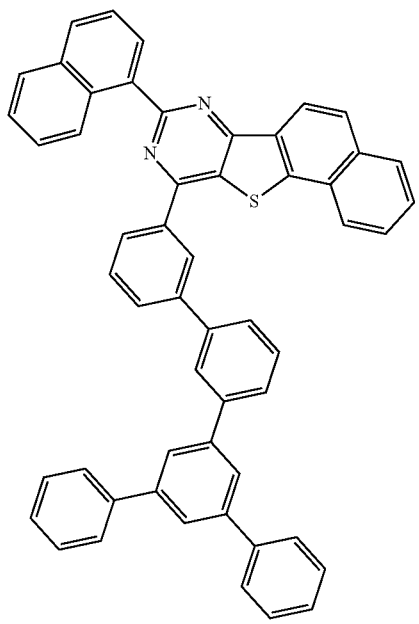
B-104
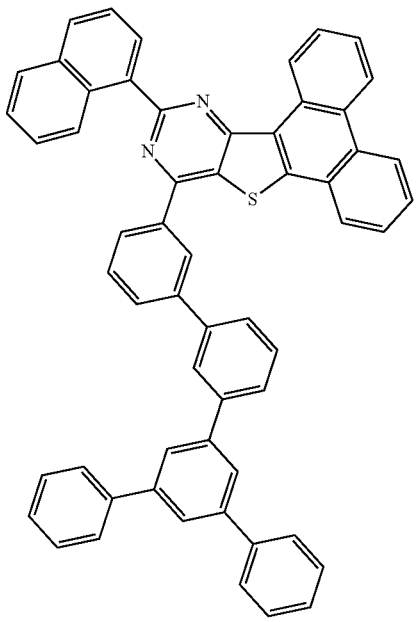
B-105
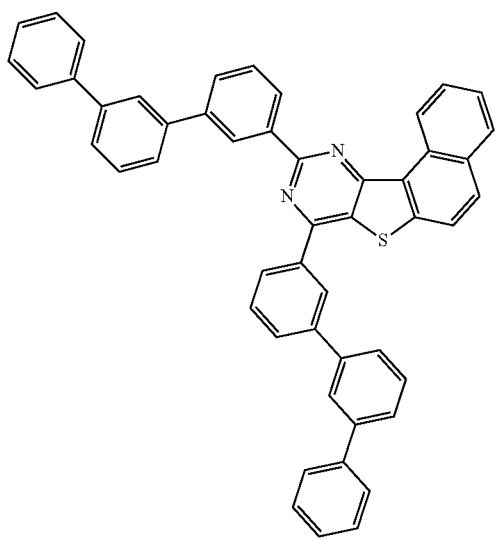
B-106
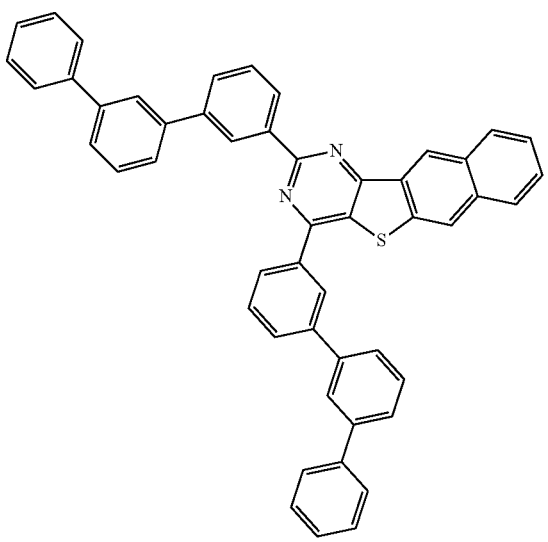

-continued
B-107
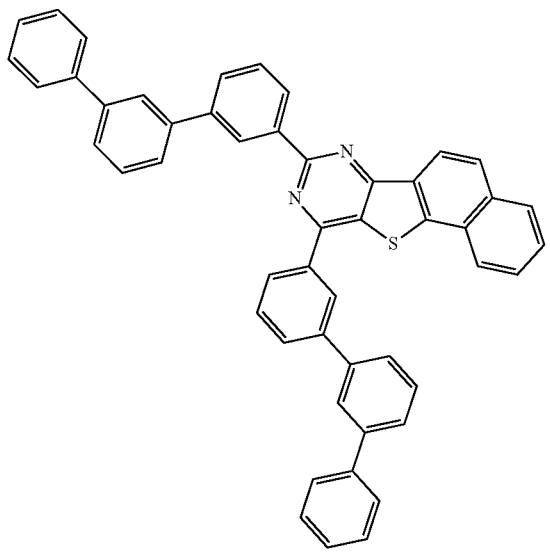
B-108
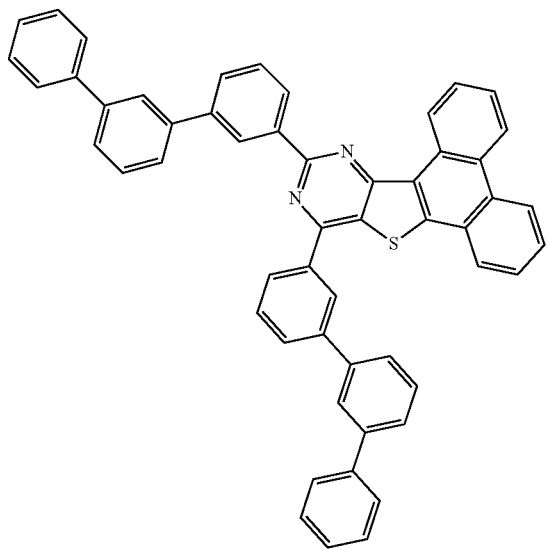
B-109
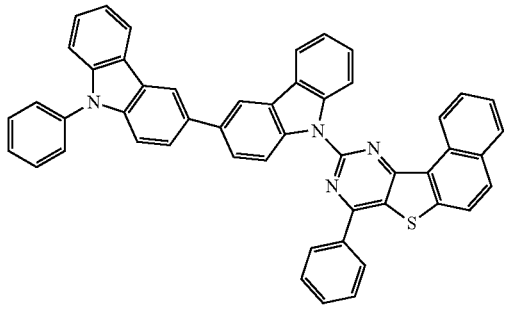
B-110
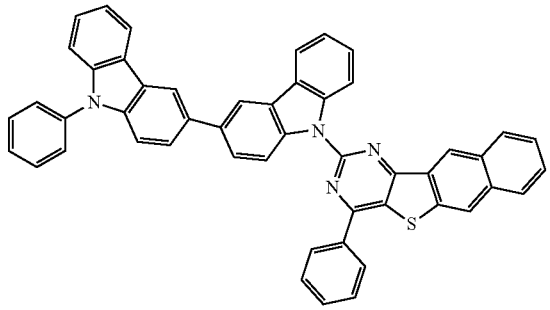
B-111
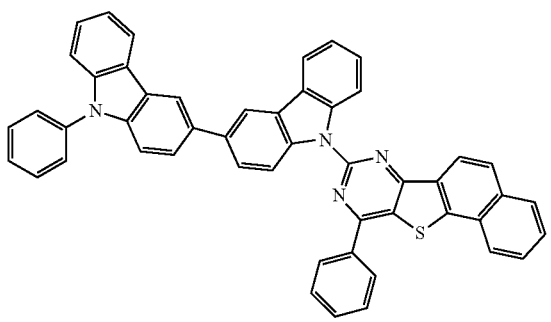
B-112
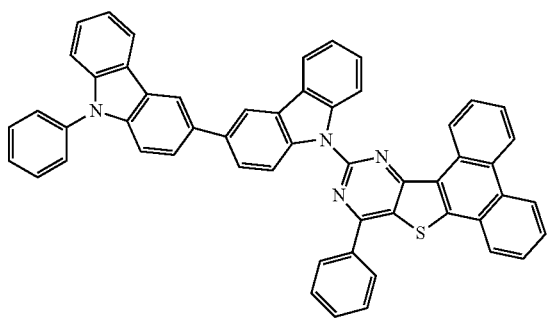
B-113
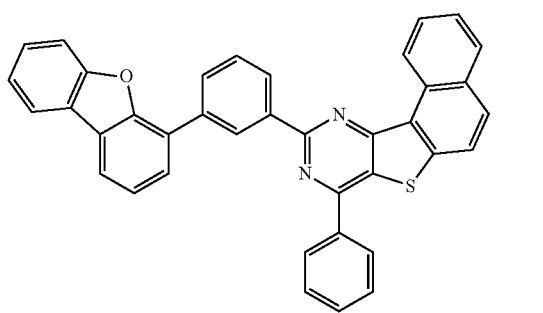
B-114
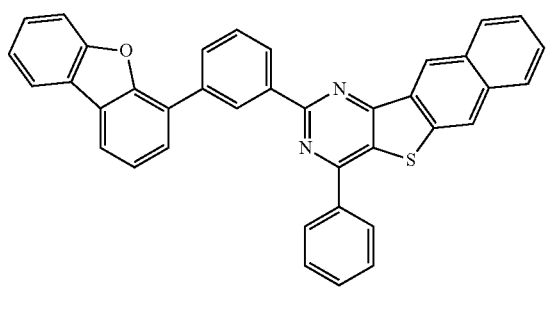

-continued
B-115
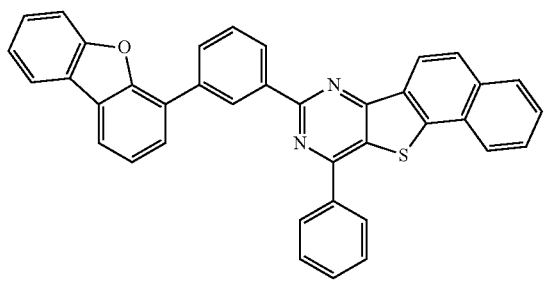
B-116
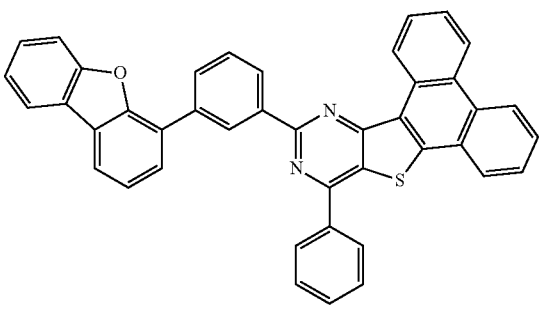
B-117
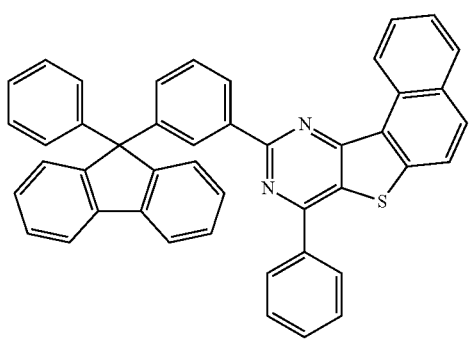
B-118
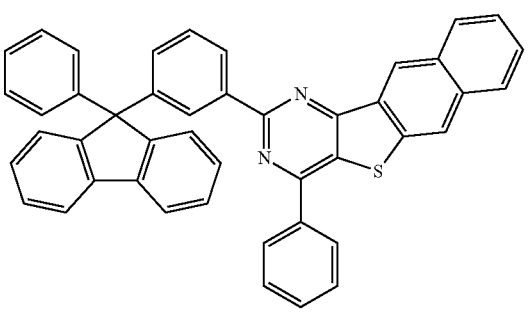
B-119
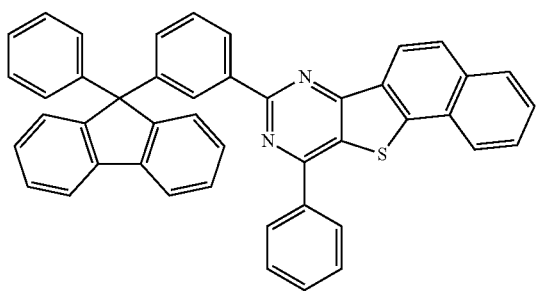
B-120
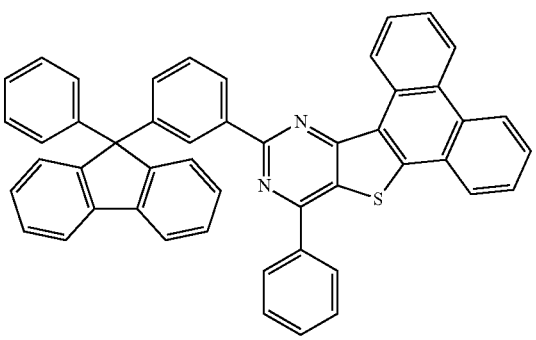
C-1
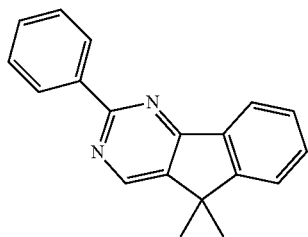
C-2
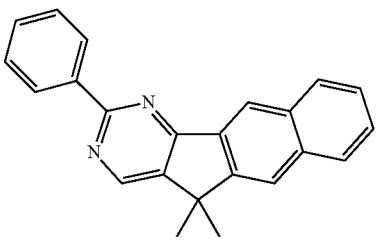
C-3
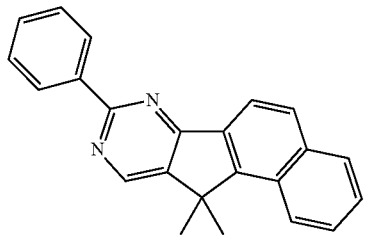
C-4
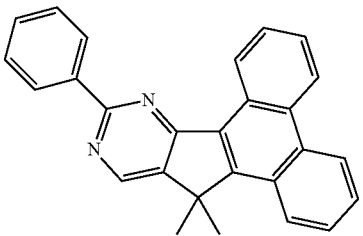

-continued
| C-5 | C-6 |
|---|---|
| 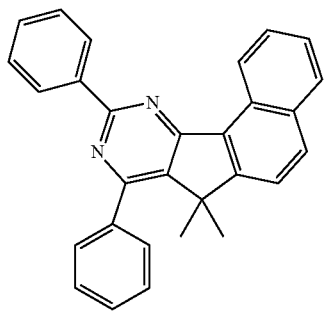 | 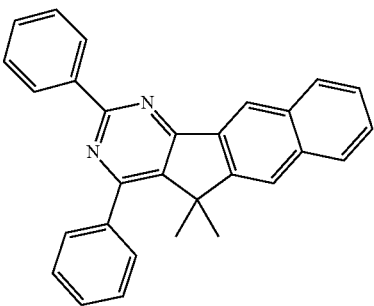 |
| C-7 | C-8 |
| 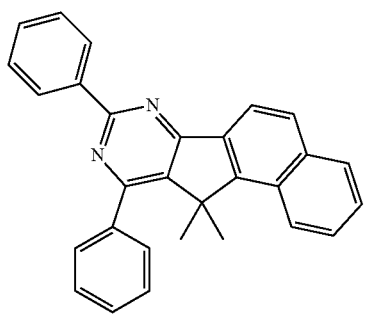 | 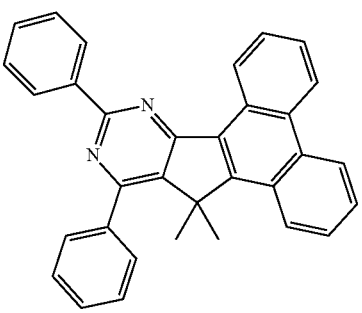 |
| C-9 | C-10 |
| 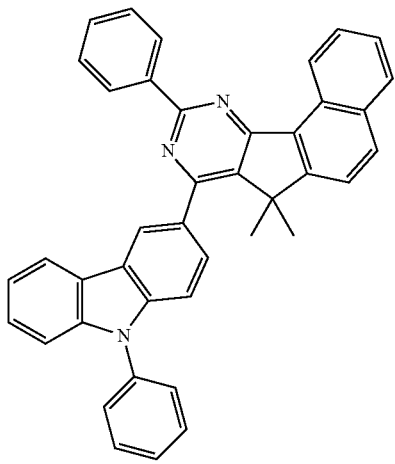 | 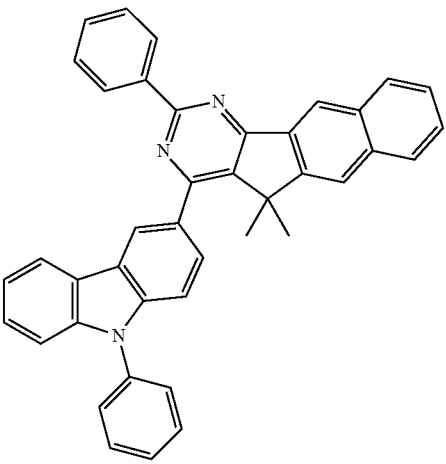 |
| C-11 | C-12 |
| 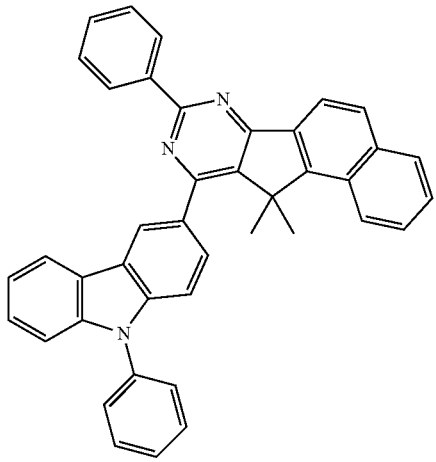 | 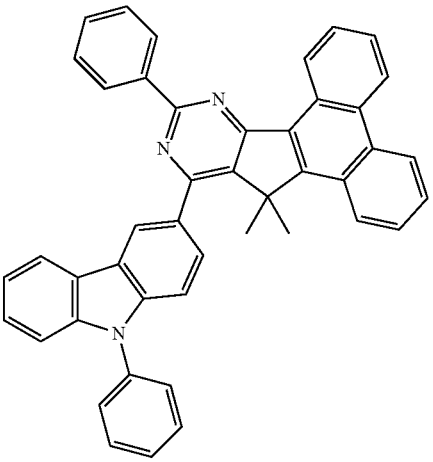 |

-continued
C-13
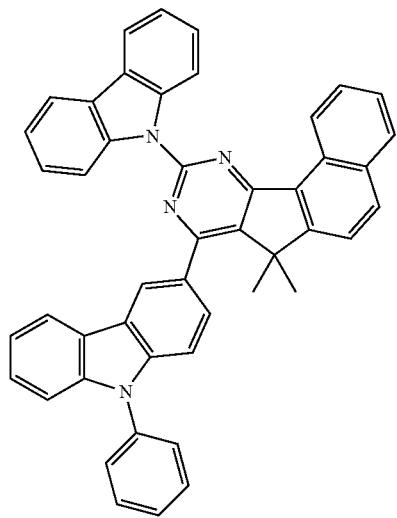
C-14
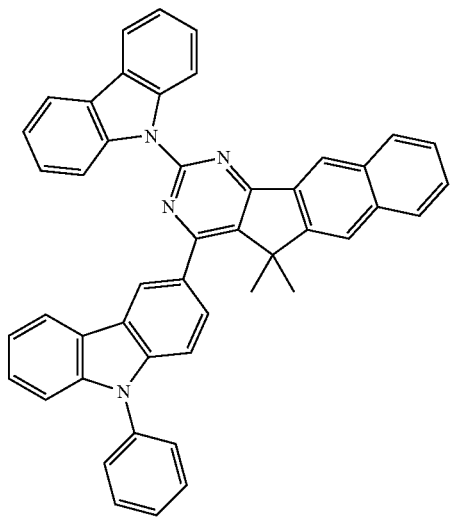
C-15
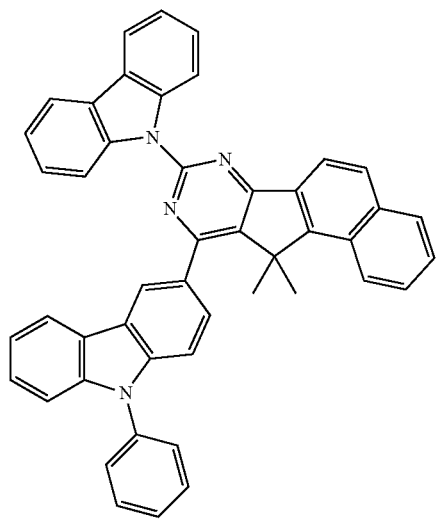
C-16
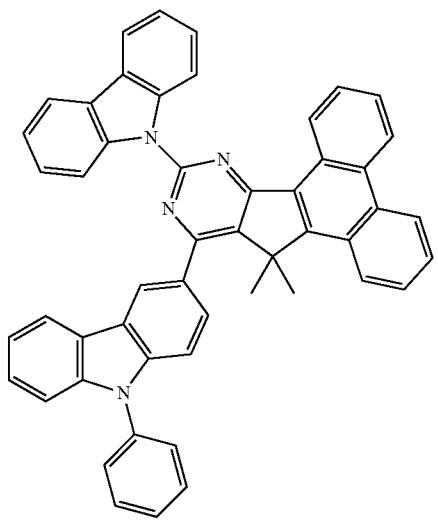
C-17
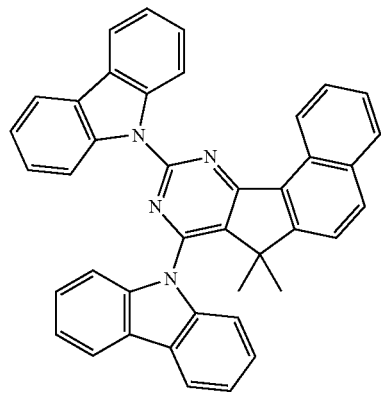
C-18
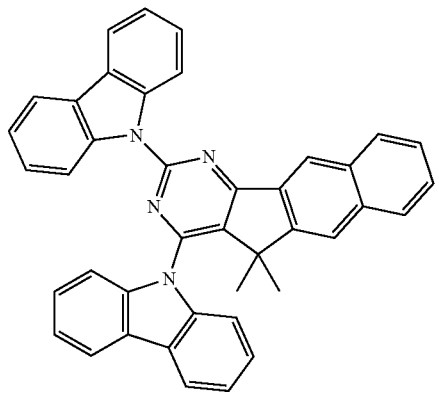

-continued
C-19
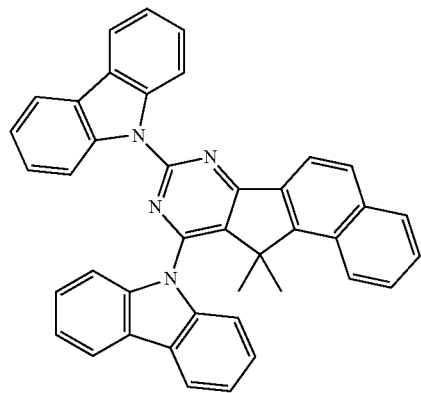
C-20
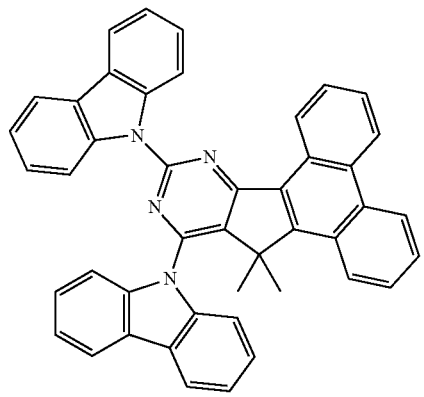
C-21
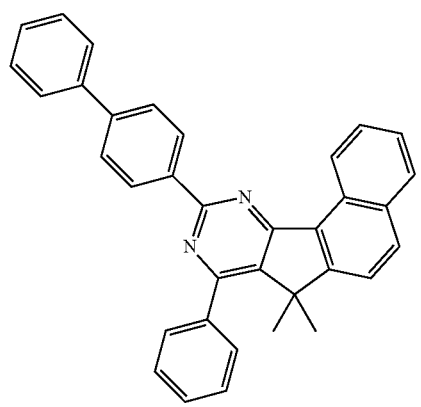
C-22
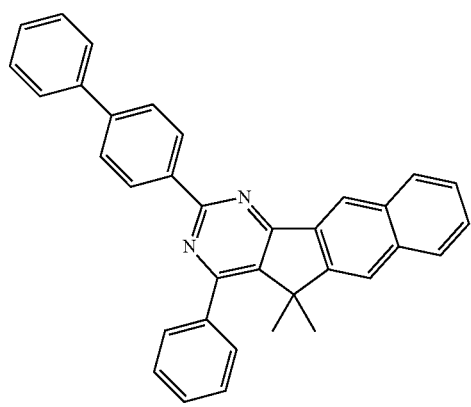
C-23
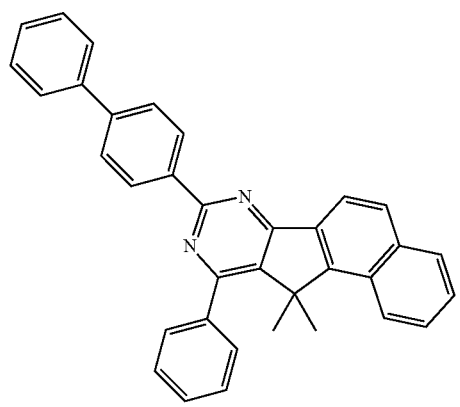
C-24
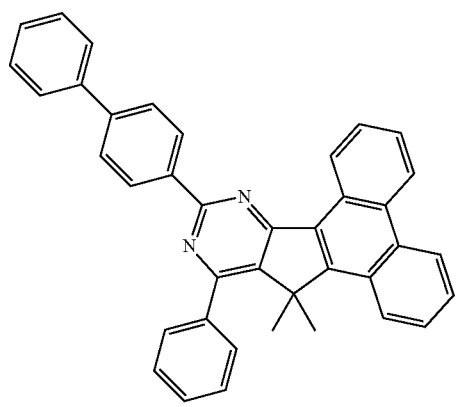
C-25
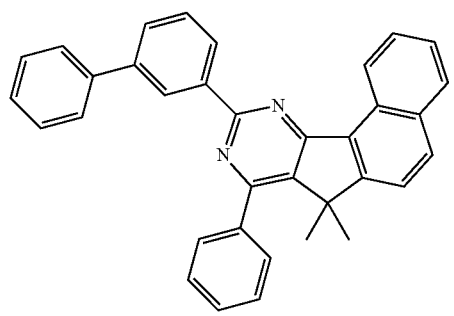
C-26
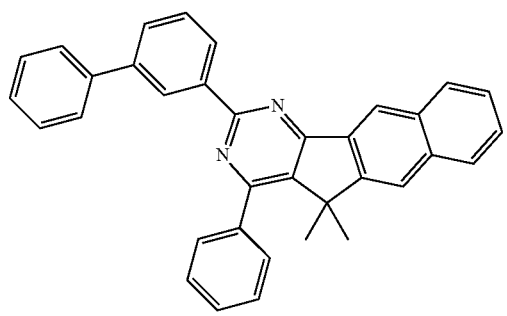

-continued
C-27
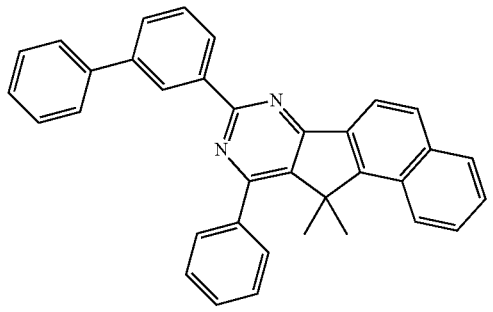
C-28
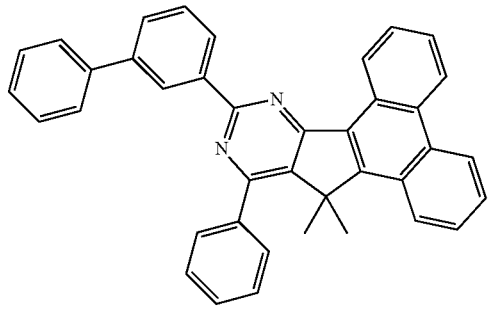
C-29
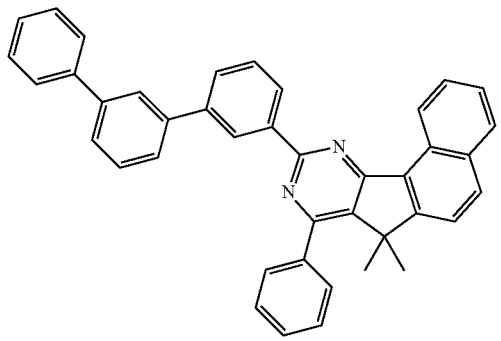
C-30
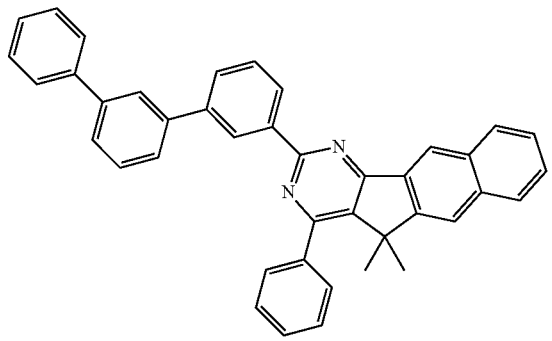
C-31
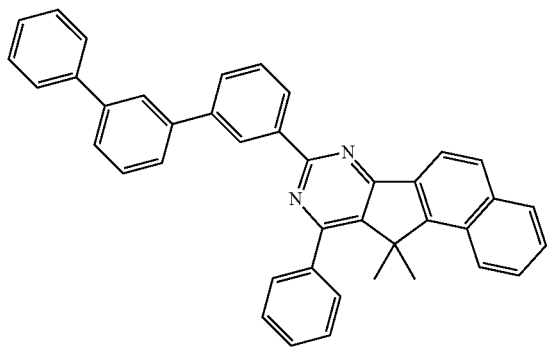
C-32
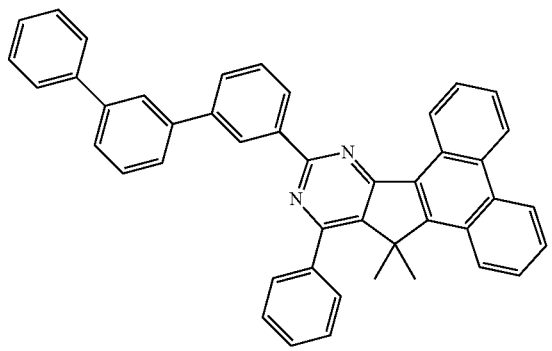
C-33
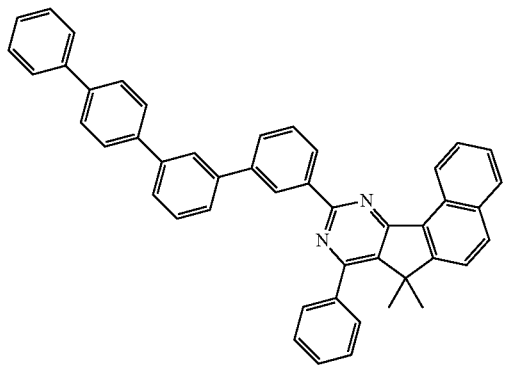
C-34
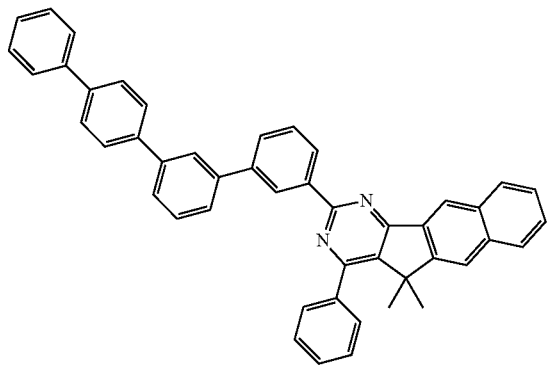

-continued
C-35
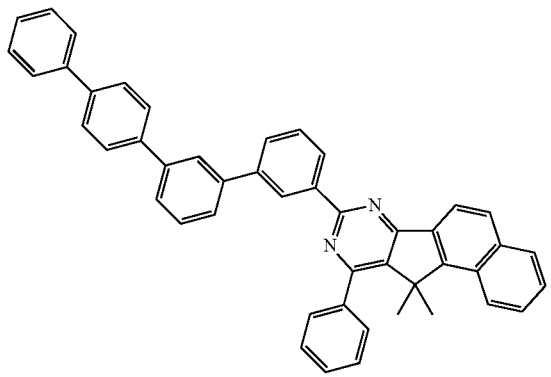
C-36
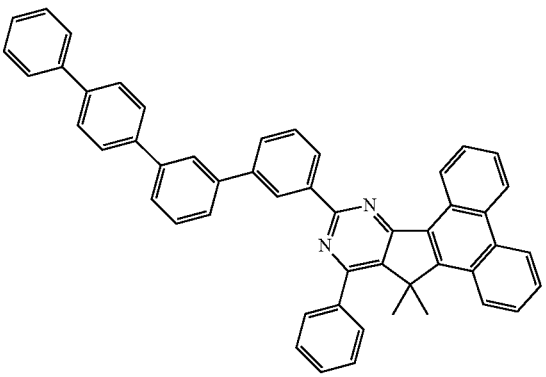
C-37
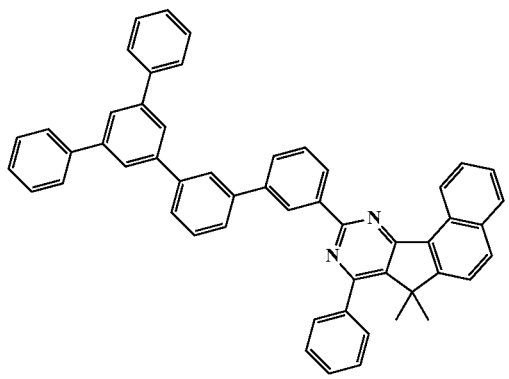
C-38
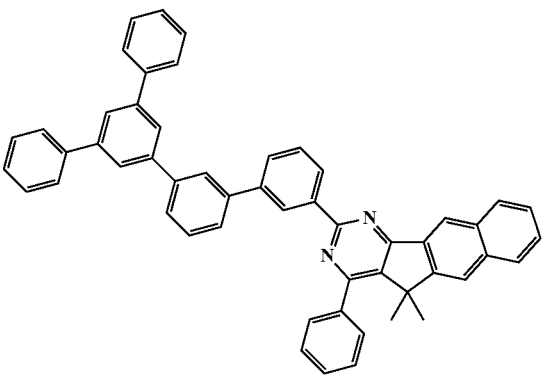
C-39
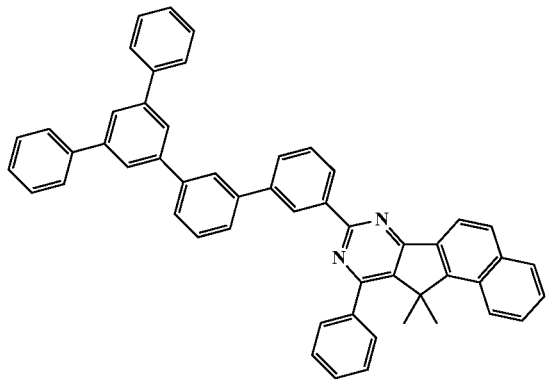
C-40
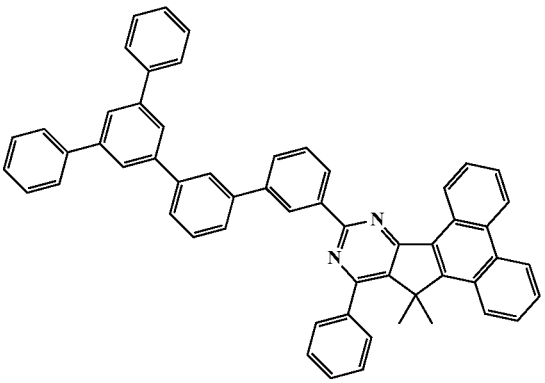
C-41
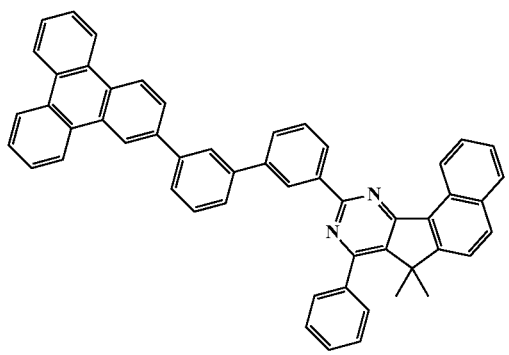
C-42
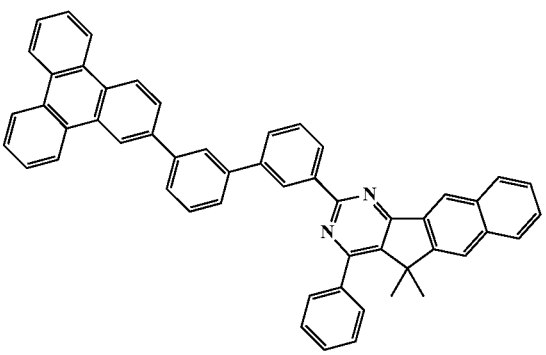

-continued
C-43
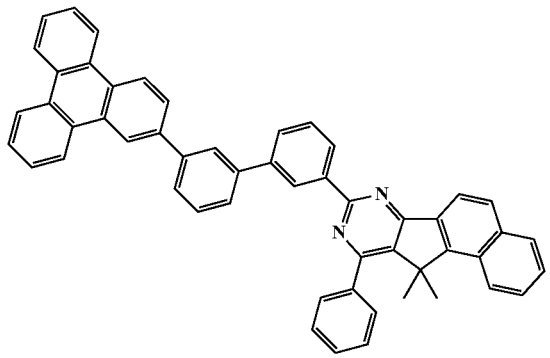
C-44
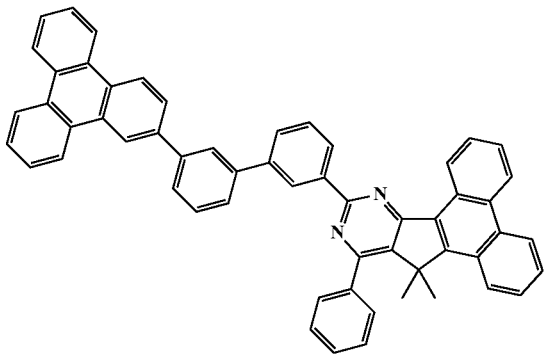
C-45
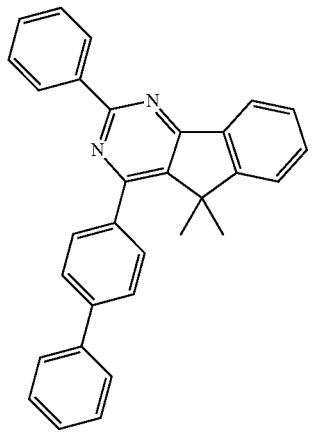
C-46
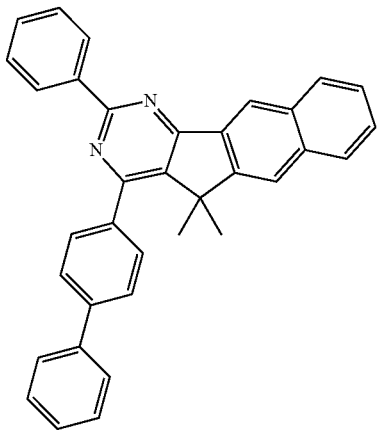
C-47
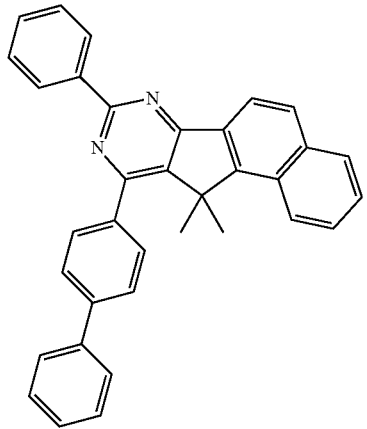
C-48
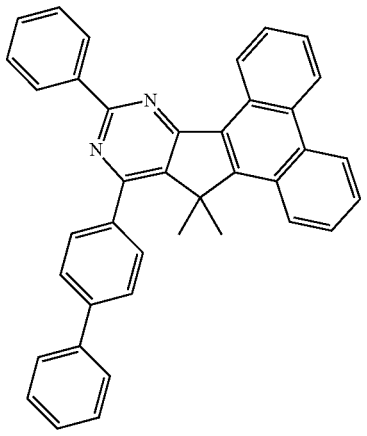
C-49
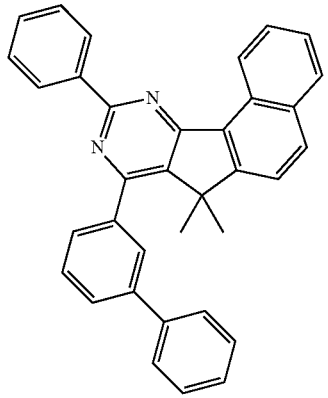
C-50
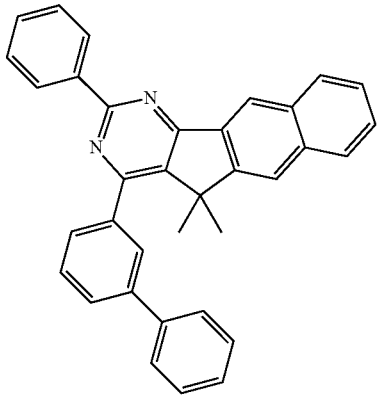

-continued
C-51
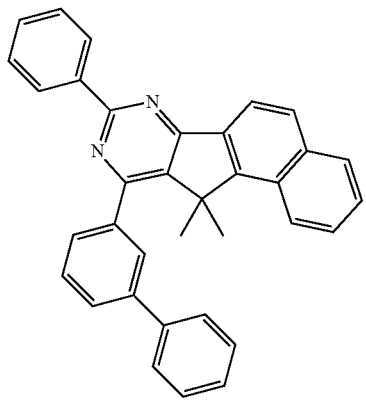
C-52
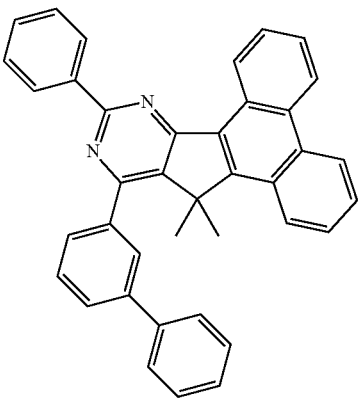
C-53
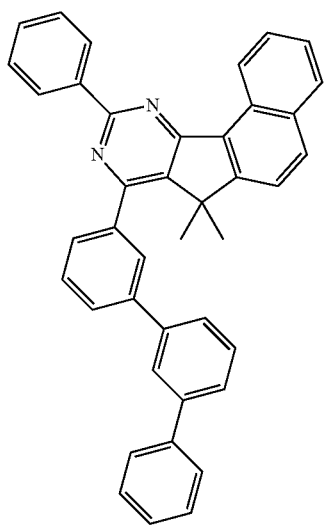
C-54
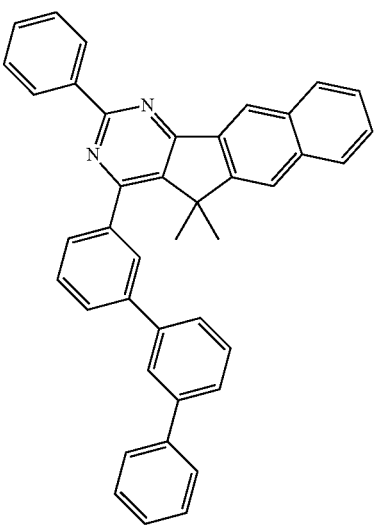
C-55
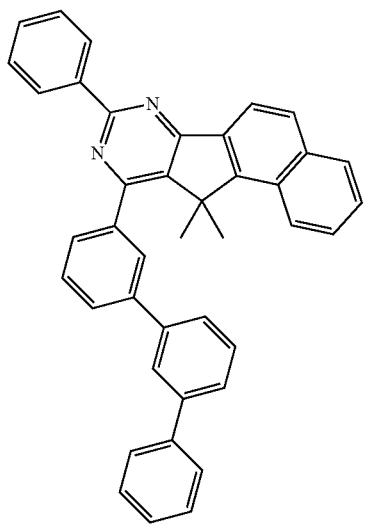
C-56
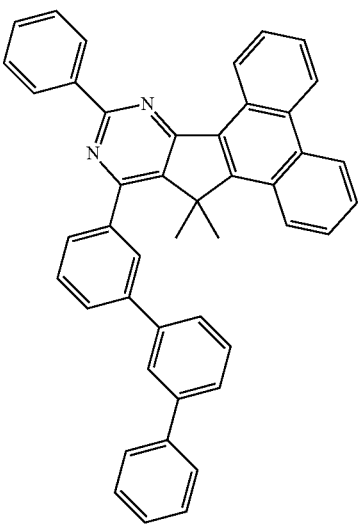

-continued
C-57
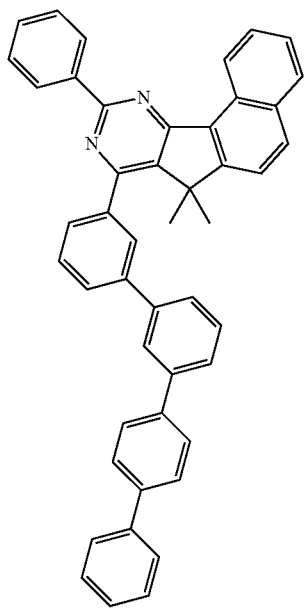
C-58
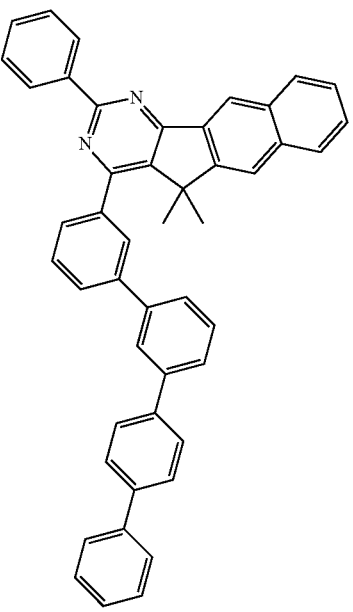
C-59
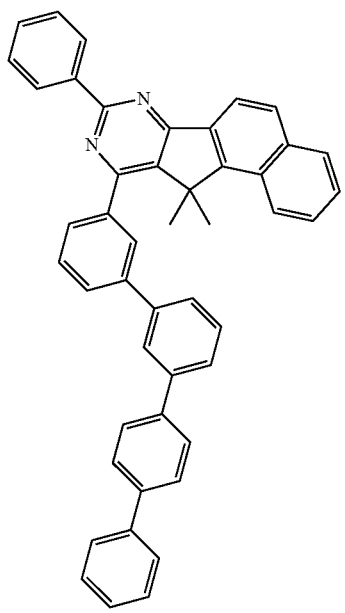
C-60
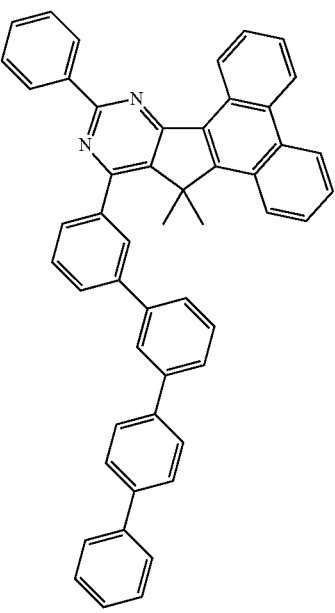

-continued
C-61
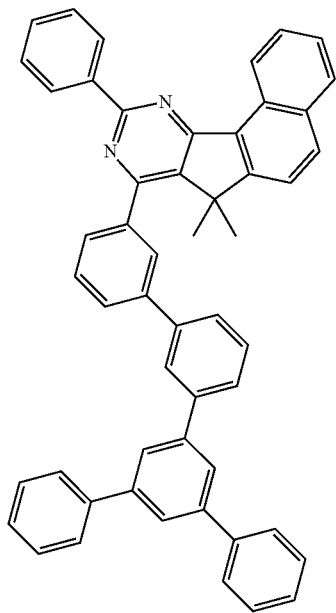
C-62
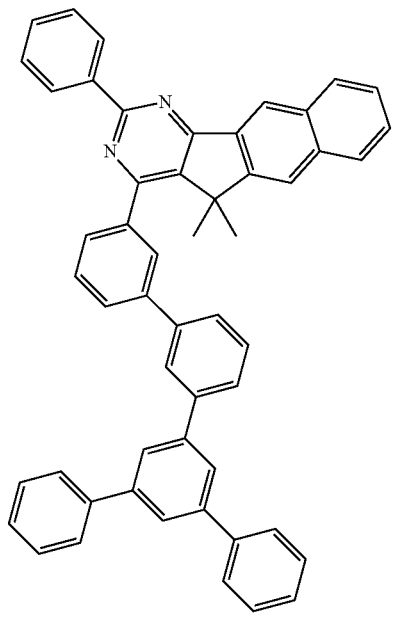
C-63
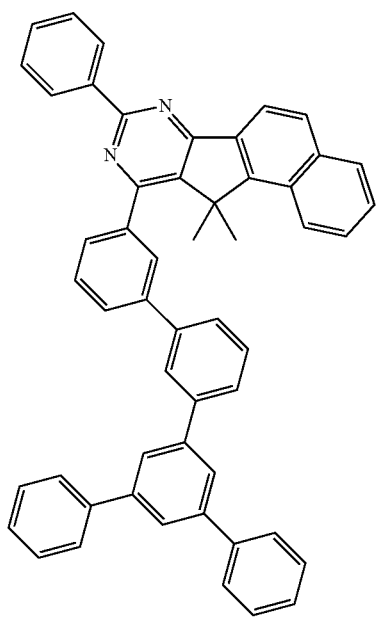
C-64
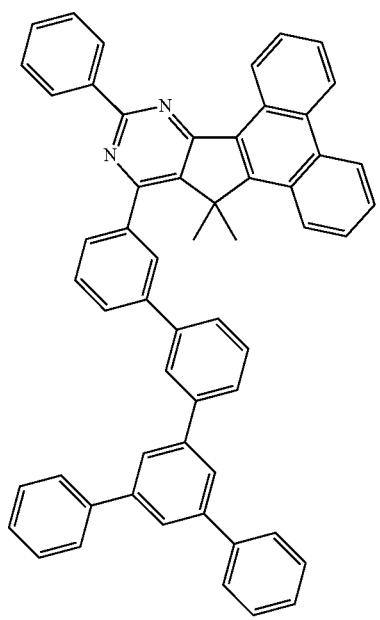

-continued
C-65
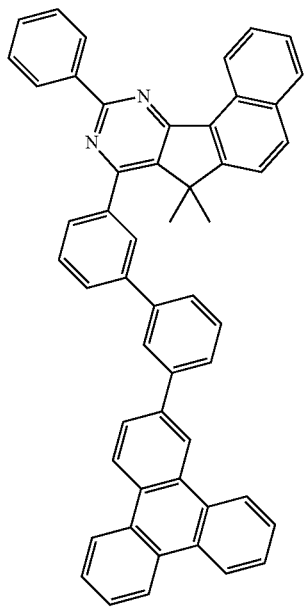
C-66
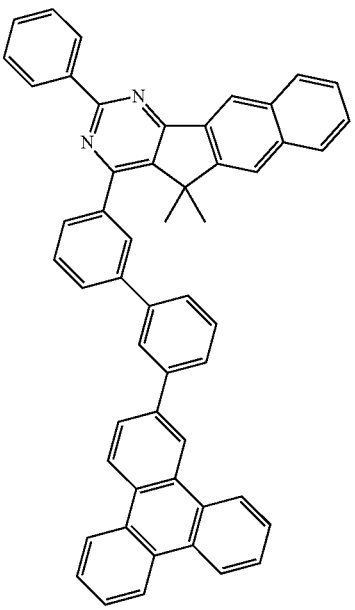
C-67
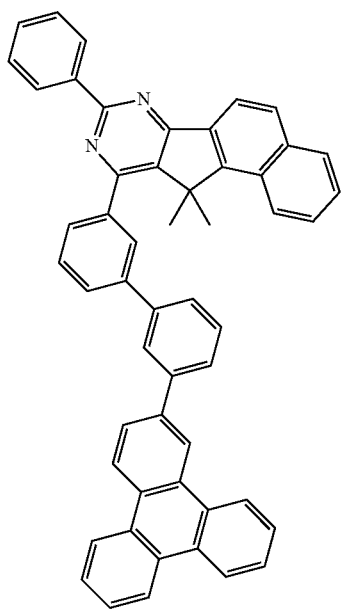
C-68
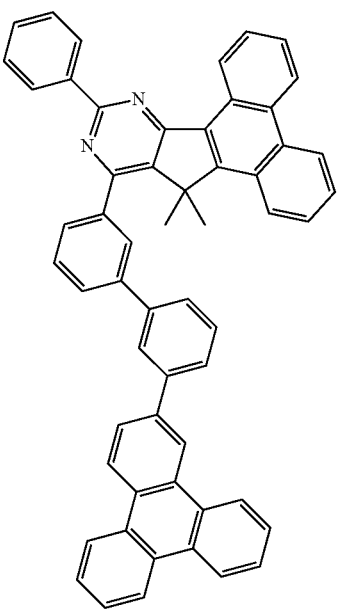
C-69
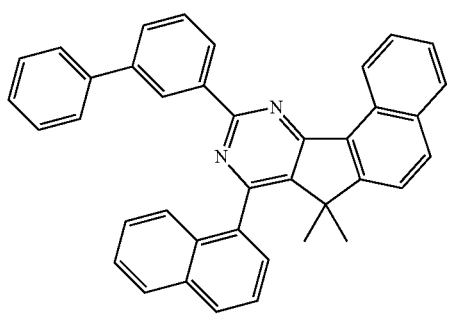
C-70
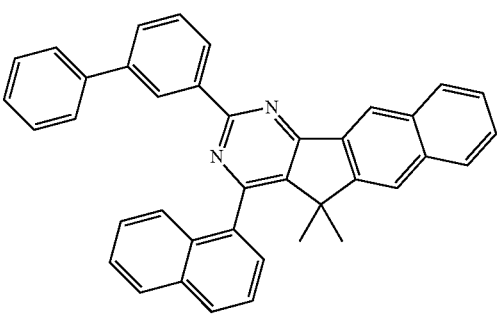

-continued
C-71
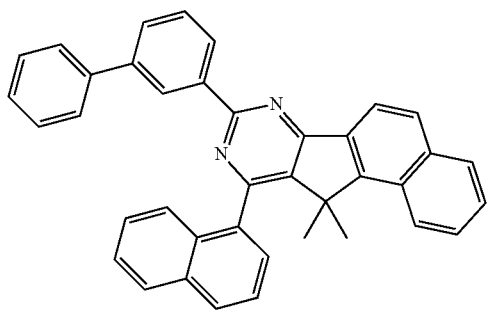
C-72
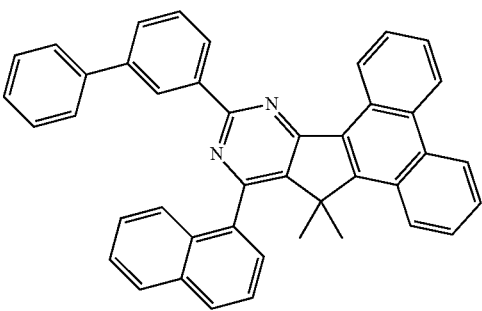
C-73
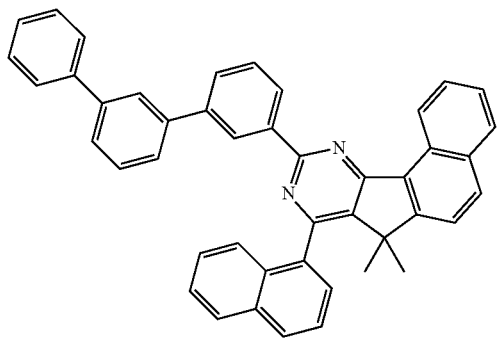
C-74
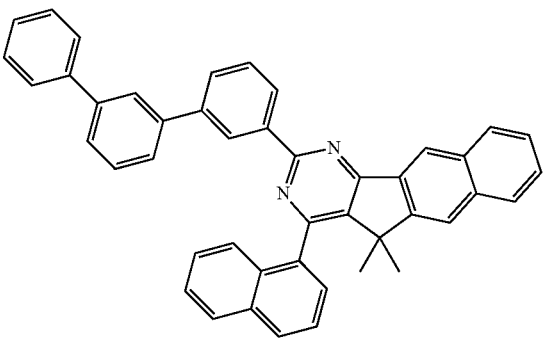
C-75
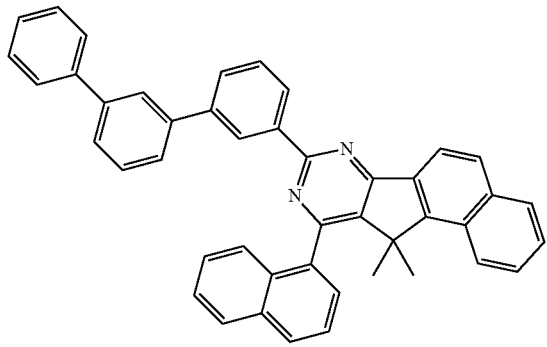
C-76
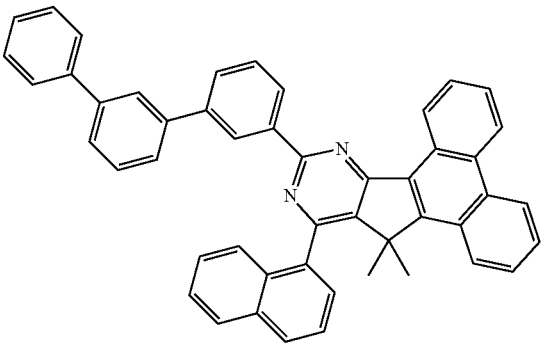
C-77
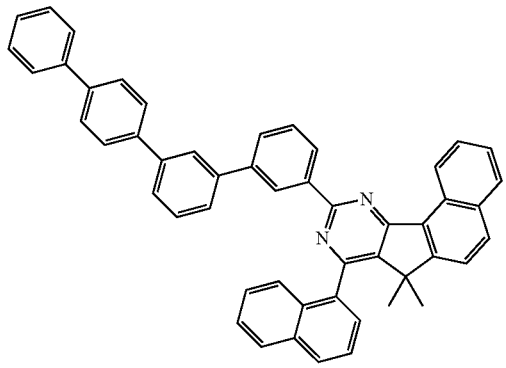
C-78
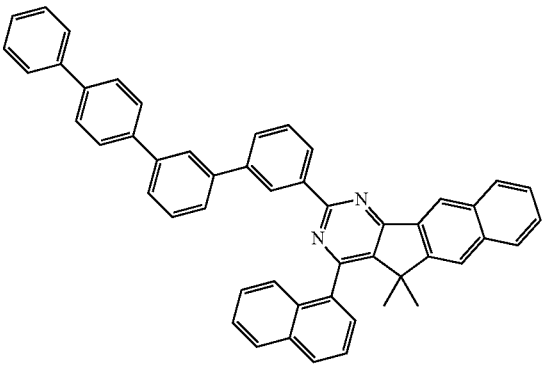

-continued
C-79
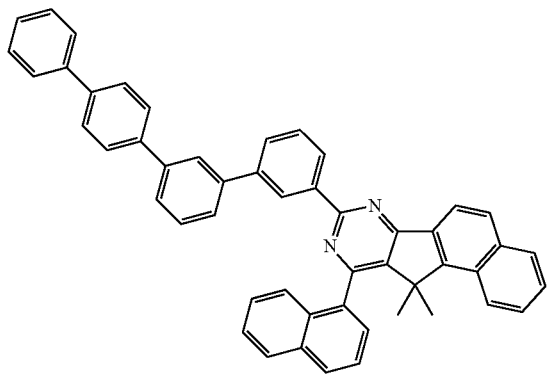
C-80
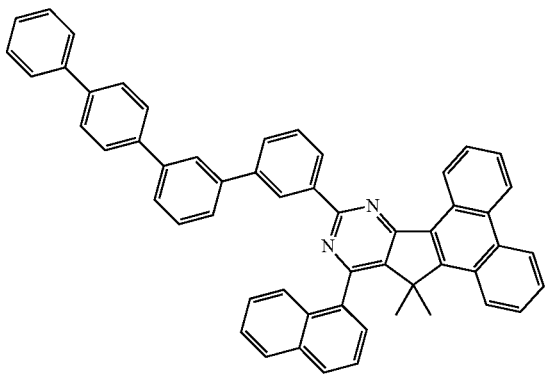
C-81
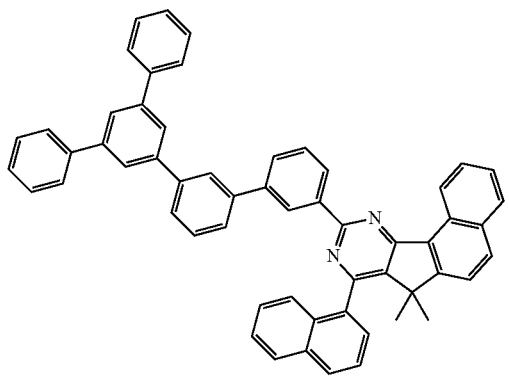
C-82
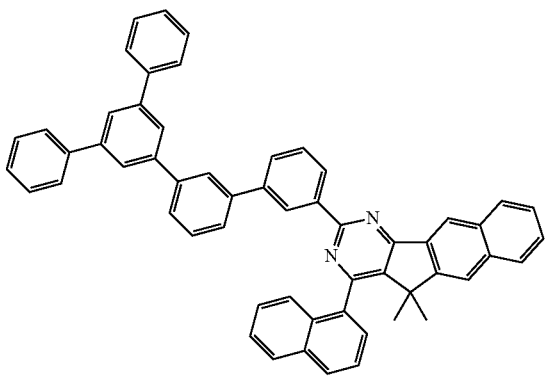
C-83
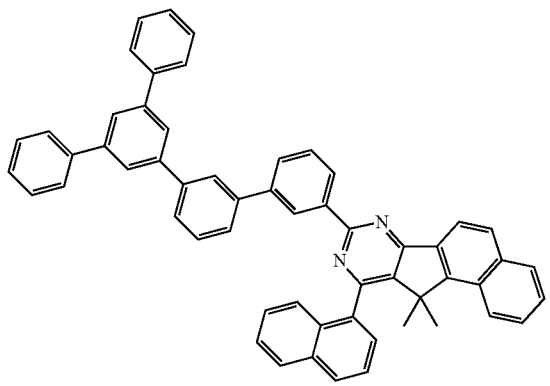
C-84
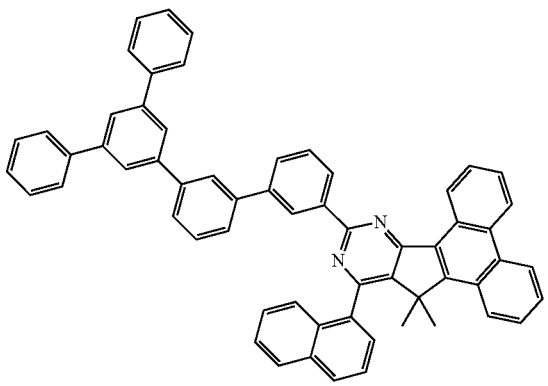
C-85
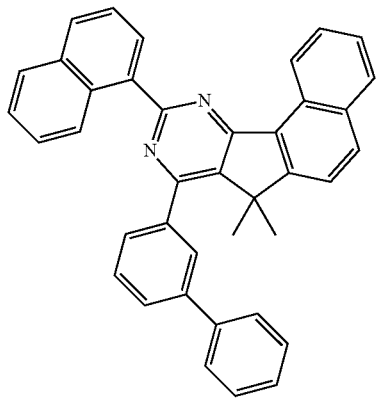
C-86
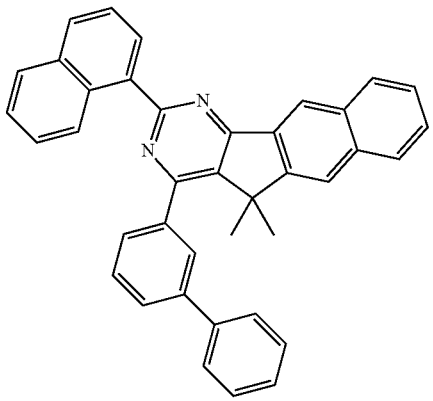

-continued
C-87
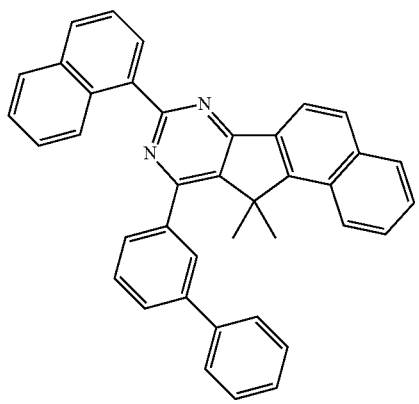
C-88
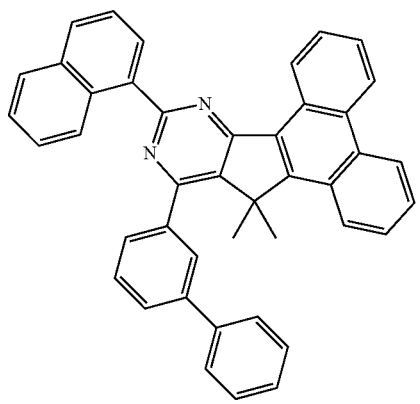
C-89
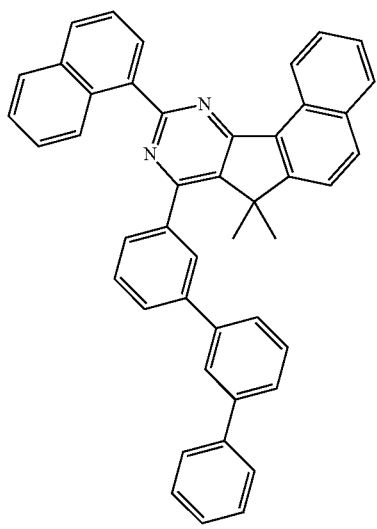
C-90
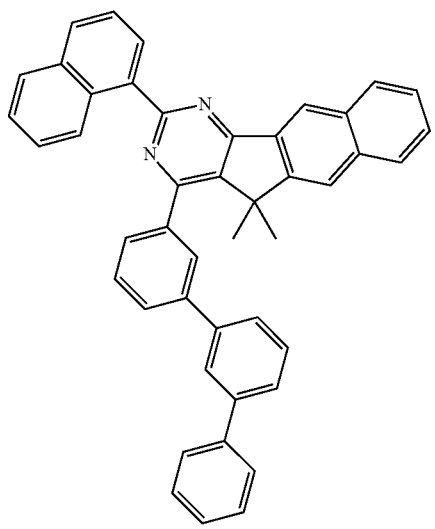
C-91
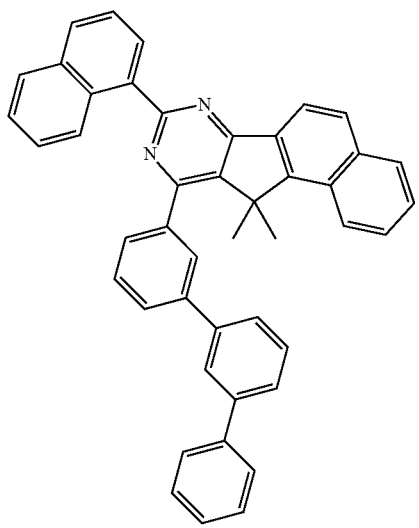
C-92
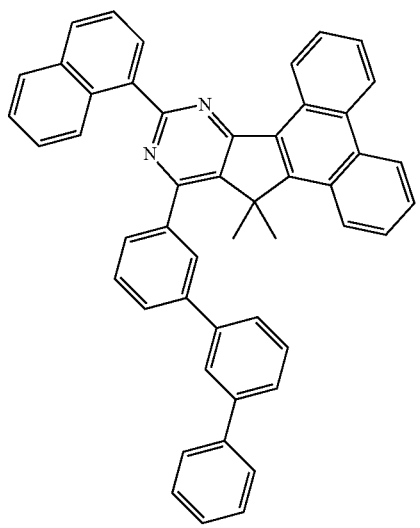

-continued
C-93
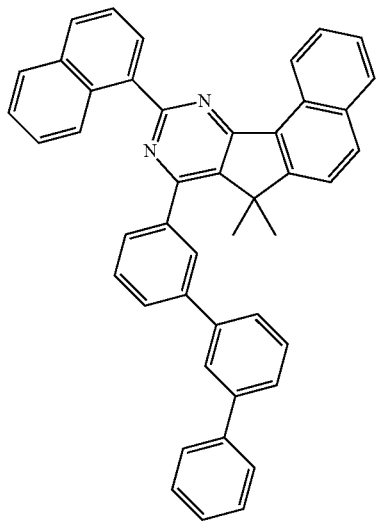
C-94
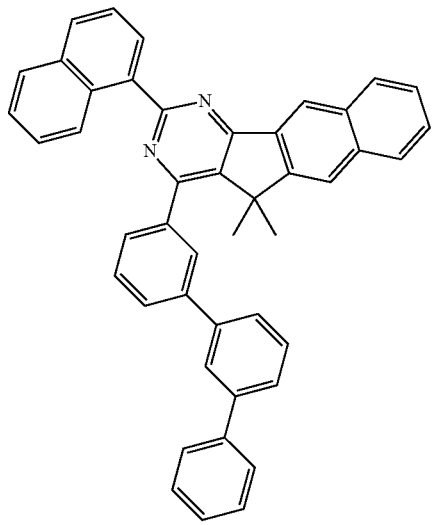
C-95
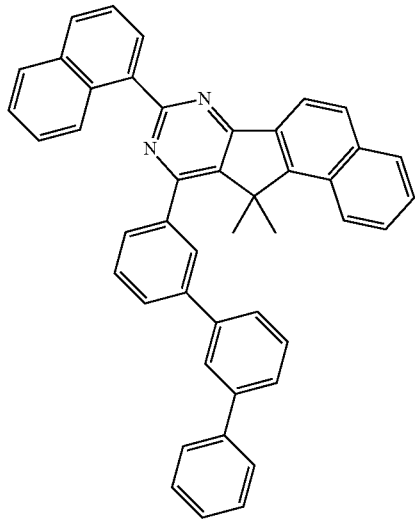
C-96
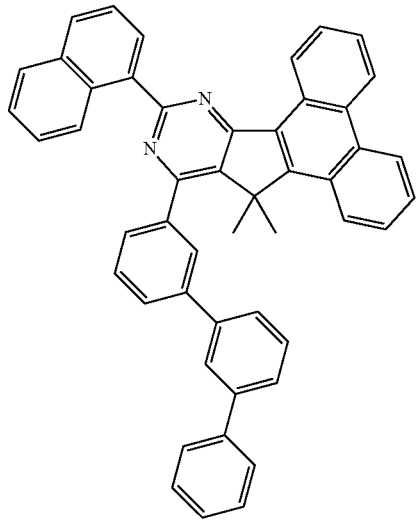
C-97
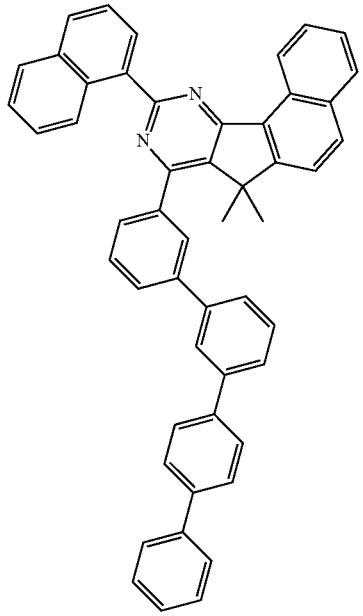
C-98
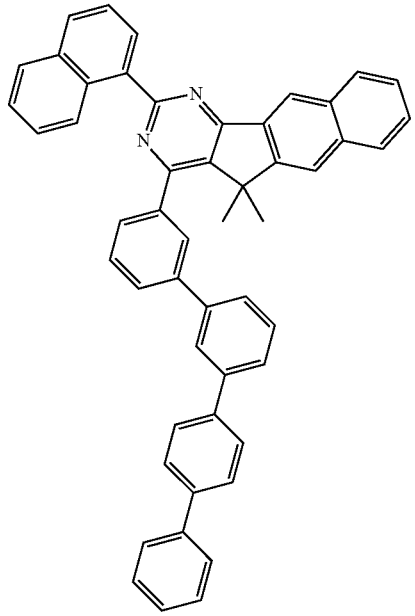

-continued
C-99
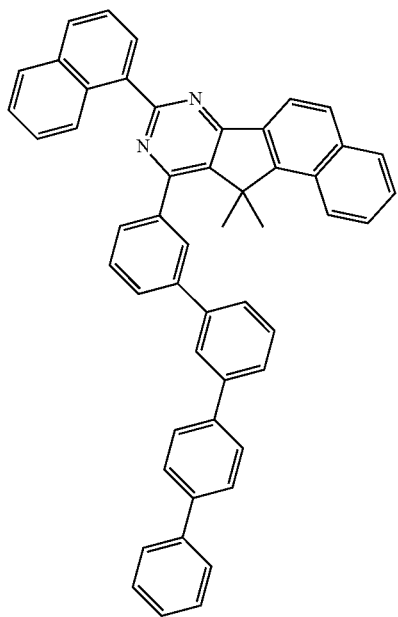
C-100
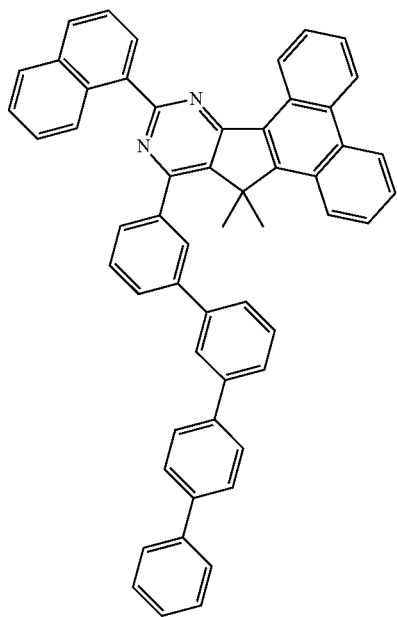
C-101
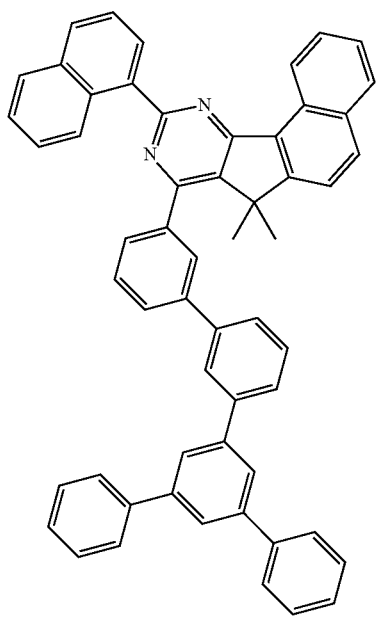
C-102
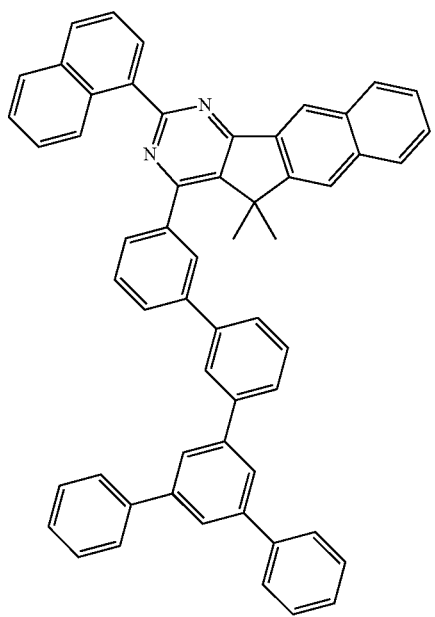

-continued
C-103
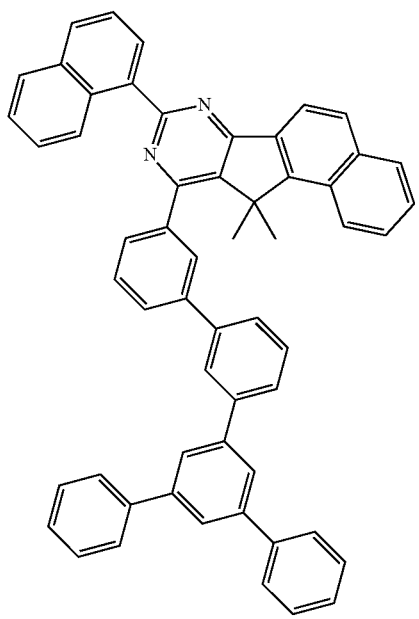
C-104
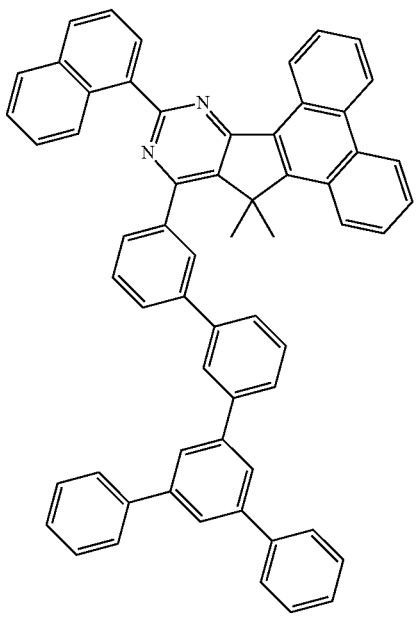
C-105
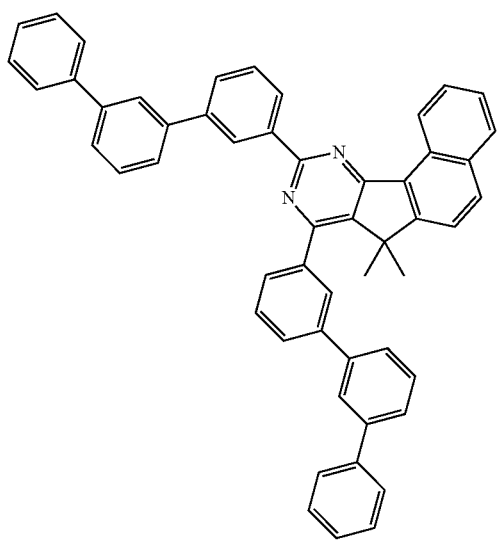
C-106
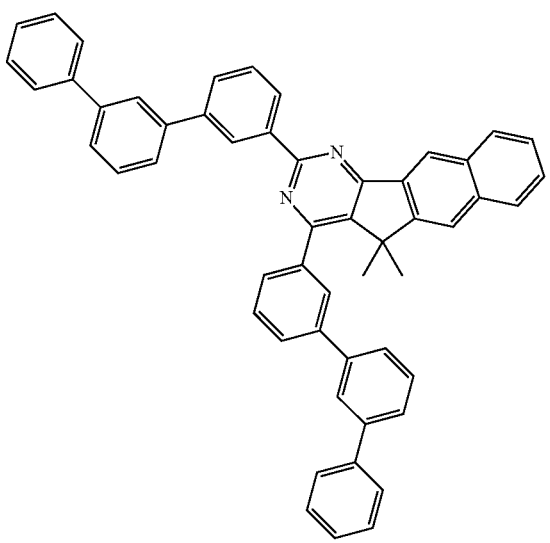

-continued
C-107
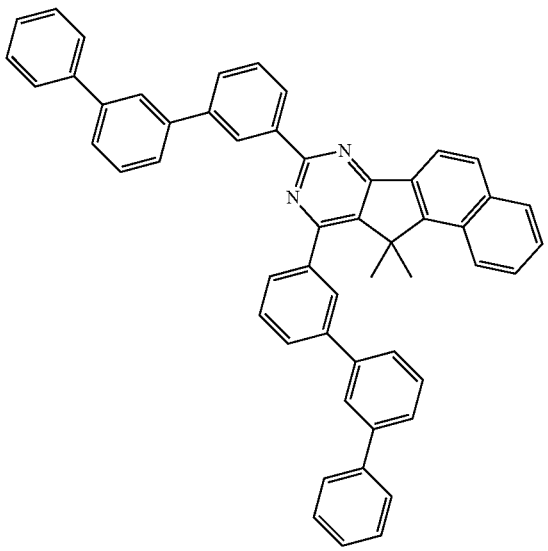
C-108
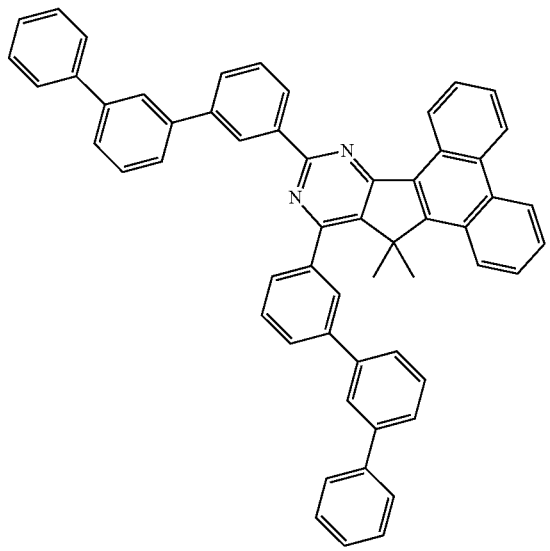
C-109
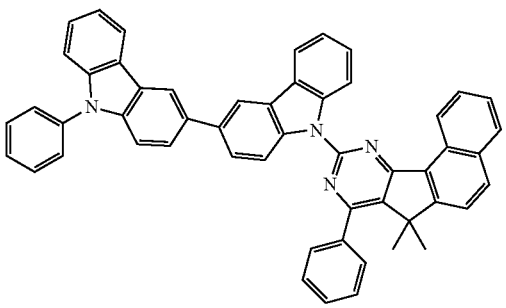
C-110
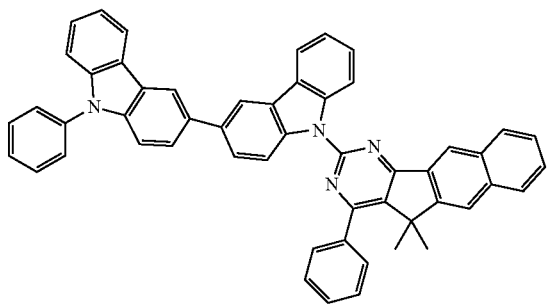
C-111
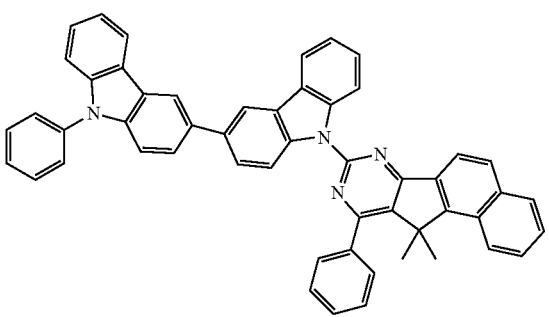
C-112
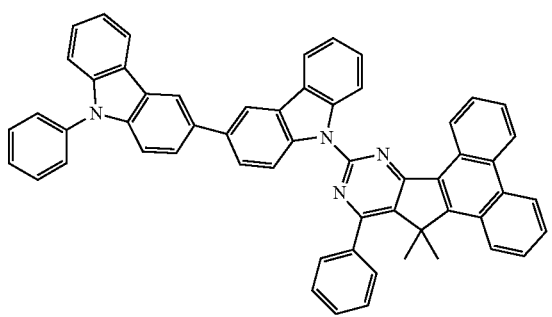
C-113
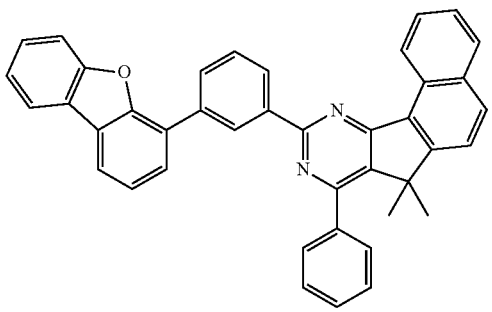
C-114
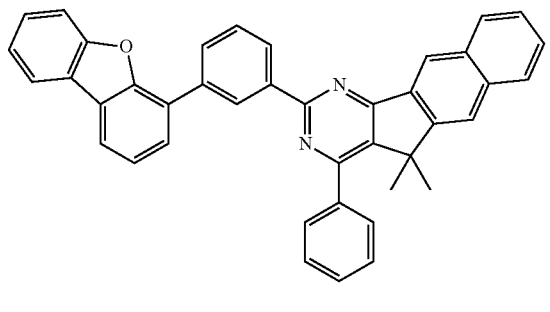

-continued
C-115
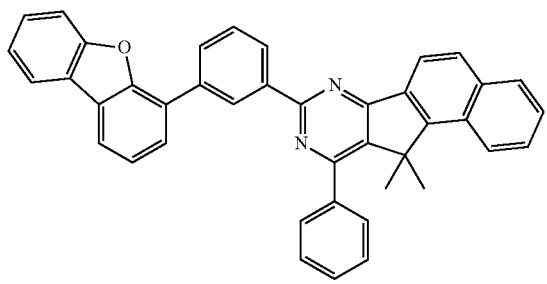
C-116
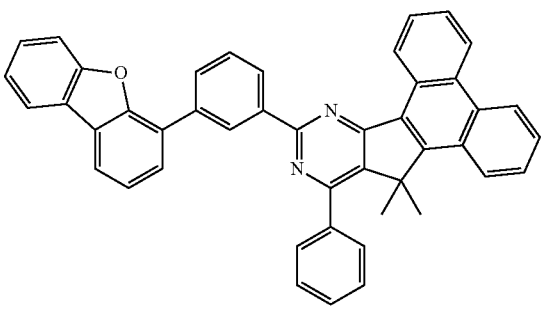
C-117
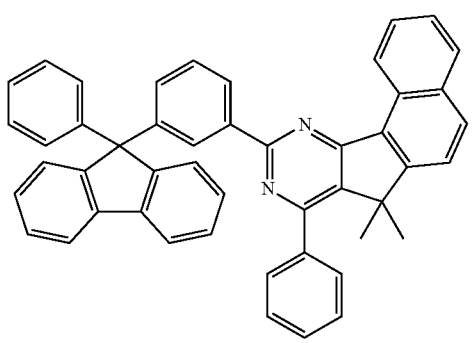
C-118
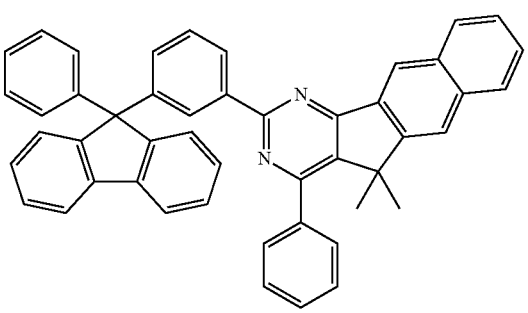
C-119
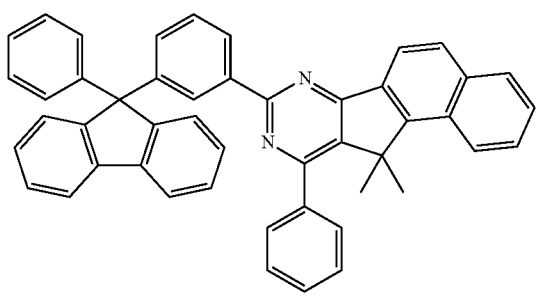
C-120
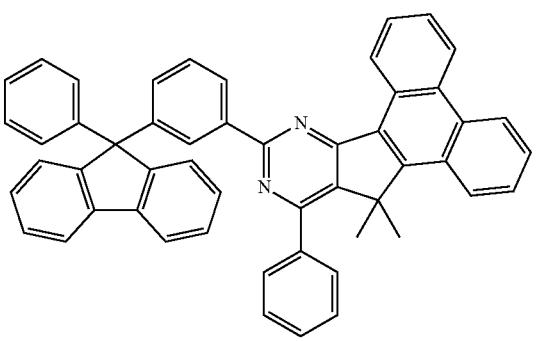
D-1
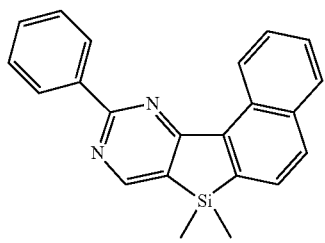
D-2
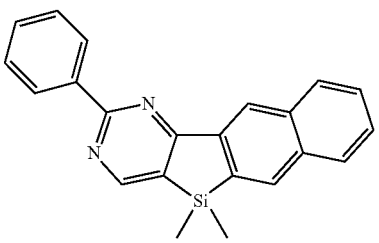
D-3
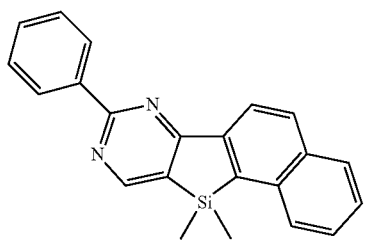
D-4
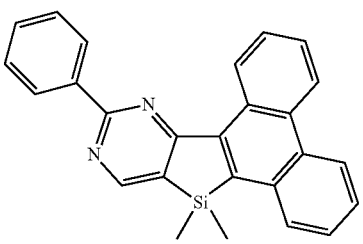

-continued
D-5
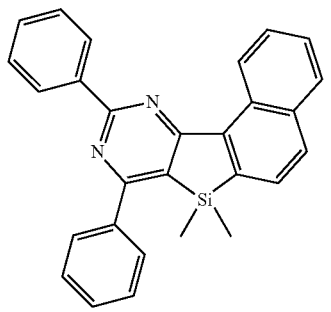
D-6
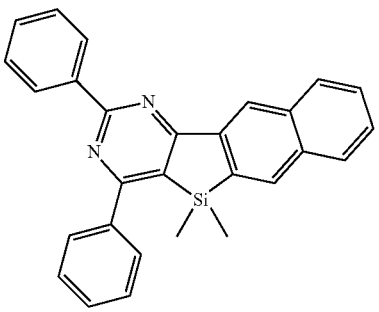
D-7
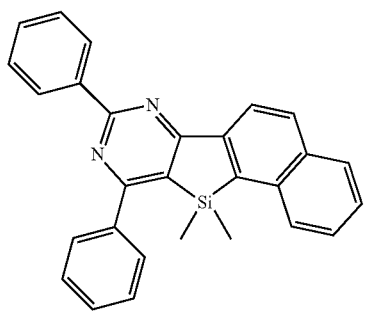
D-8
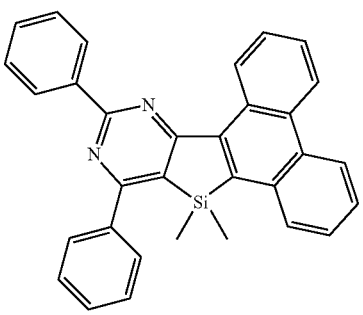
D-9
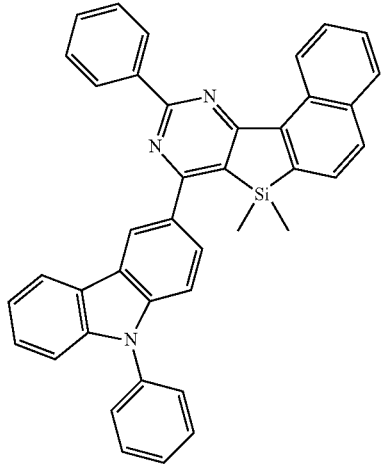
D-10
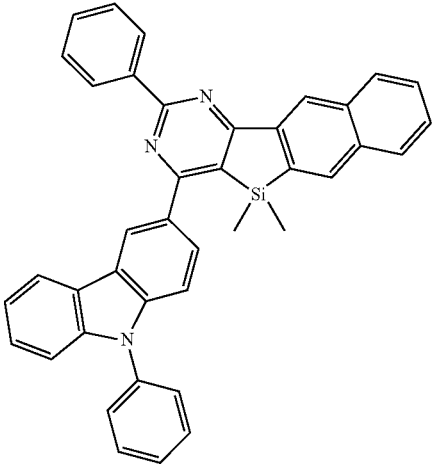
D-11
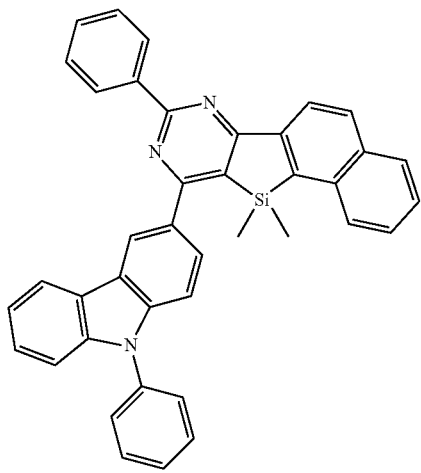
D-12
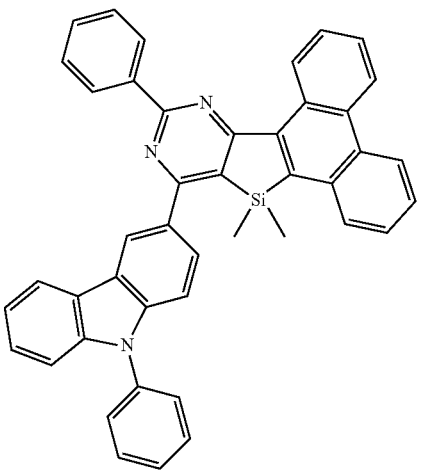

-continued
D-13
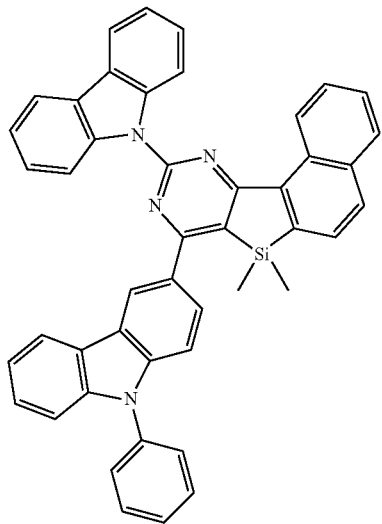
D-14
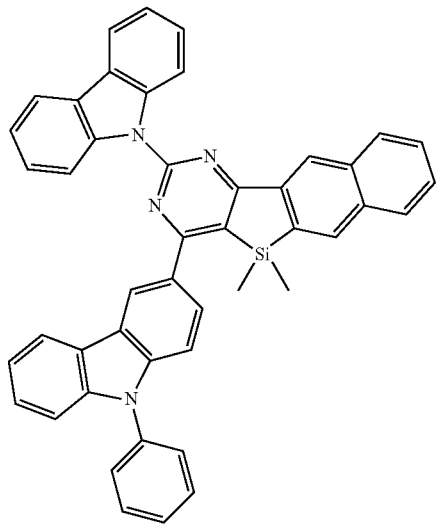
D-15
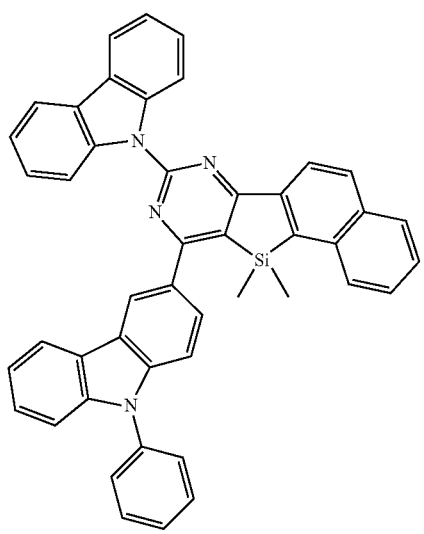
D-16
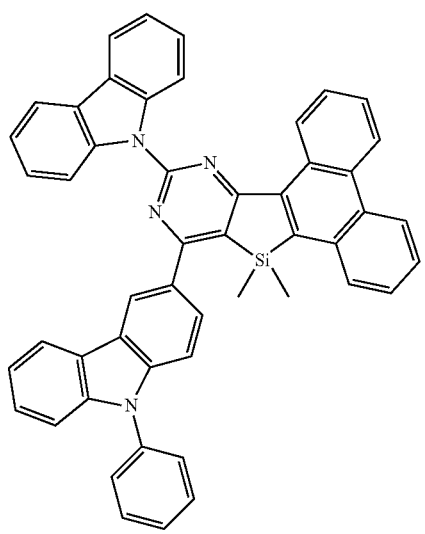
D-17
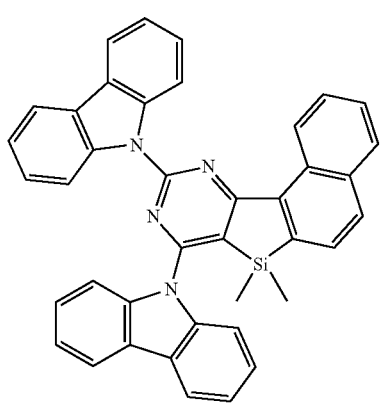
D-18
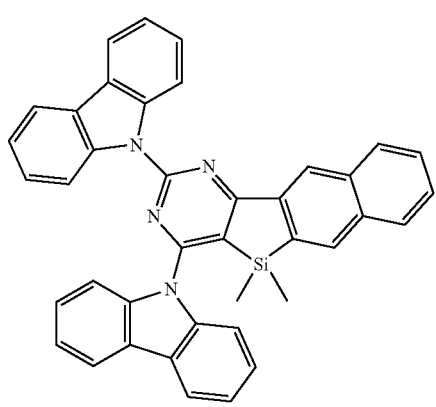

-continued
D-19
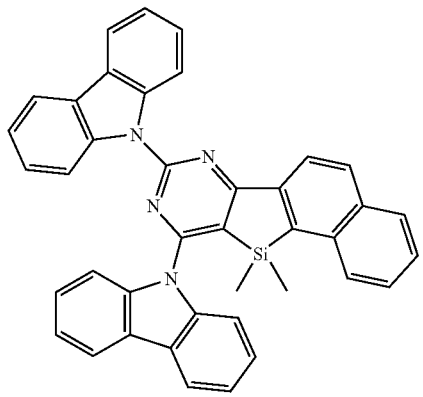
D-20
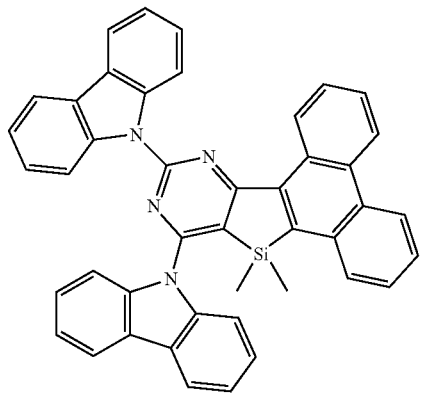
D-21
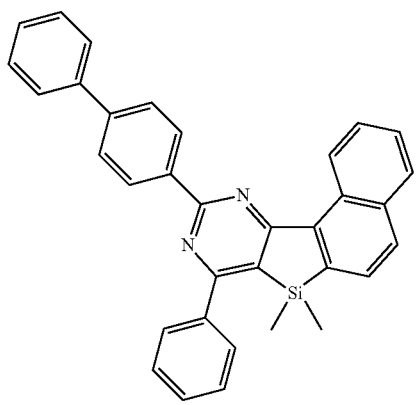
D-22
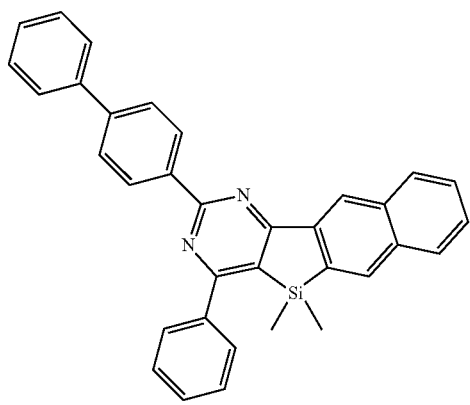
D-23
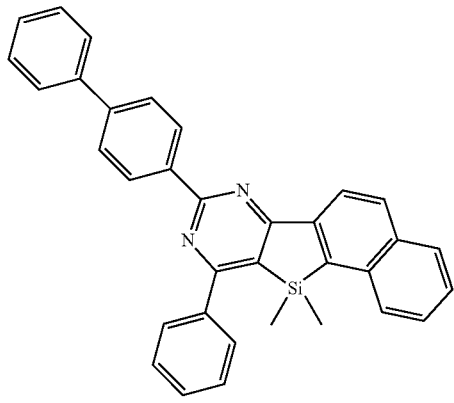
D-24
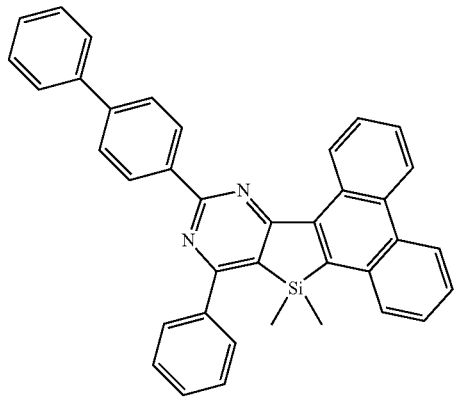
D-25
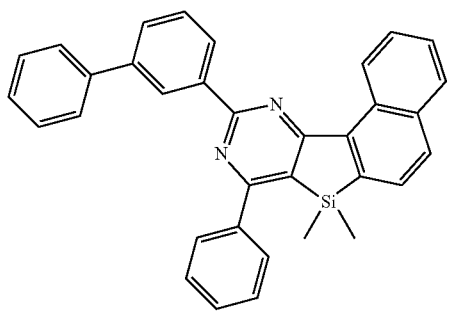
D-26
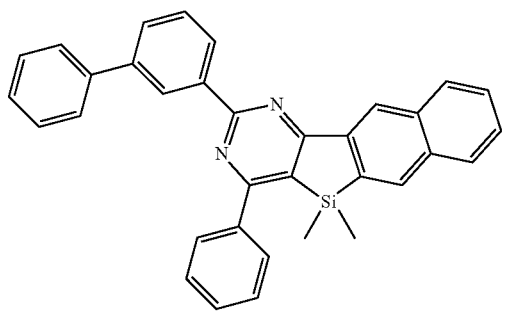

-continued
D-27
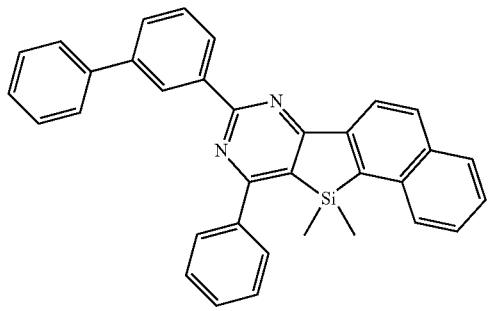
D-28
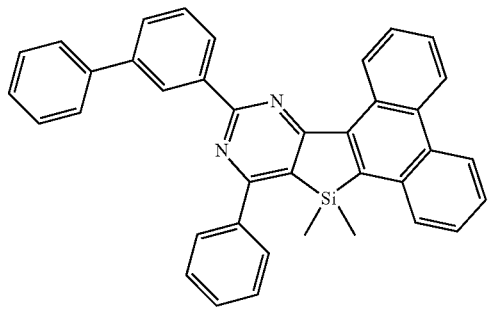
D-29
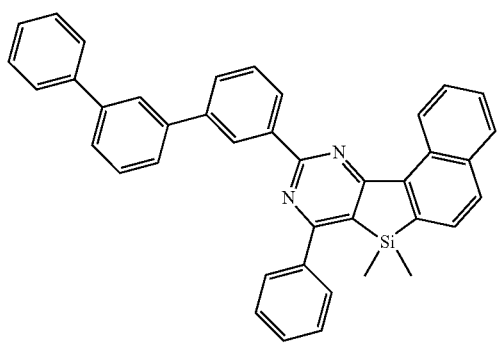
D-30
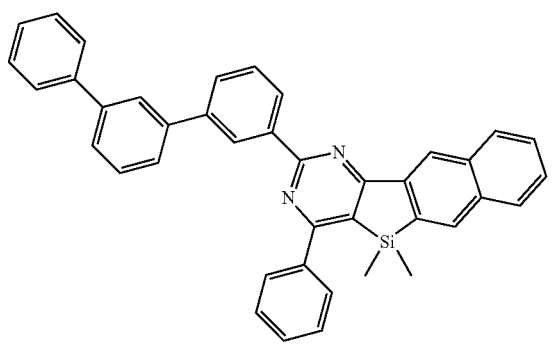
D-31
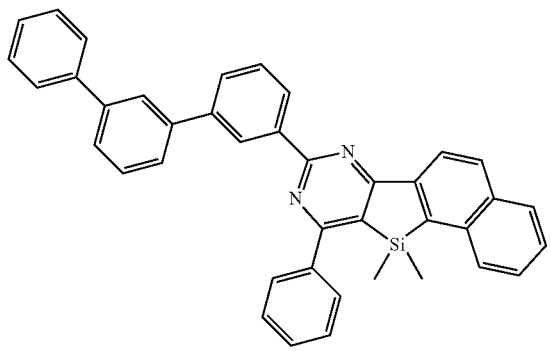
D-32
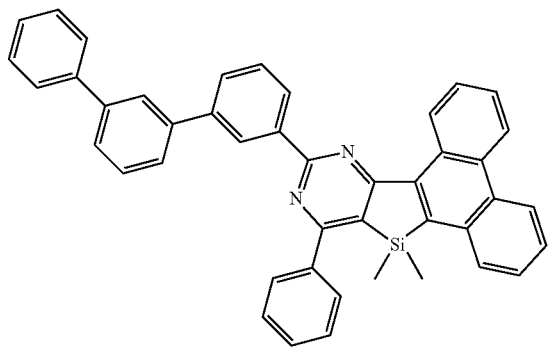
D-33
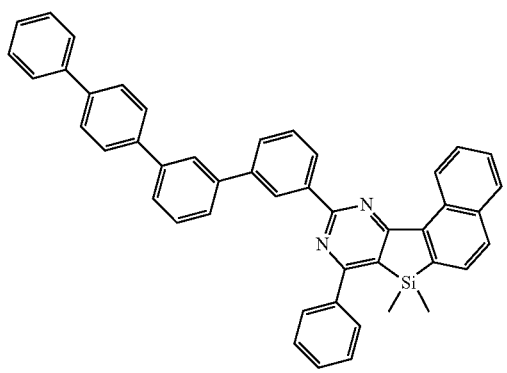
D-34
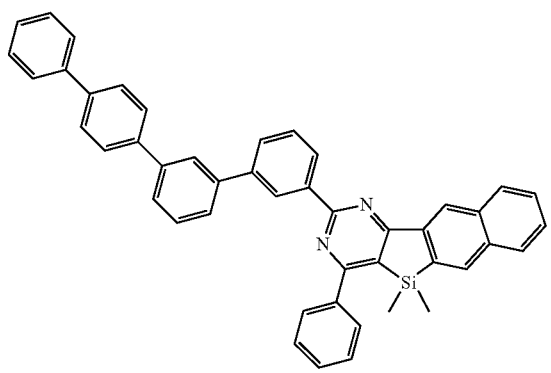

-continued
D-35
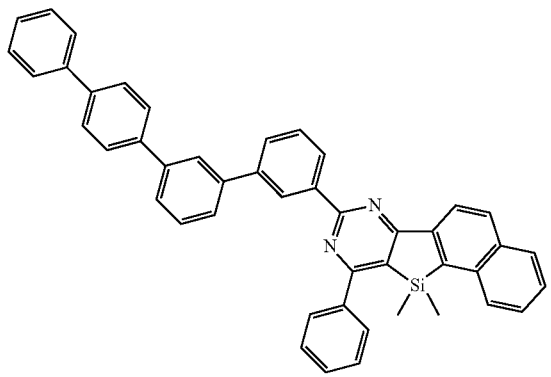
D-36
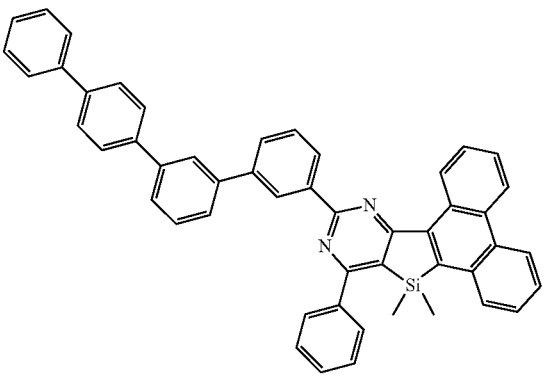
D-37
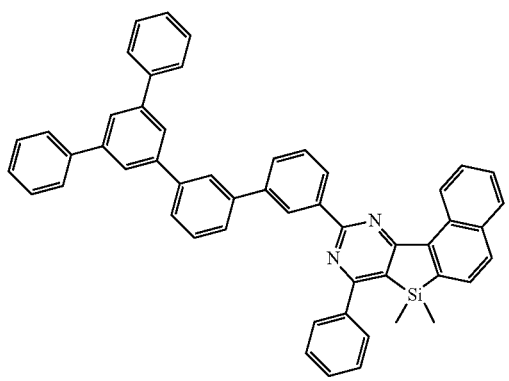
D-38
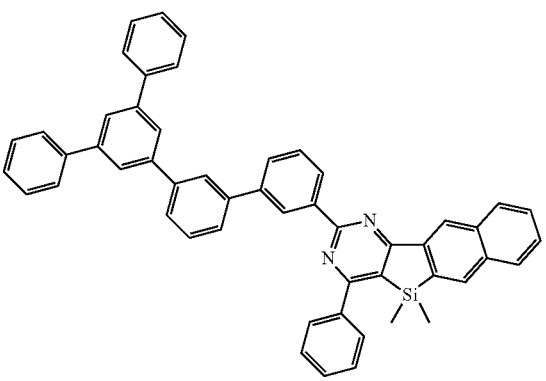
D-39
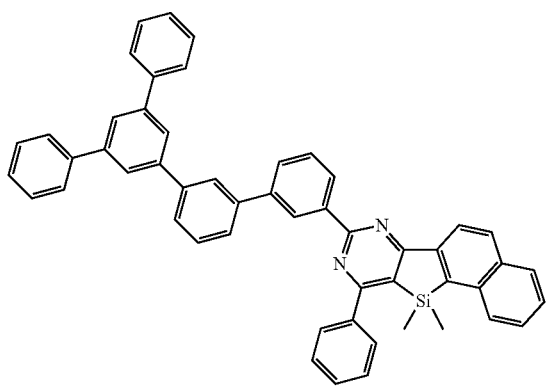
D-40
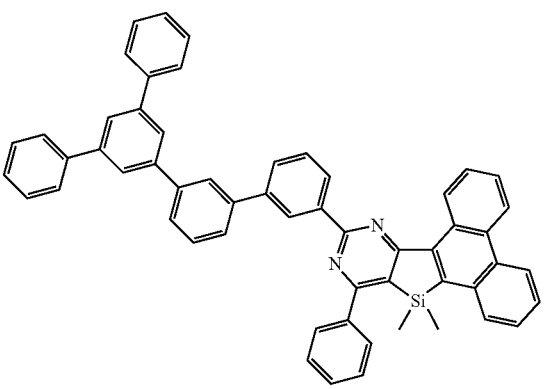
D-41
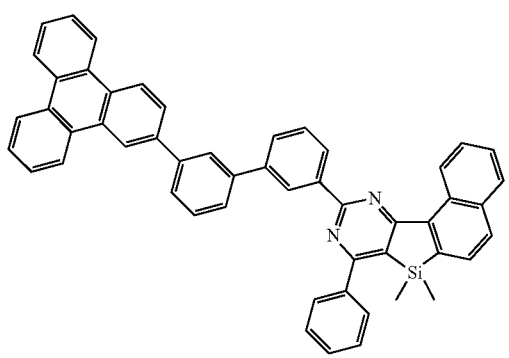
D-42
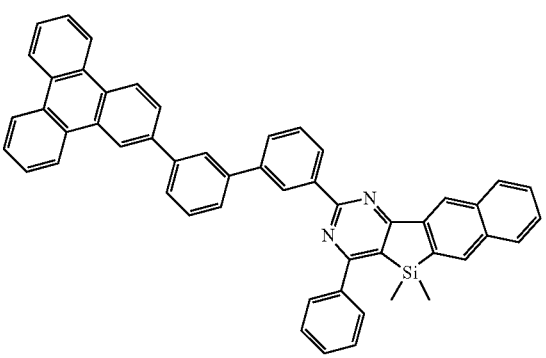

-continued
D-43
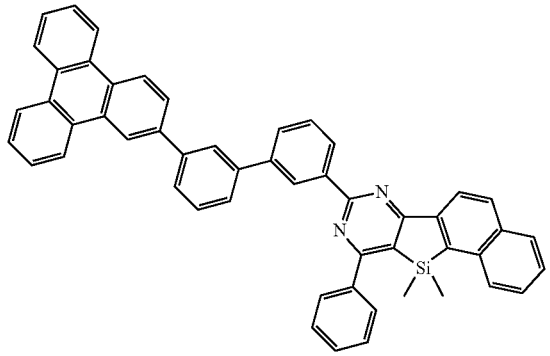
D-44
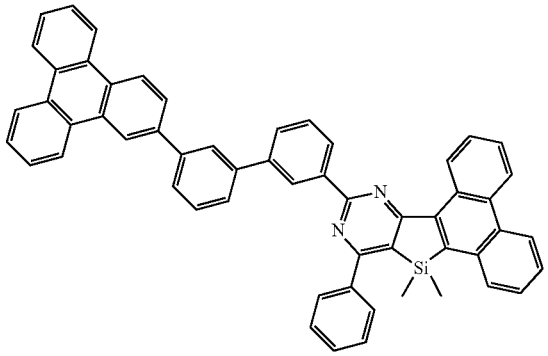
D-45
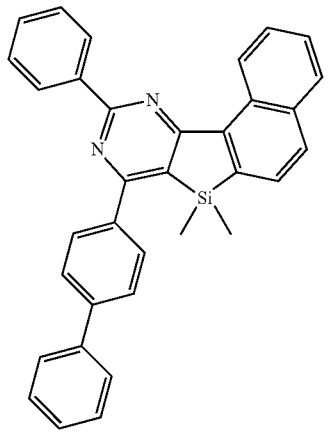
D-46
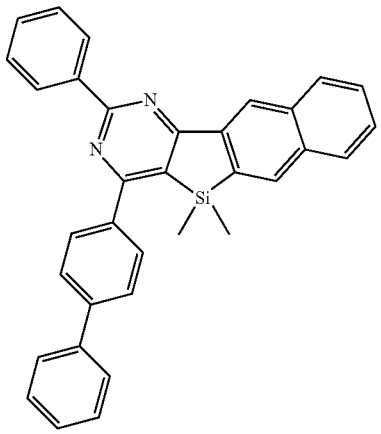
D-47
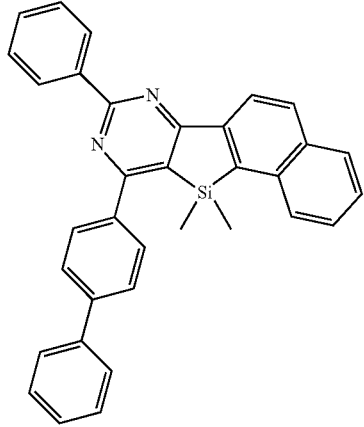
D-48
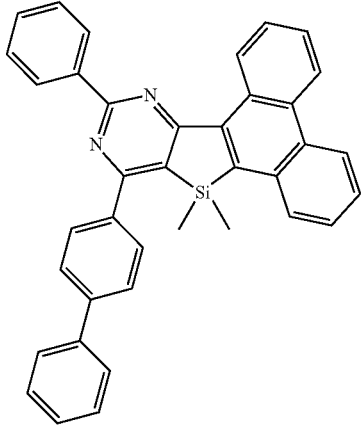
D-49
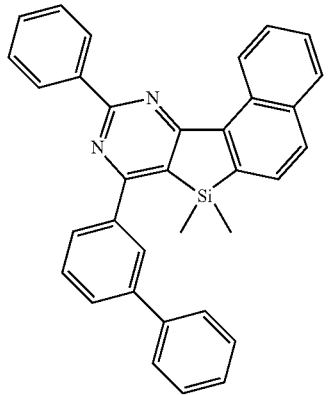
D-50
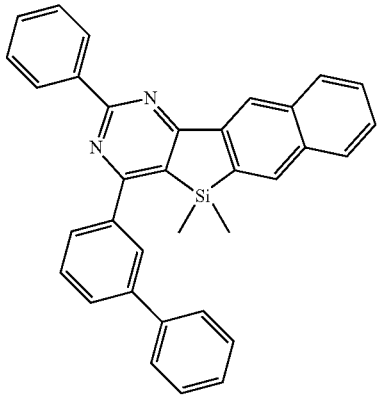

-continued
D-51
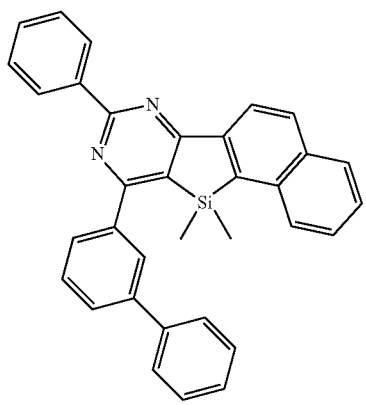
D-52
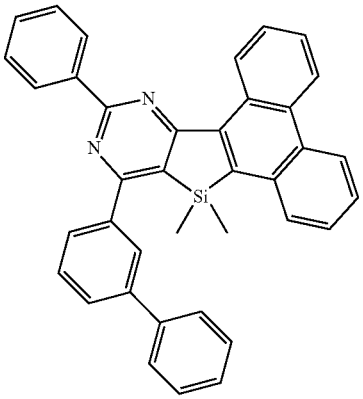
D-53
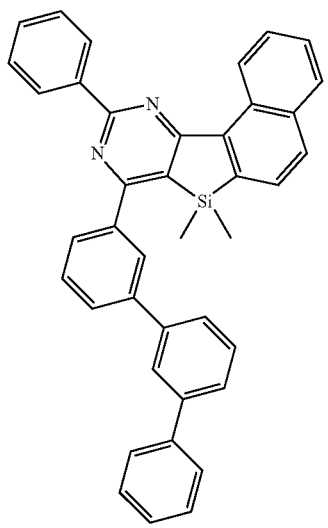
D-54
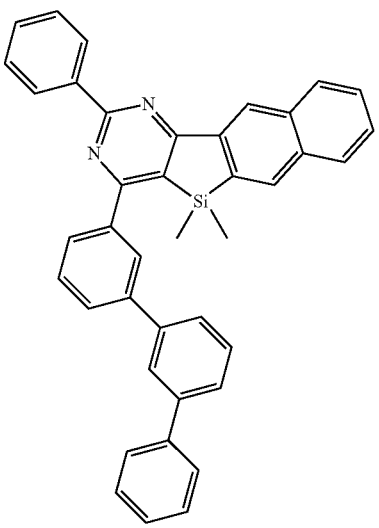
D-55
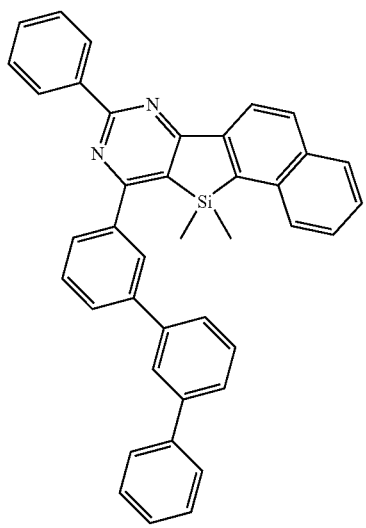
D-56
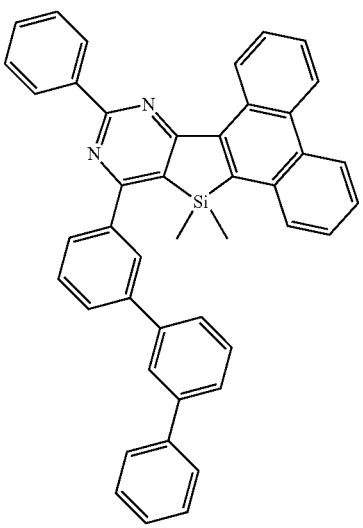

-continued
D-57
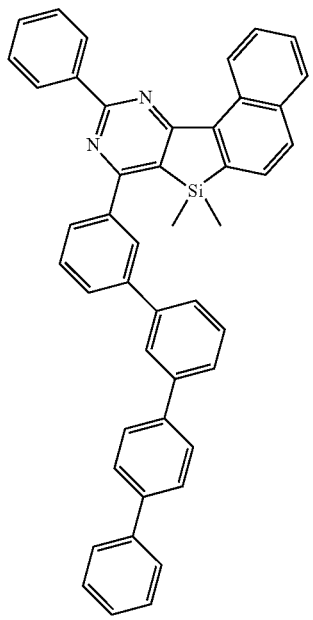
D-58
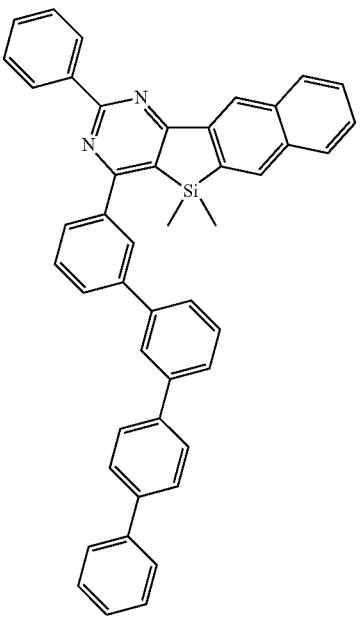
D-59
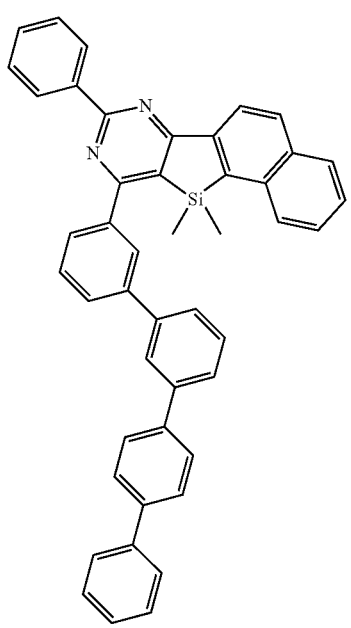
D-60
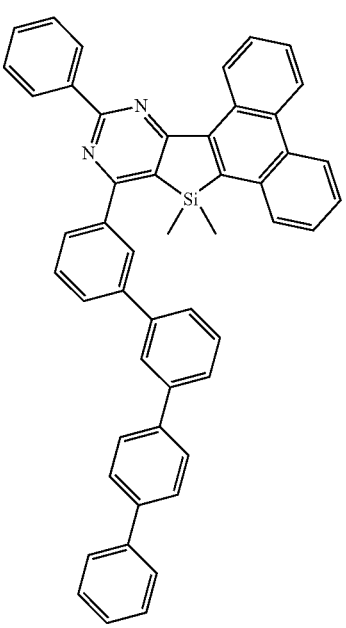

-continued
D-61
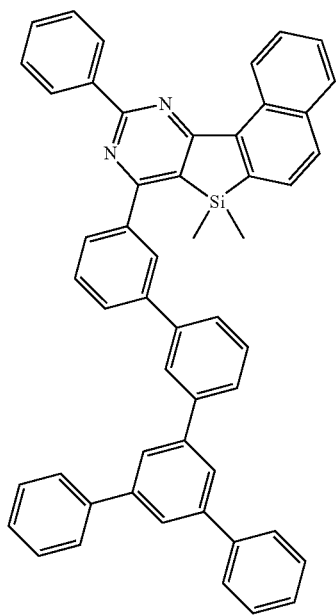
D-62
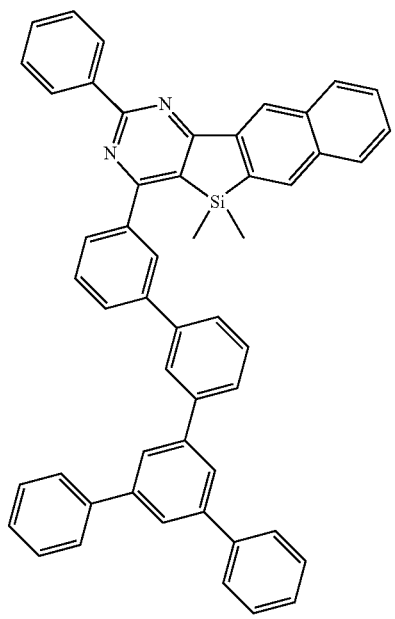
D-63
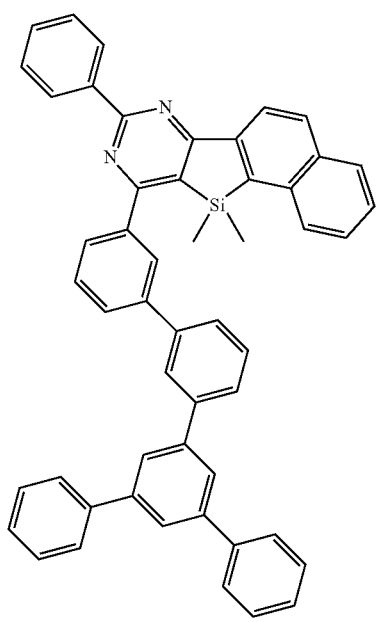
D-64
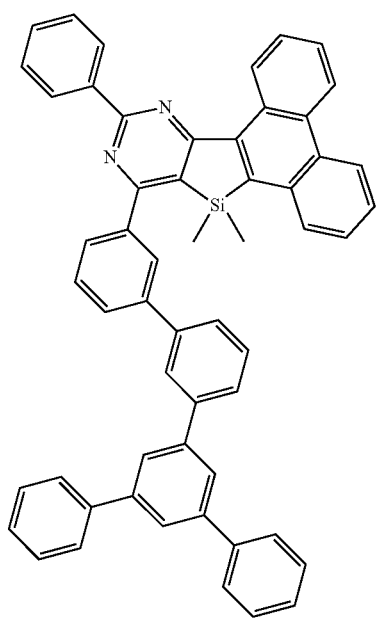

-continued
D-65
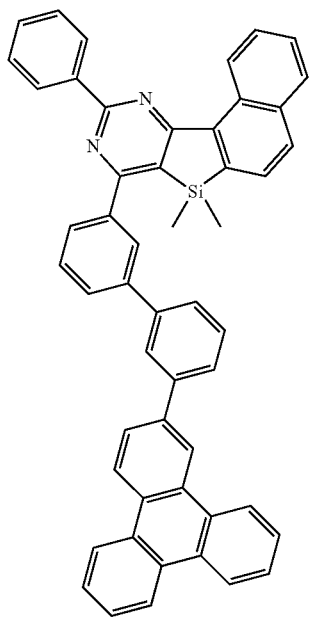
D-66
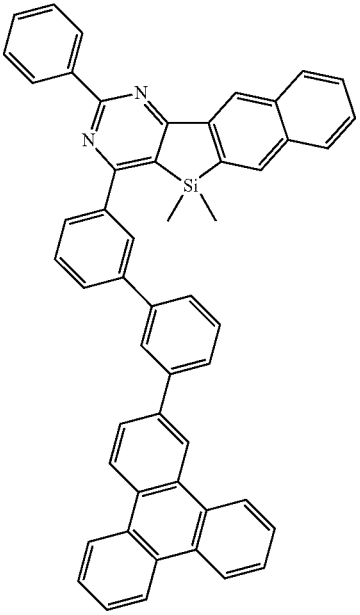
D-67
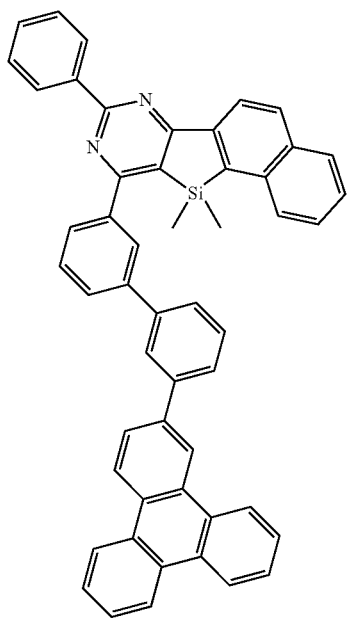
D-68
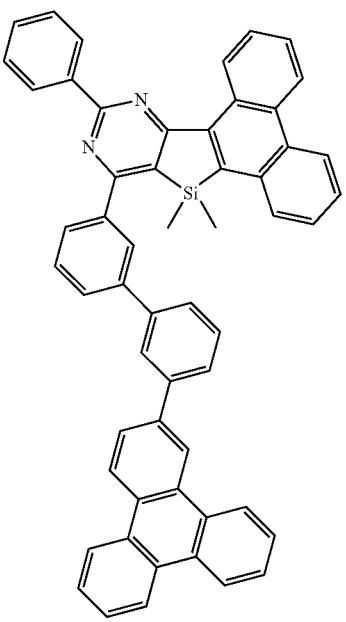
D-69
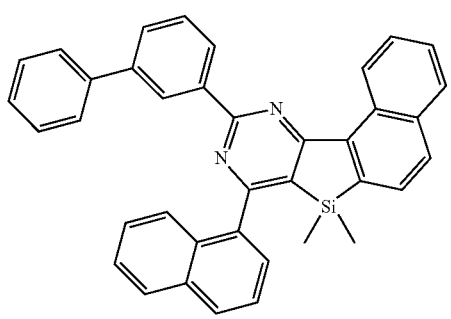
D-70
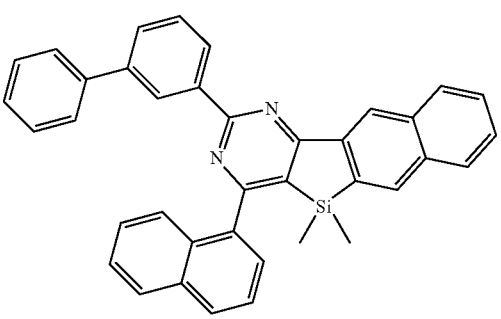

-continued
D-71
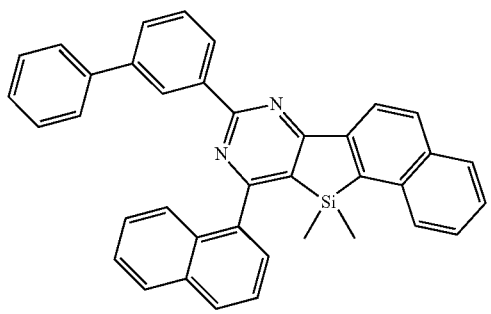
D-72
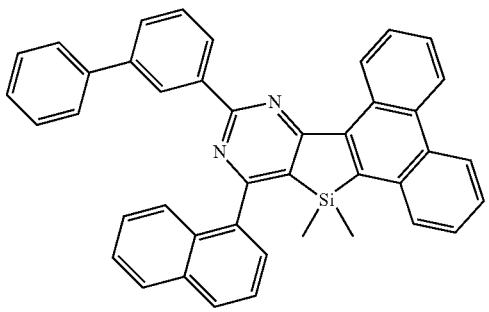
D-73
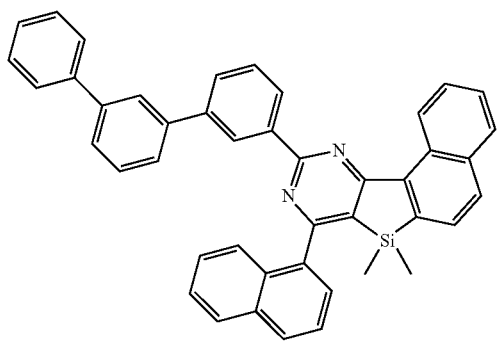
D-74
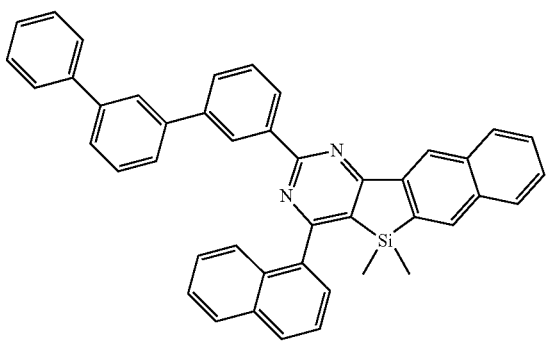
D-75
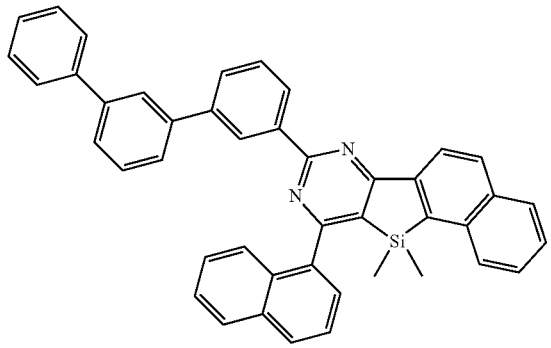
D-76
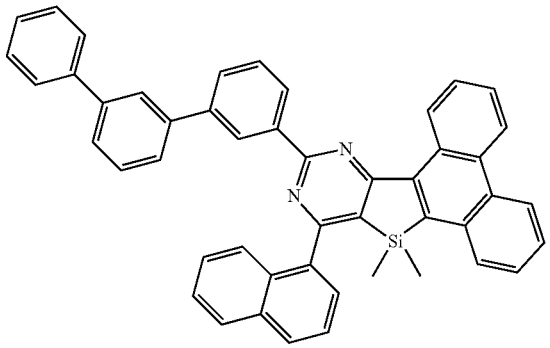
D-77
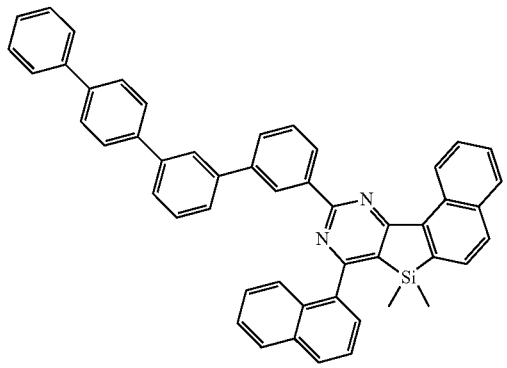
D-78
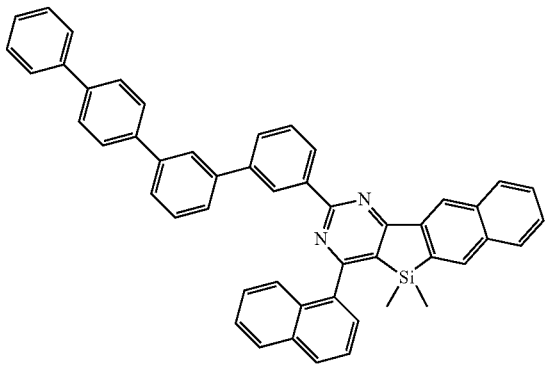

-continued
D-79
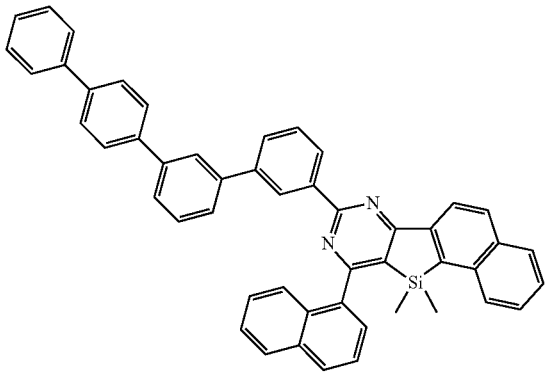
D-80
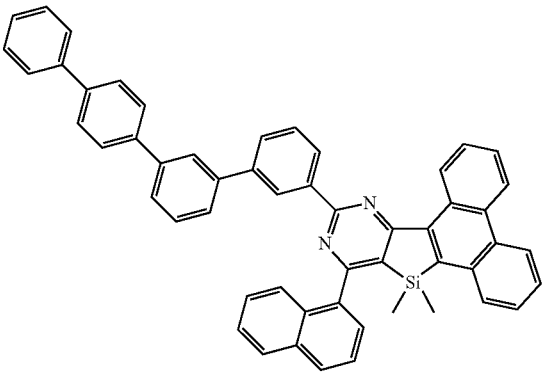
D-81
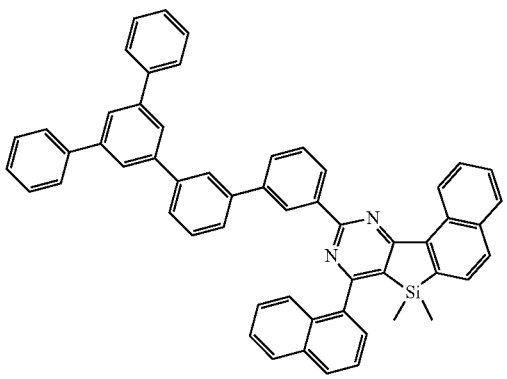
D-82
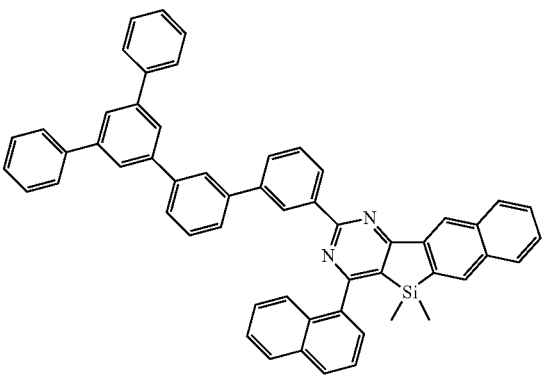
D-83
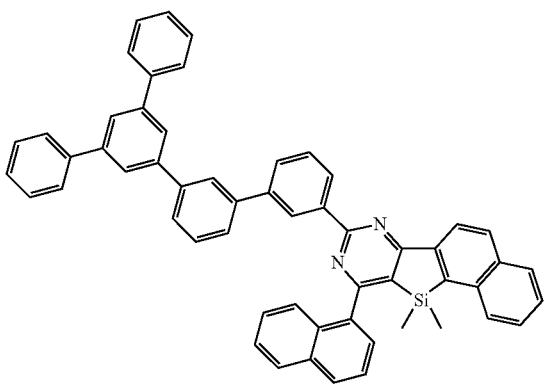
D-84
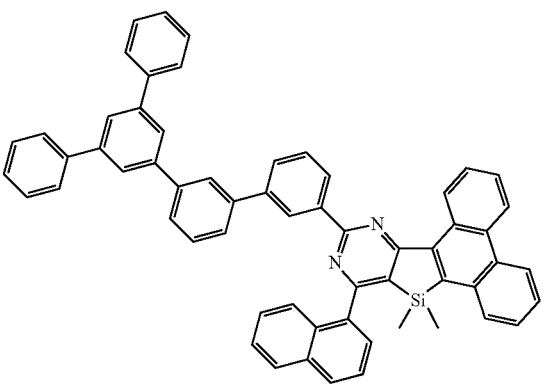
D-85
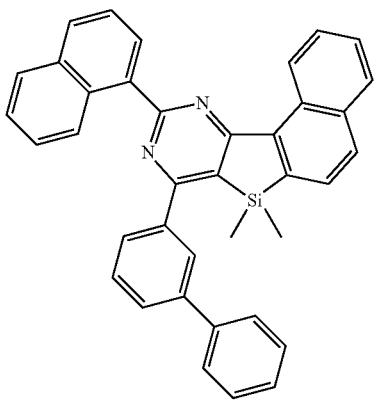
D-86
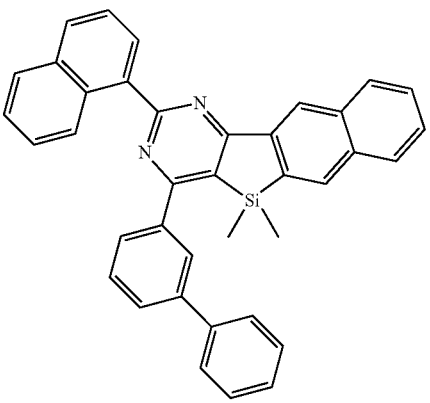

-continued
D-87
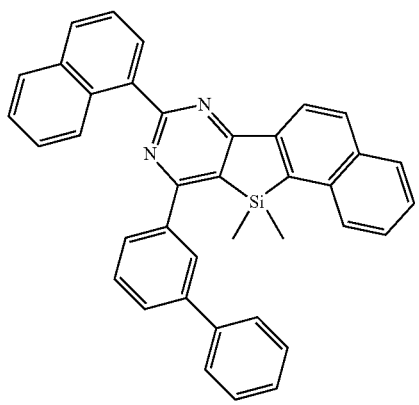
D-88
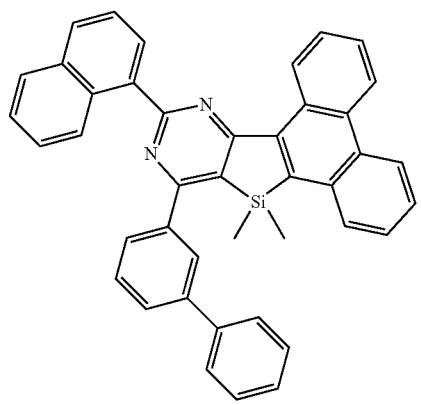
D-89
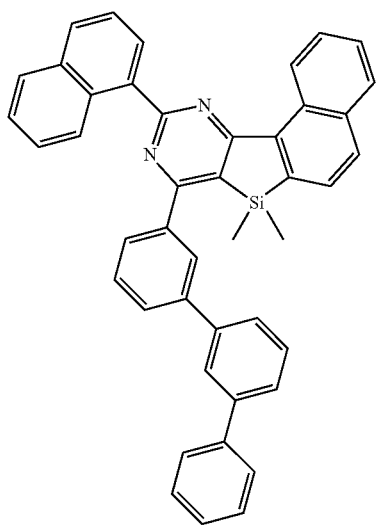
D-90
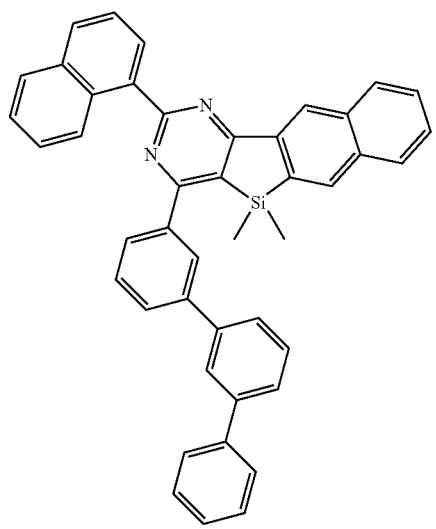
D-91
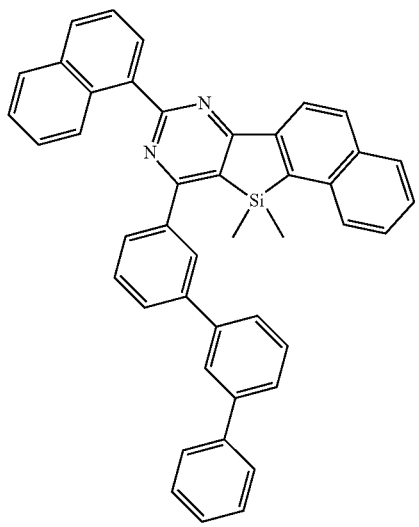
D-92
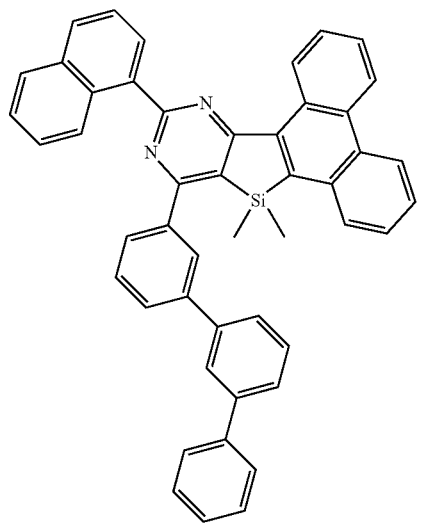

-continued
D-93
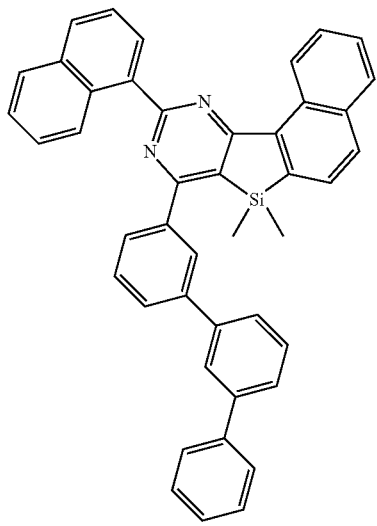
D-94
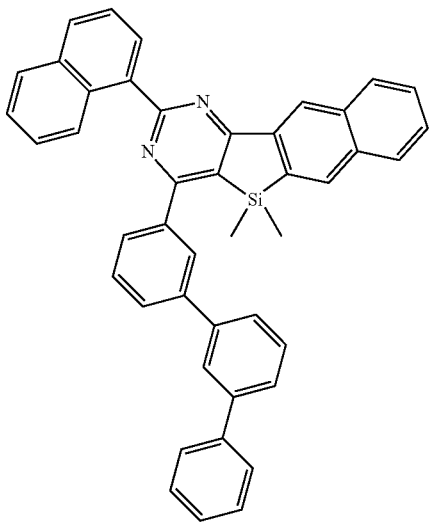
D-95
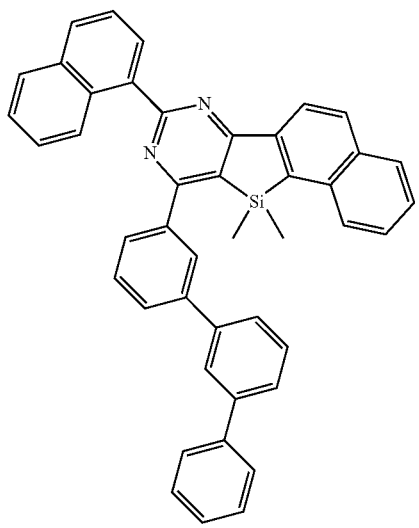
D-96
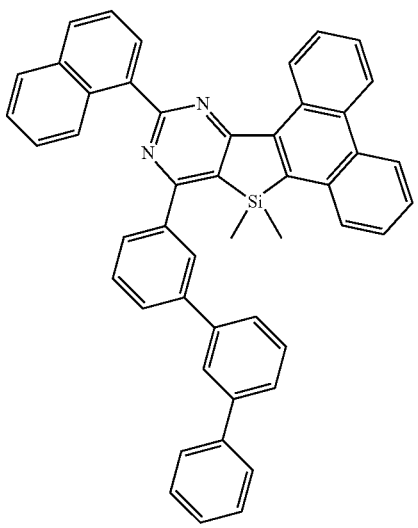
D-97
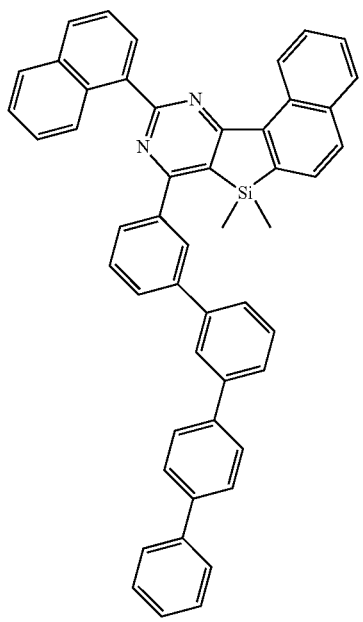
D-98
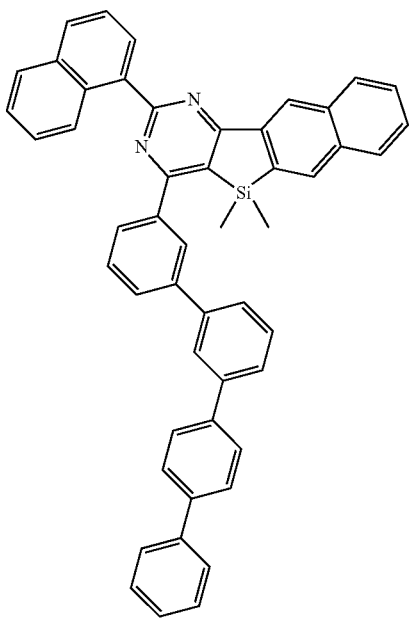

-continued
D-99
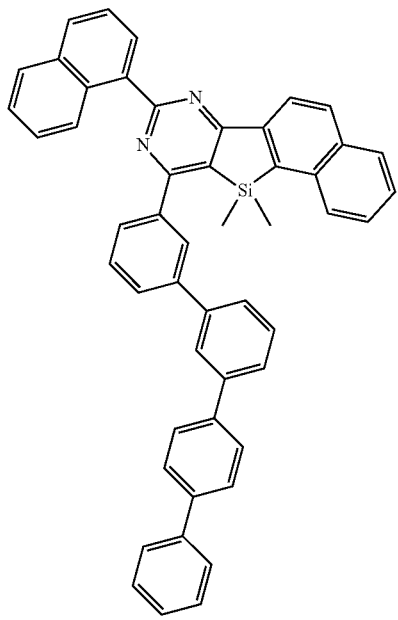
D-100
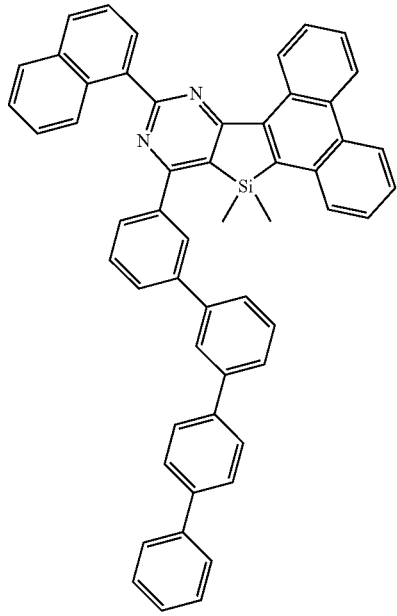
D-101
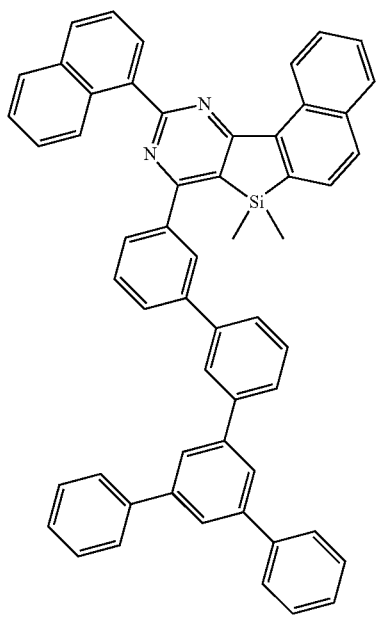
D-102

-continued
D-103
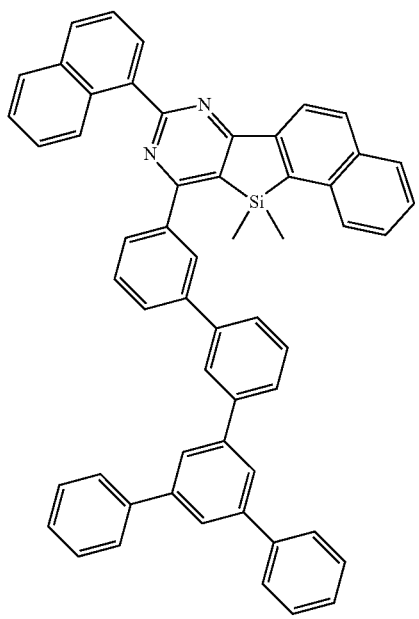
D-104
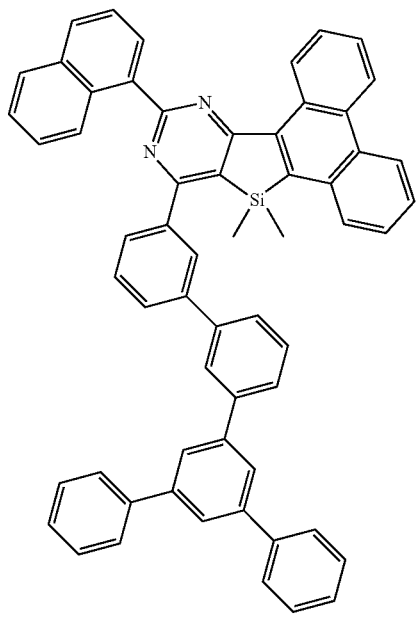
D-105
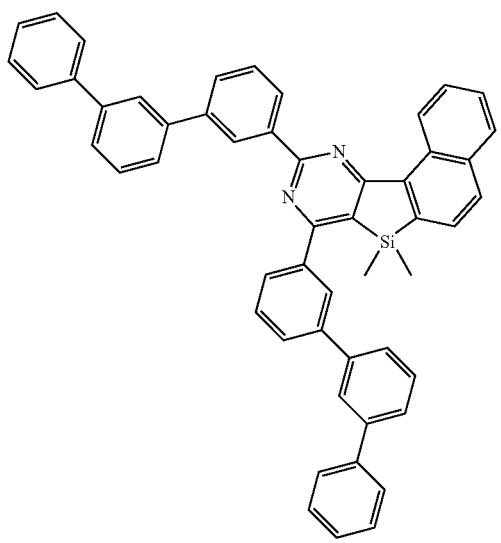
D-106
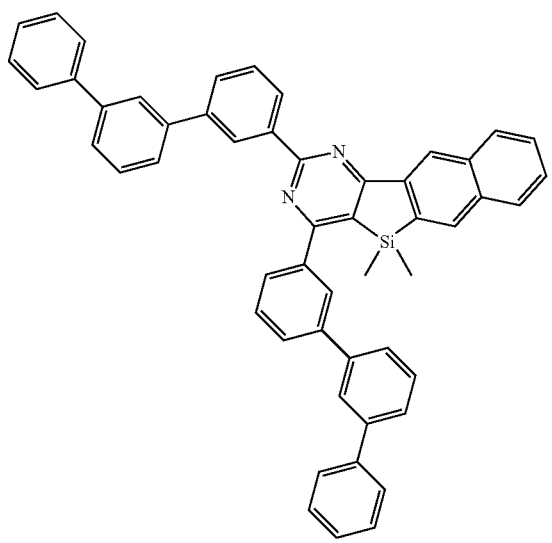

-continued
D-107
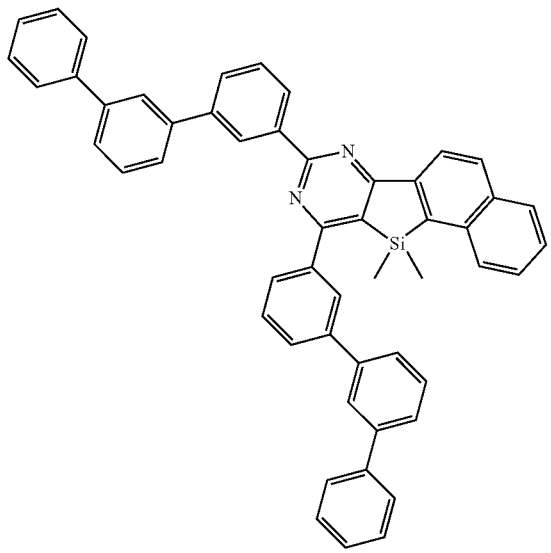
D-108
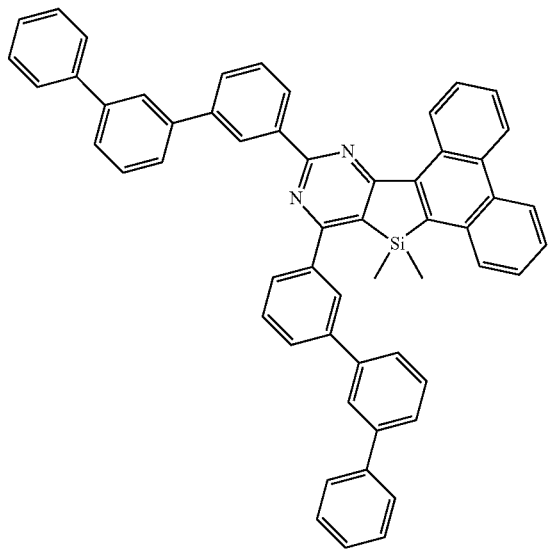
D-109
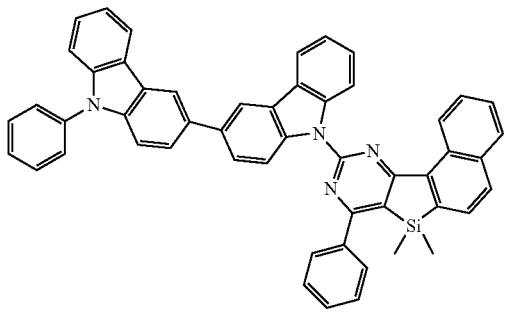
D-110
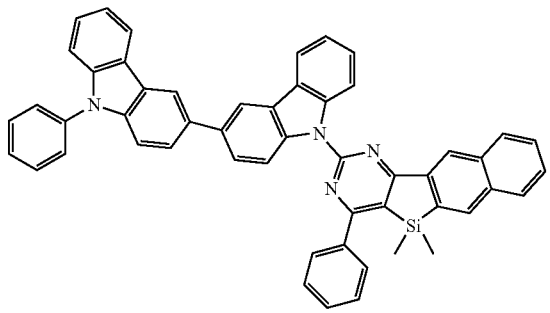
D-111
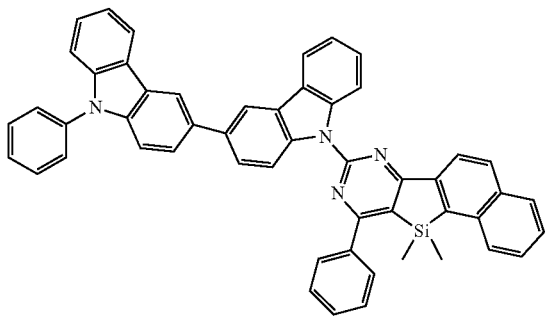
D-112
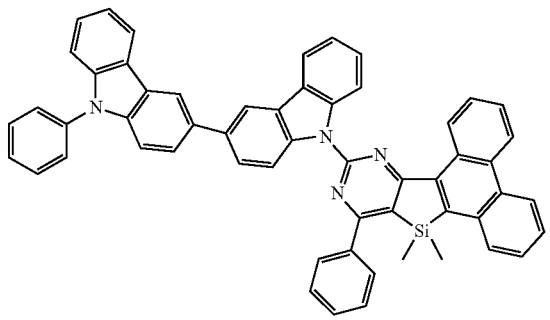
D-113
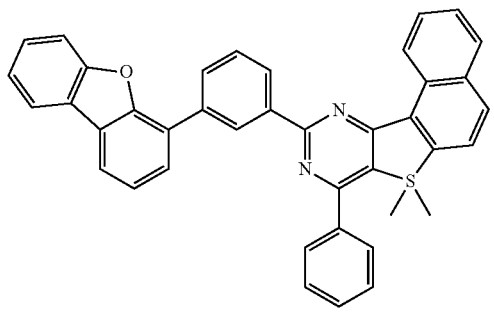
D-114
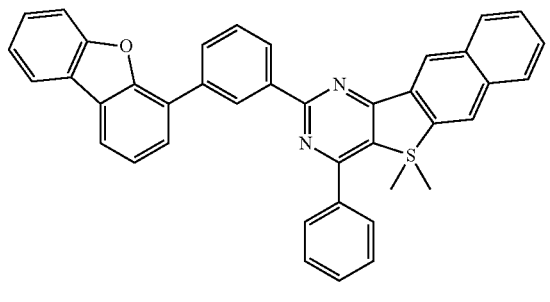

-continued
D-115
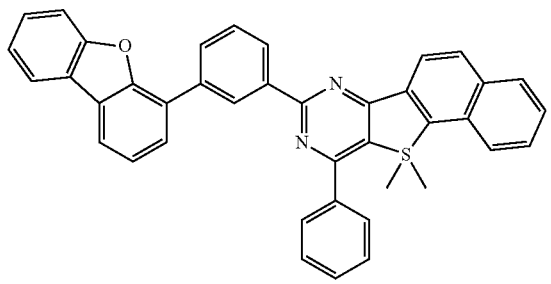
D-116
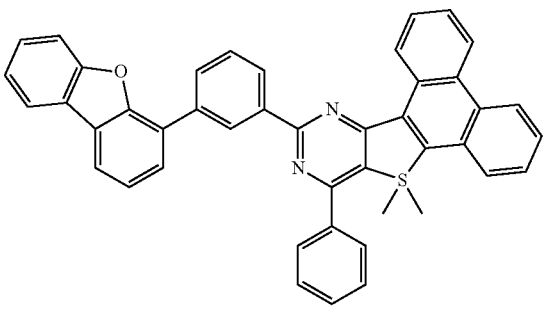
D-117
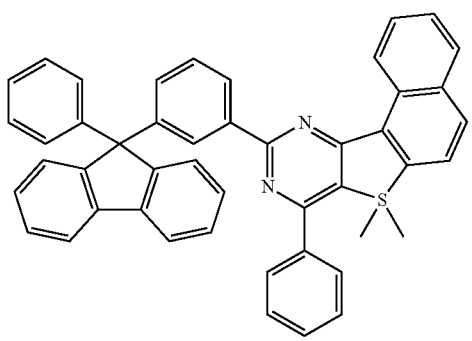
D-118
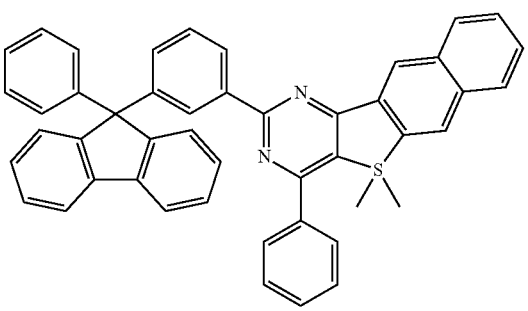
D-119
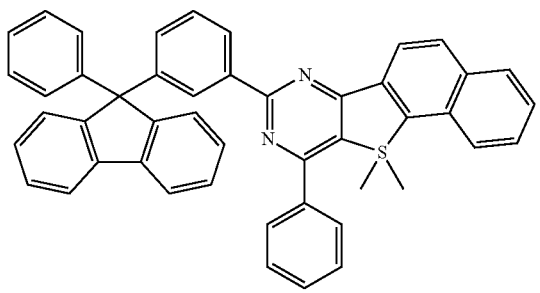
D-120
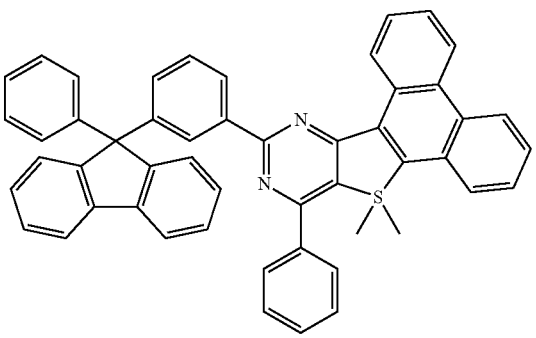
F-1
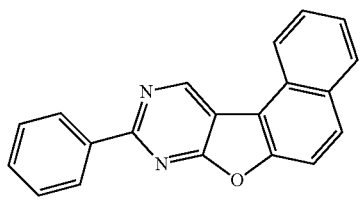
F-2
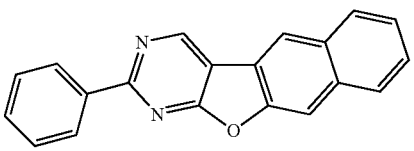
F-3
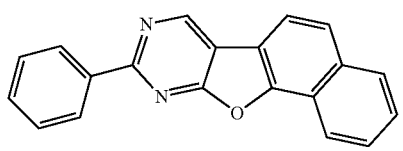
F-4
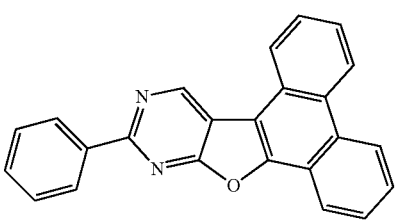

-continued
F-5
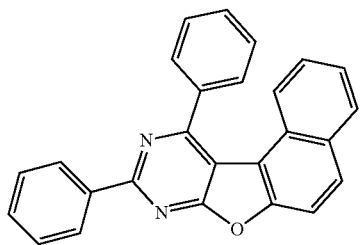
F-6
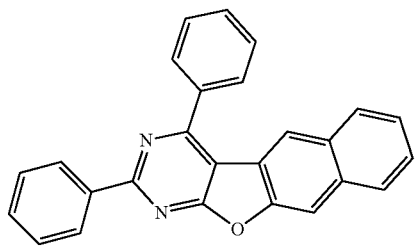
F-7
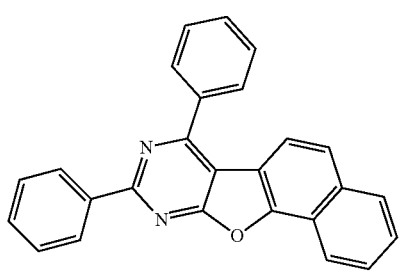
F-8
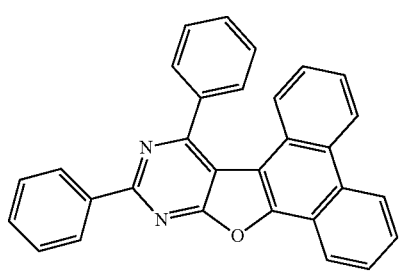
F-9
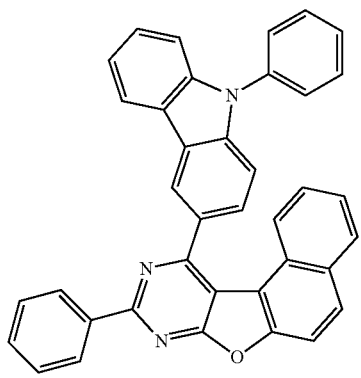
F-10
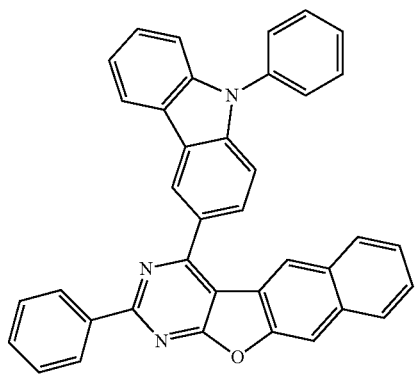
F-11
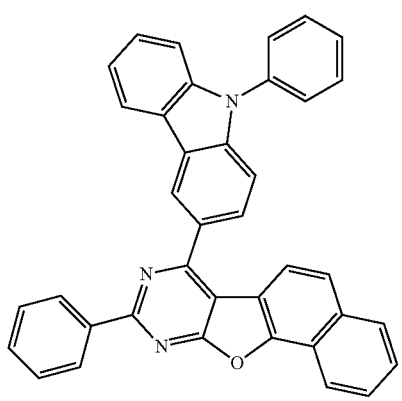
F-12
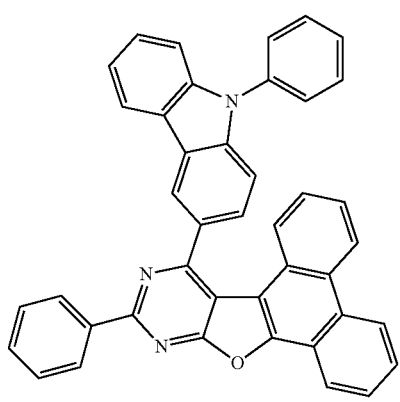

-continued
F-13
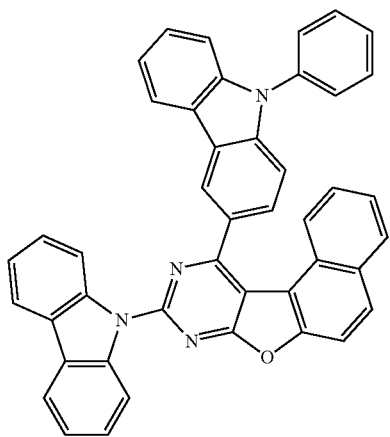
F-14
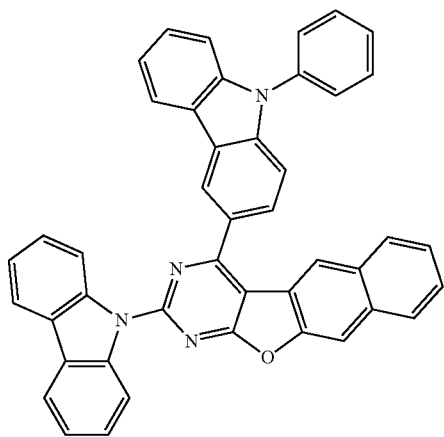
F-15
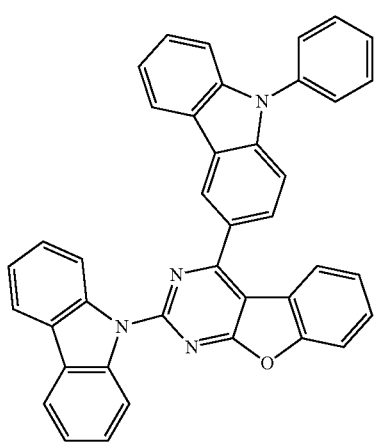
F-16
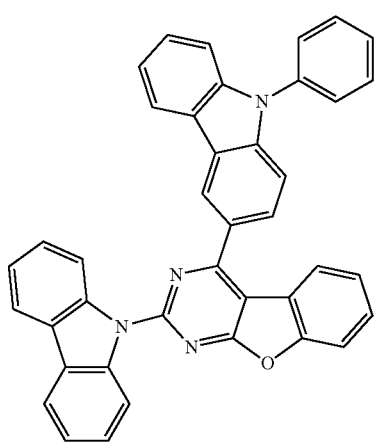
F-17
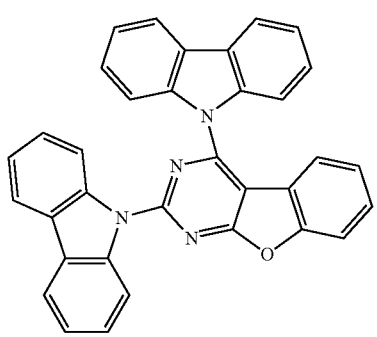
F-18
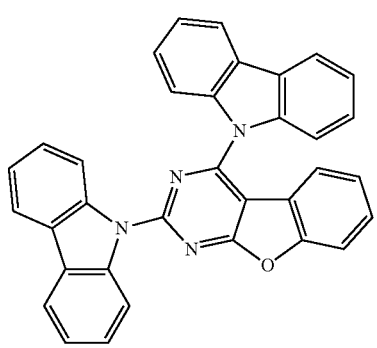
F-19
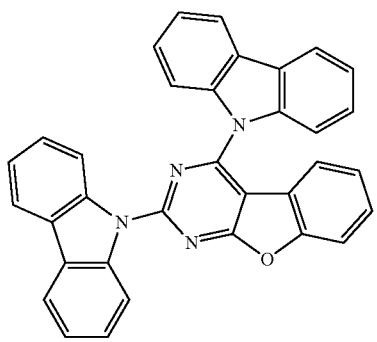
F-20
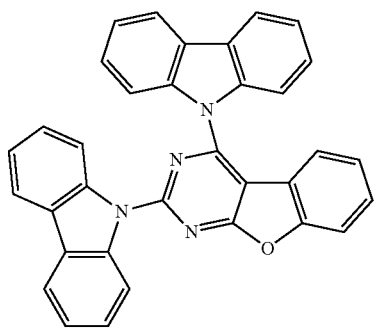

-continued
F-21
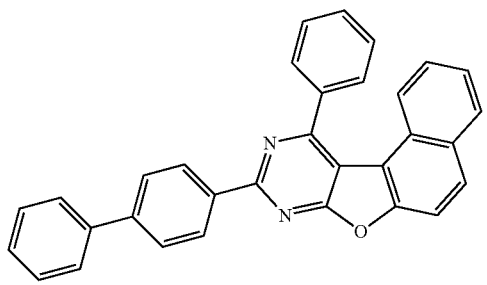
F-22
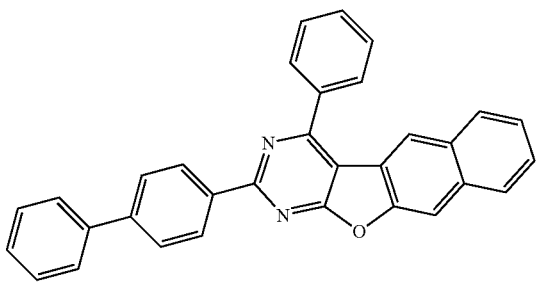
F-23
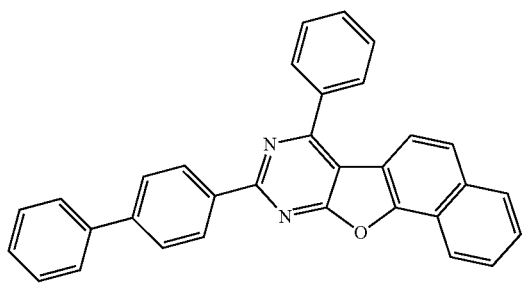
F-24
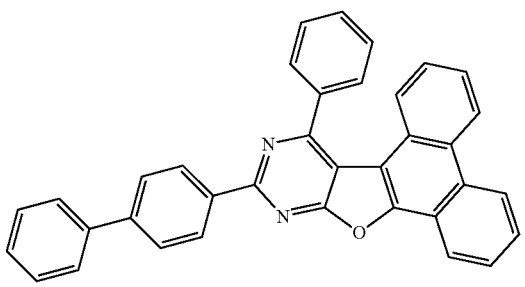
F-25
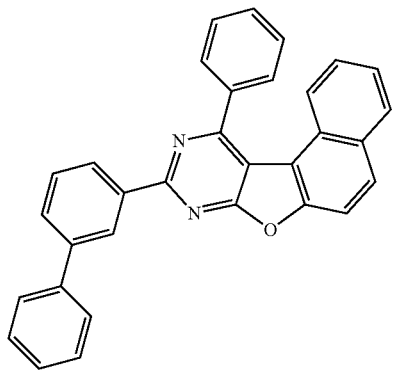
F-26
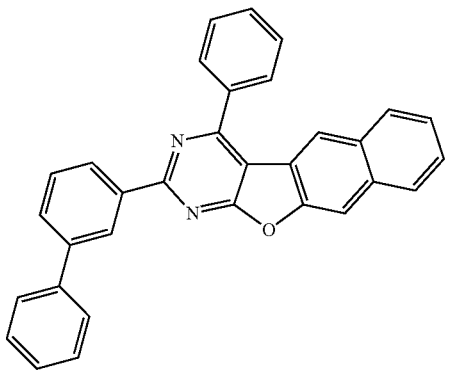
F-27
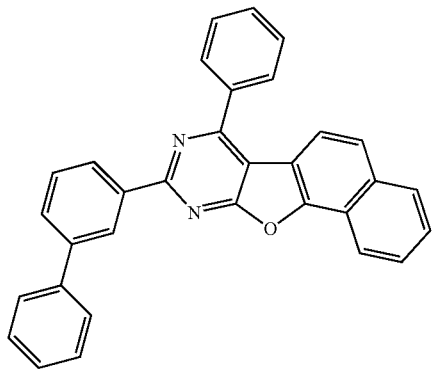
F-28
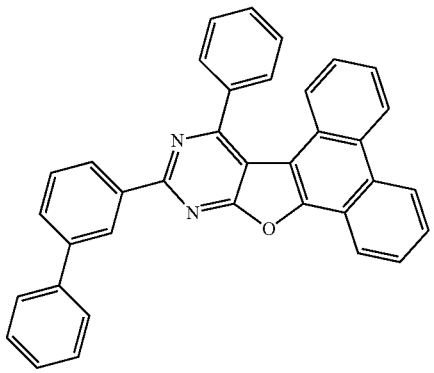

-continued
F-29
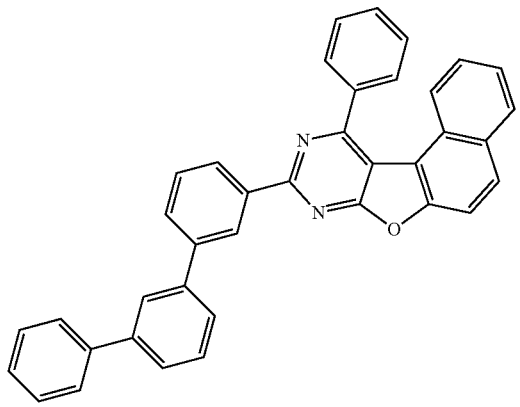
F-30
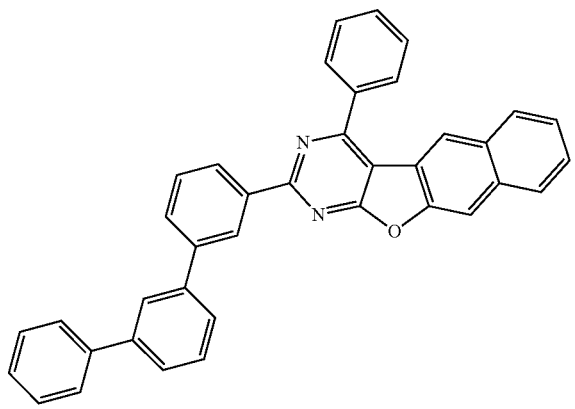
F-31
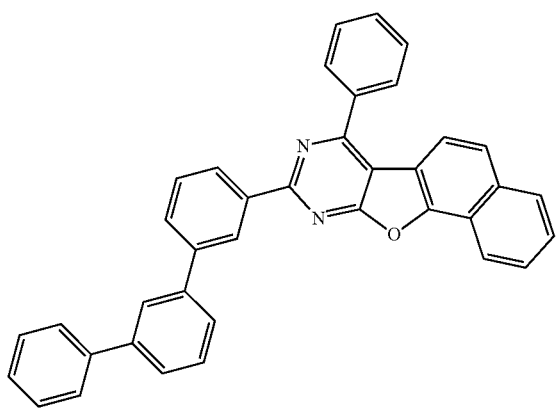
F-32
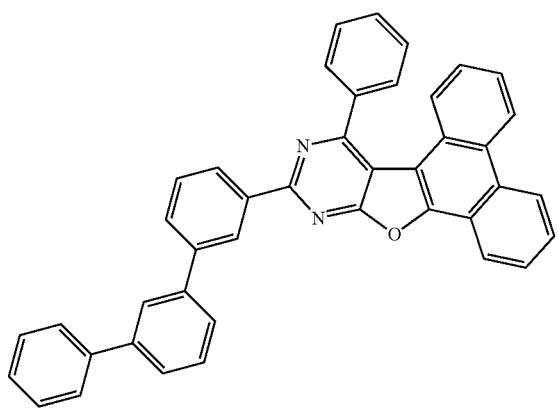
F-33
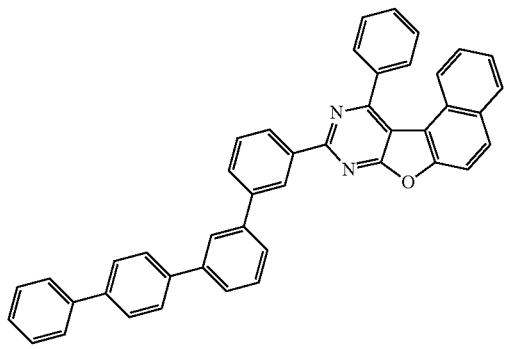
F-34
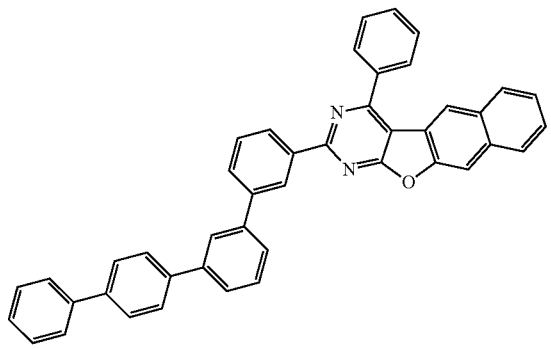
F-35
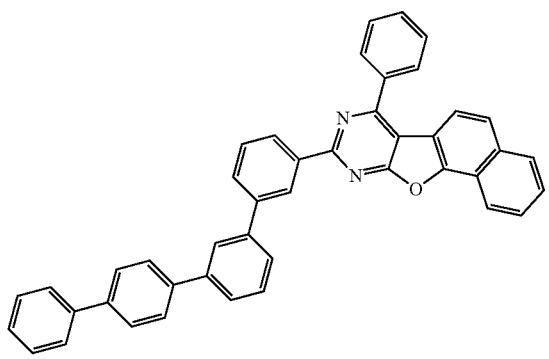
F-36
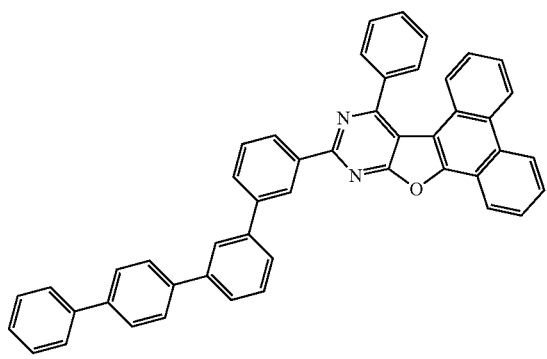

-continued
F-37
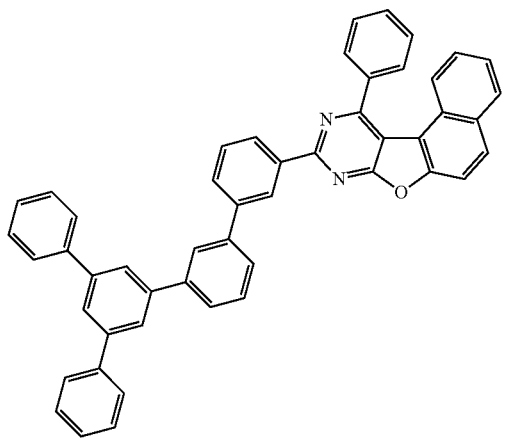
F-38
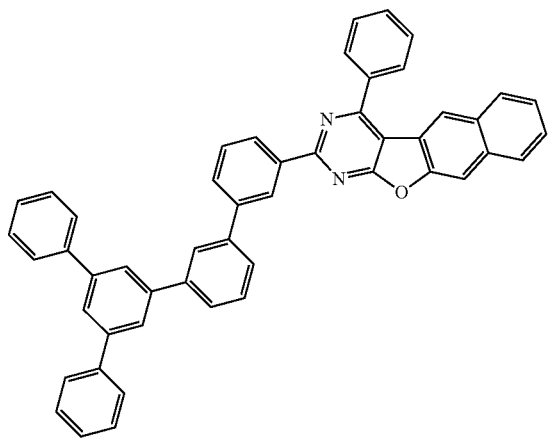
F-39
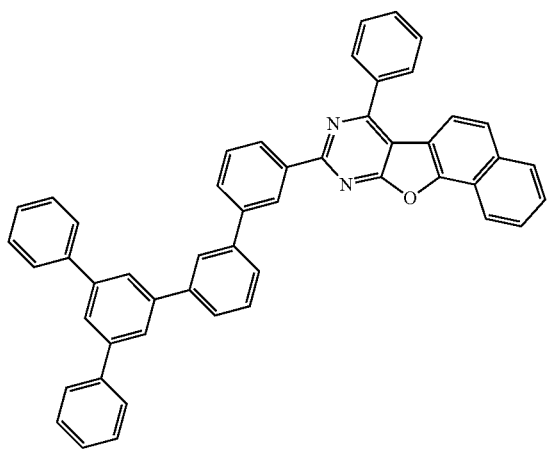
F-40
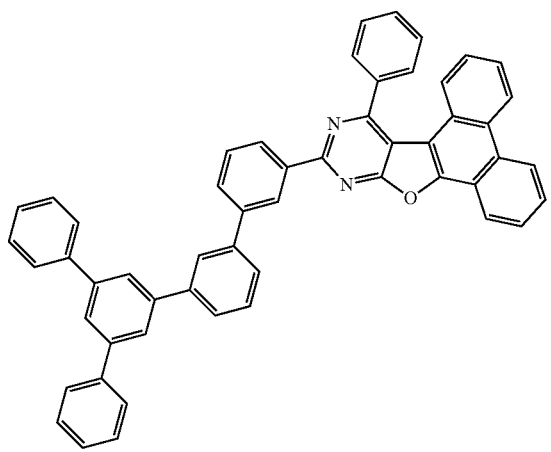
F-41
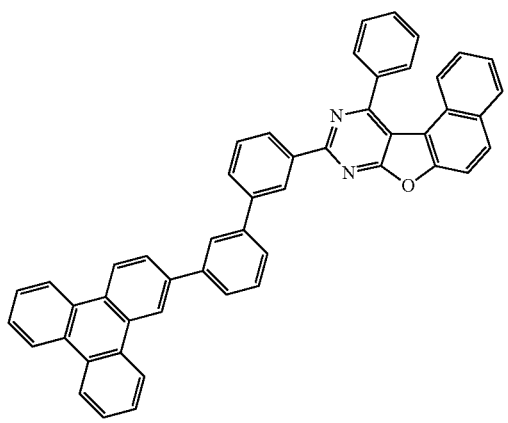
F-42
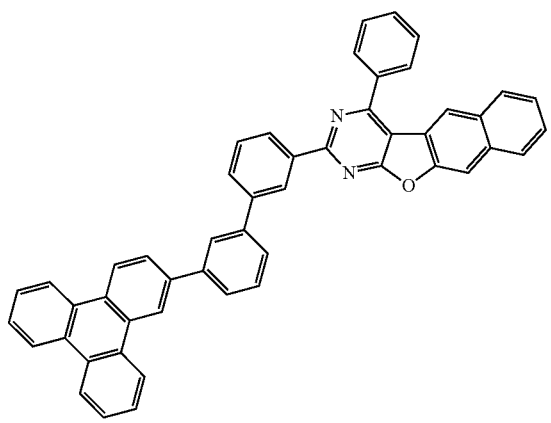

-continued
F-43
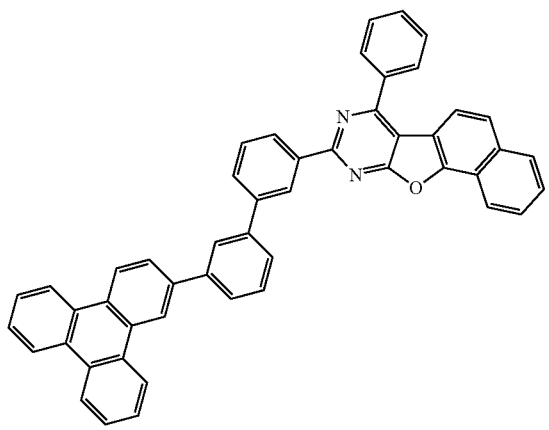
F-44
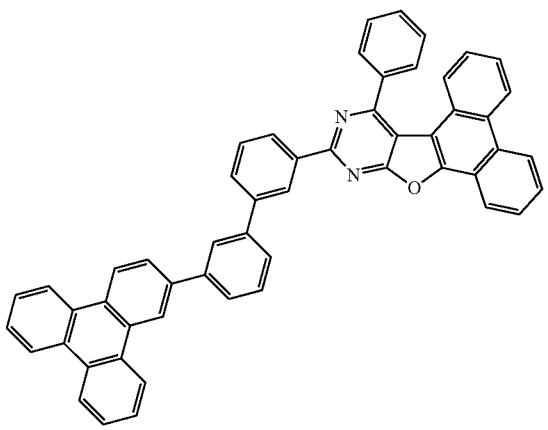
F-45
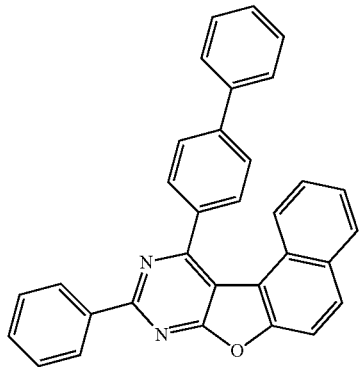
F-46
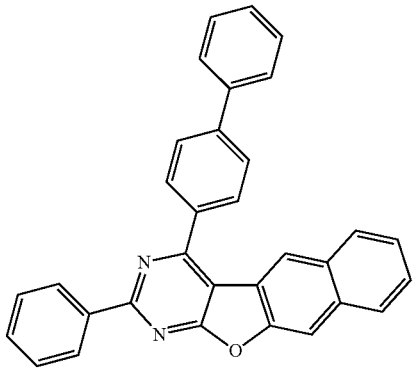
F-47
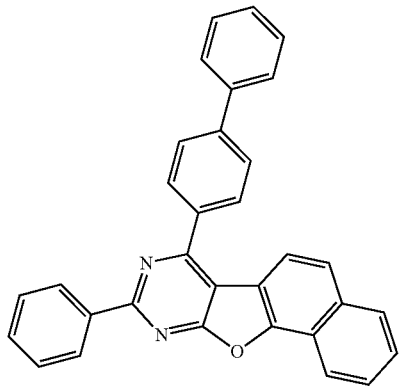
F-48
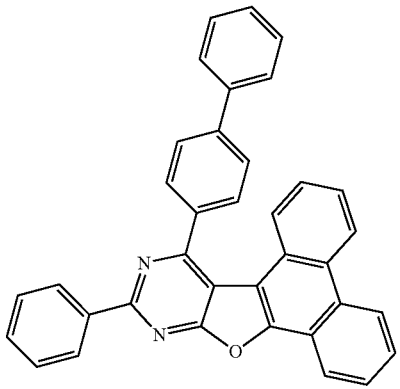
F-49
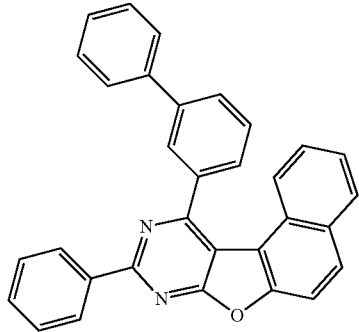
F-50
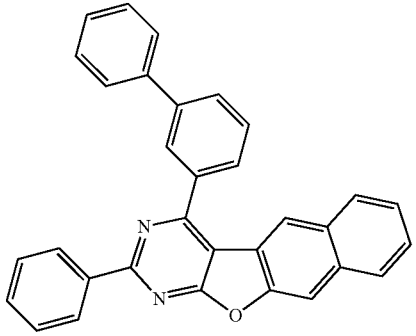

-continued
F-51
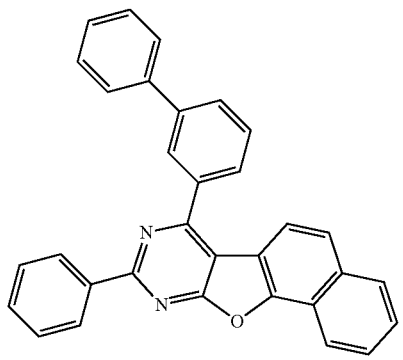
F-52
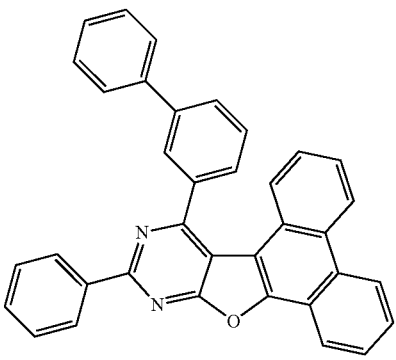
F-53
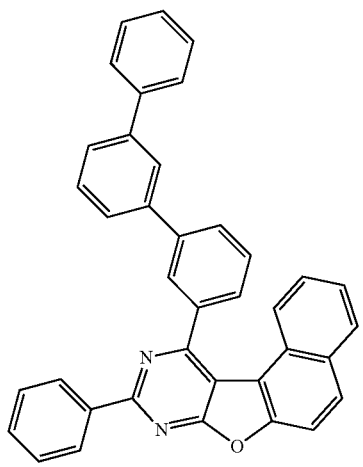
F-54
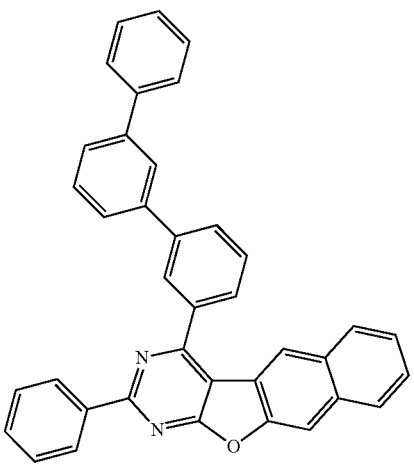
F-55
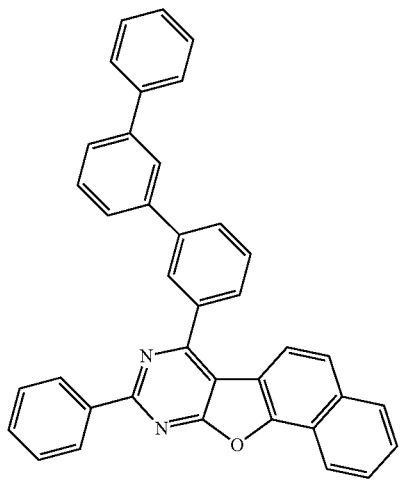
F-56
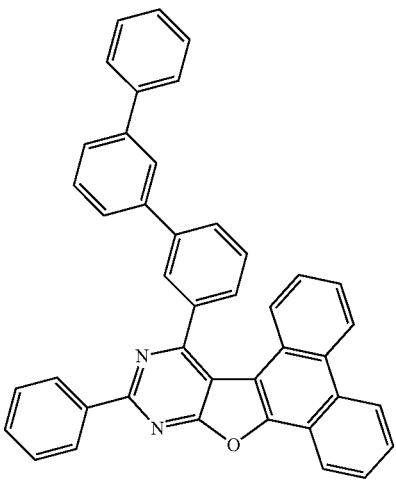

-continued
F-57
F-58
F-59
F-60
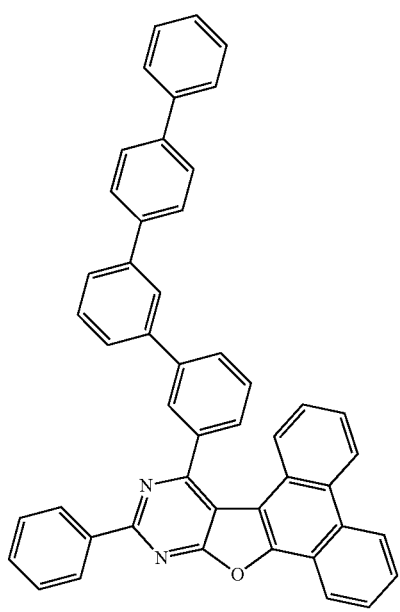

-continued
F-61
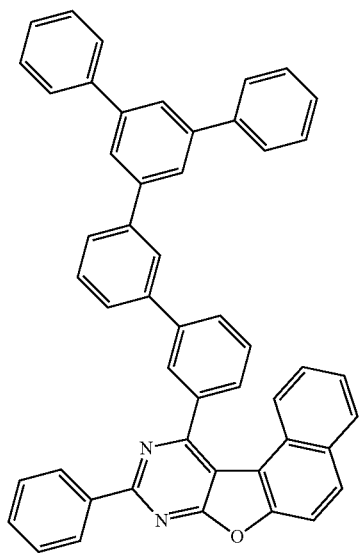
F-62
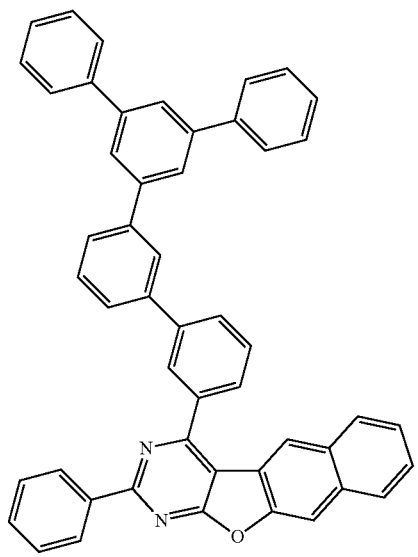
F-63
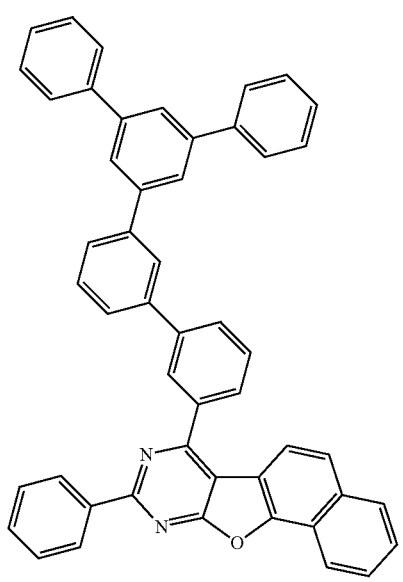
F-64
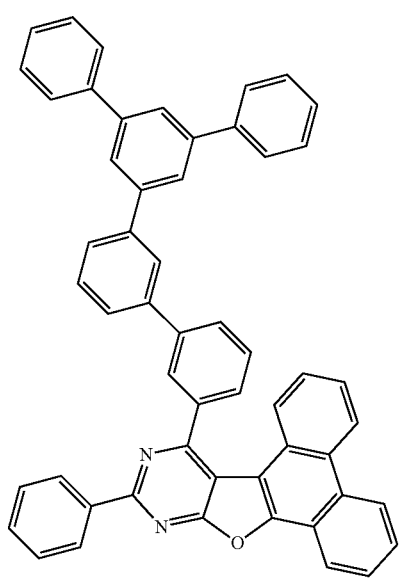

-continued
F-65
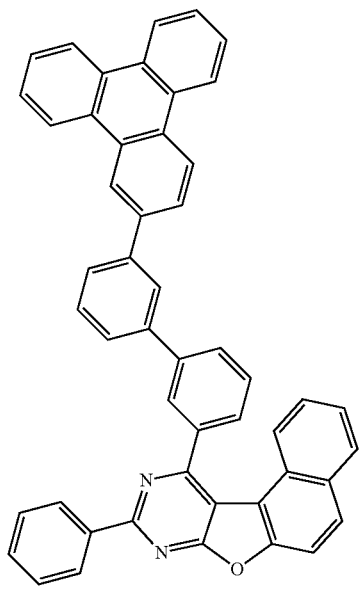
F-66
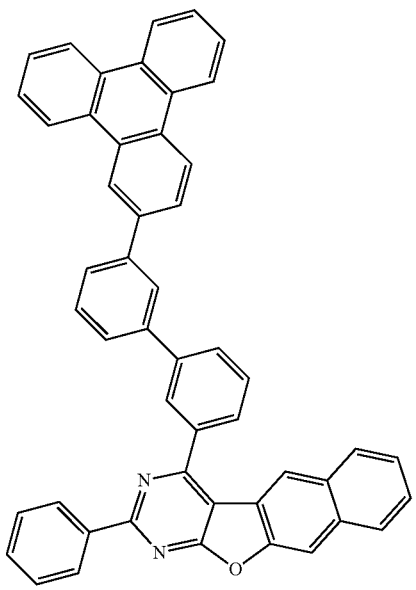
F-67
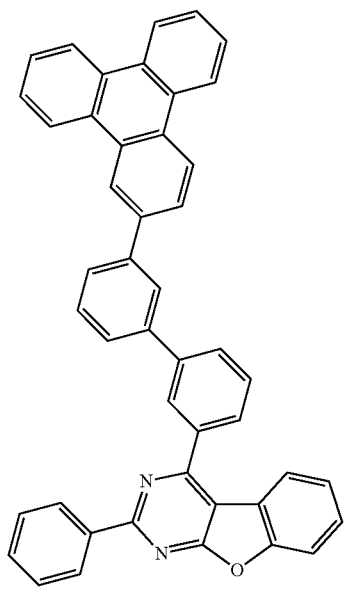
F-68
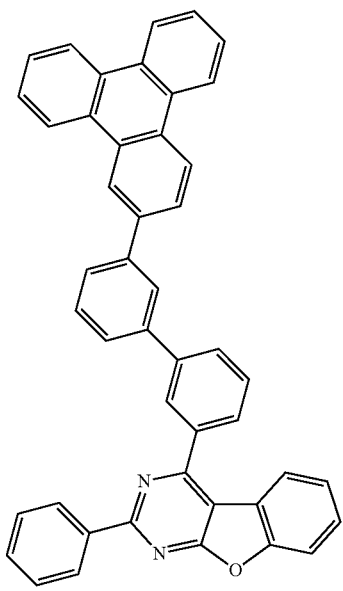
F-69
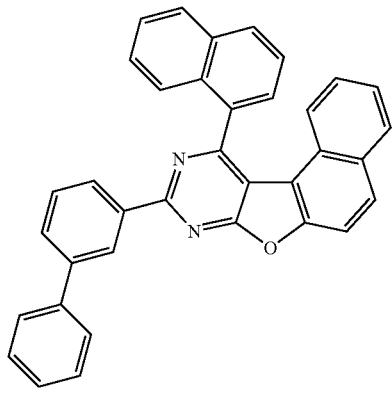
F-70
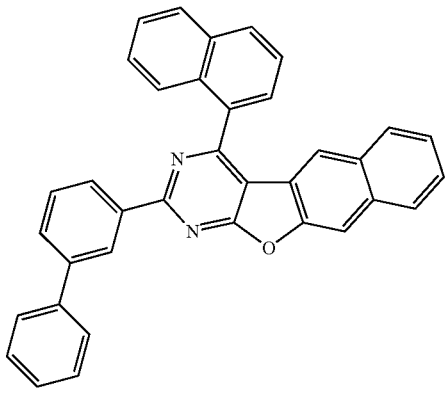

-continued
F-71
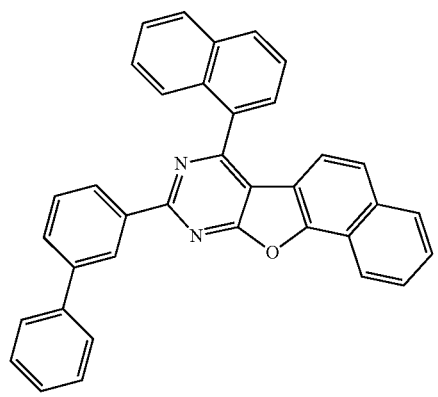
F-72
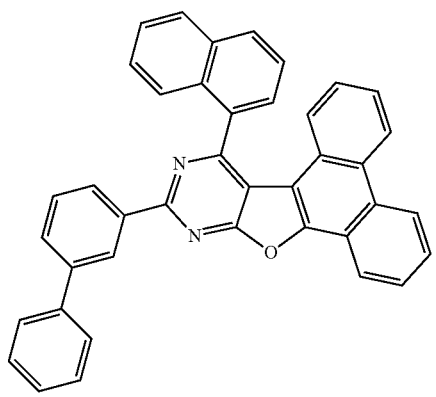
F-73
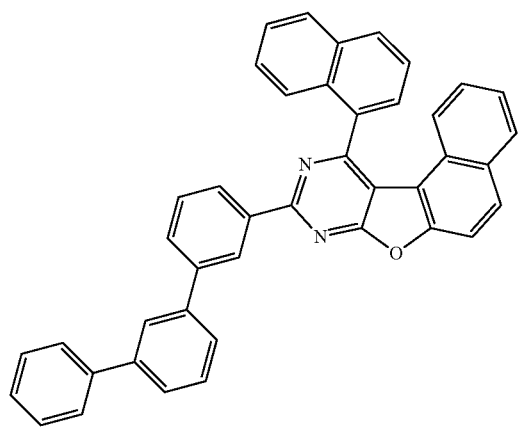
F-74
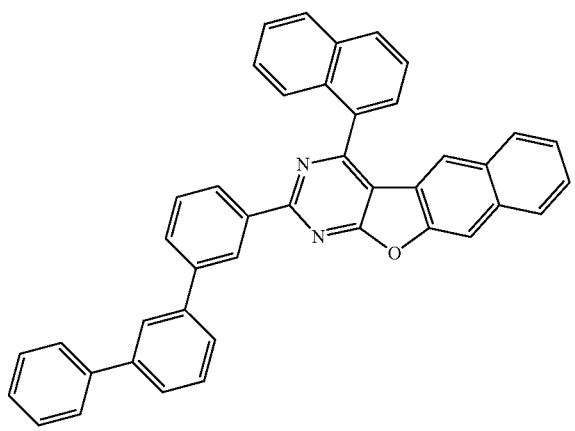
F-75
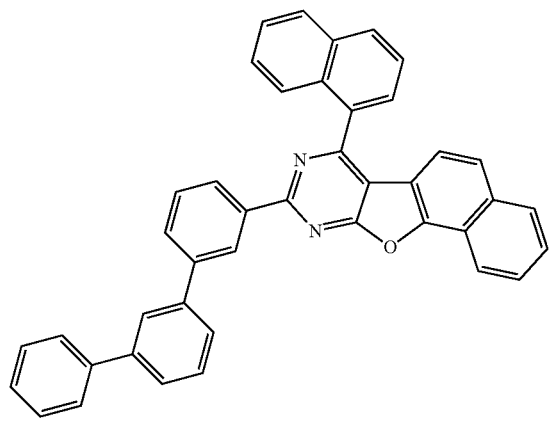
F-76
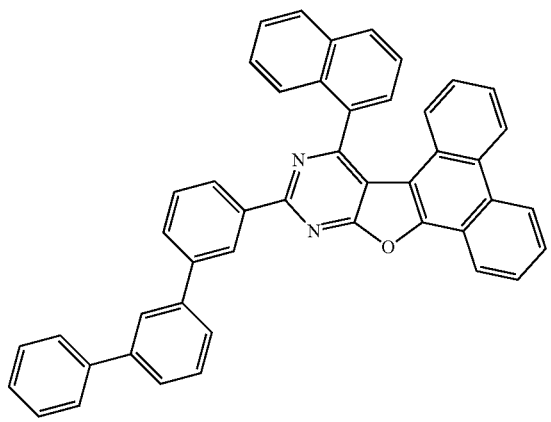

-continued
F-77
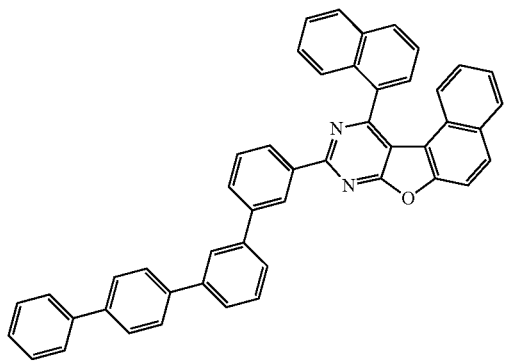
F-78
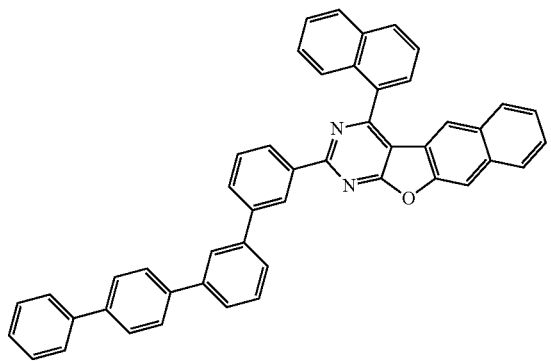
F-79
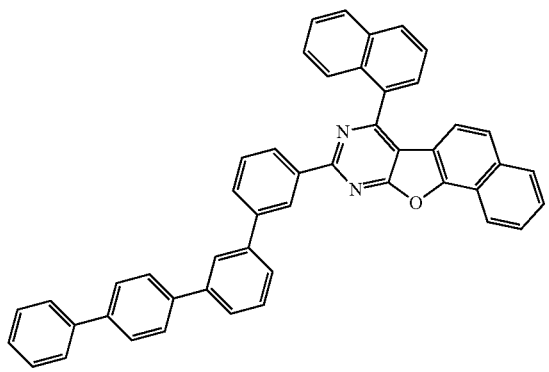
F-80
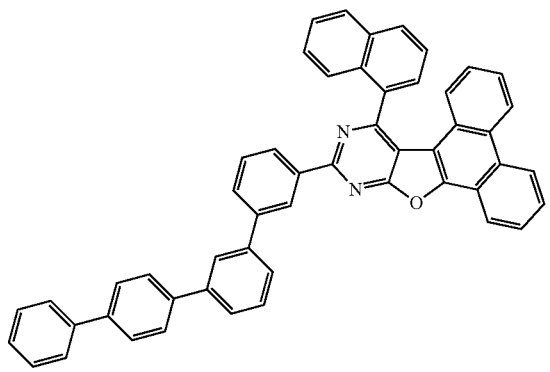
F-81
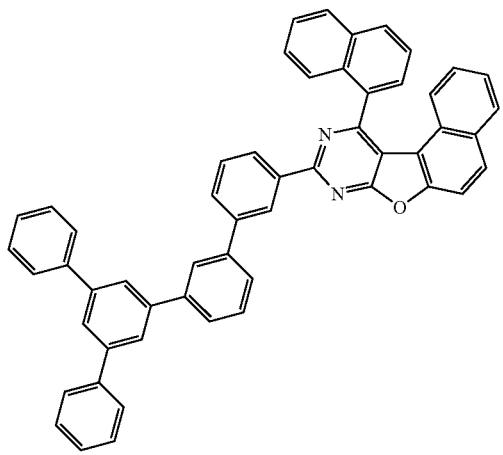
F-82
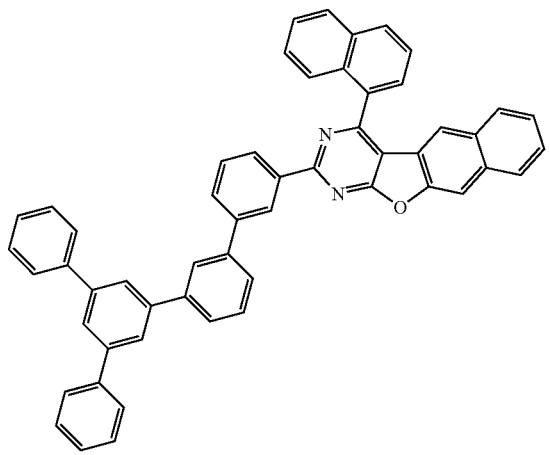

-continued
F-83
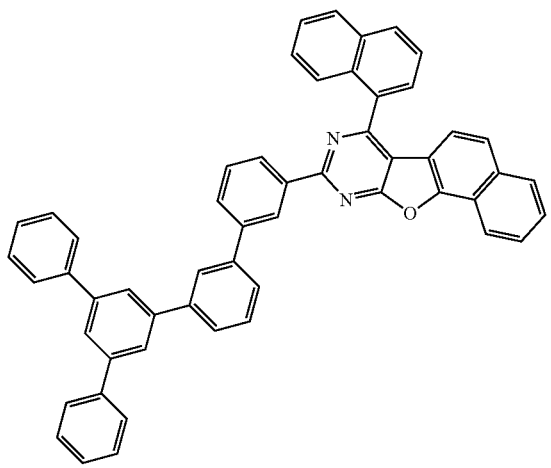
F-84
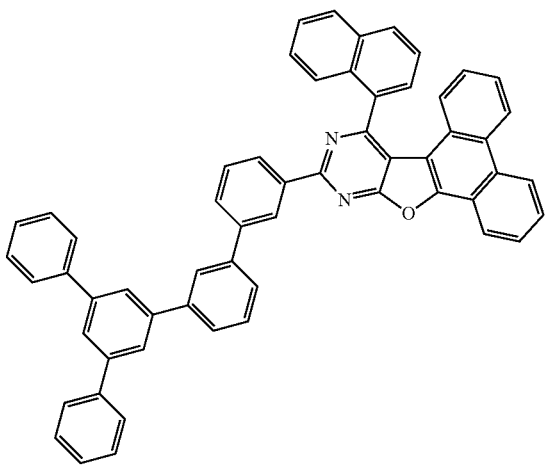
F-85
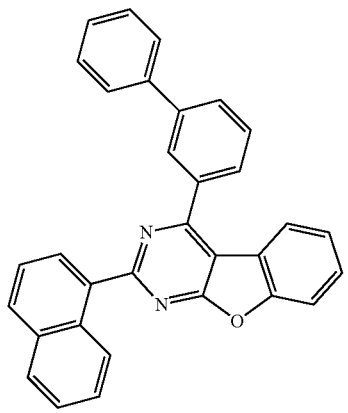
F-86
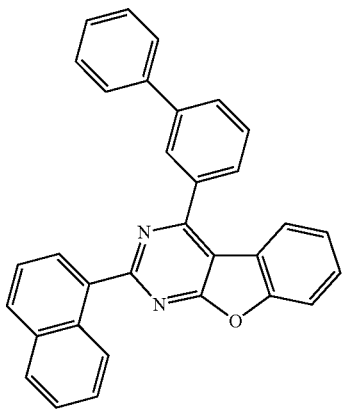
F-87
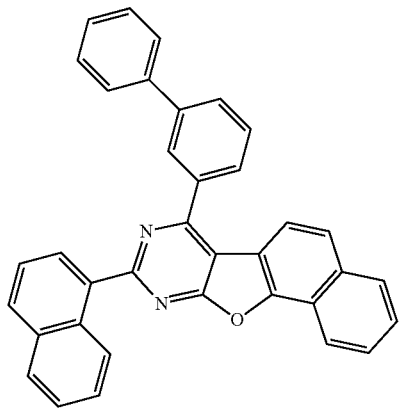
F-88
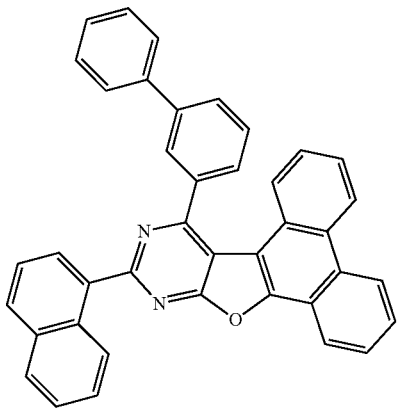

-continued
F-89
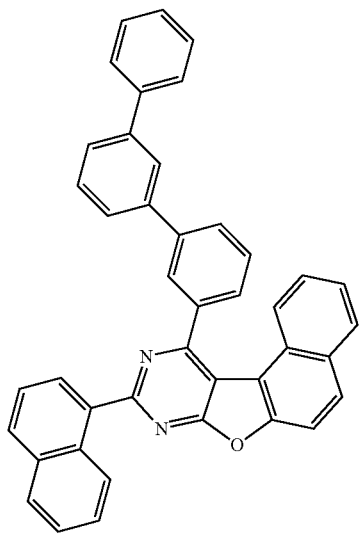
F-90
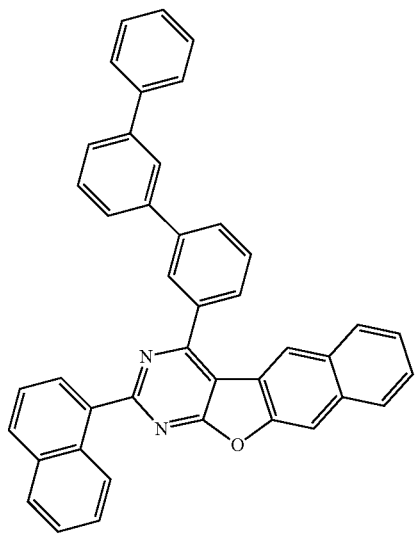
F-91
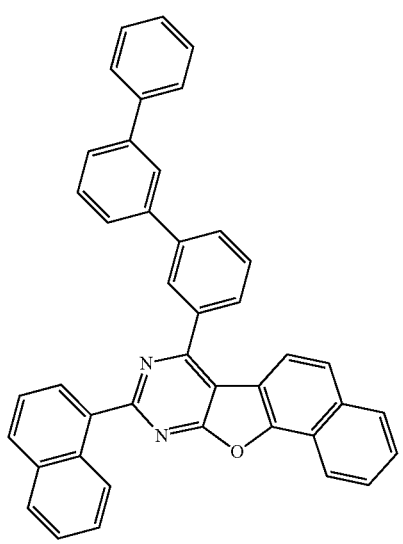
F-92
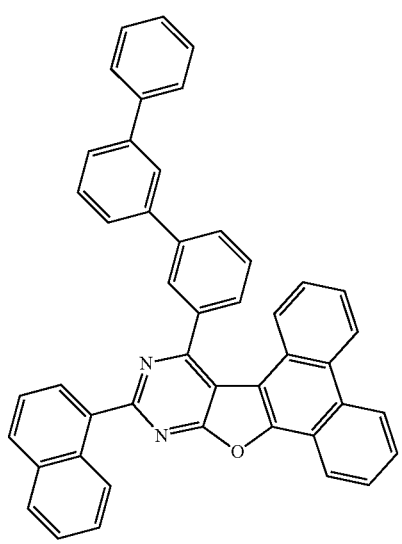

-continued
F-93
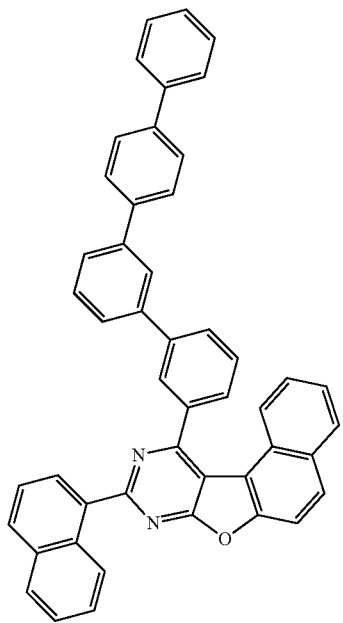
F-94
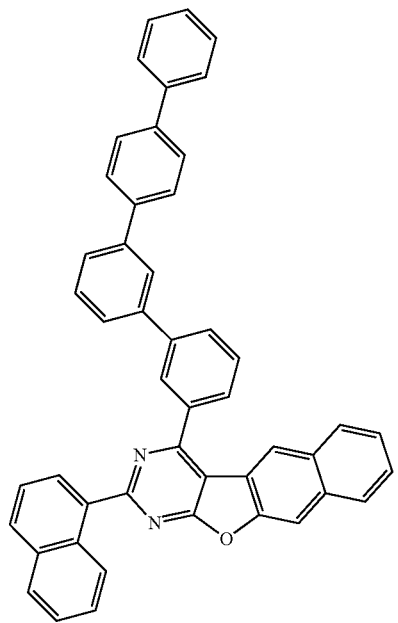
F-95
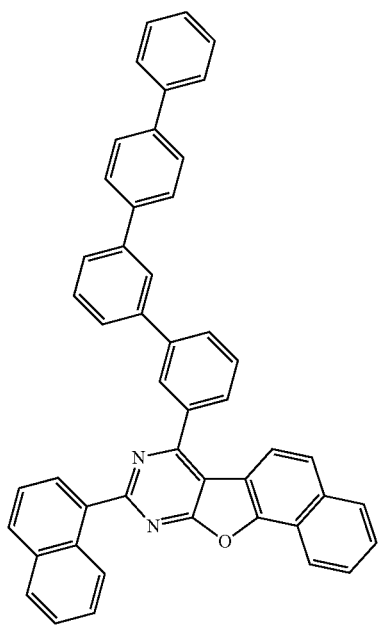
F-96
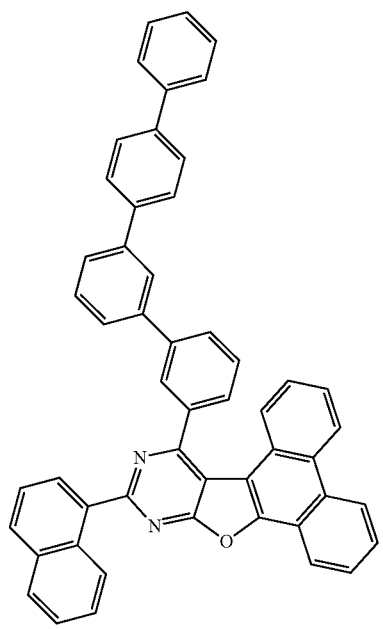

-continued
F-97
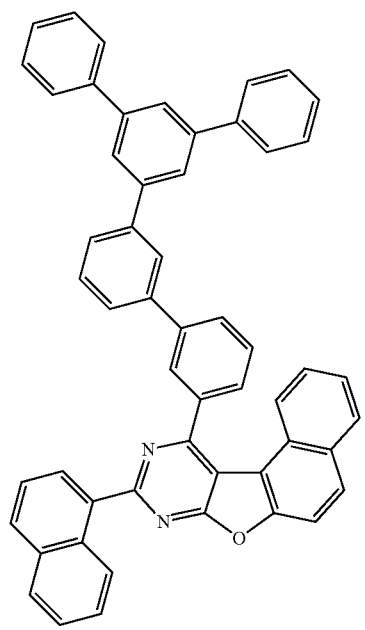
F-98
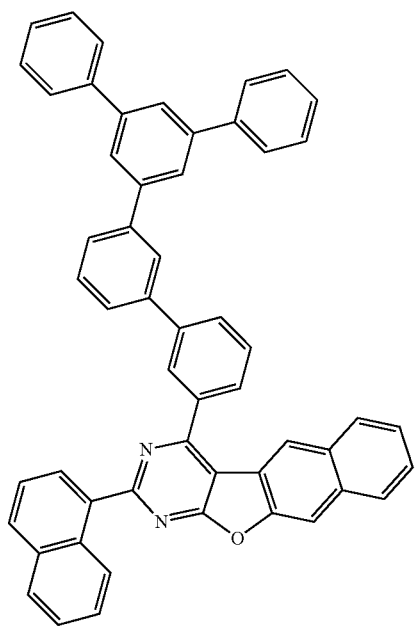
F-99
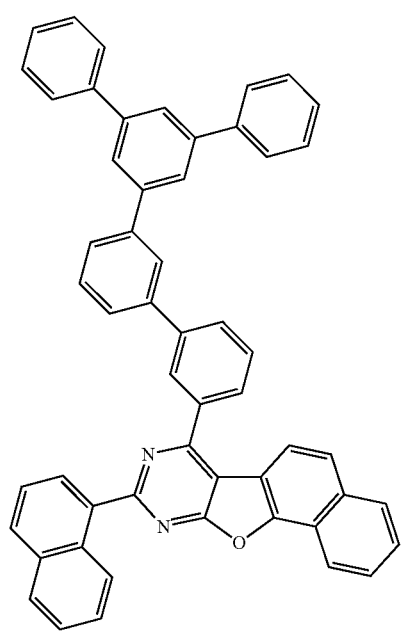
F-100
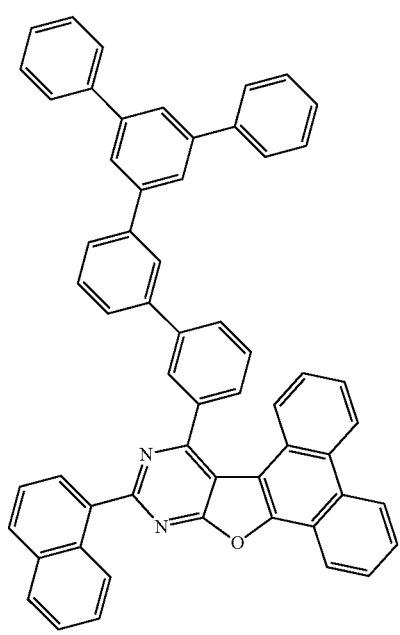

-continued
F-101
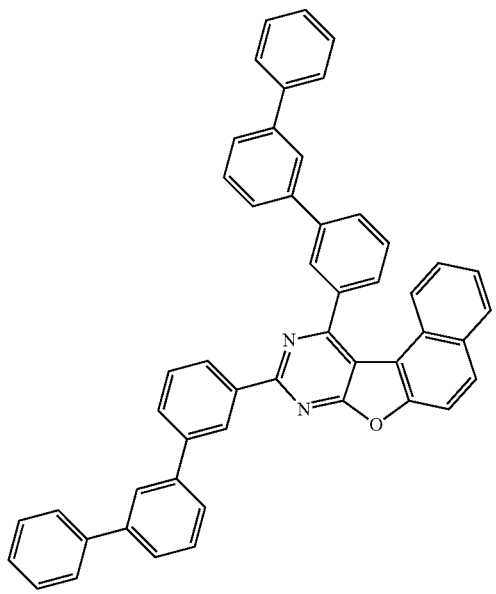
F-102
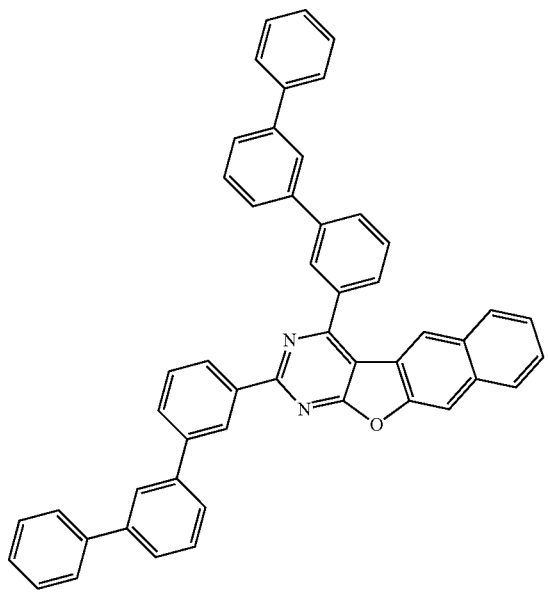
F-103
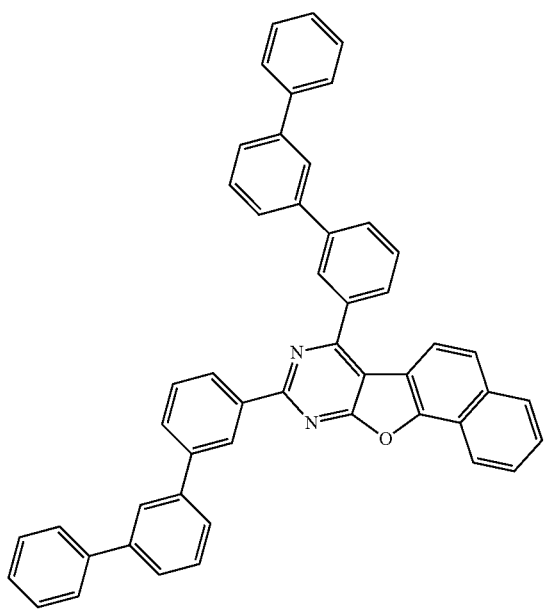
F-104
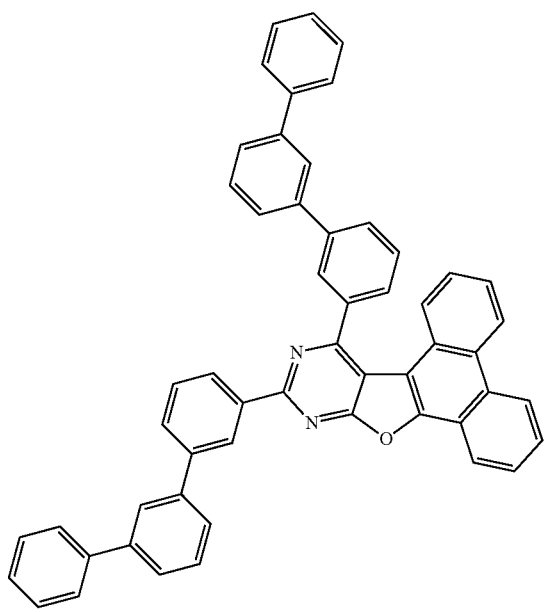

-continued
F-105
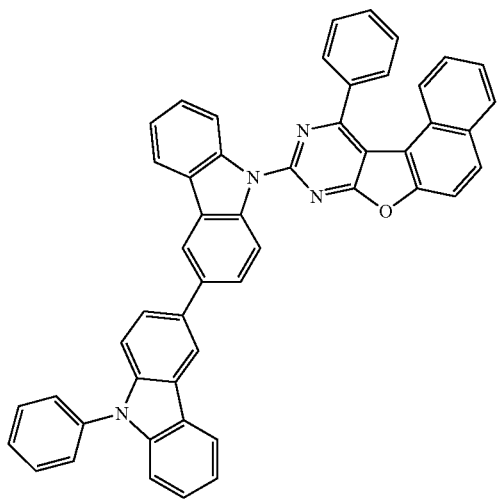
F-106
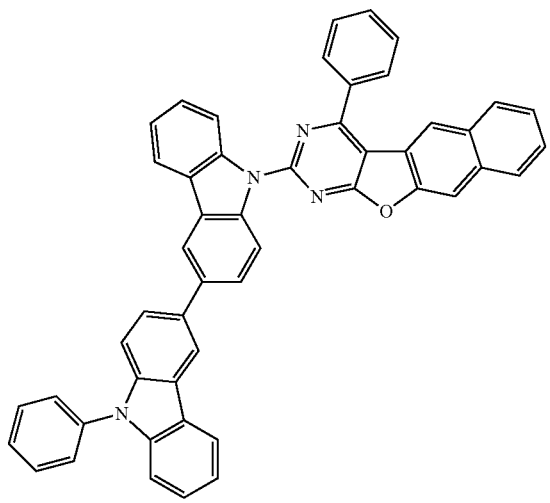
F-107
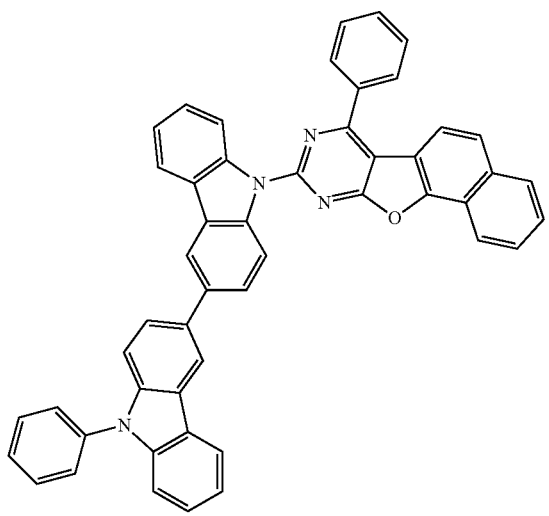
F-108
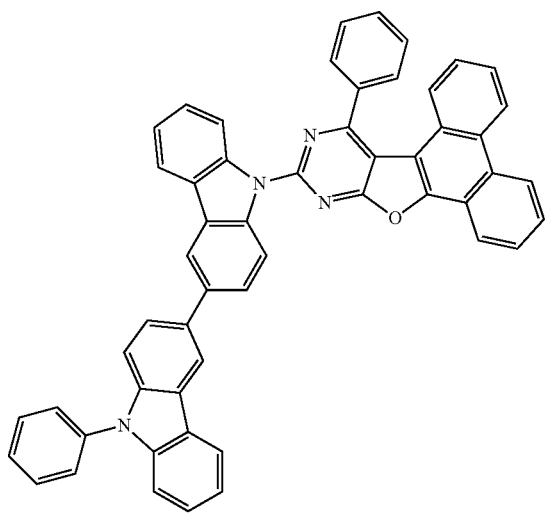
G-1
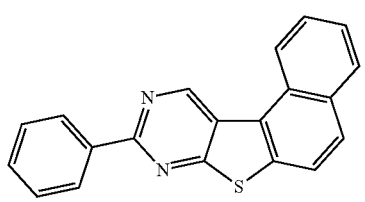
G-2
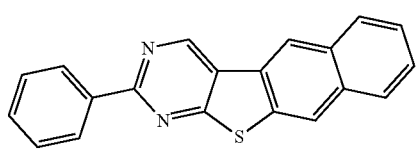
G-3
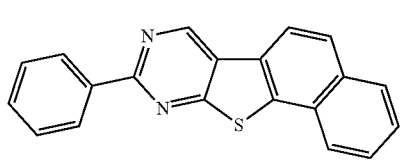
G-4
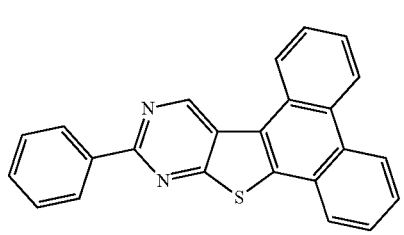

-continued
G-5
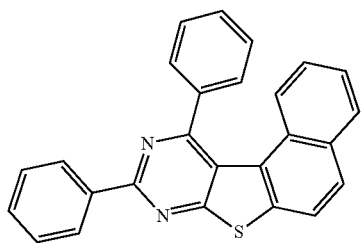
G-6
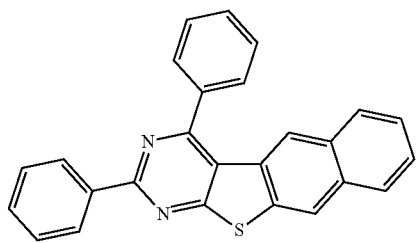
G-7
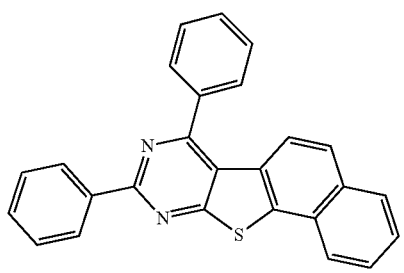
G-8
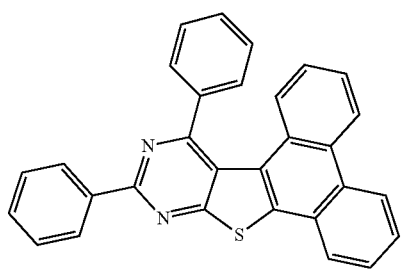
G-9
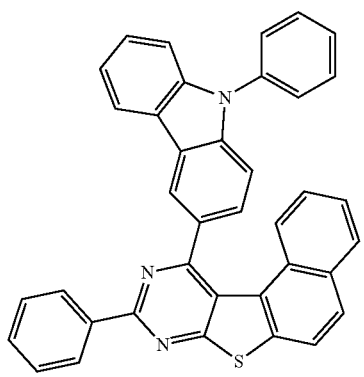
G-10
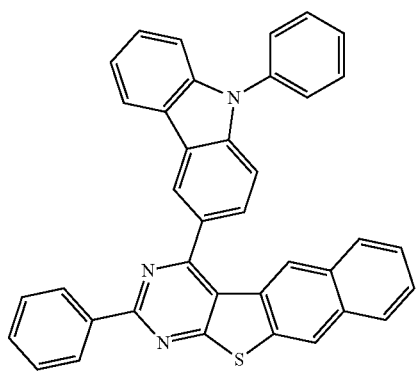
G-11
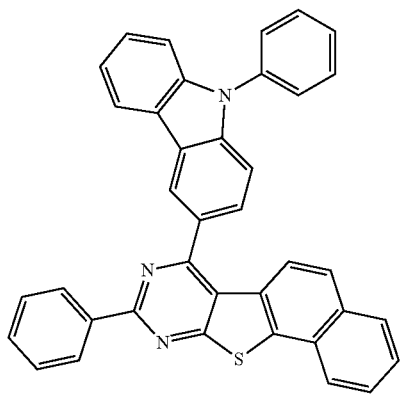
G-12
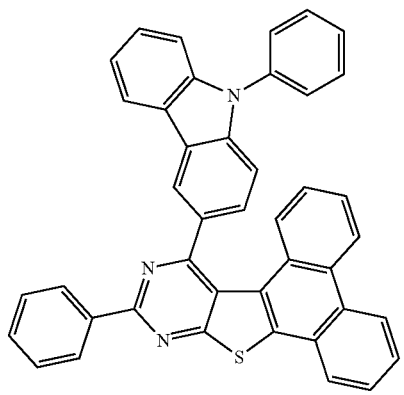

-continued
G-13
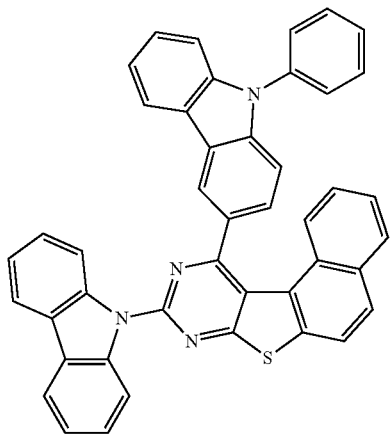
G-14
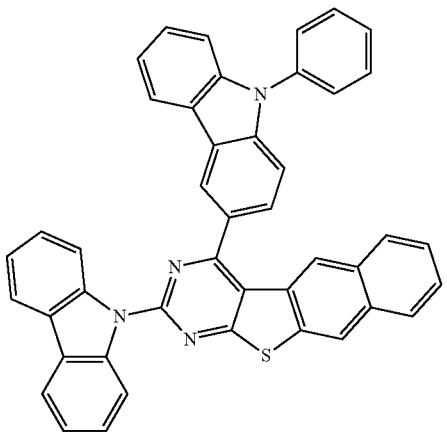
G-15
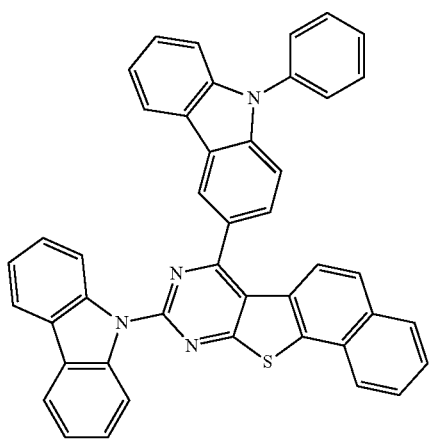
G-16
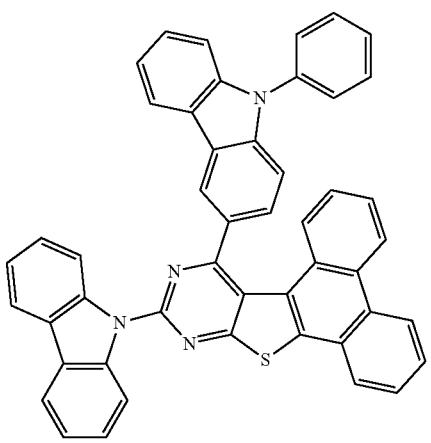
G-17
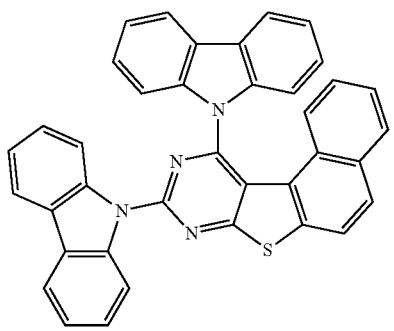
G-18
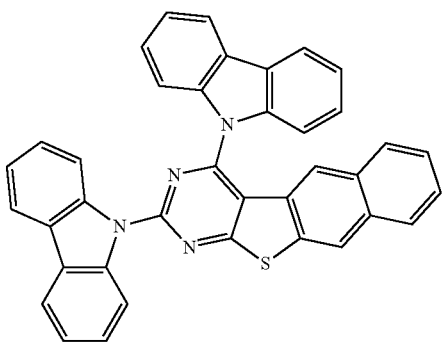
G-19
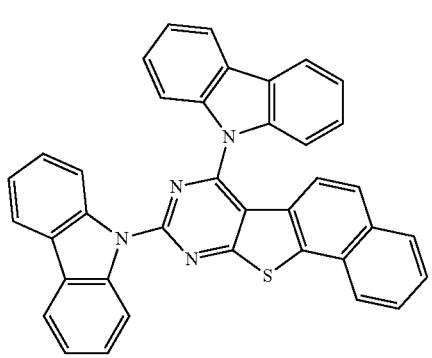
G-20
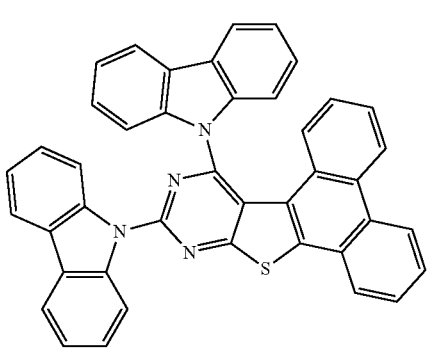

-continued
G-21
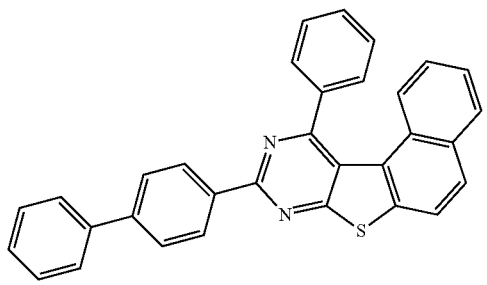
G-22
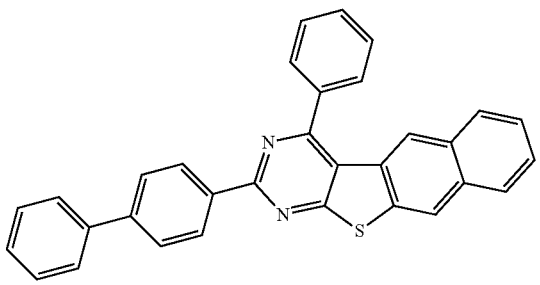
G-23
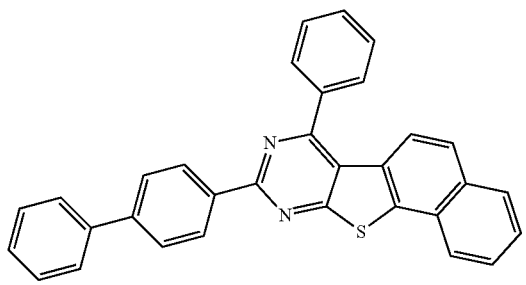
G-24
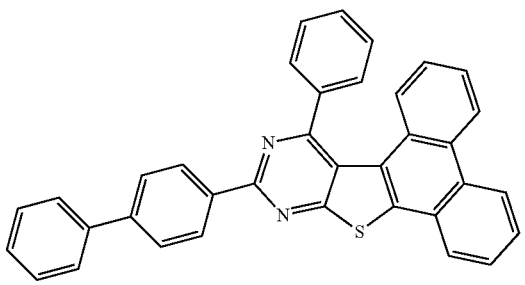
G-25
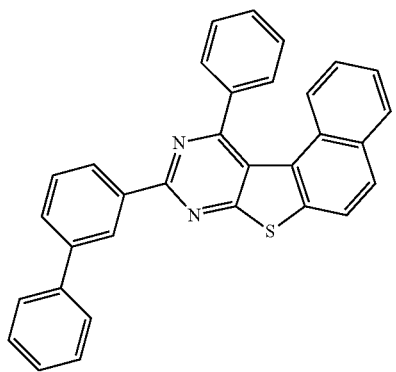
G-26
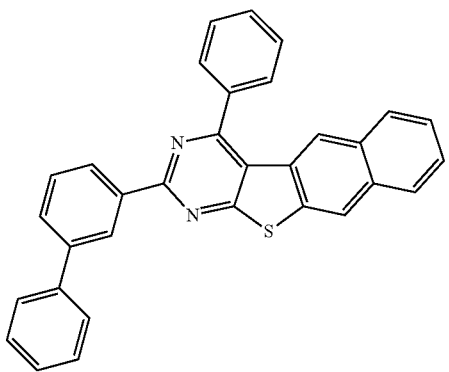
G-27
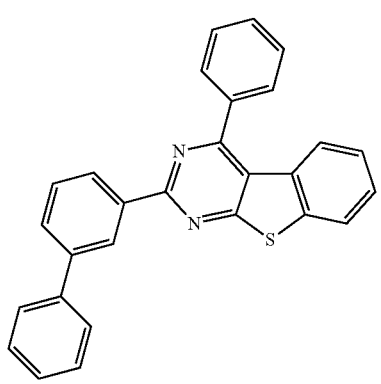
G-28
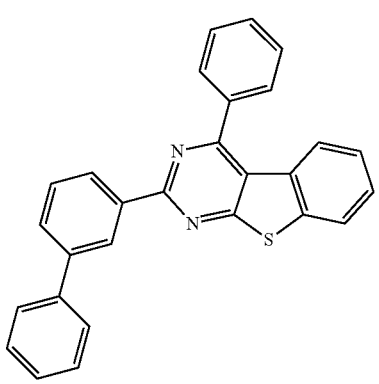

-continued
G-29
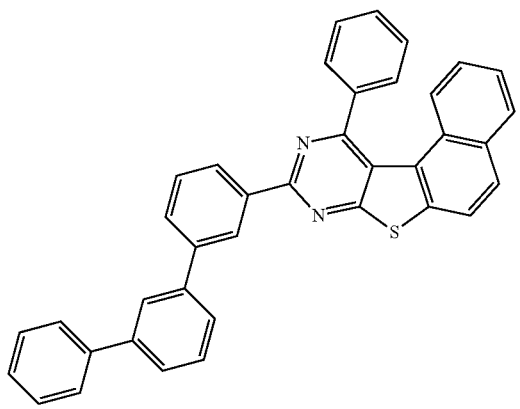
G-30
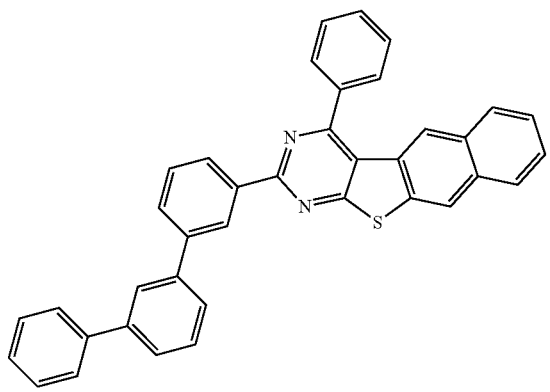
G-31
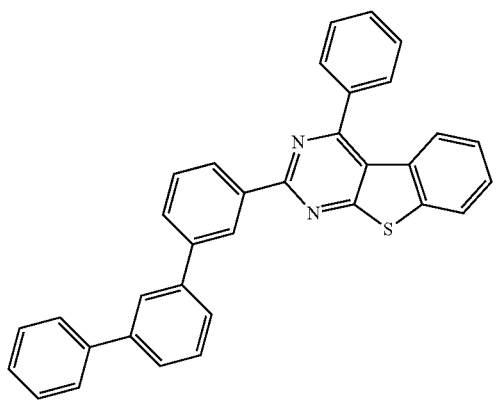
G-32
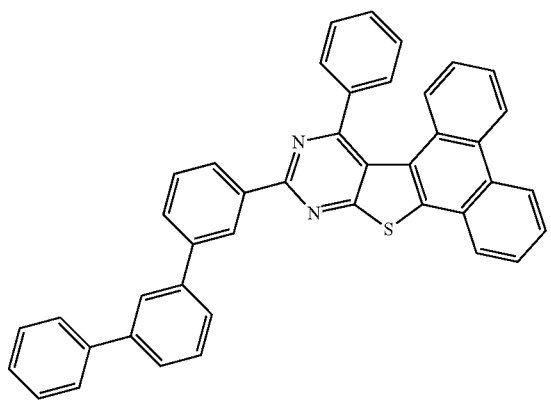
G-33
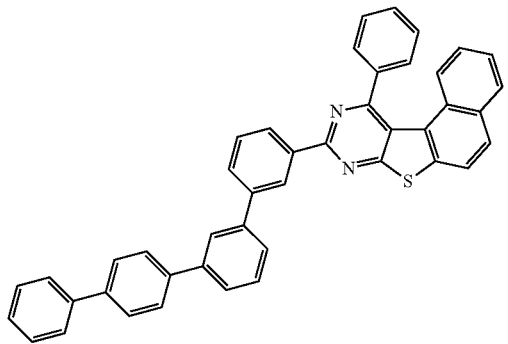
G-34
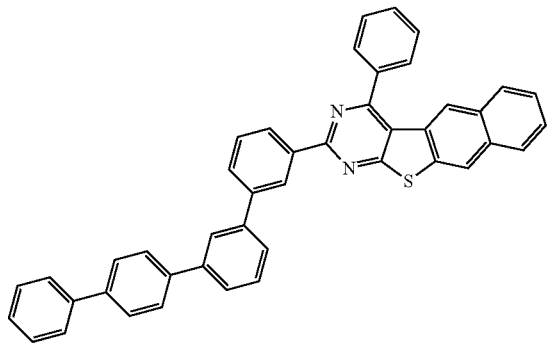
G-35
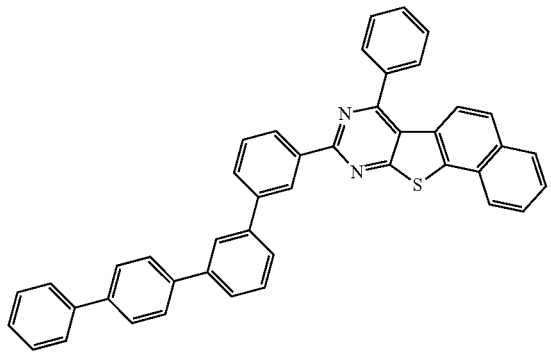
G-36
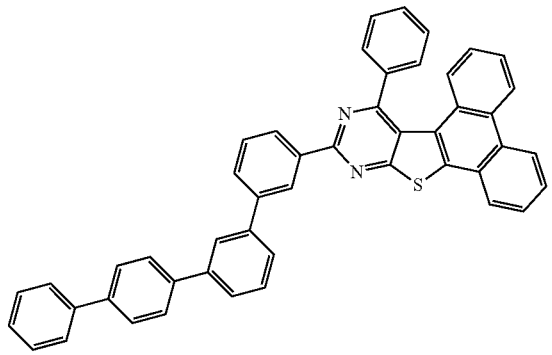

-continued
G-37
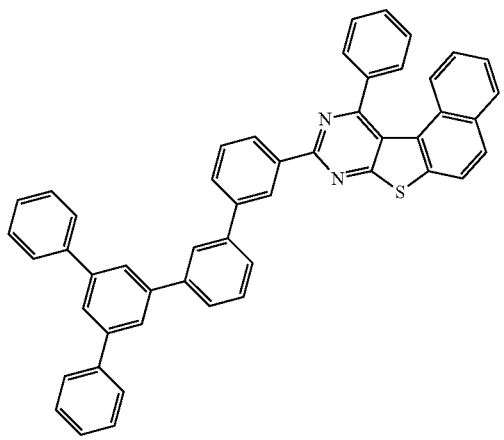
G-38
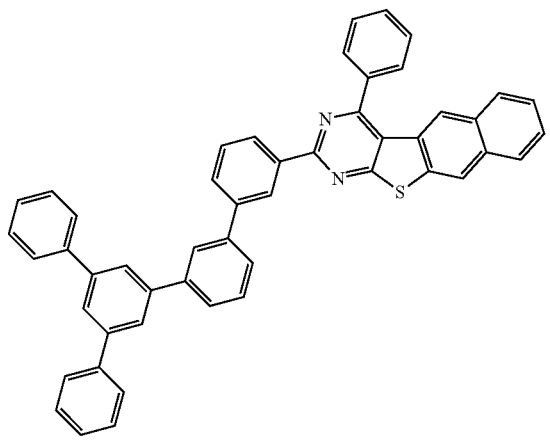
G-39
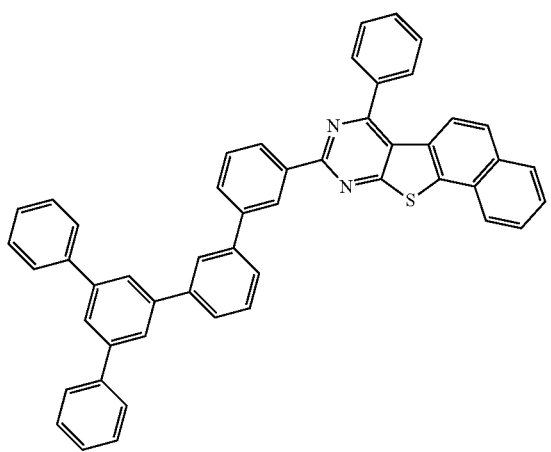
G-40
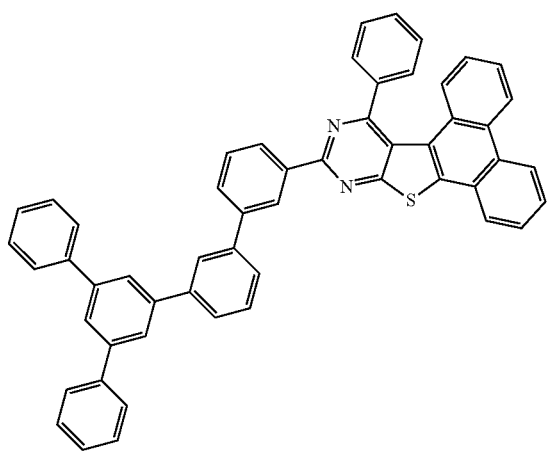
G-41
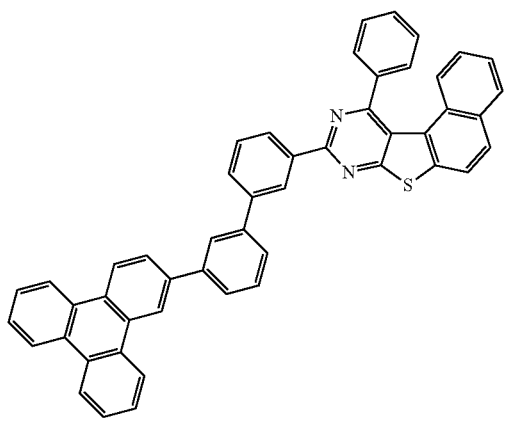
G-42
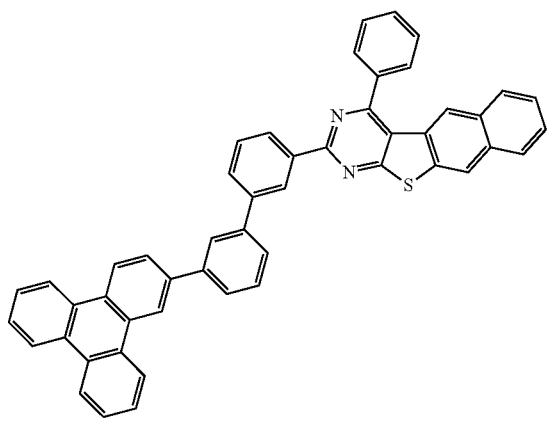

-continued
G-43
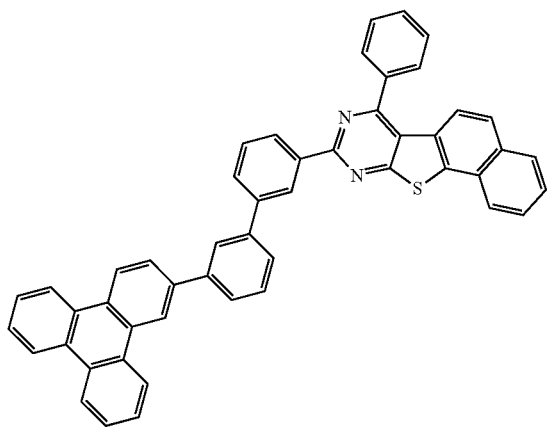
G-44
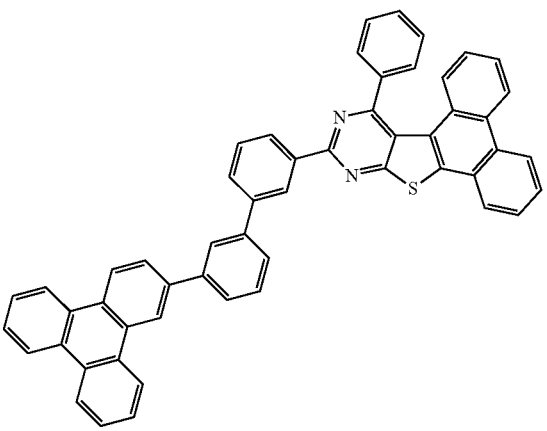
G-45
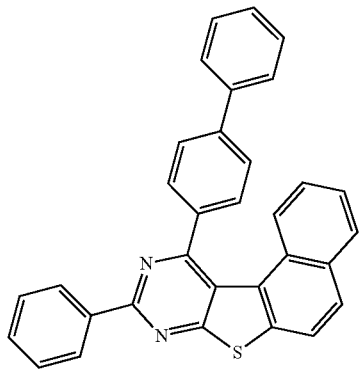
G-46
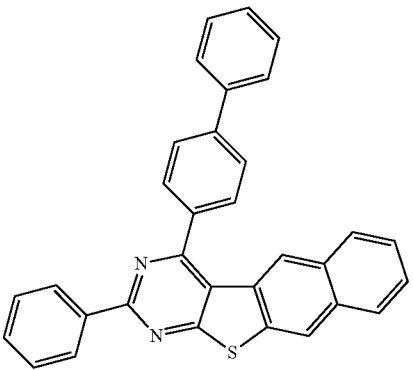
G-47
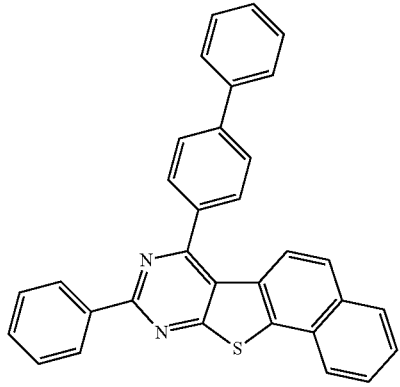
G-48
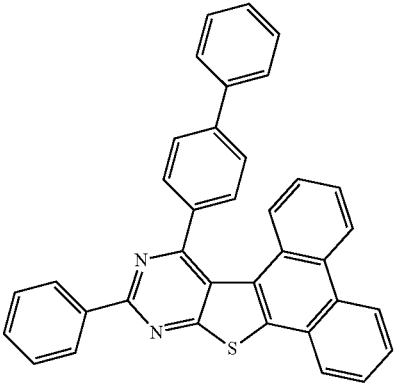
G-49
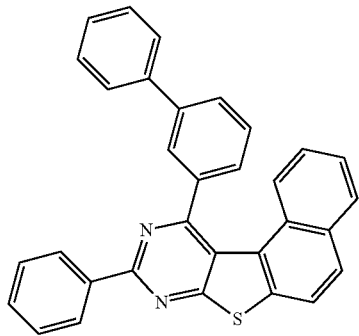
G-50
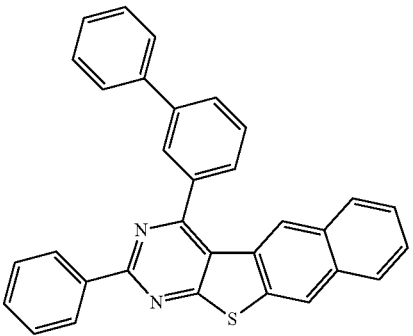

-continued
G-51
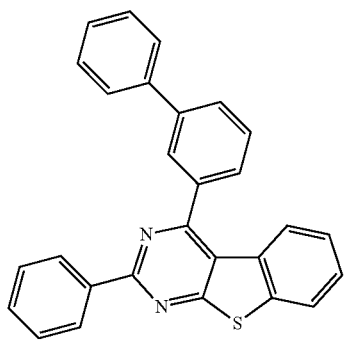
G-52
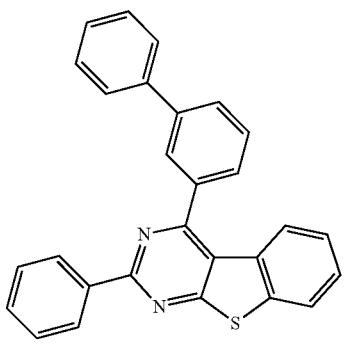
G-53
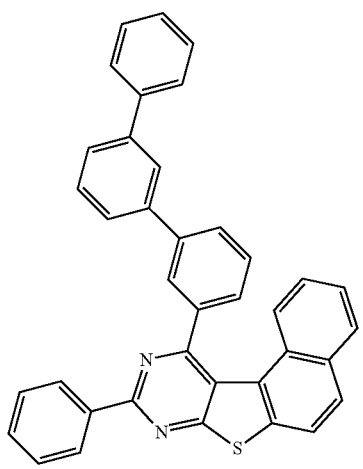
G-54
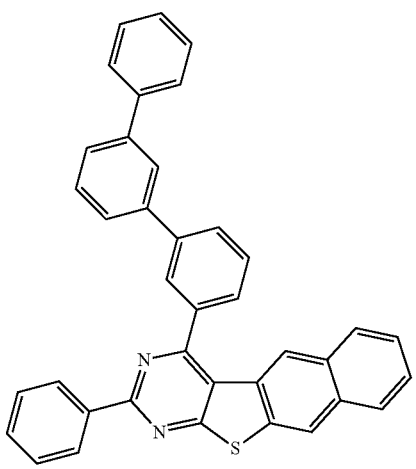
G-55
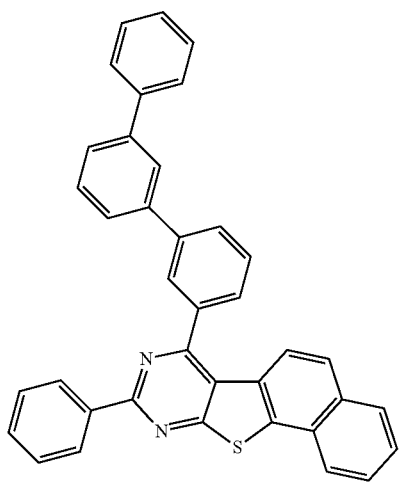
G-56
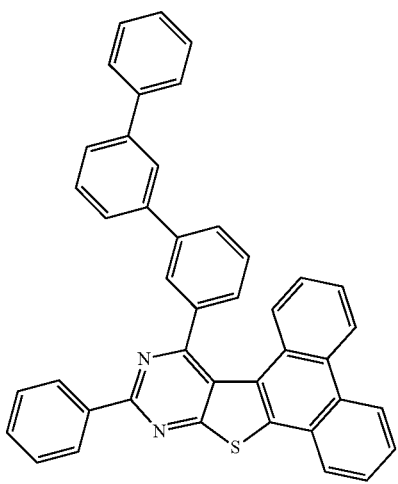

-continued
G-57
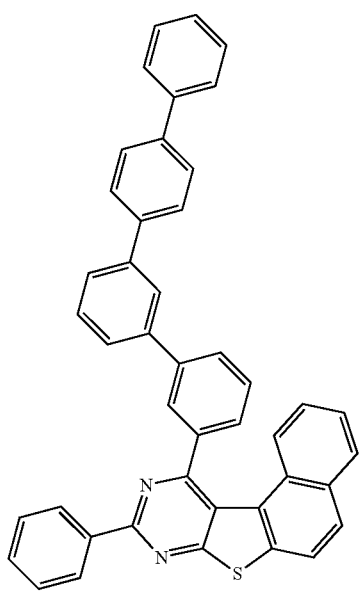
G-58
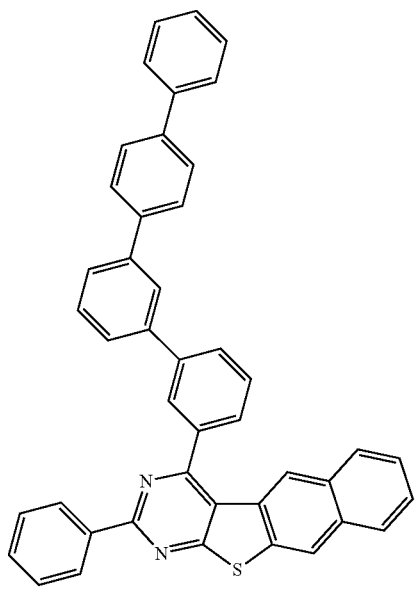
G-59
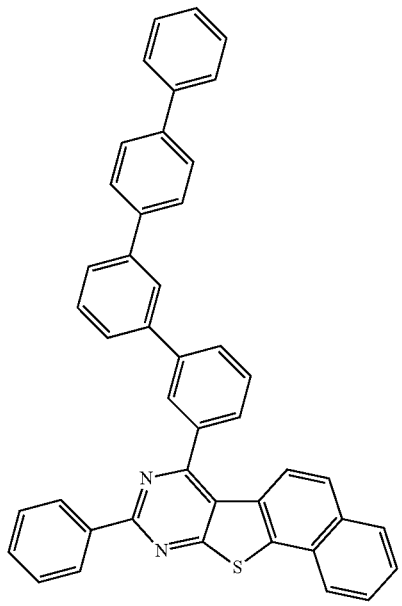
G-60
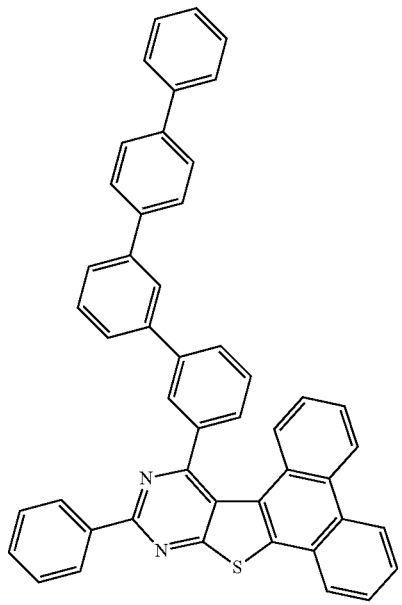

-continued
G-61
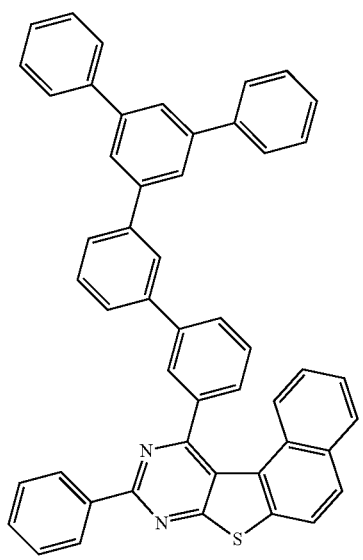
G-62
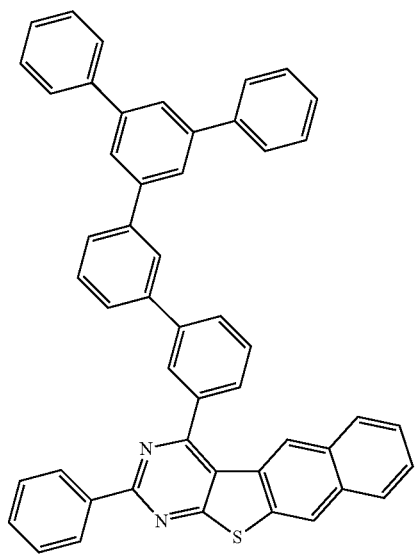
G-63
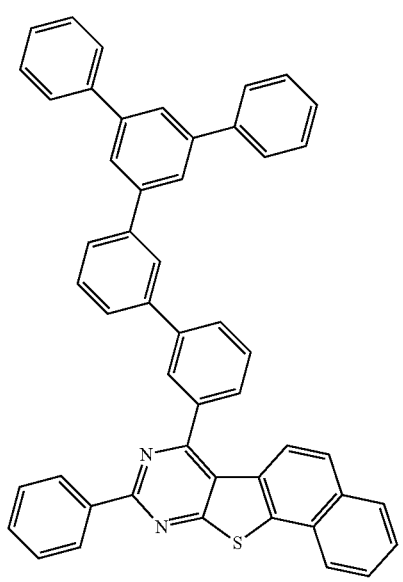
G-64
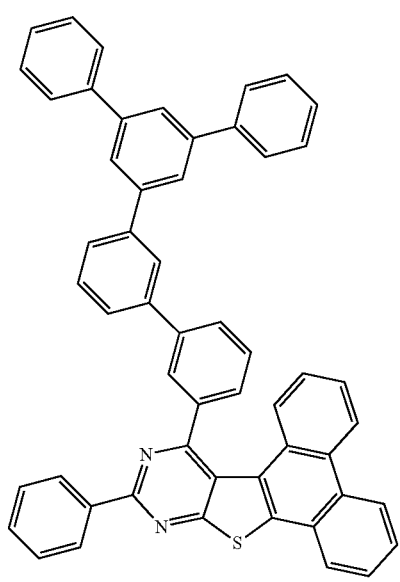

-continued
G-65
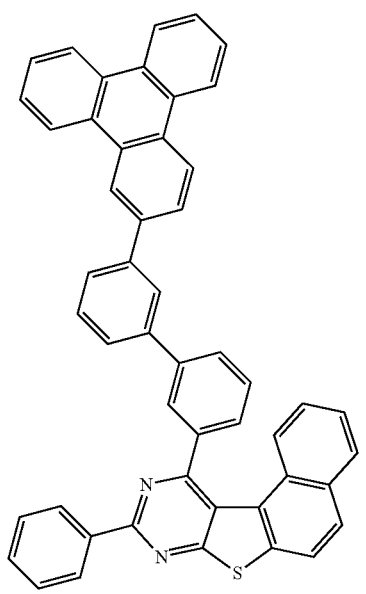
G-66
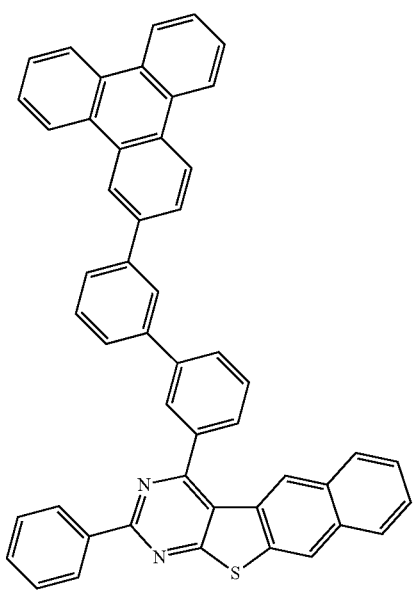
G-67
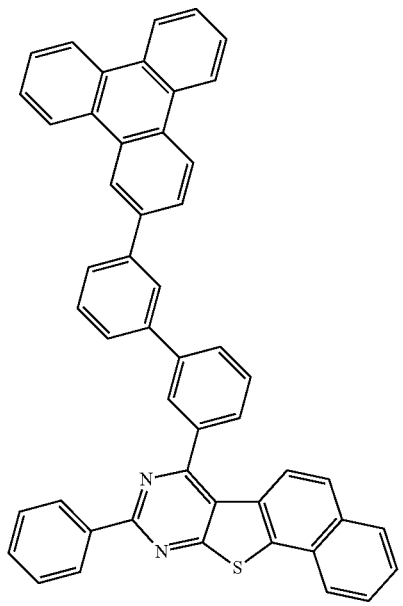
G-68
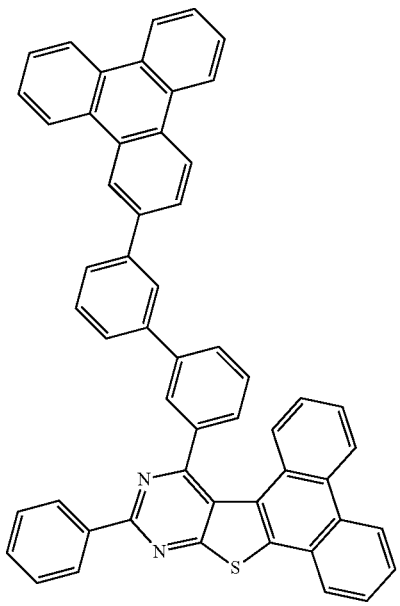
G-69
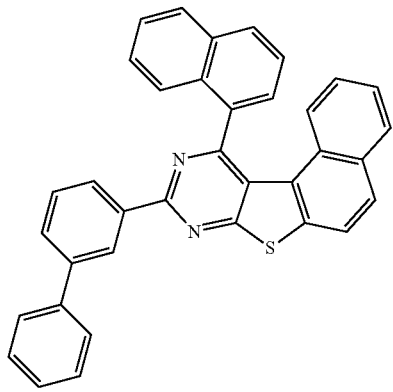
G-70
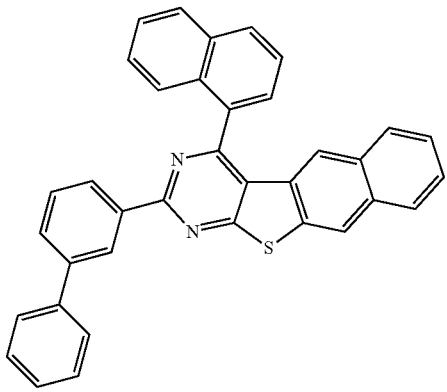

-continued
G-71
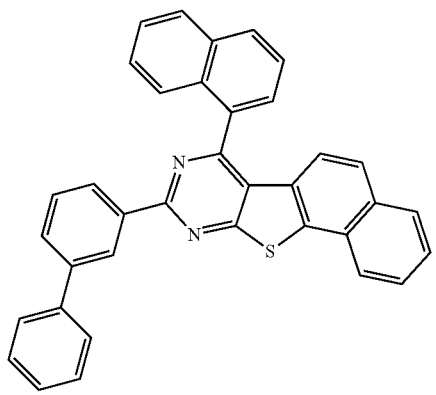
G-72
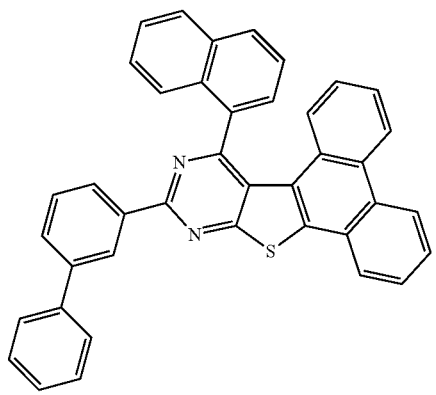
G-73
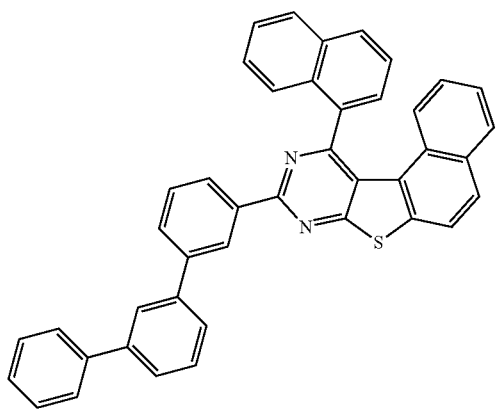
G-74
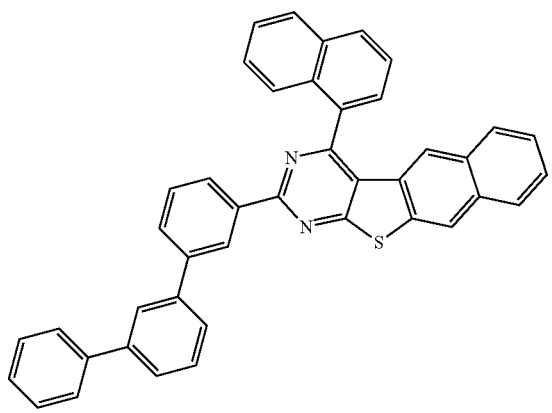
G-75
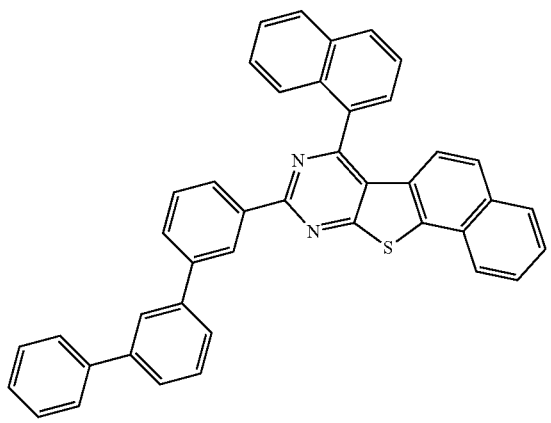
G-76
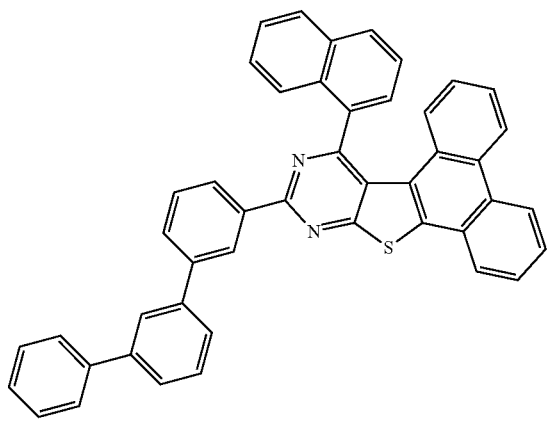
G-77
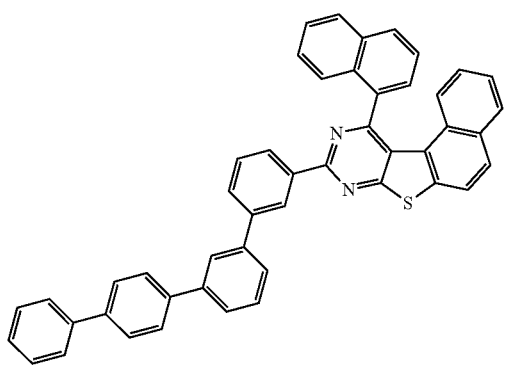
G-78
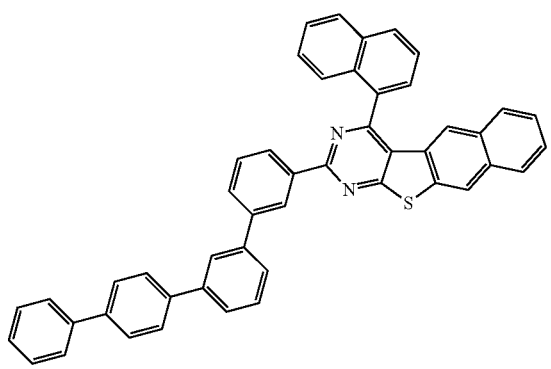

-continued
G-79
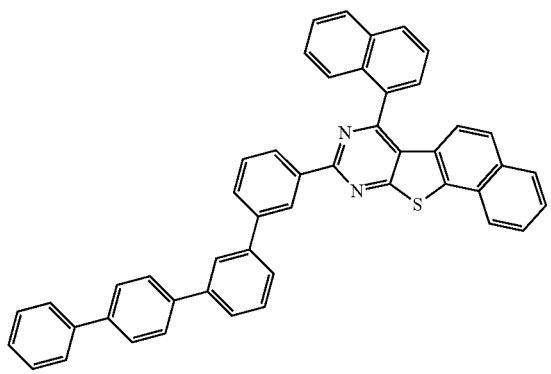
G-80
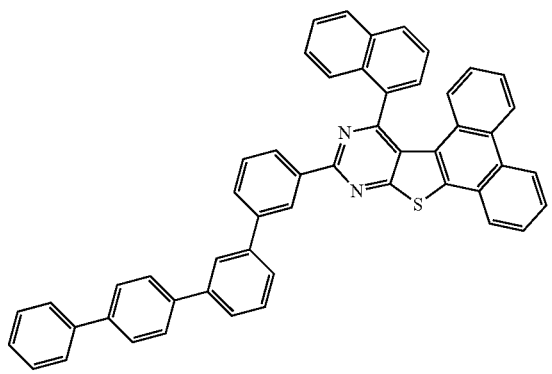
G-81
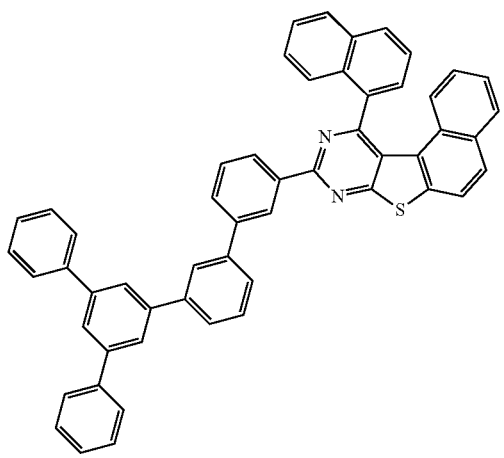
G-82
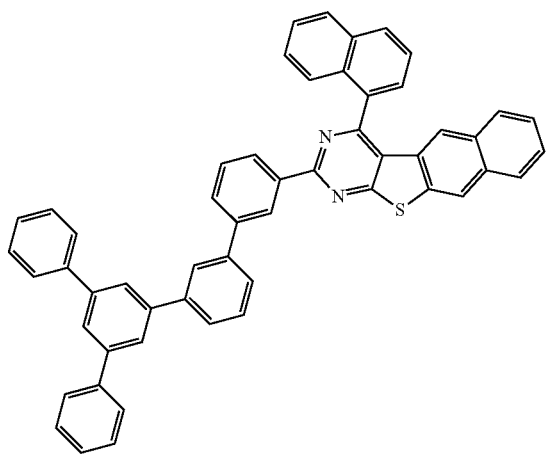
G-83
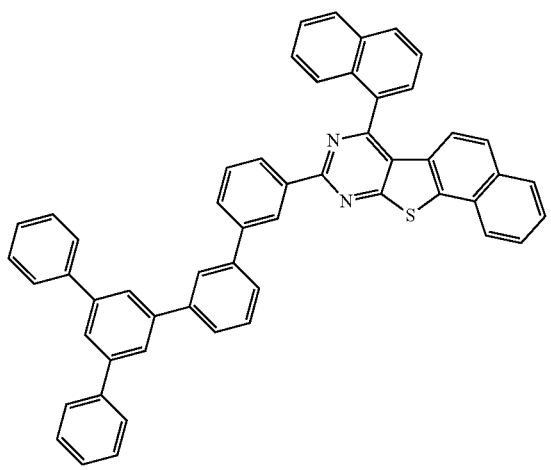
G-84
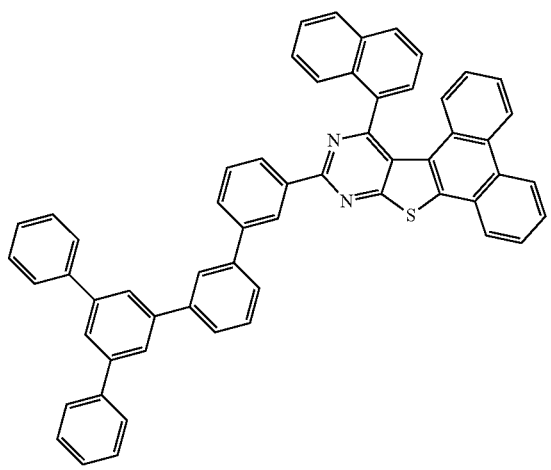

-continued
G-85
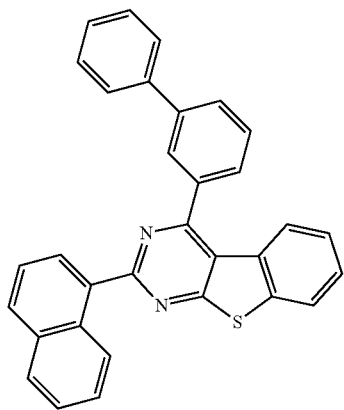
G-86
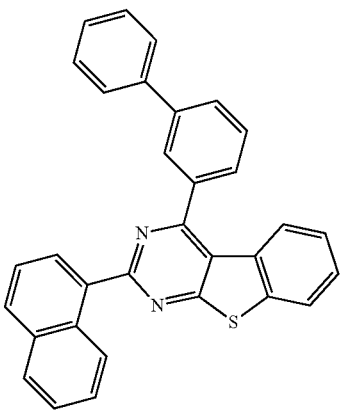
G-87
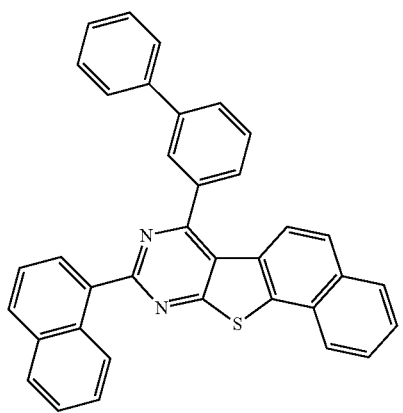
G-88
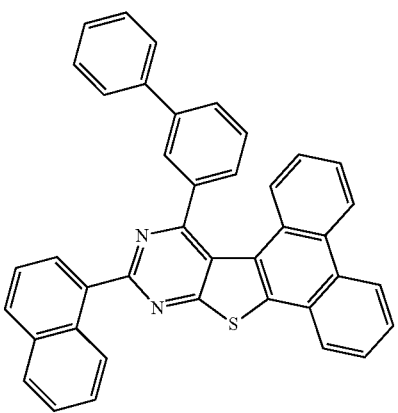
G-89
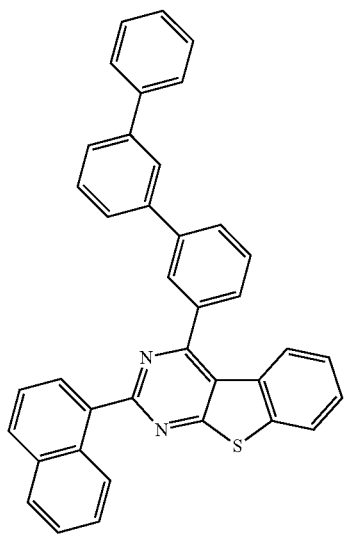
G-90
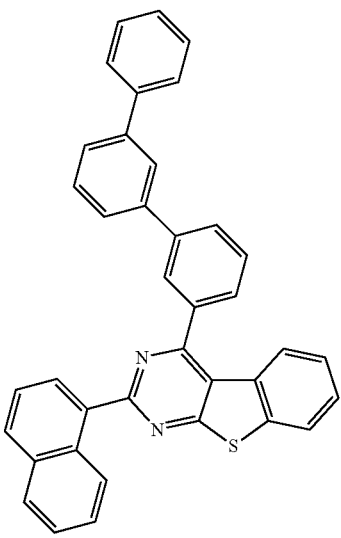

-continued
G-91
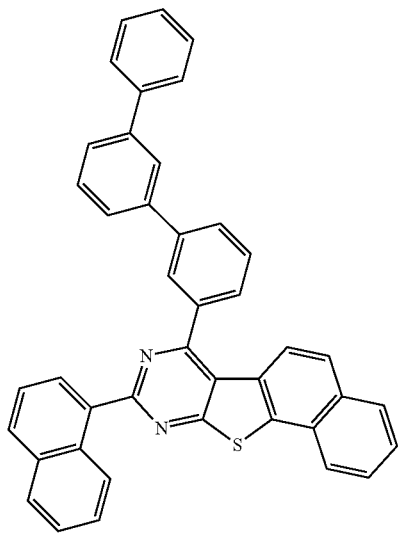
G-92
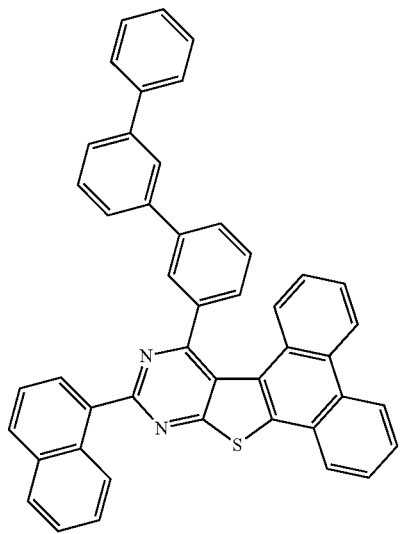
G-93
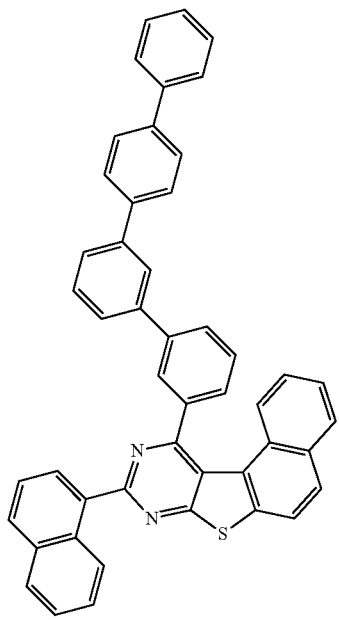
G-94
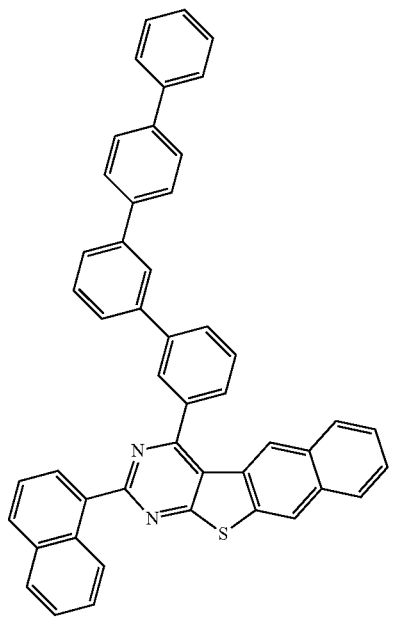

-continued
G-95
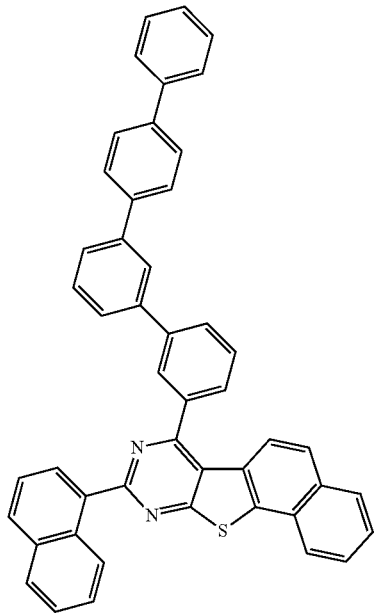
G-96
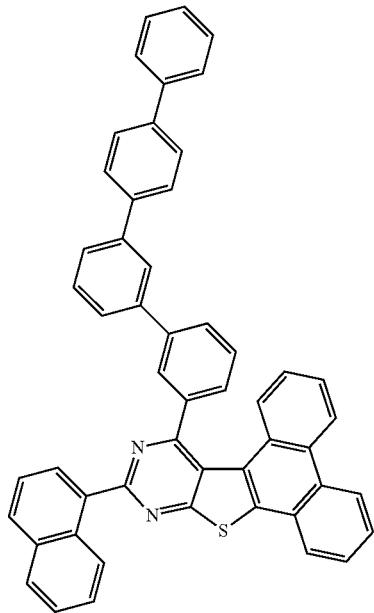
G-97
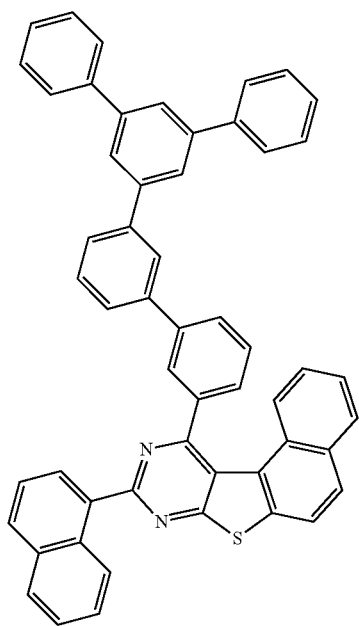
G-98
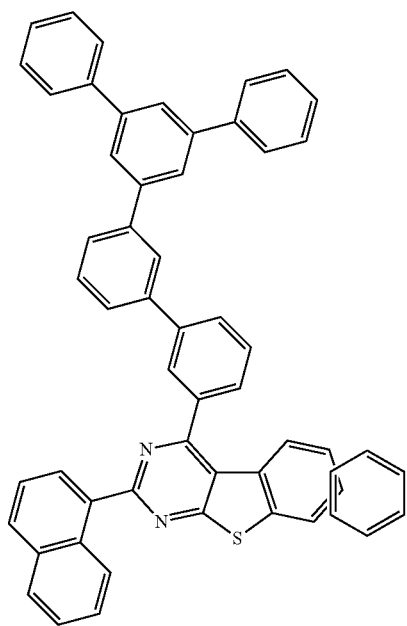

-continued
G-99
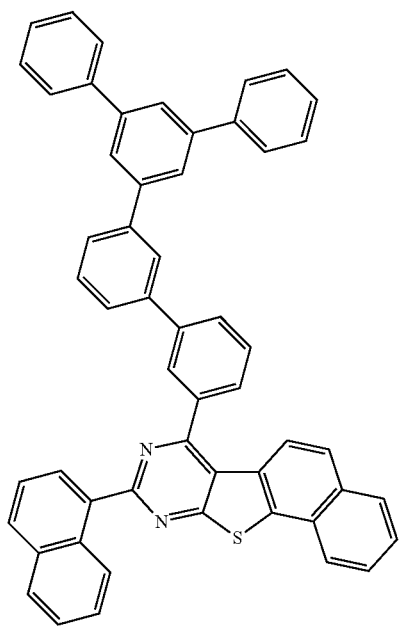
G-100
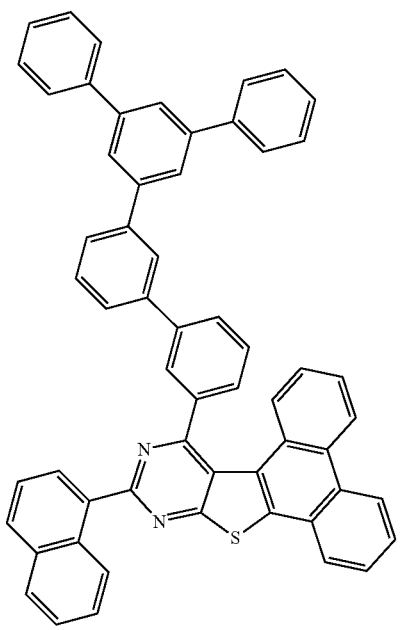
G-101
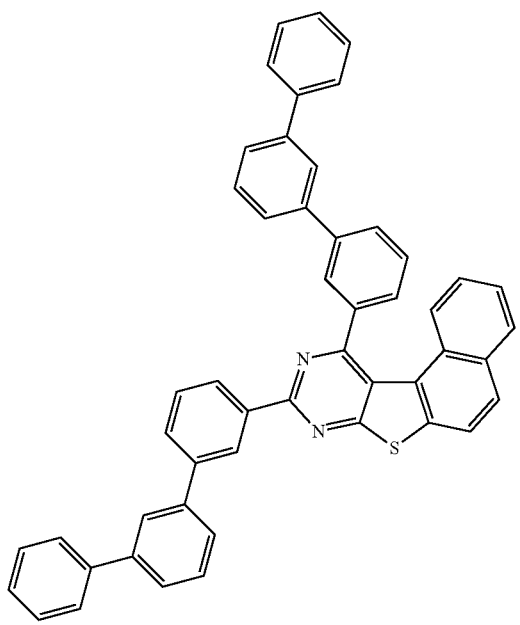
G-102
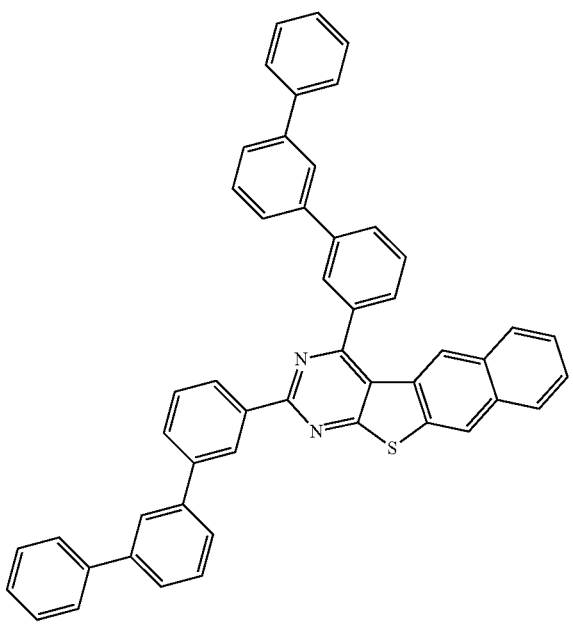

-continued
G-103
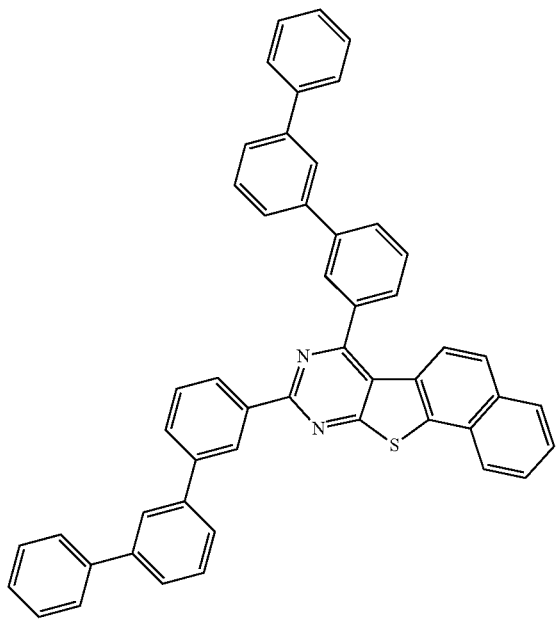
G-104
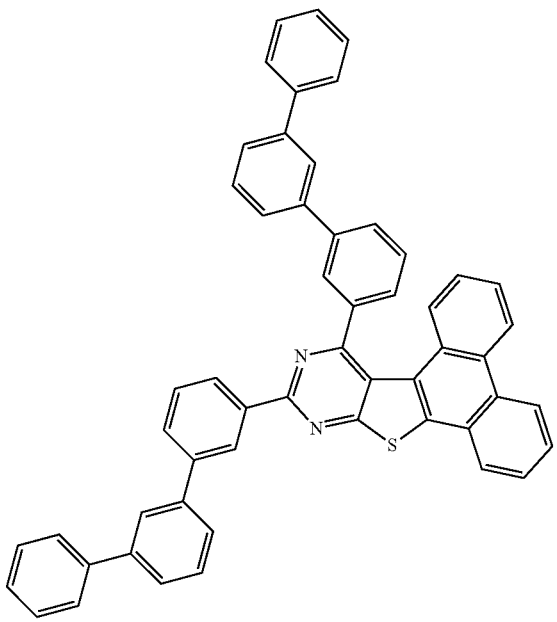
G-105
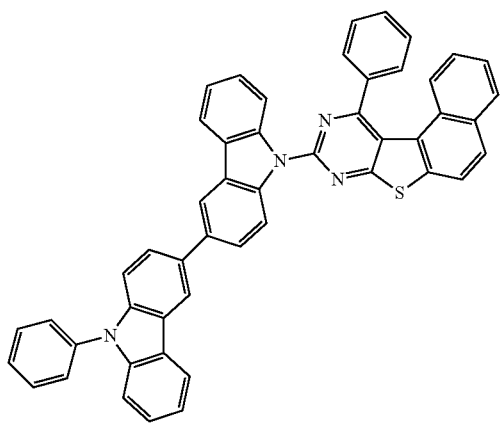
G-106
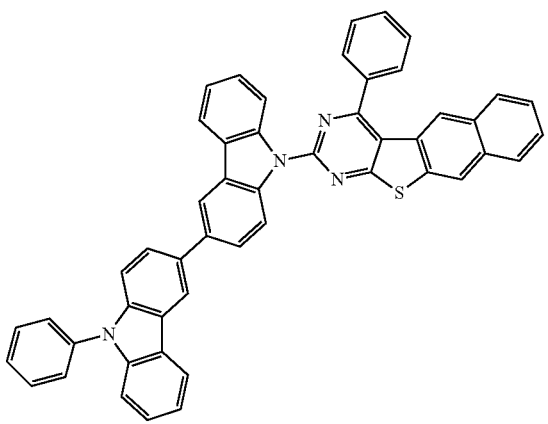
G-107
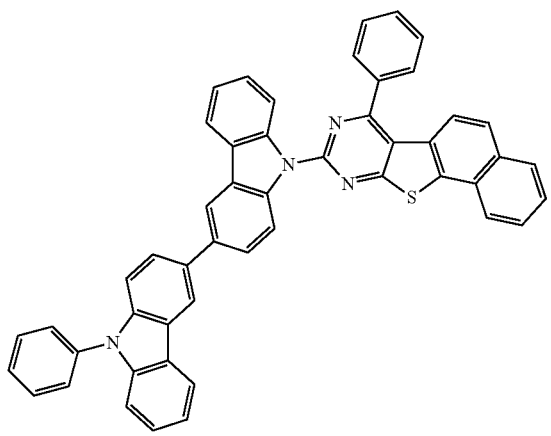
G-108
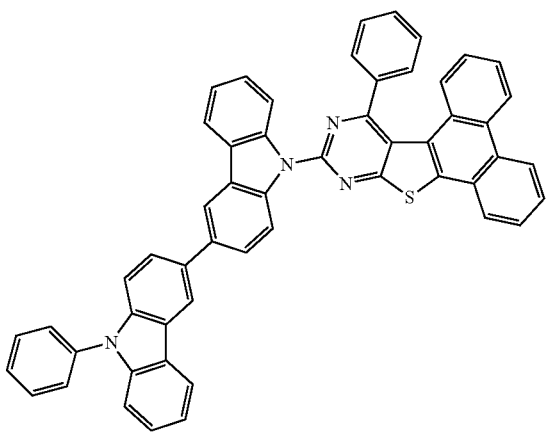

-continued
H-1
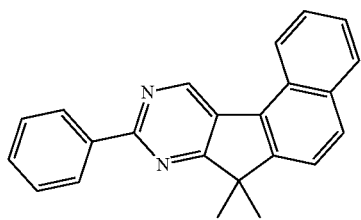
H-2
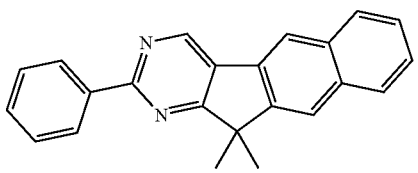
H-3
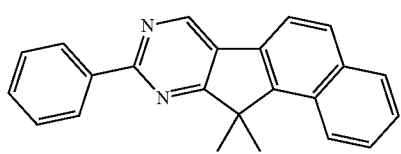
H-4
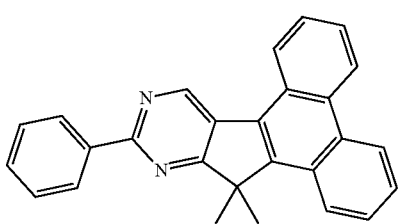
H-5
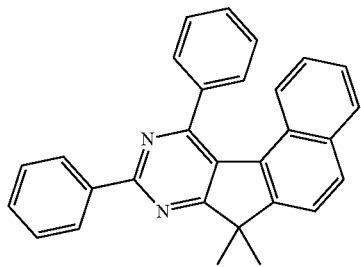
H-6
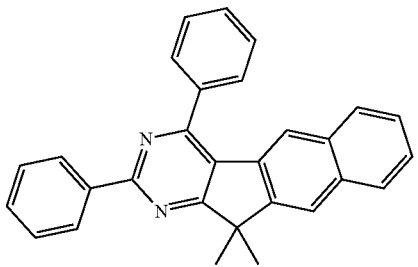
H-7
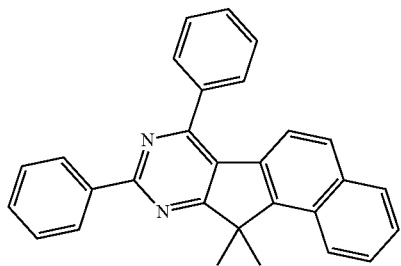
H-8
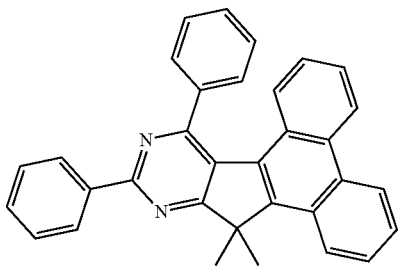
H-9
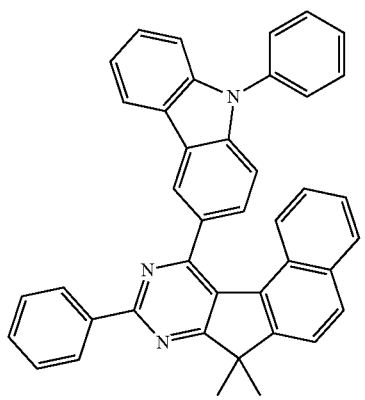
H-10
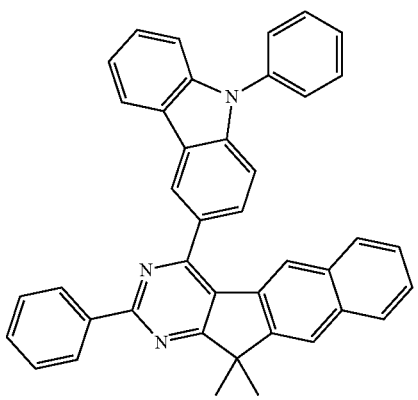

-continued
H-11
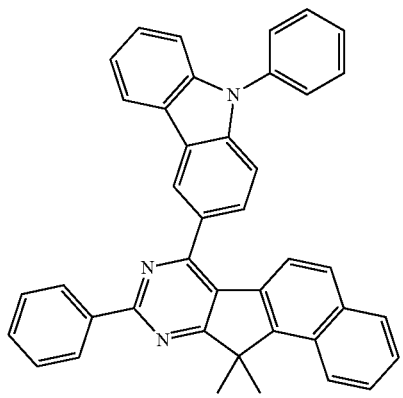
H-12
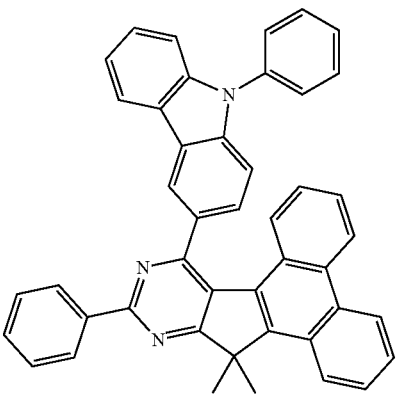
H-13
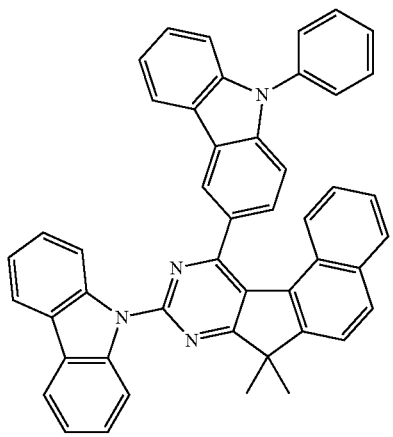
H-14
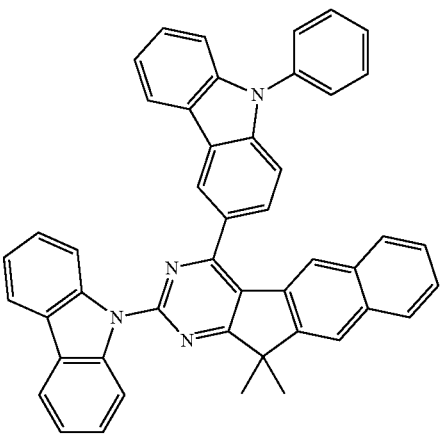
H-15
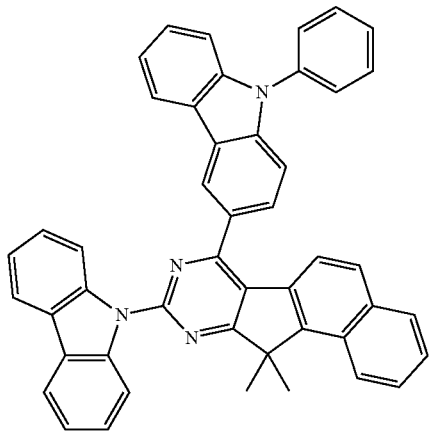
H-16
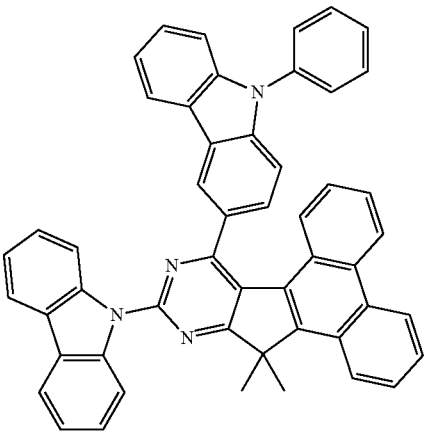
H-17
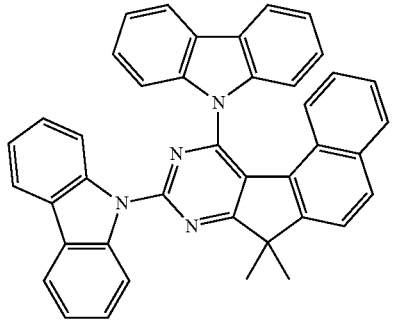
H-18
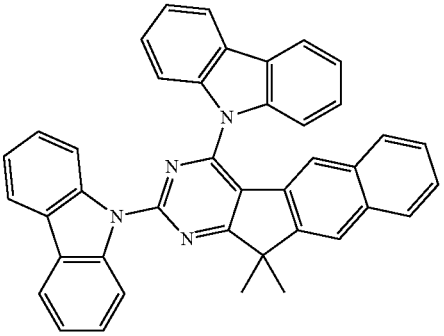

-continued
H-19
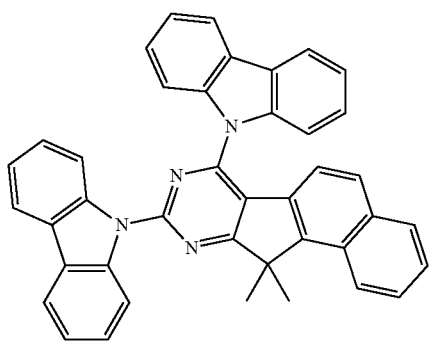
H-20
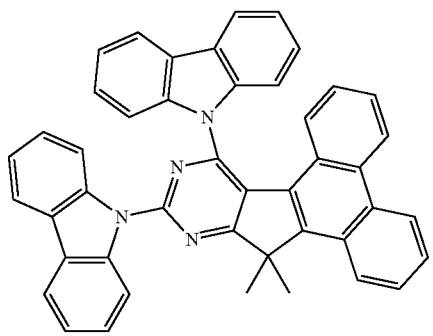
H-21
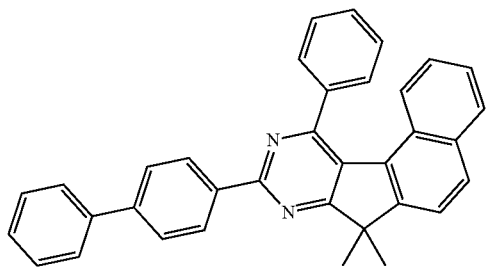
H-22
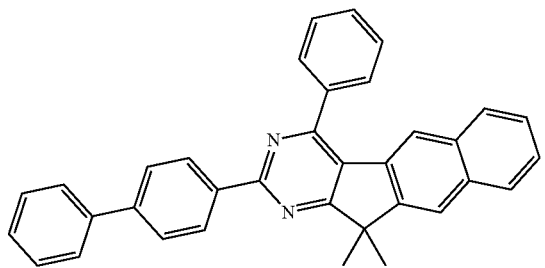
H-23
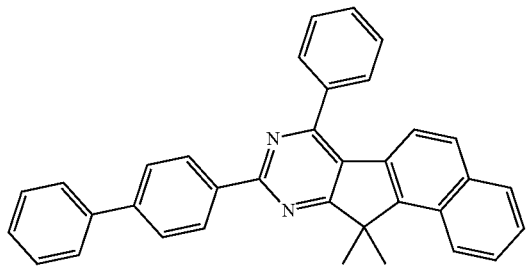
H-24
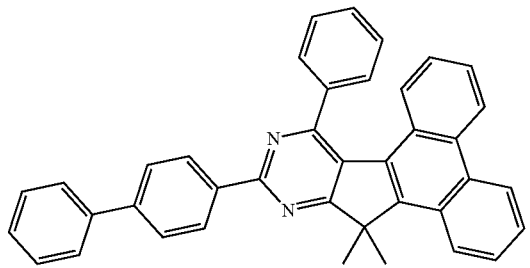
H-25
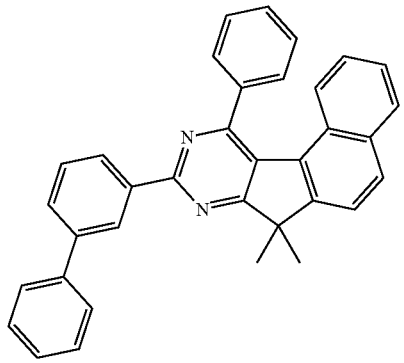
H-26
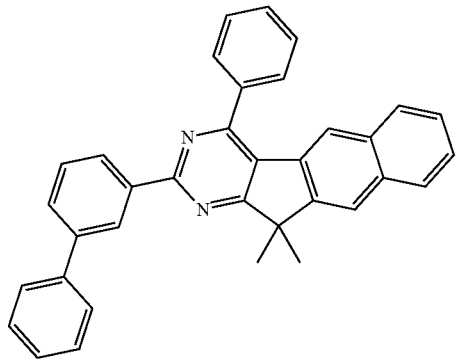

-continued
H-27
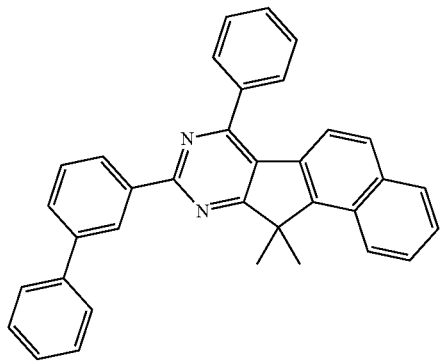
H-28
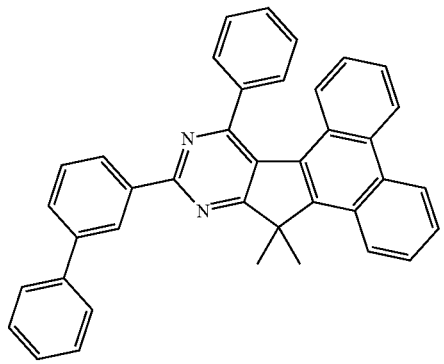
H-29
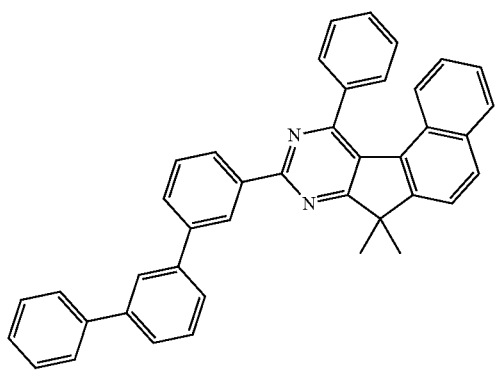
H-30
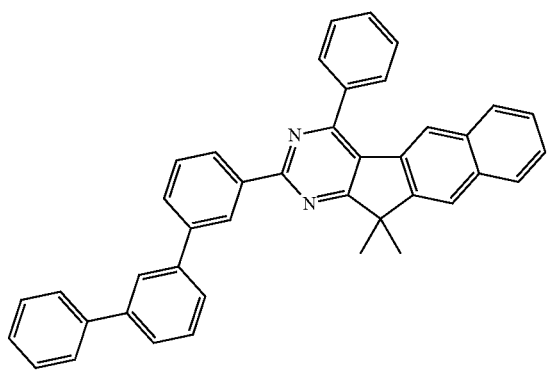
H-31
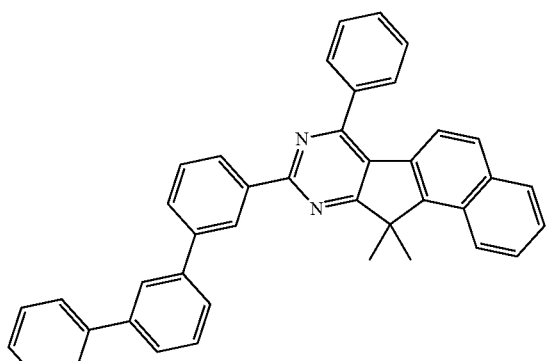
H-32
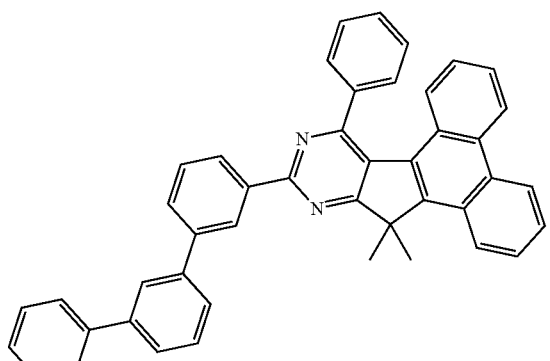
H-33
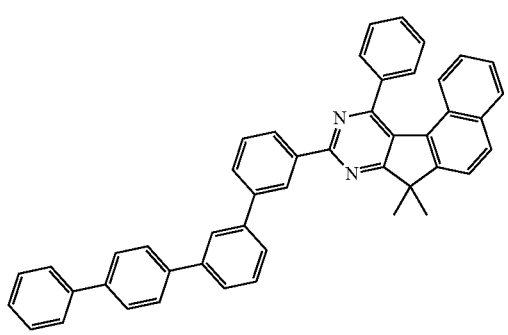
H-34
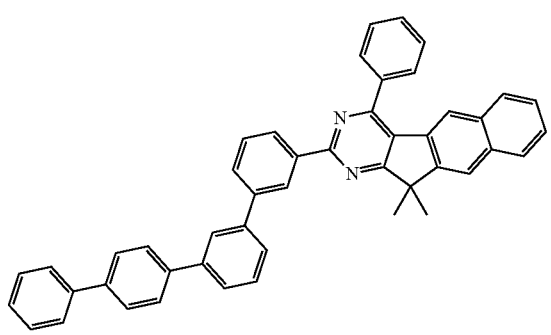

-continued
H-35
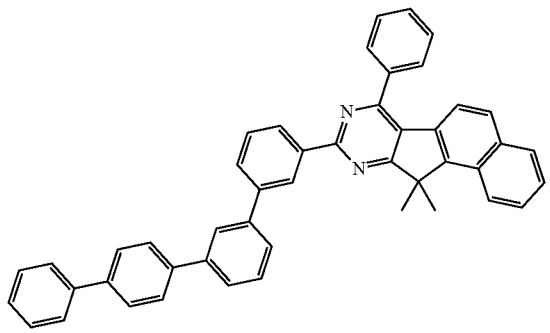
H-36
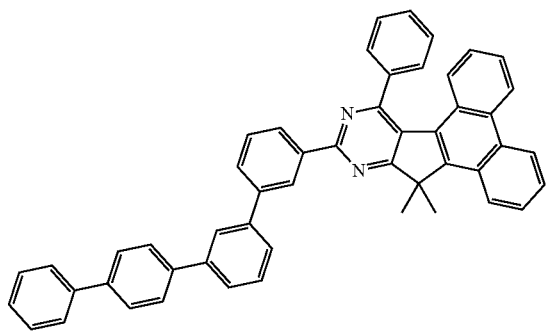
H-37
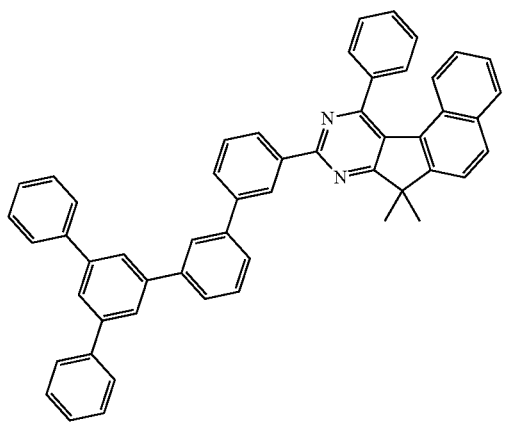
H-38
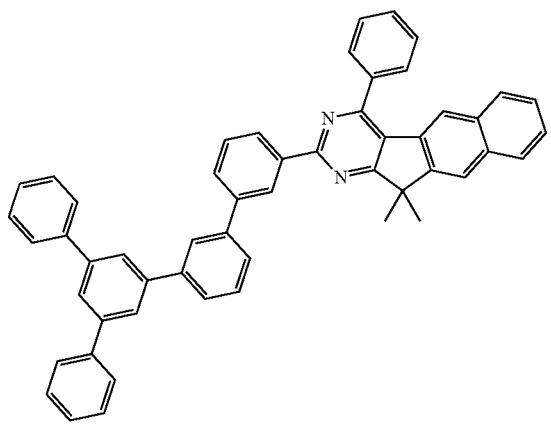
H-39
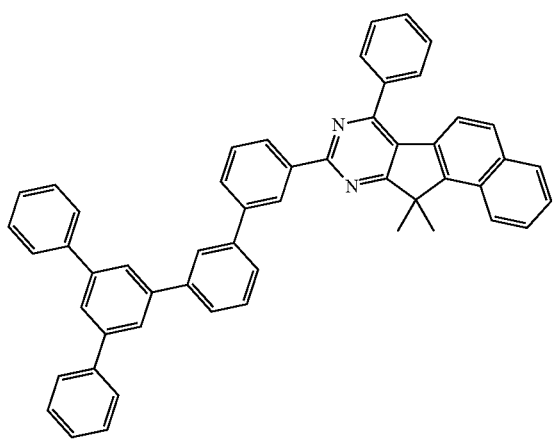
H-40
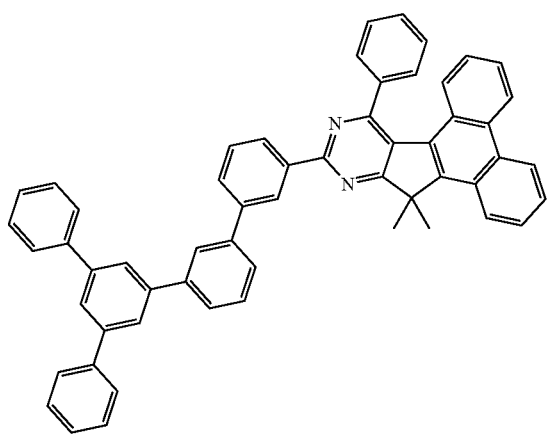

-continued
H-41
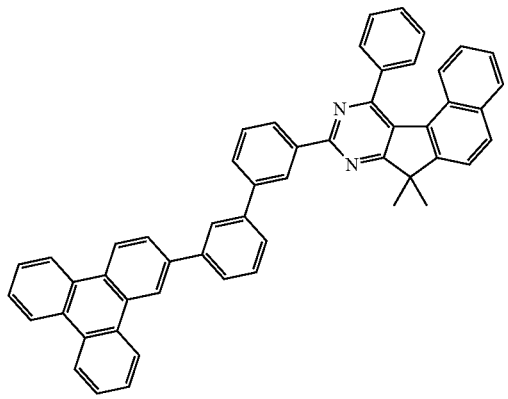
H-42
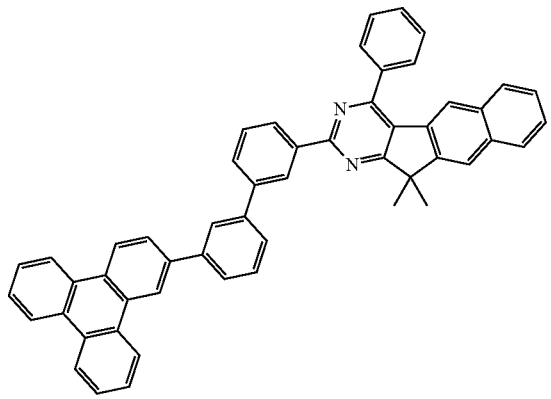
H-43
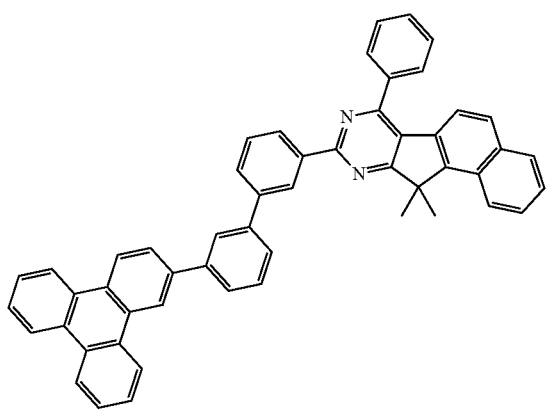
H-44
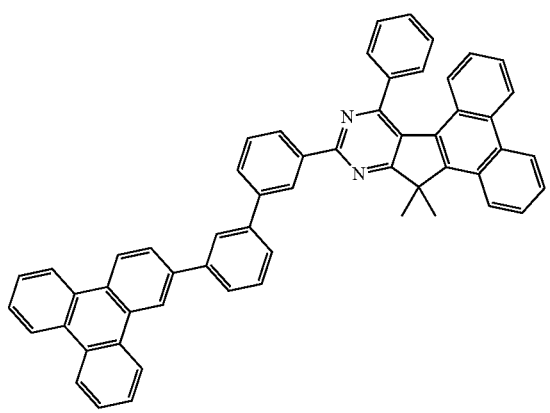
H-45
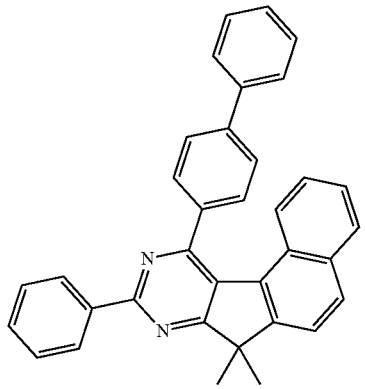
H-46
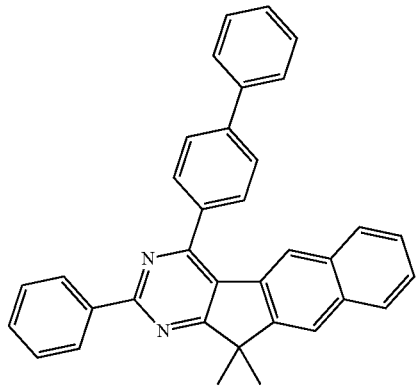
H-47
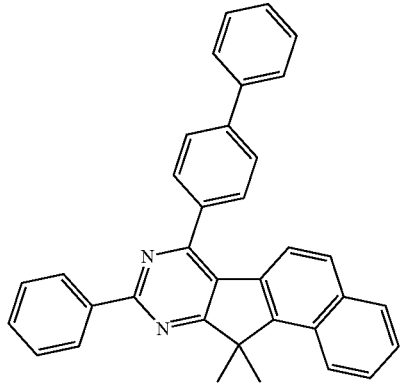
H-48
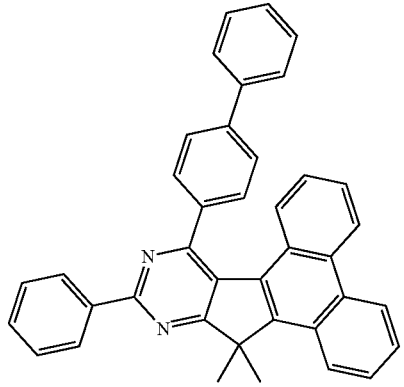

-continued
H-49
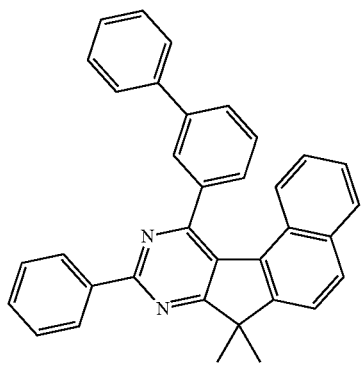
H-50
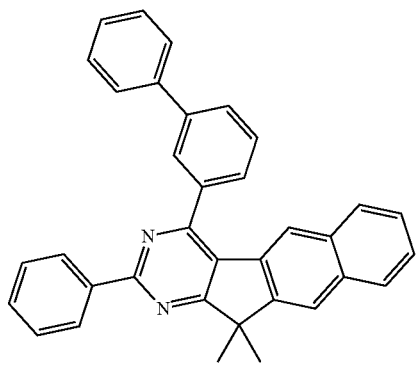
H-51
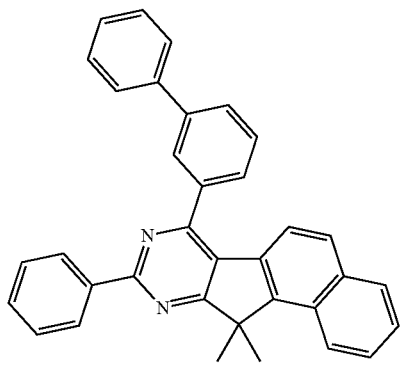
H-52
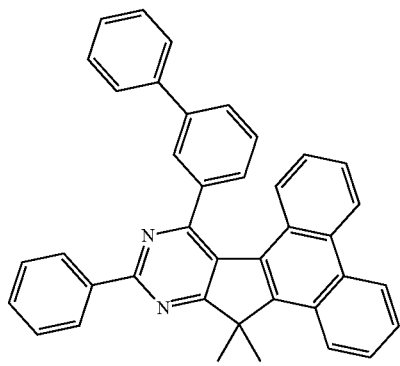
H-53
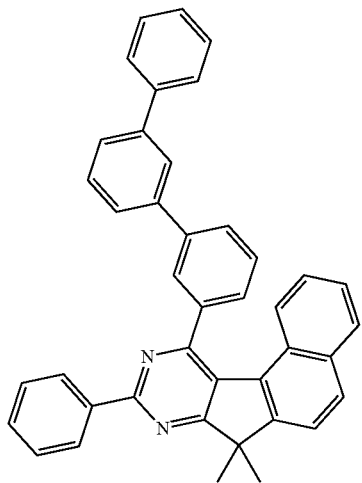
H-54
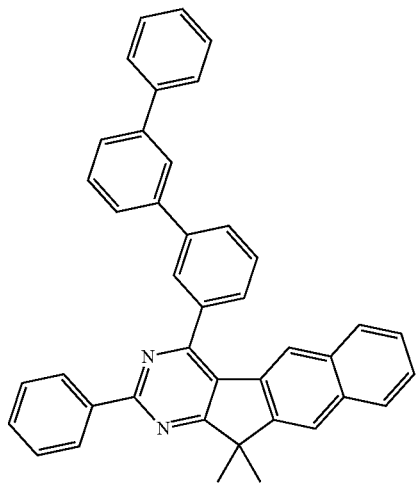

H-55
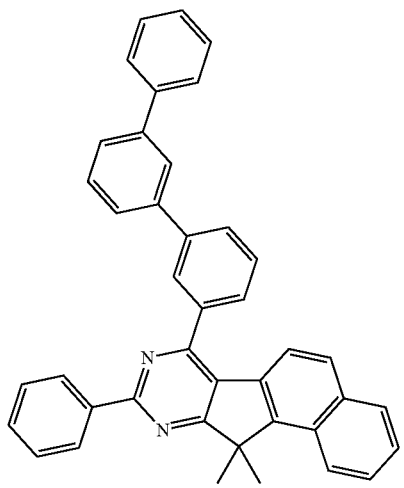
H-56
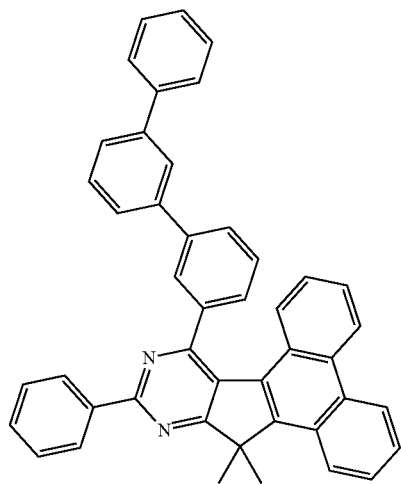
H-57
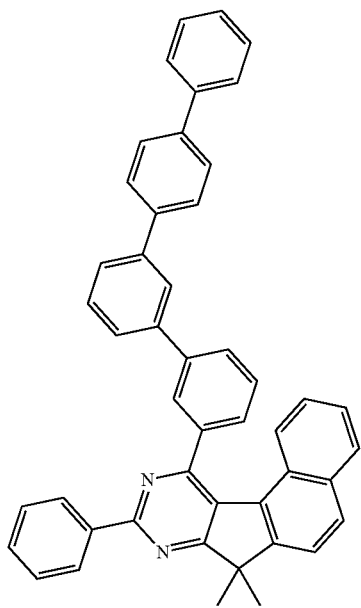
H-58
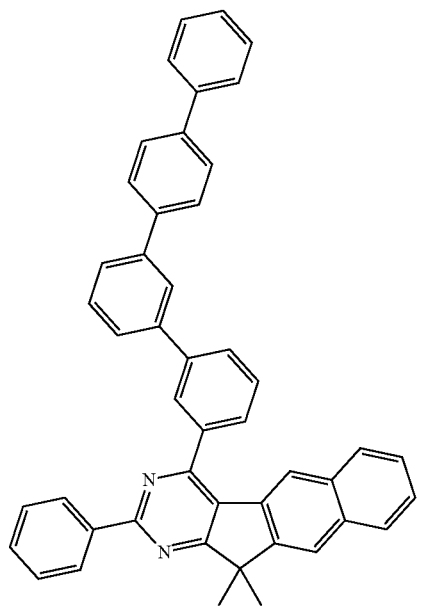

-continued
H-59
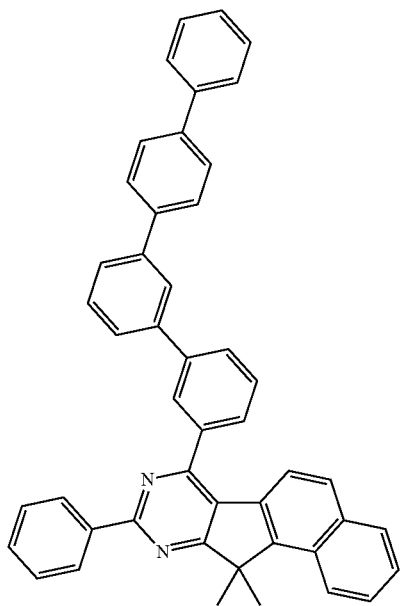
H-60
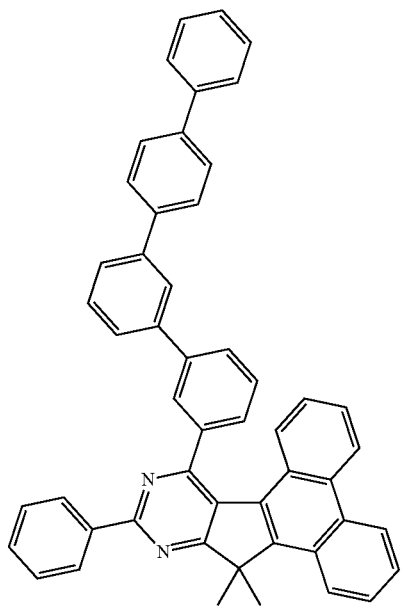
H-61
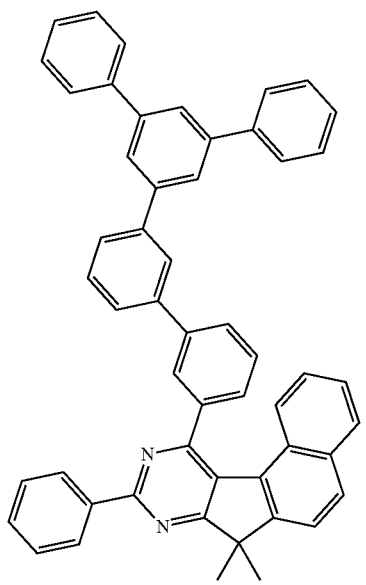
H-62
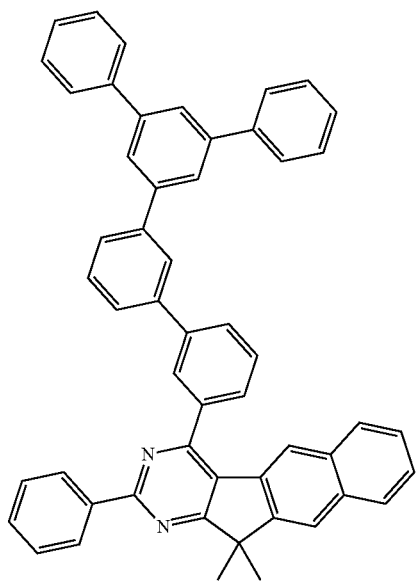

H-63
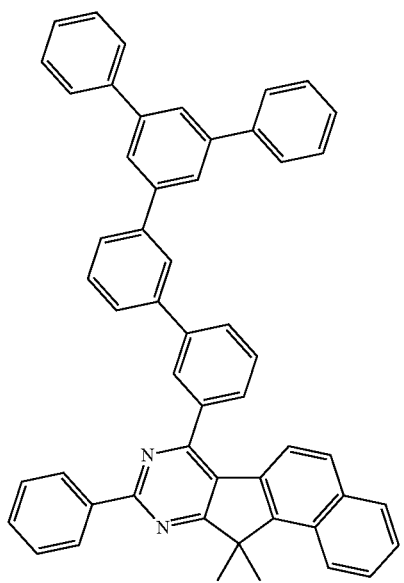
H-64
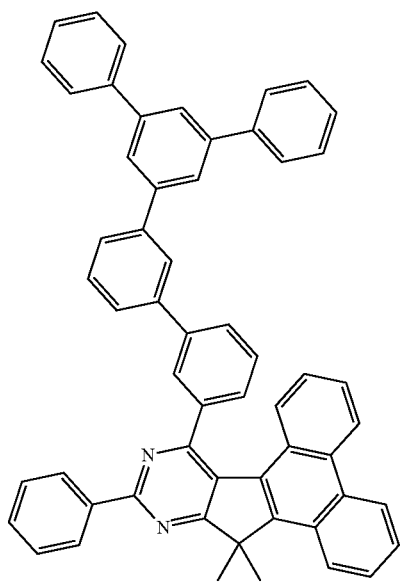
H-65
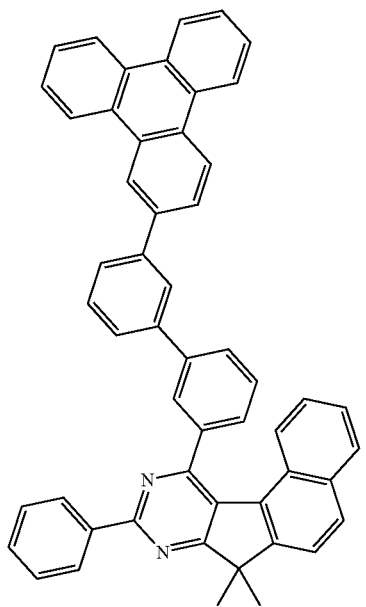
H-66
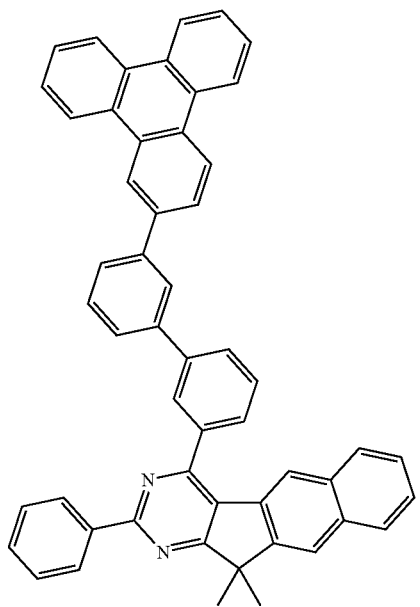

-continued
H-67
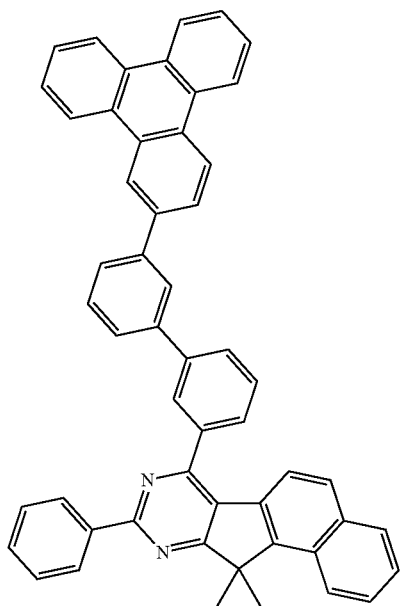
H-68
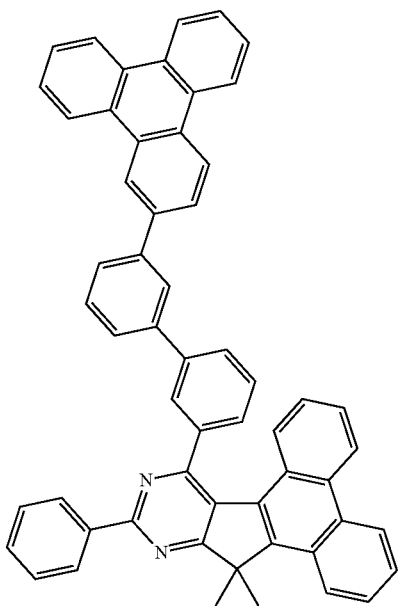
H-69
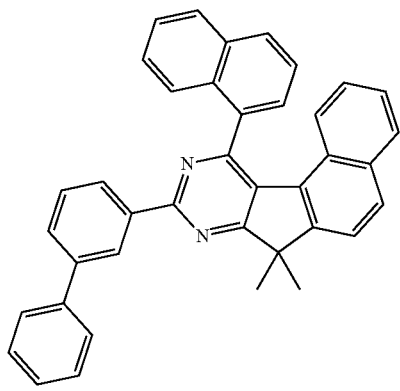
H-70
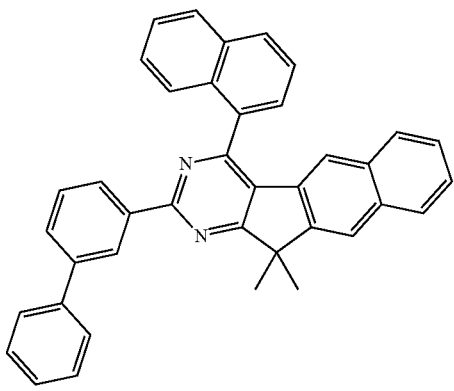
H-71
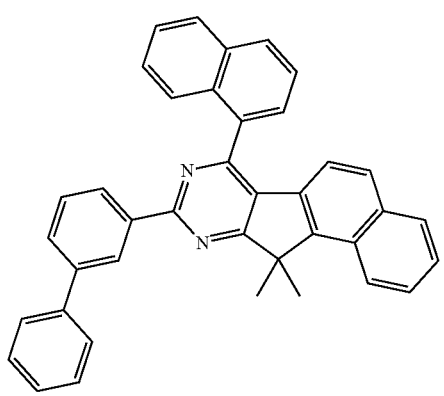
H-72
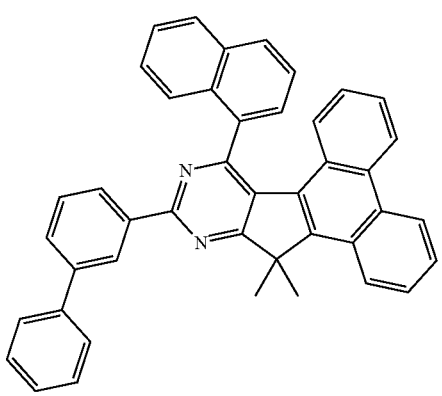

-continued
H-73
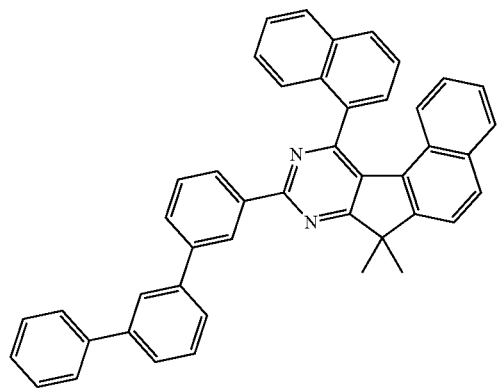
H-74
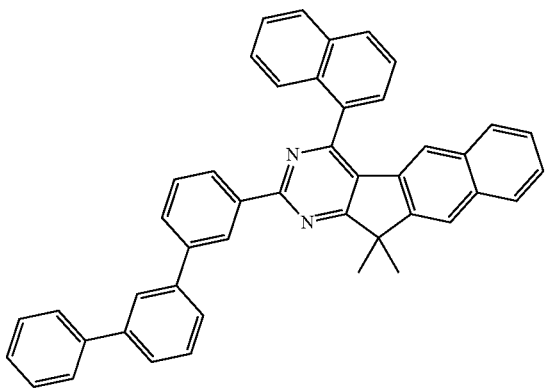
H-75
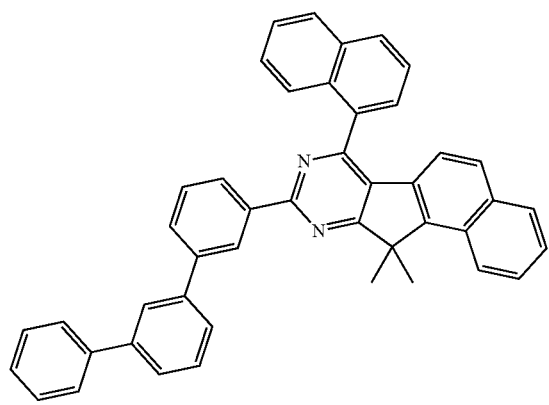
H-76
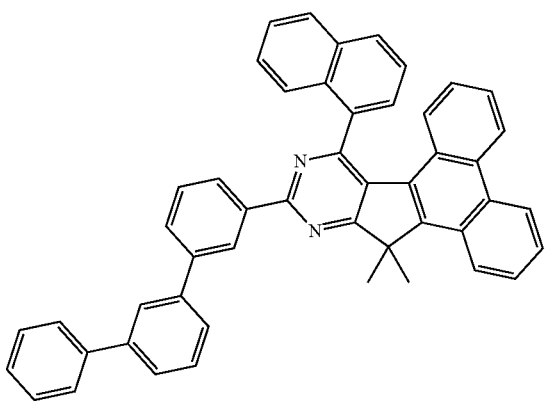
H-77
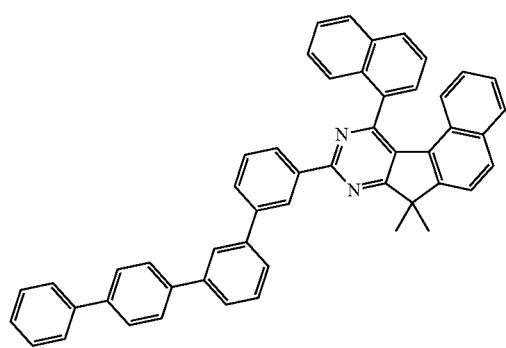
H-78
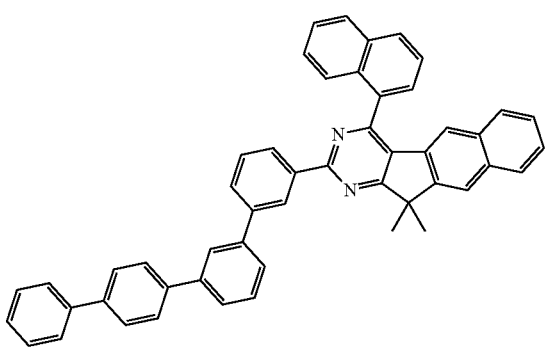
H-79
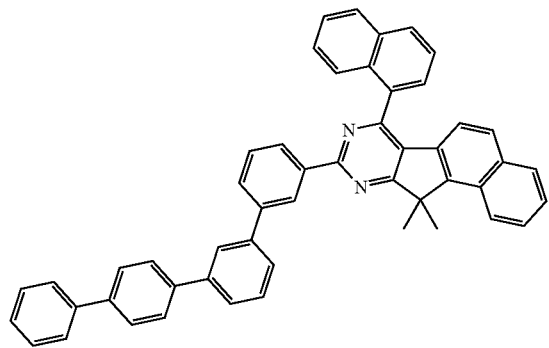
H-80
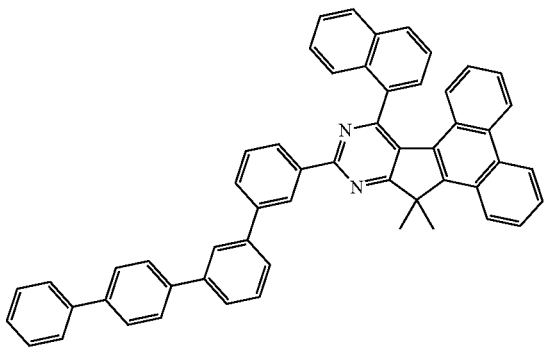

-continued
H-81
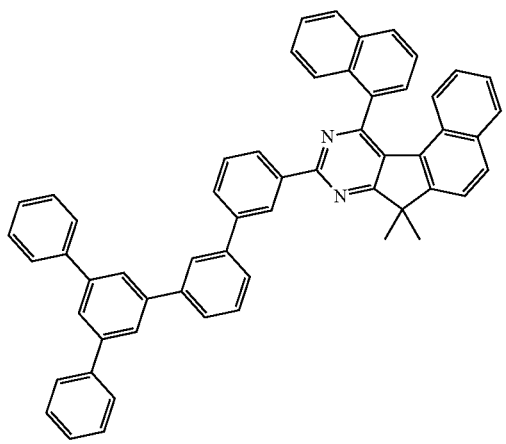
H-82
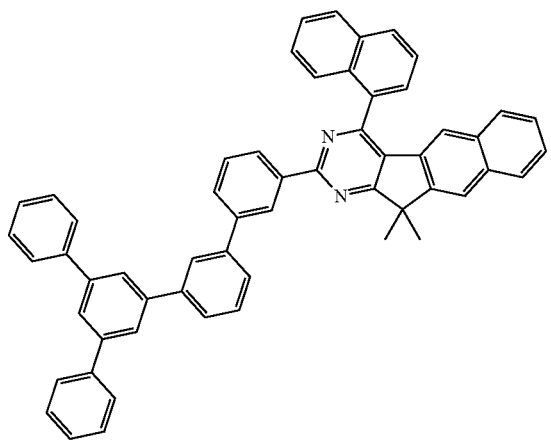
H-83
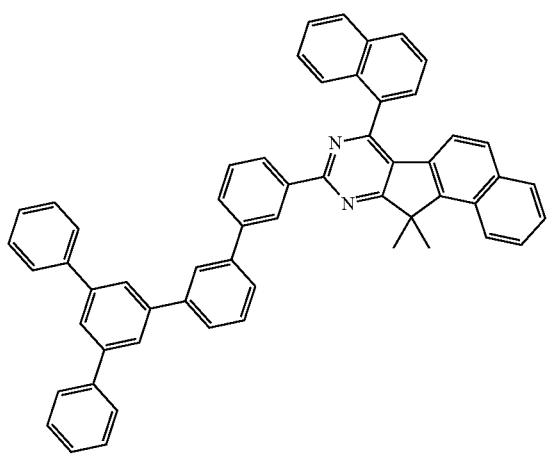
H-84
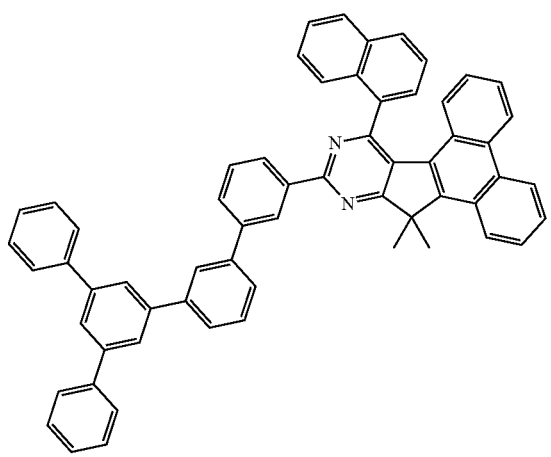
H-85
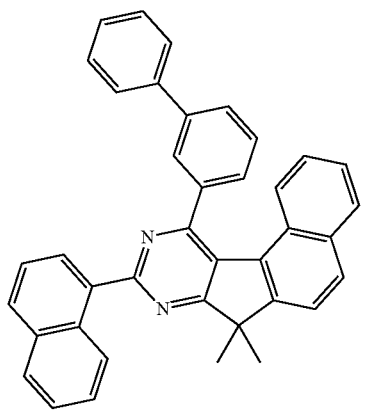
H-86
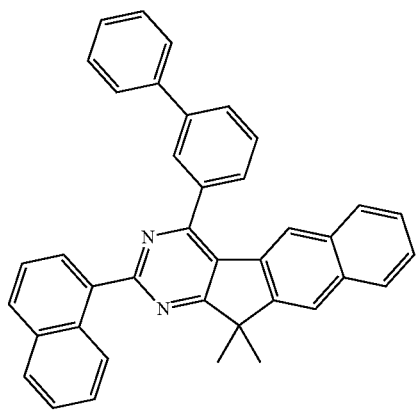

-continued
H-87
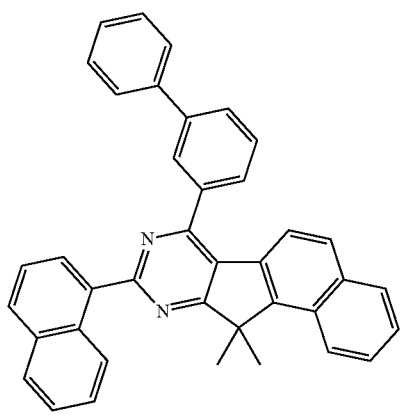
H-88
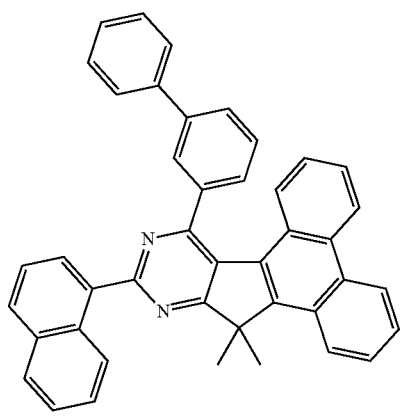
H-89
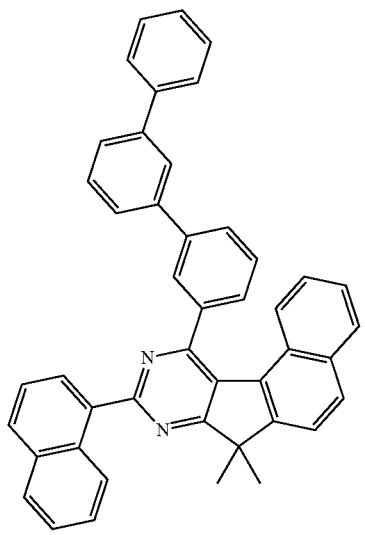
H-90
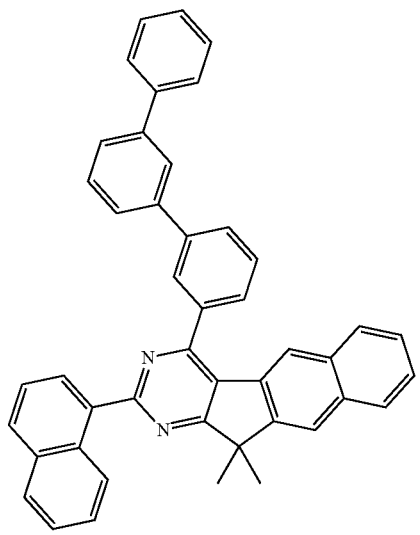
H-91
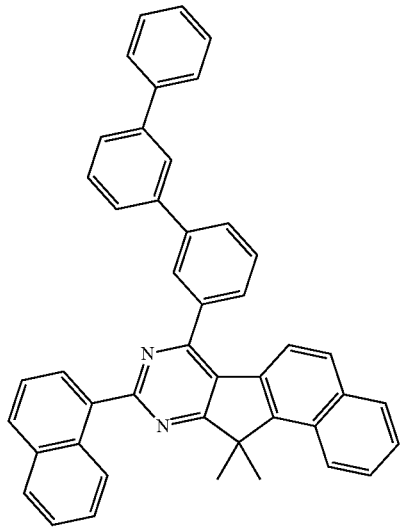
H-92
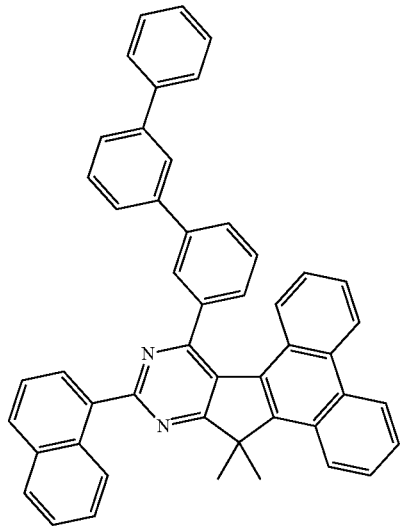

-continued
H-93
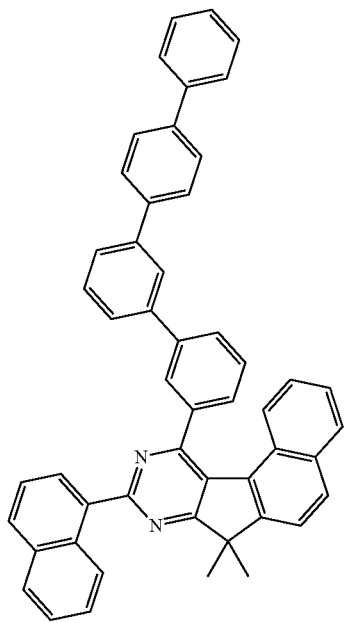
H-94
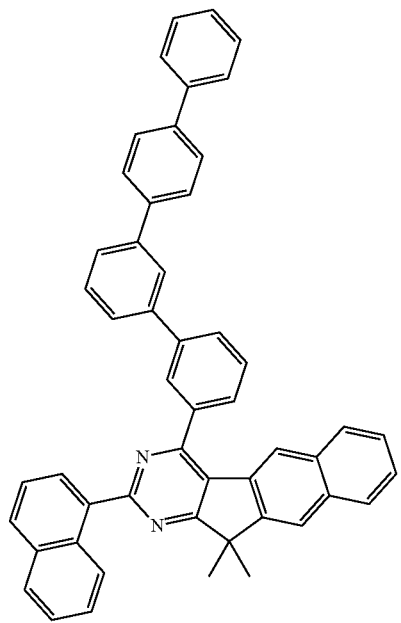
H-95
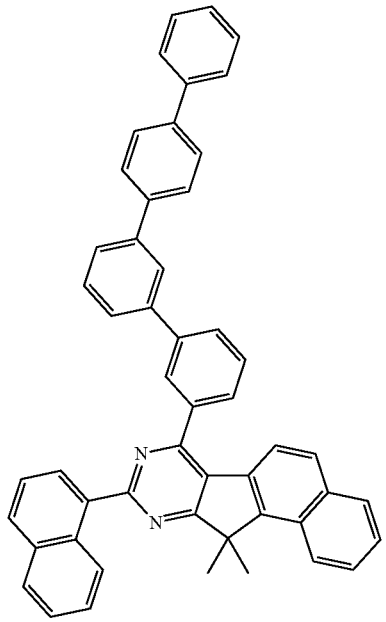
H-96
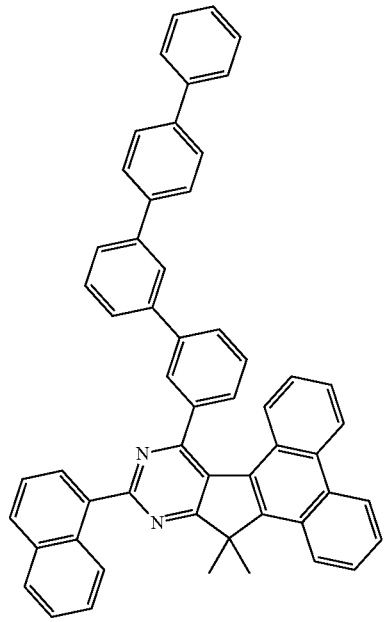

H-97
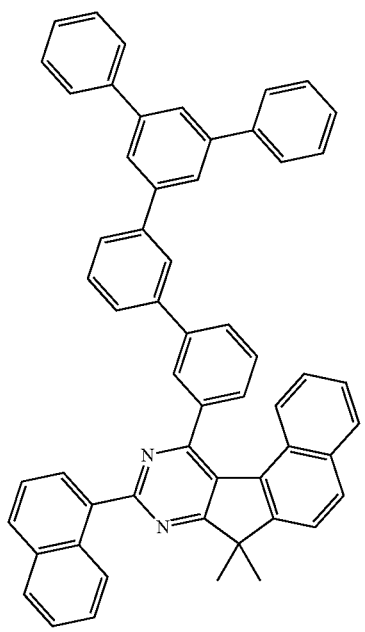
H-98
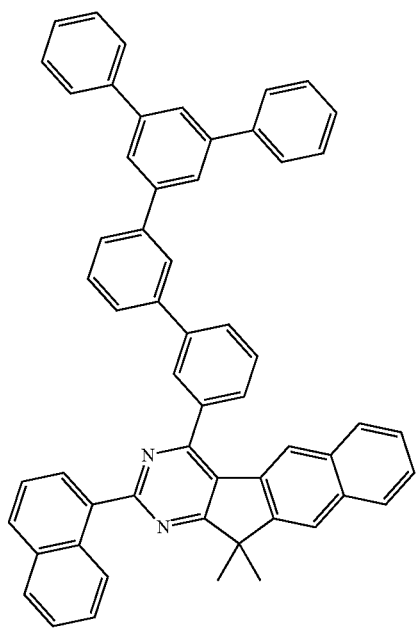
H-99
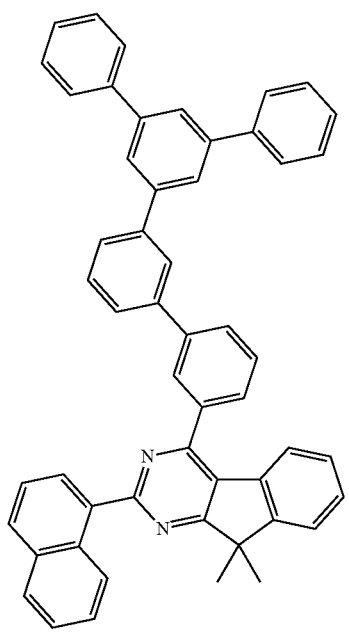
H-100
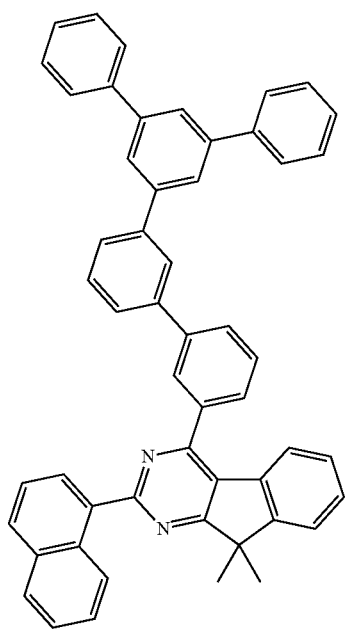

-continued
H-101
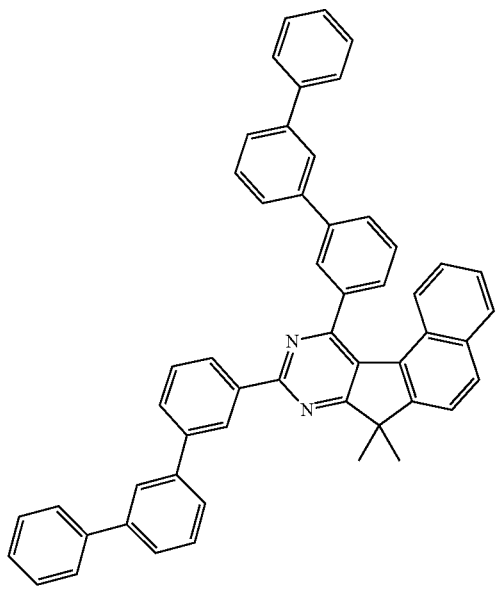
H-102
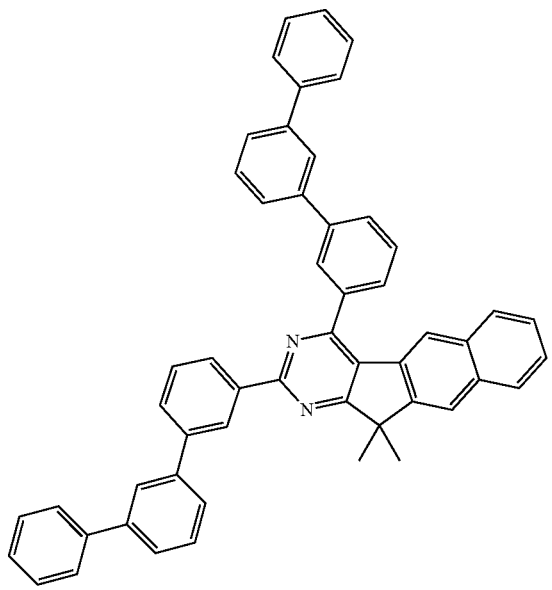
H-103
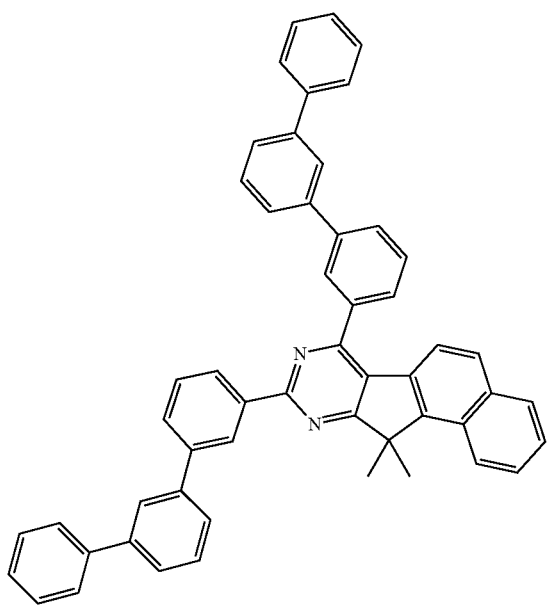
H-104
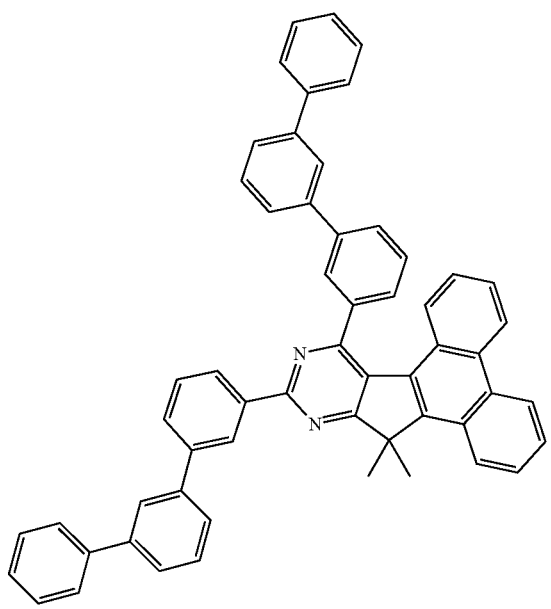

-continued
H-105
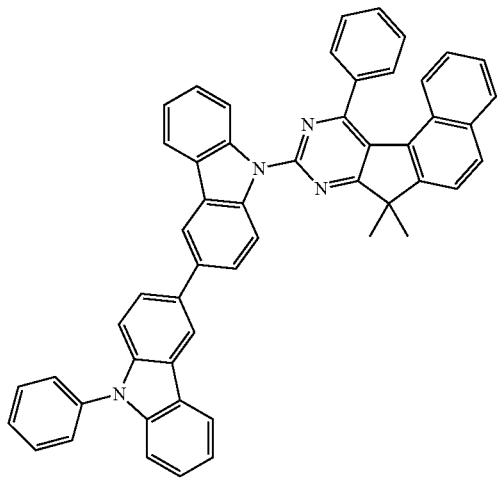
H-106
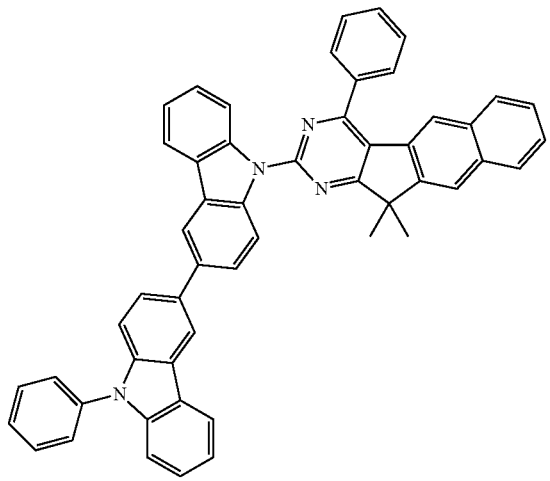
H-107
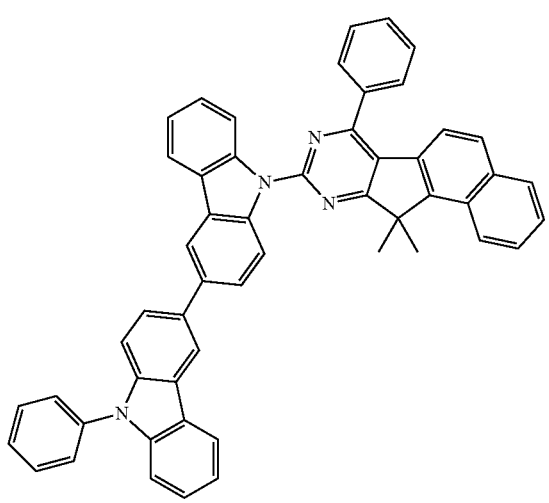
H-108
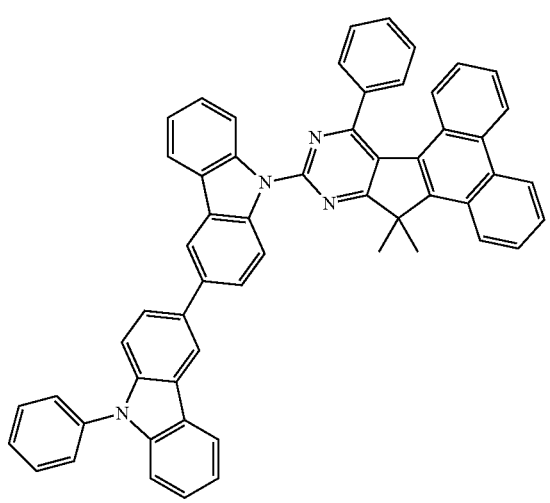
I-1
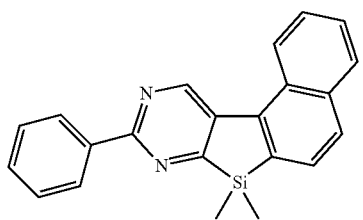
I-2
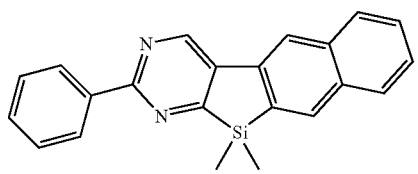
I-3
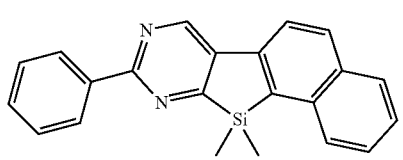
I-4
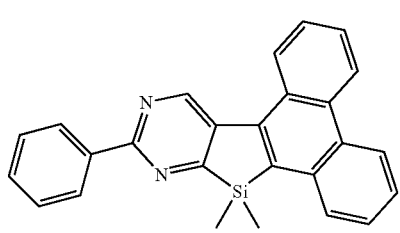

-continued
I-5
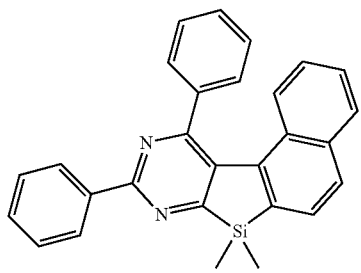
I-6
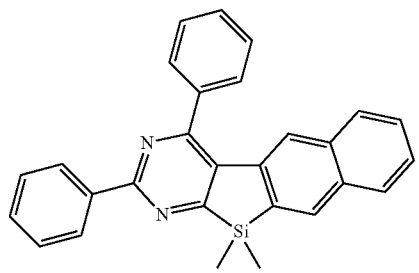
I-7
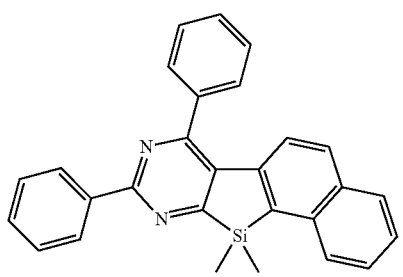
I-8
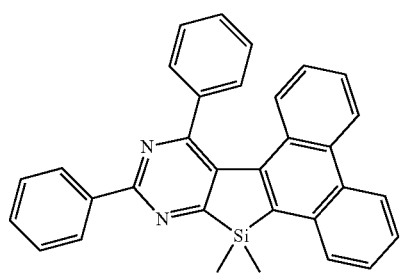
I-9
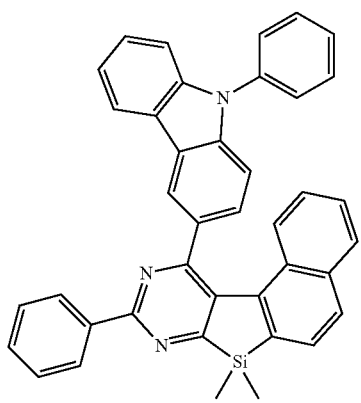
I-10
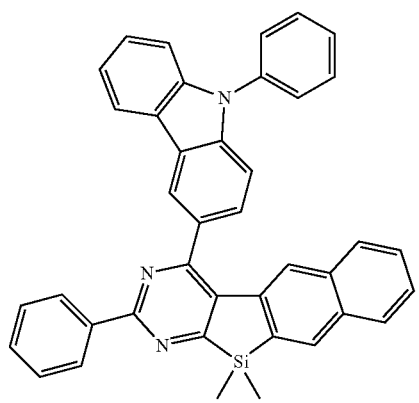
I-11
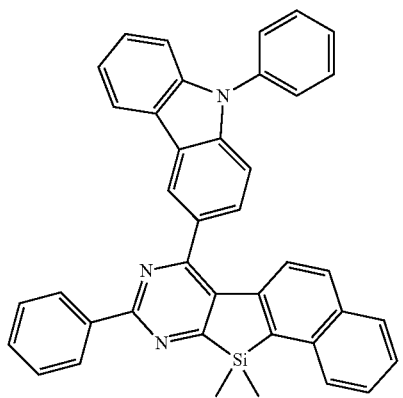
I-12
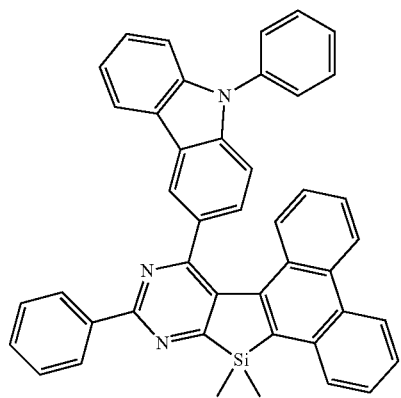

-continued
I-13
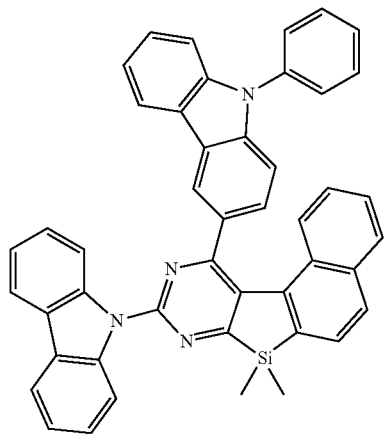
I-14
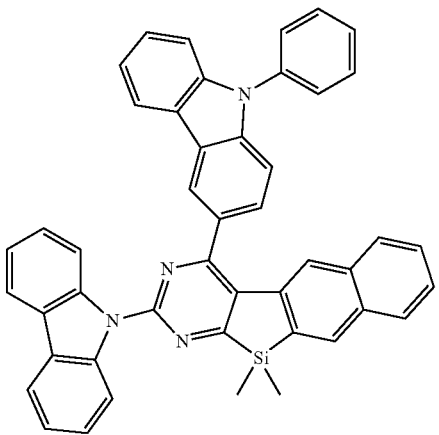
I-15
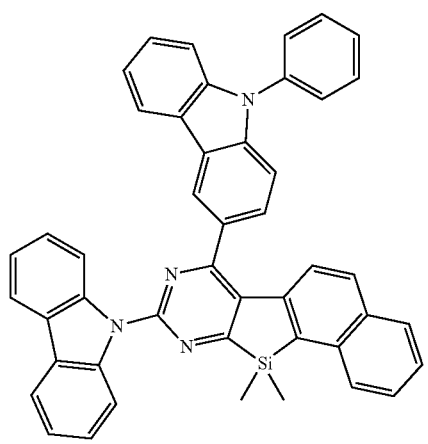
I-16
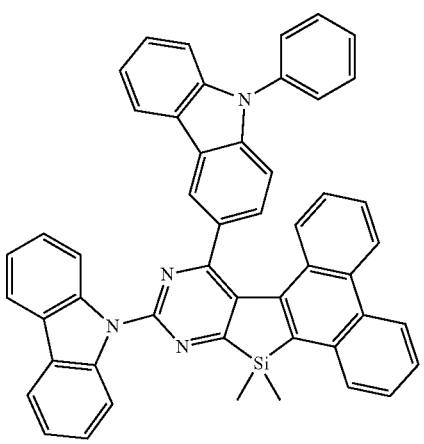
I-17
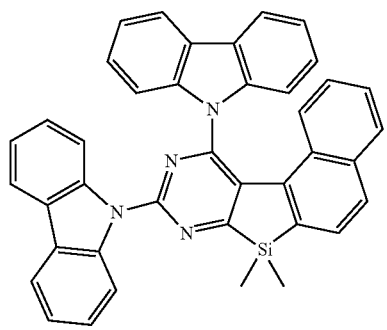
I-18
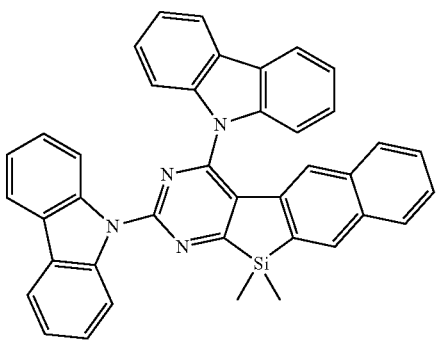
I-19
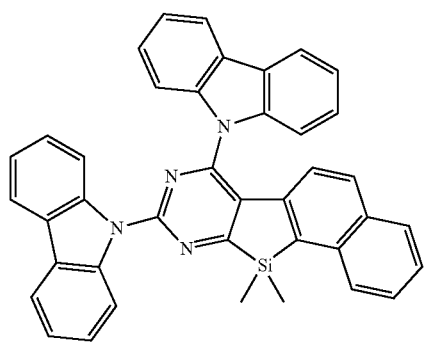
I-20
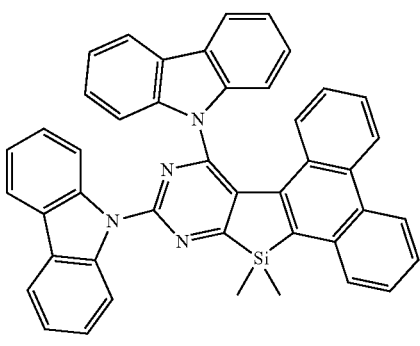

-continued
I-21
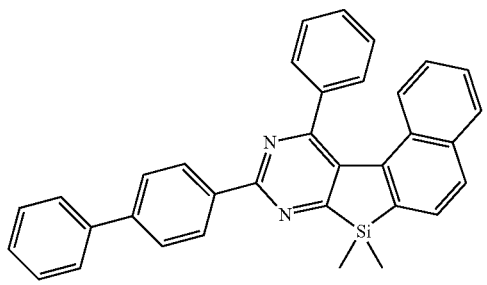
I-22
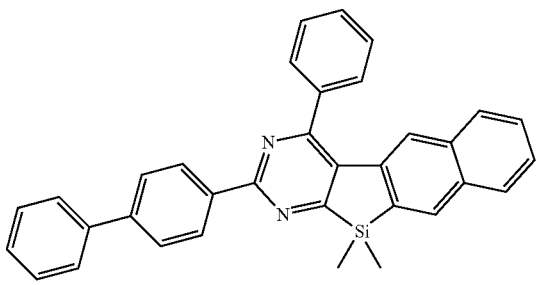
I-23
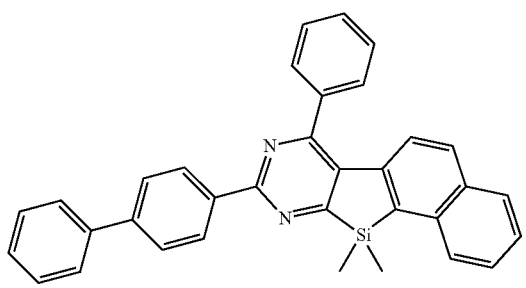
I-24
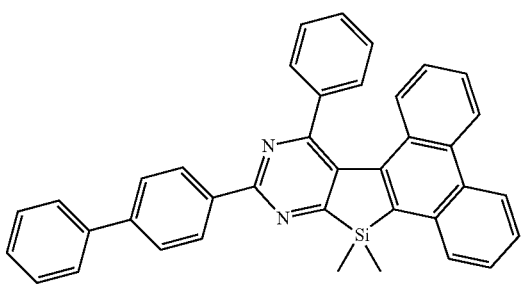
I-25
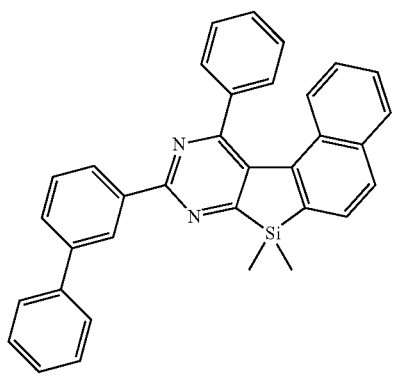
I-26
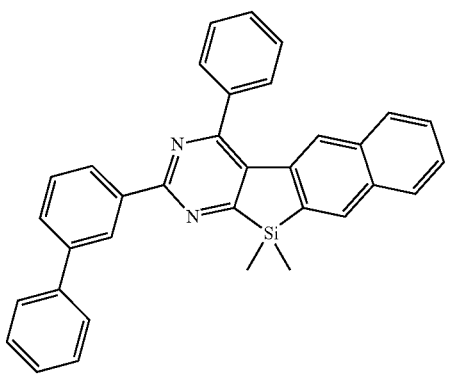
I-27
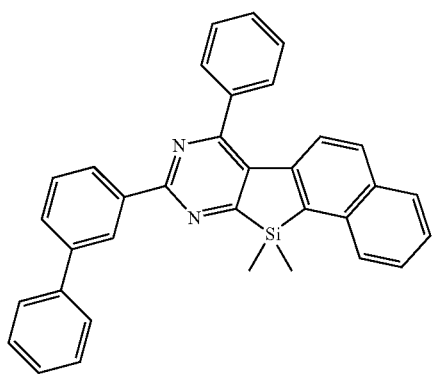
I-28
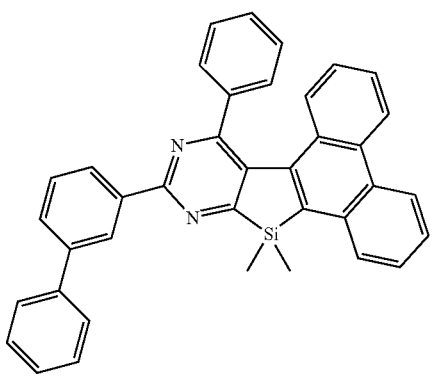

-continued
I-29
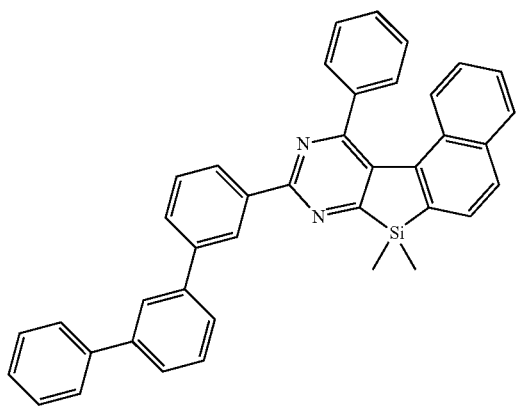
I-30
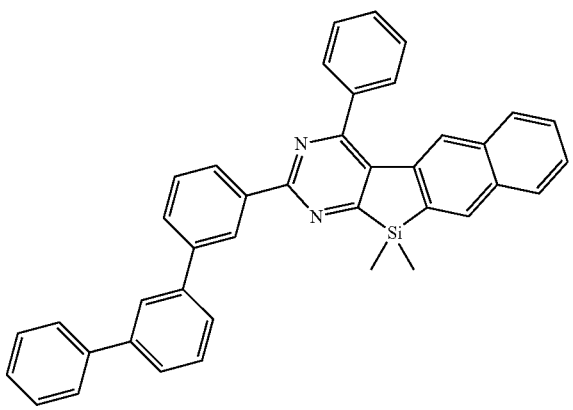
I-31
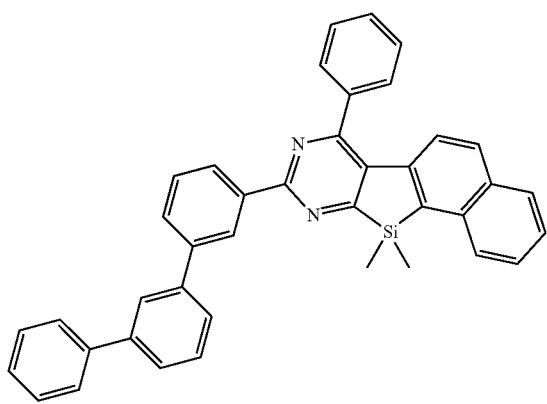
I-32
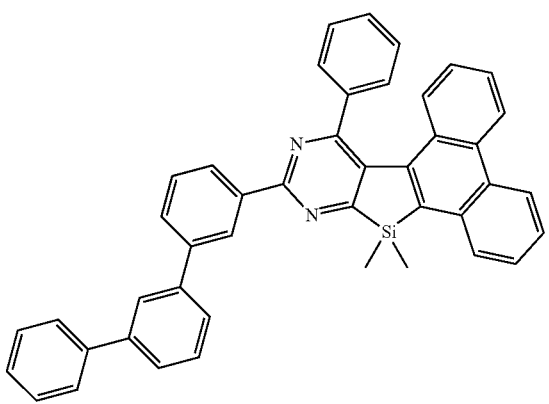
I-33
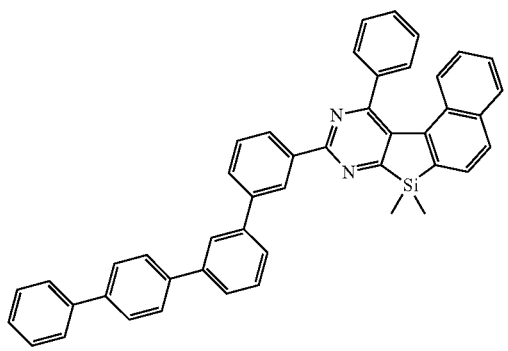
I-34
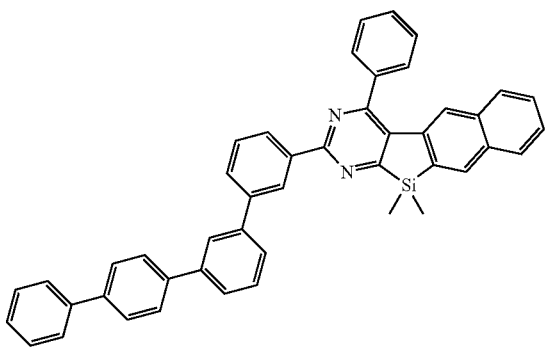
I-35
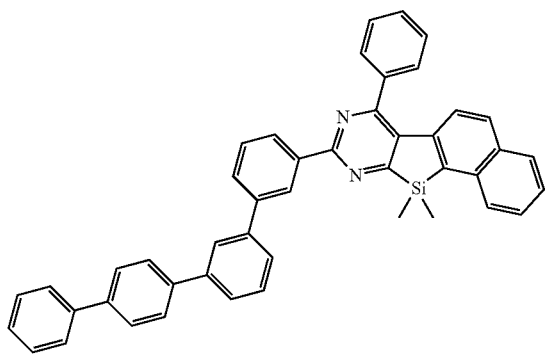
I-36
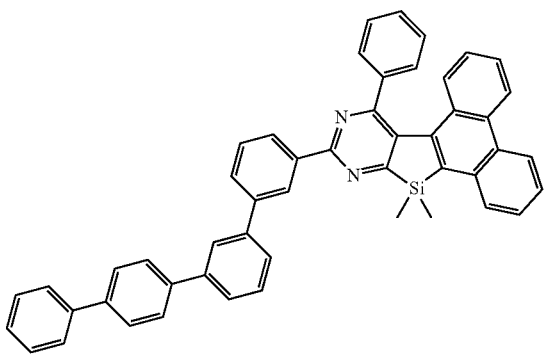

-continued
I-37
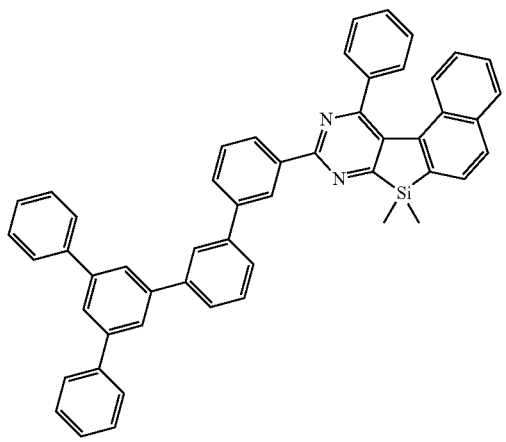
I-38
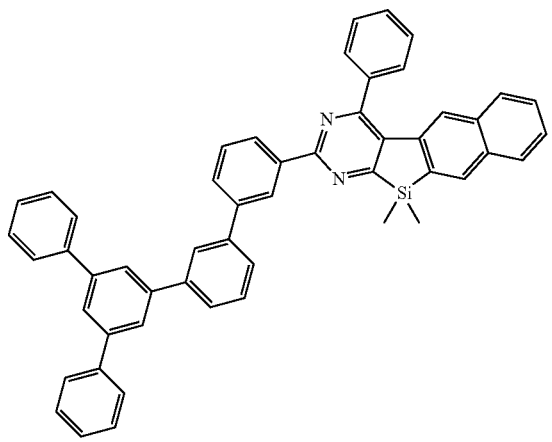
I-39
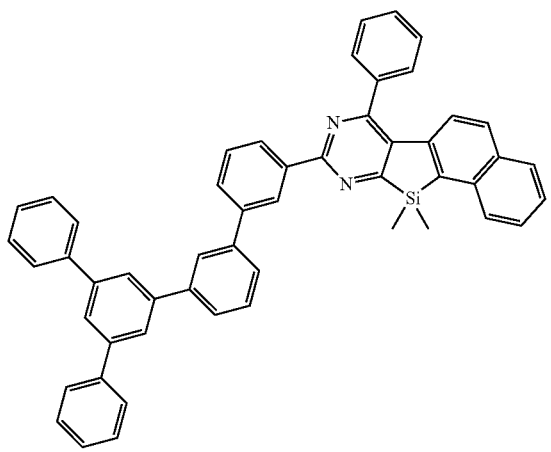
I-40
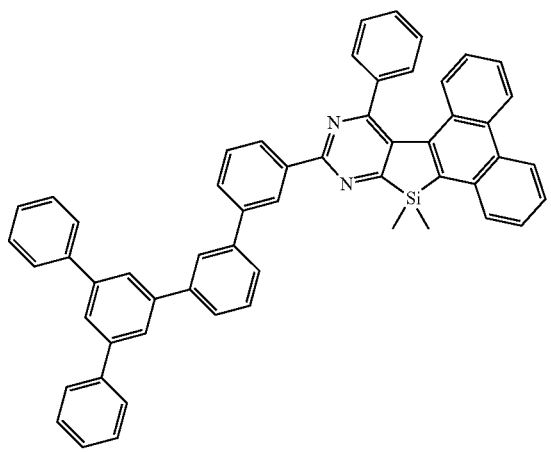
I-41
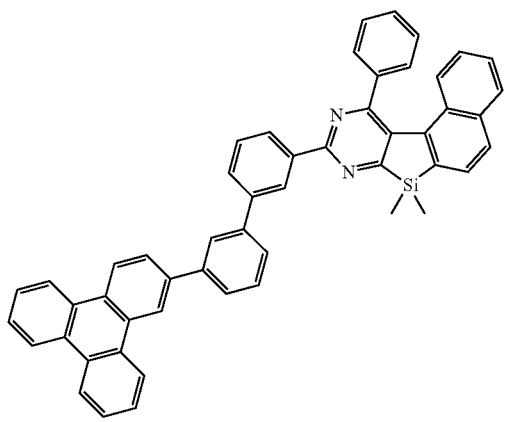
I-42
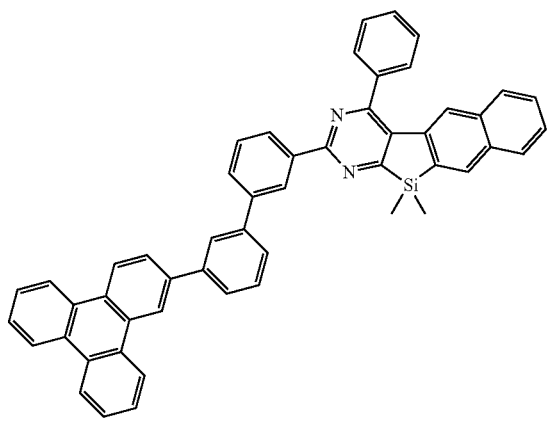

-continued
I-43
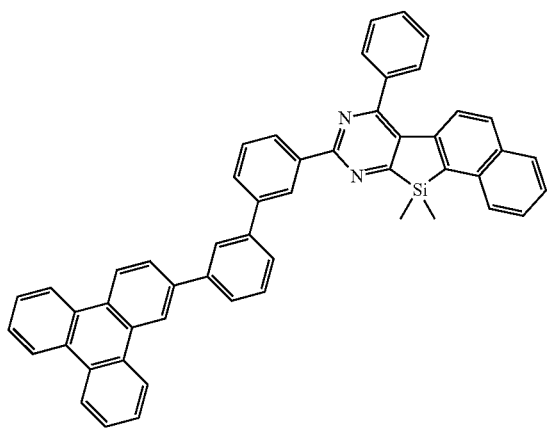
I-44
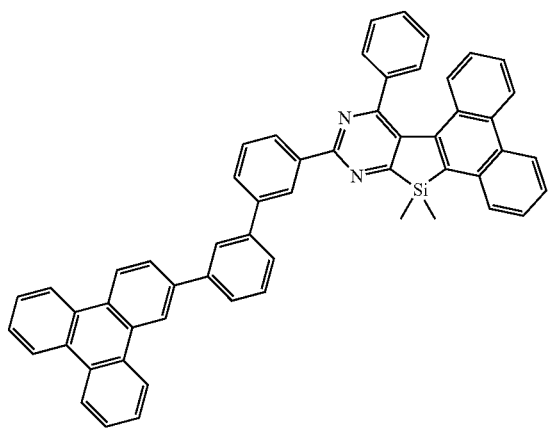
I-45
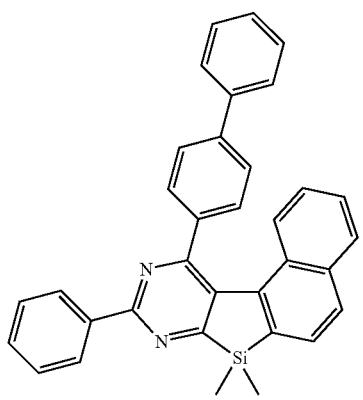
I-46
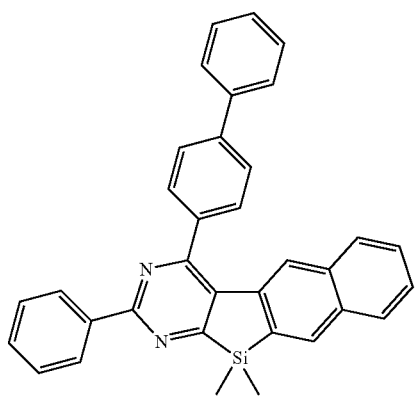
I-47
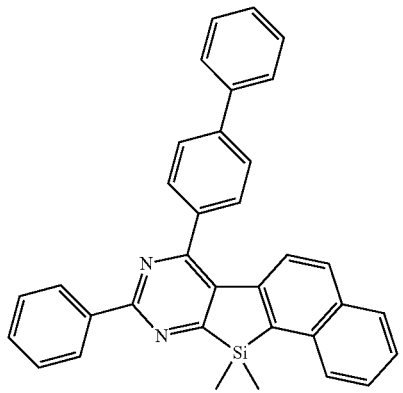
I-48
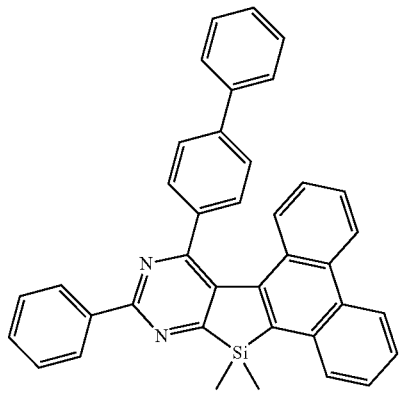
I-49
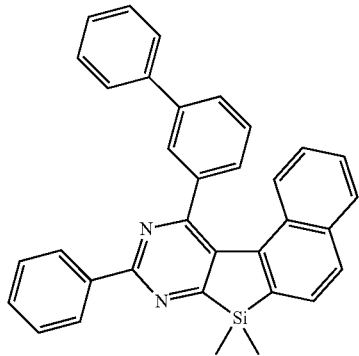
I-50
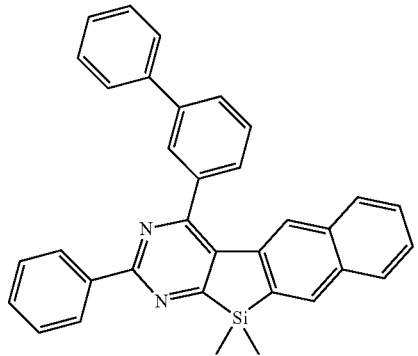

-continued
I-51
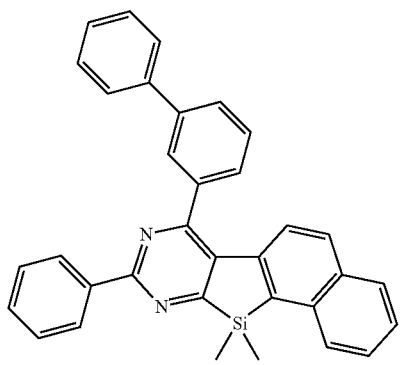
I-52
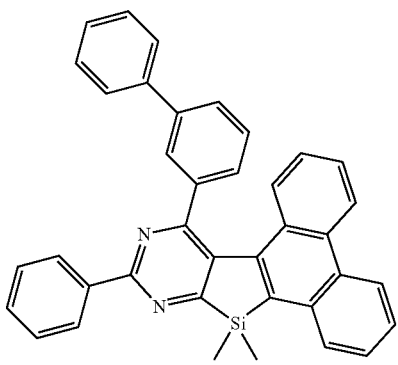
I-53
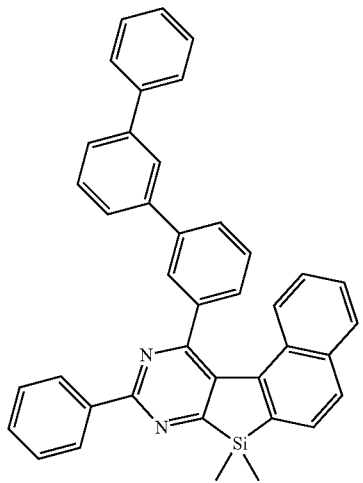
I-54
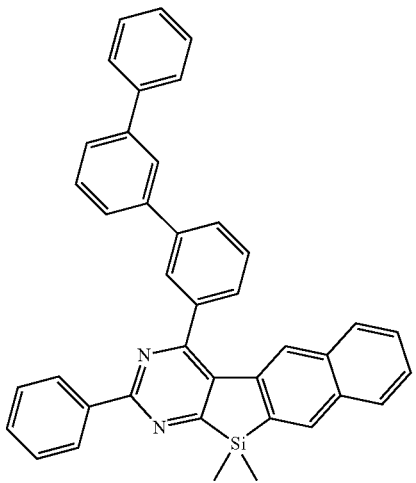
I-55
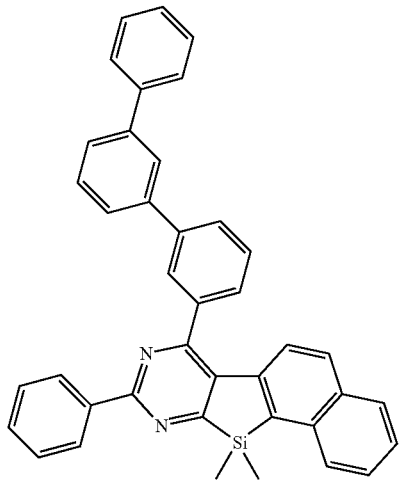
I-56
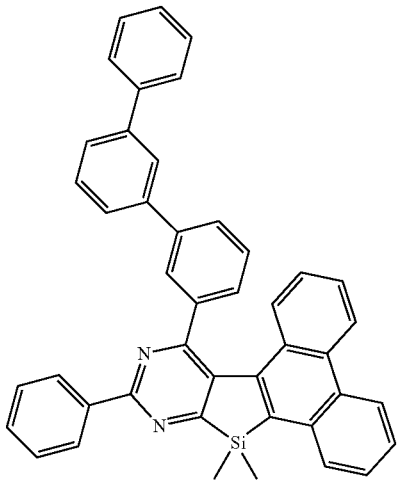

I-57
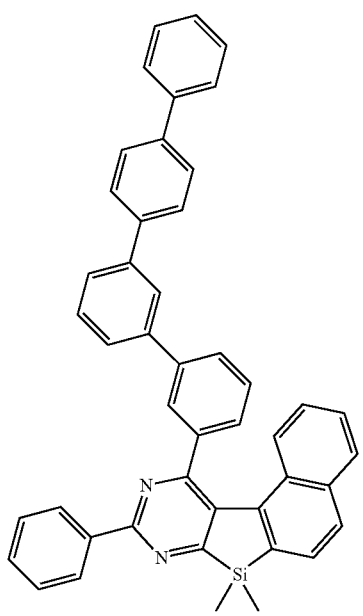
I-58
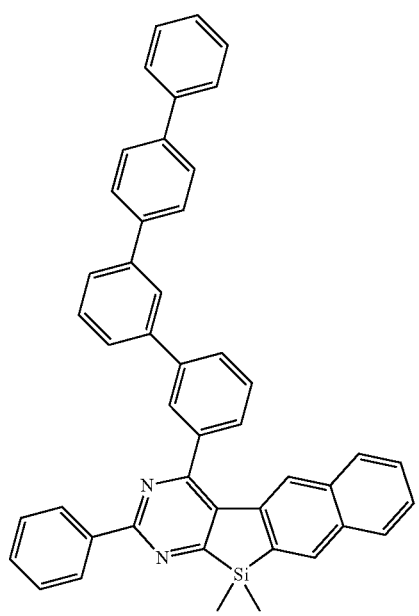
I-59
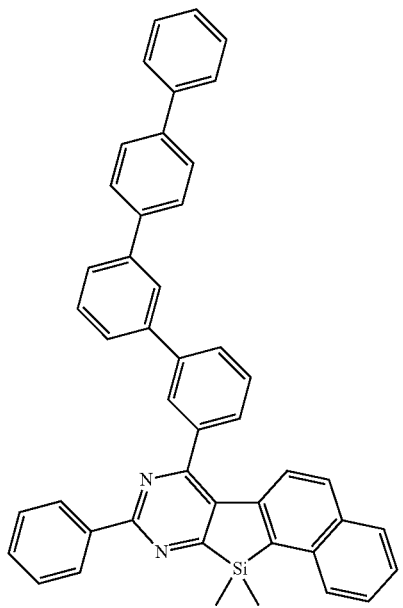
I-60
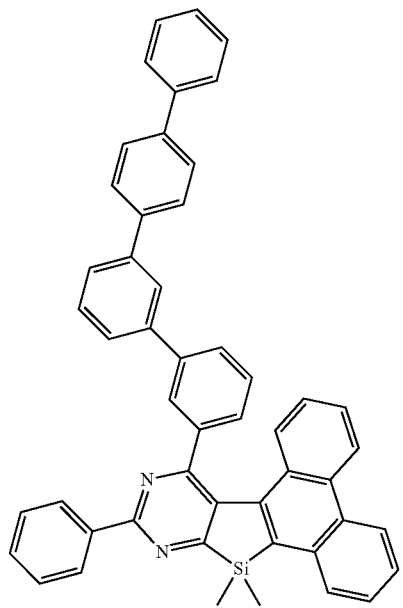

I-61
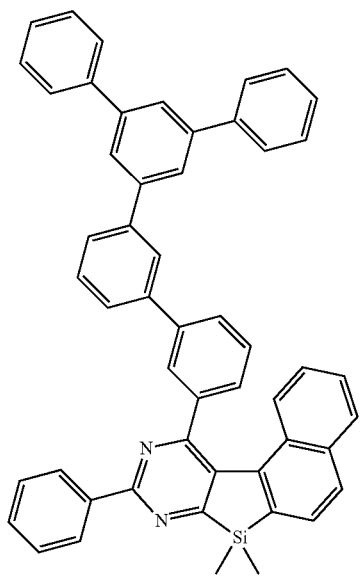
I-62
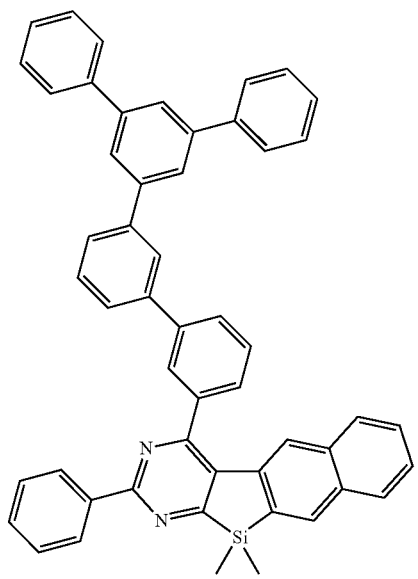
I-63
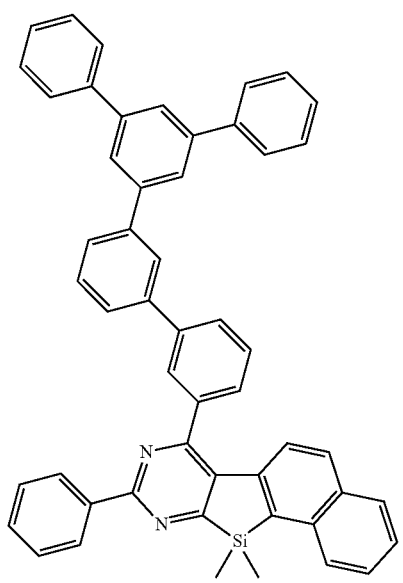
I-64
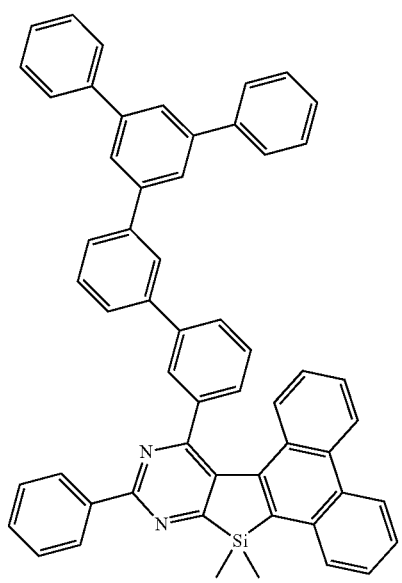

-continued
I-65
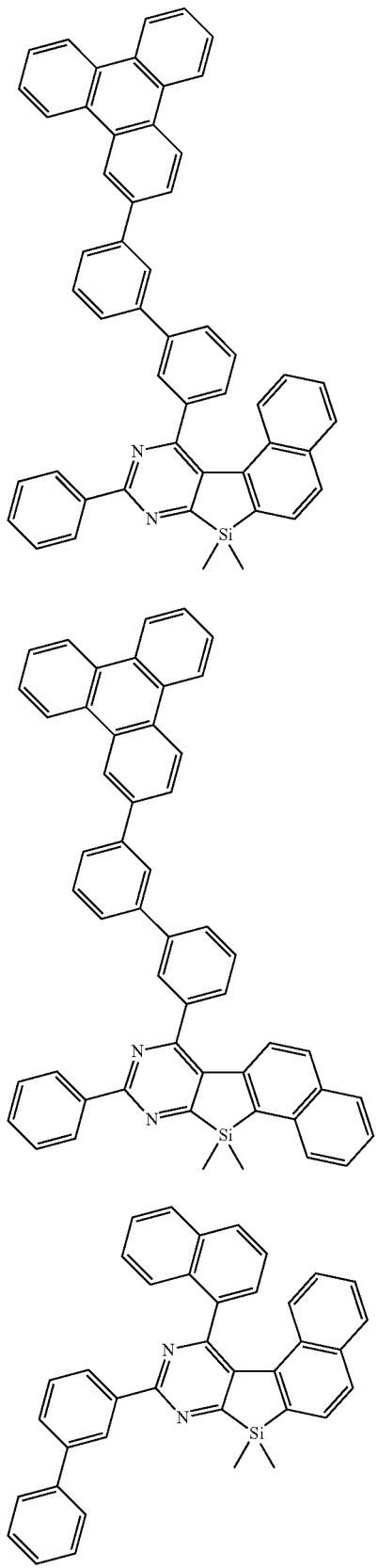
I-66
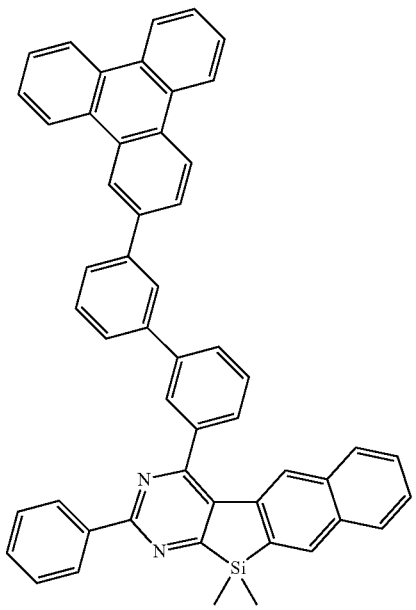
I-67
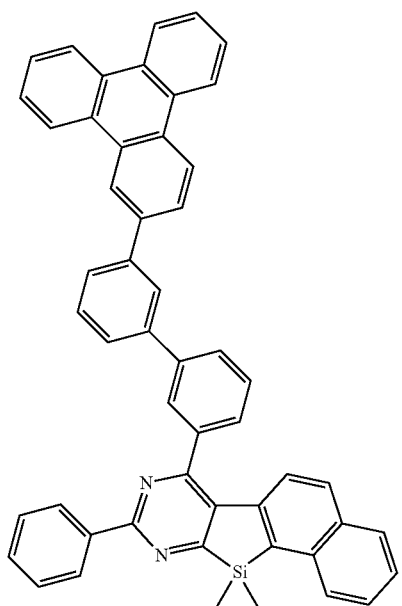
I-68
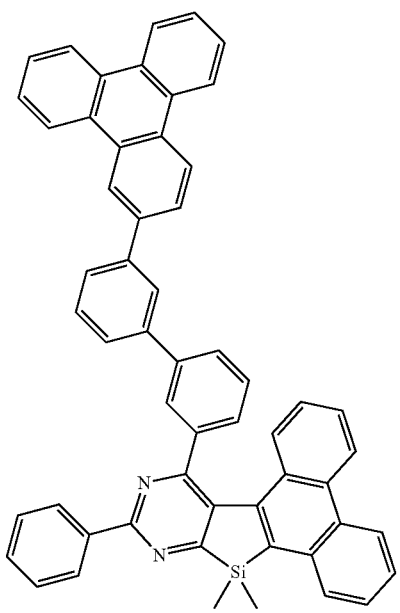
I-69
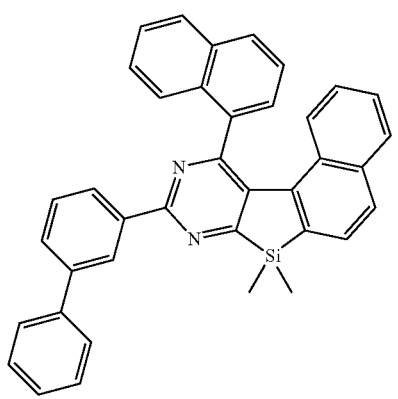
I-70
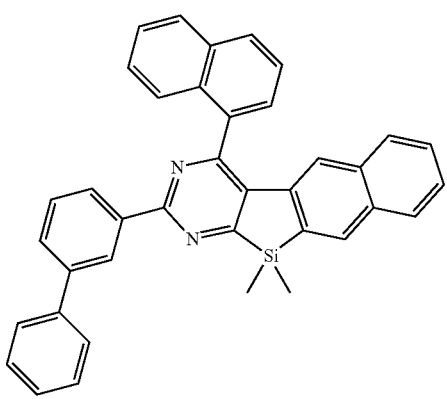

-continued
I-71
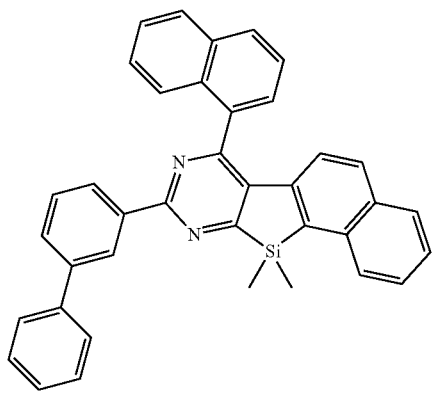
I-72
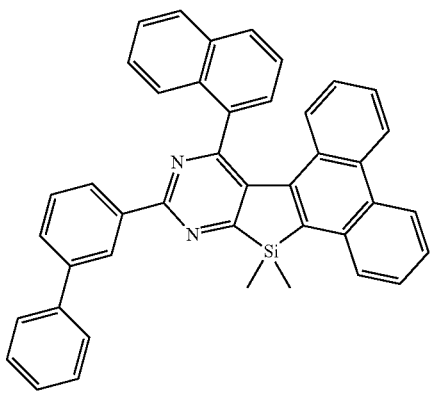
I-73
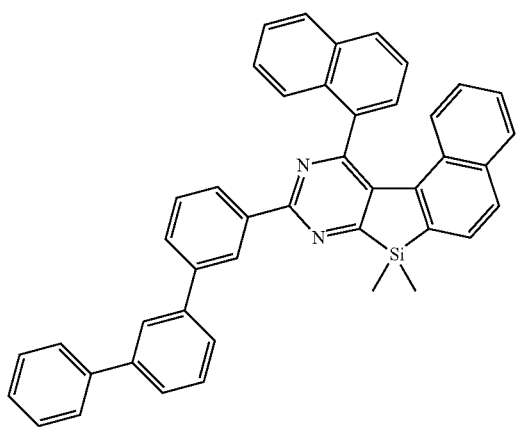
I-74
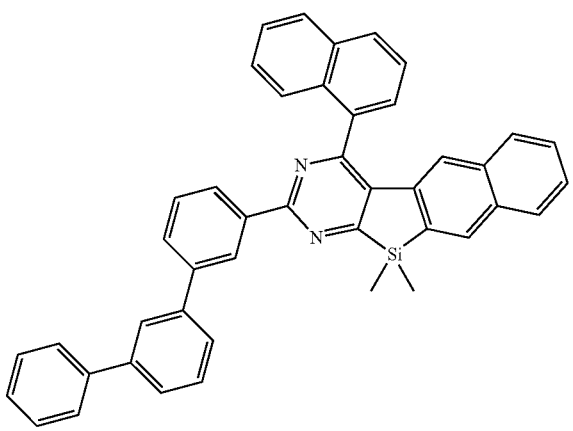
I-75
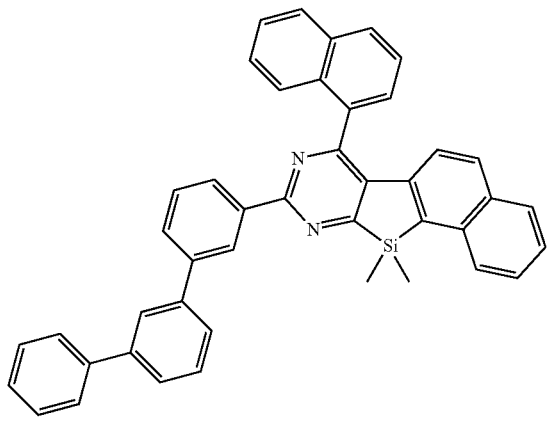
I-76
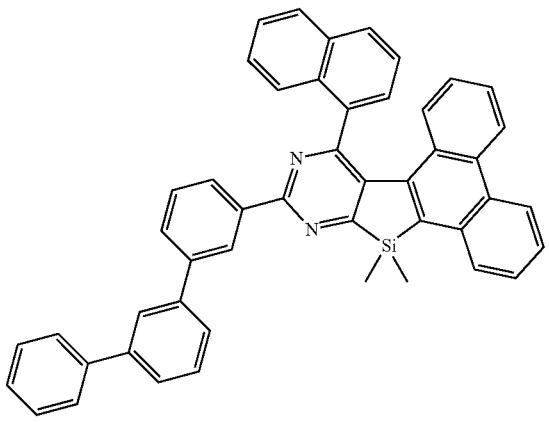
I-77
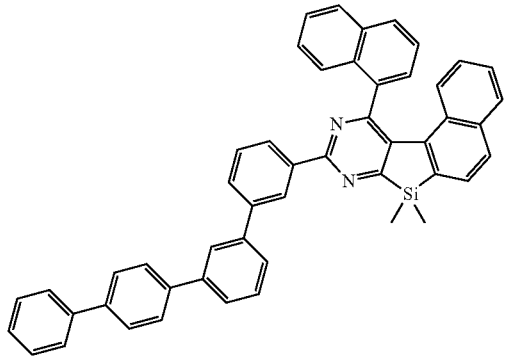
I-78
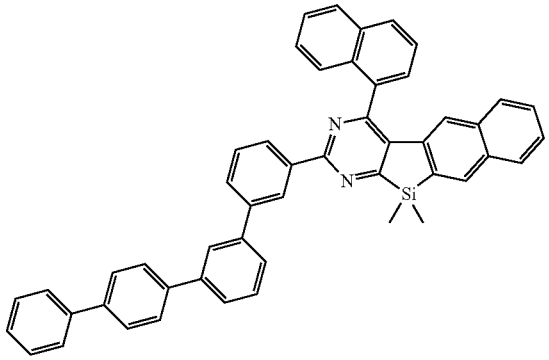

I-79
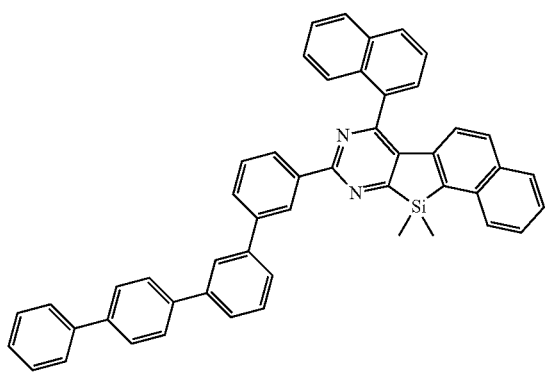
I-80
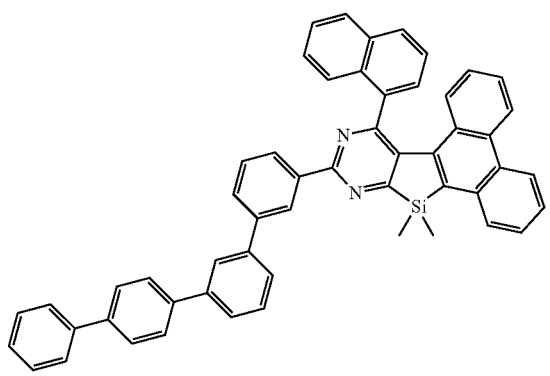
I-81
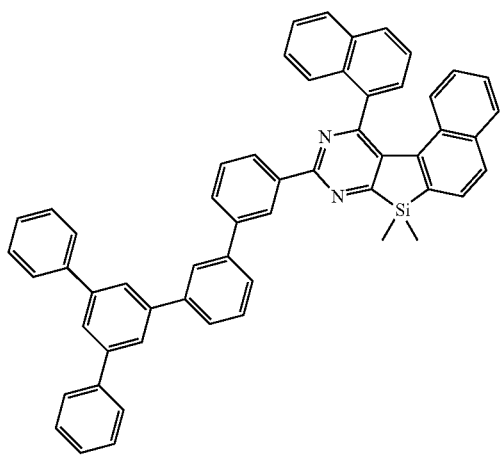
I-82
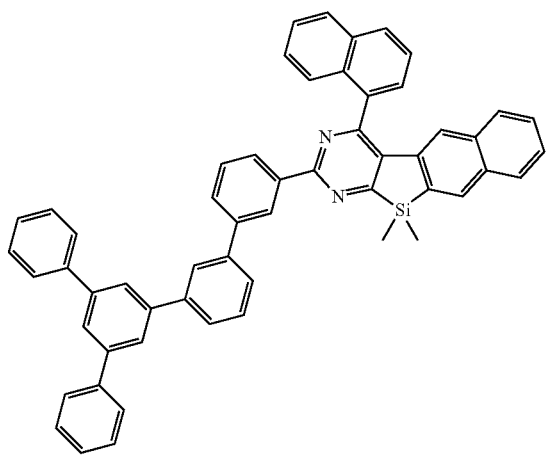
I-83
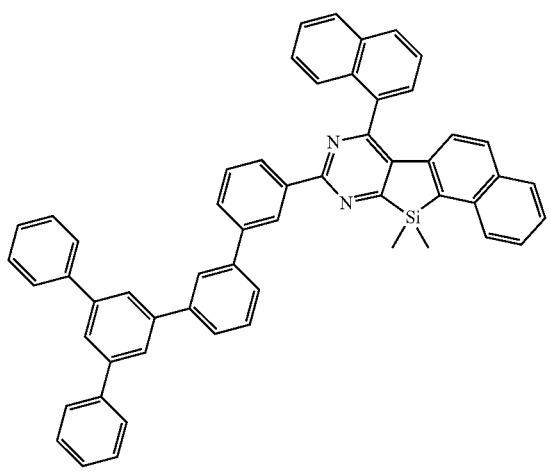
I-84
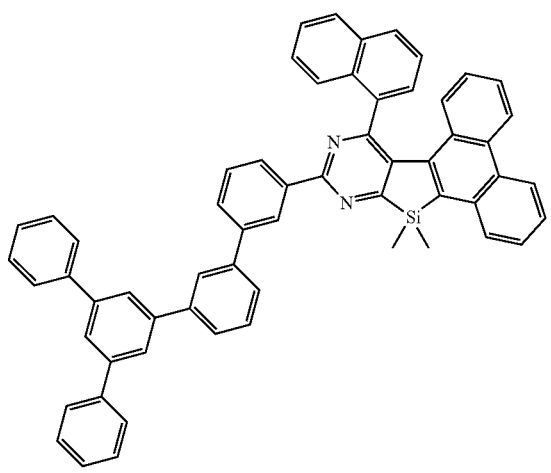

I-85
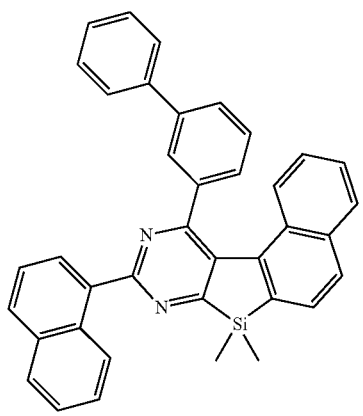
I-86
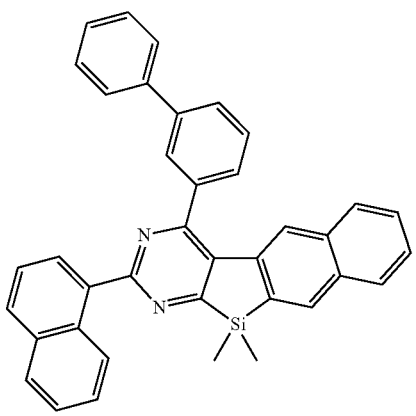
I-87
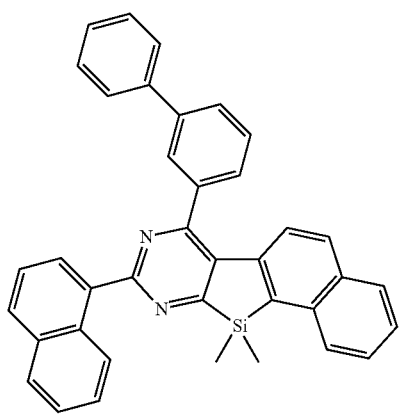
I-88
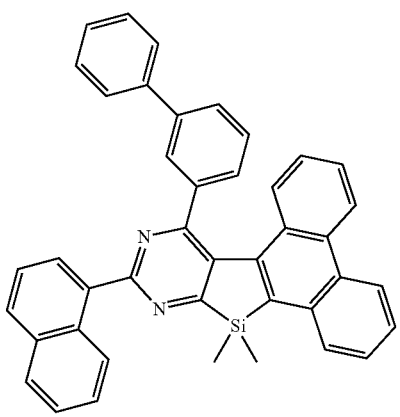
I-89
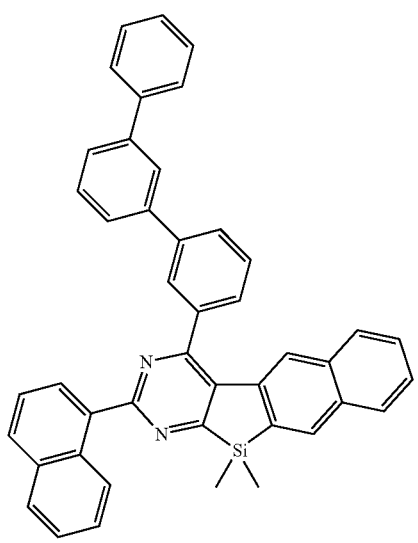
I-90
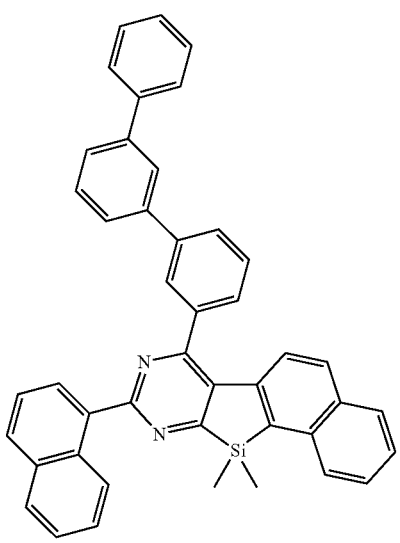

-continued
I-91
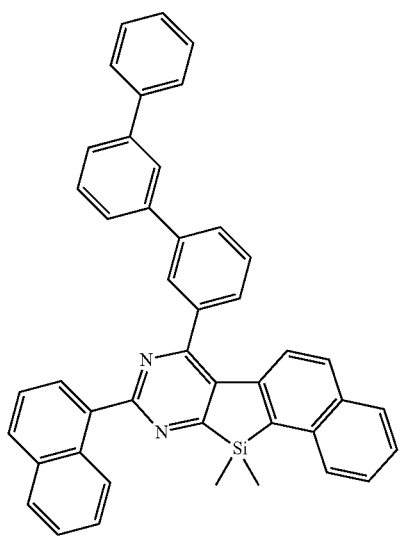
I-92
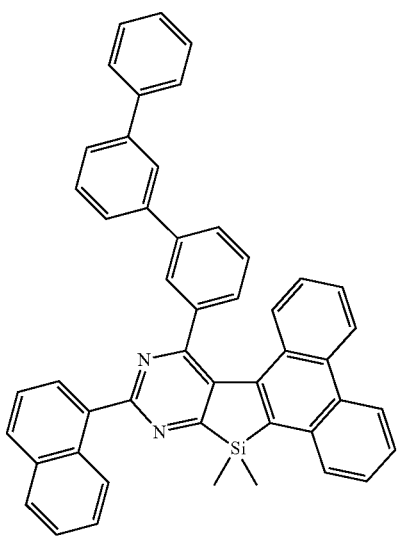
I-93
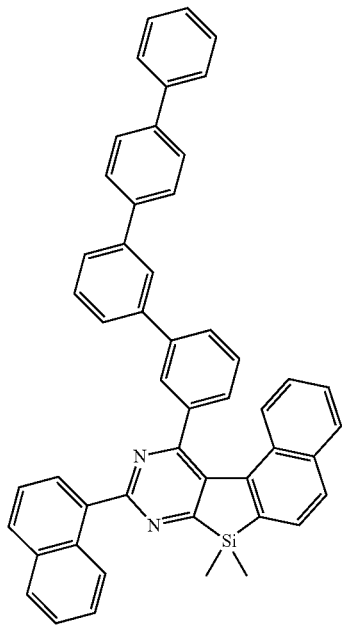
I-94
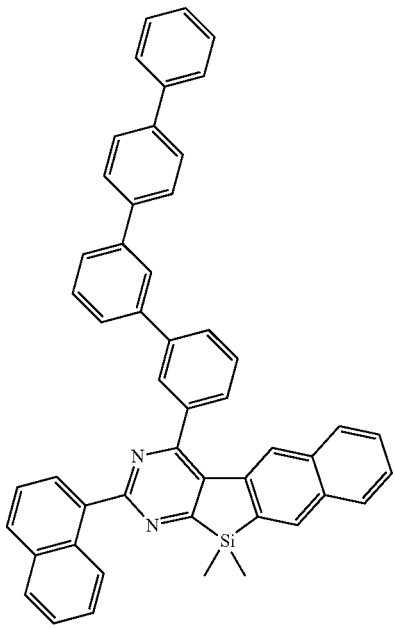

-continued
I-95
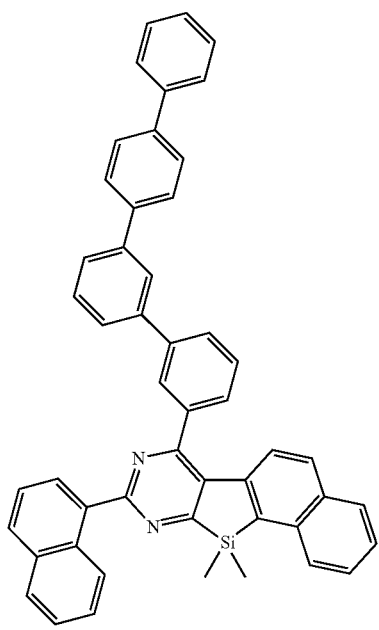
I-96
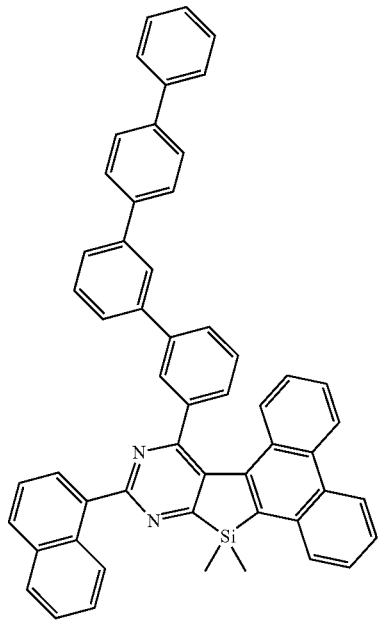
I-97
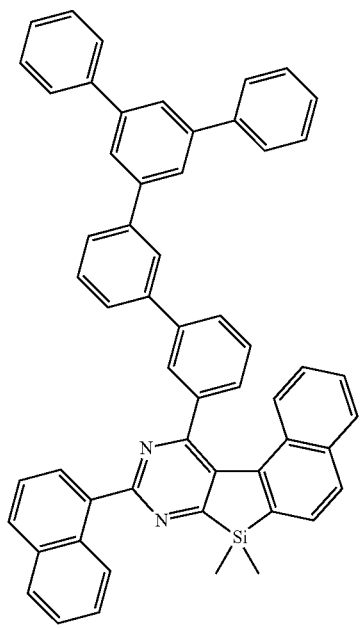
I-98
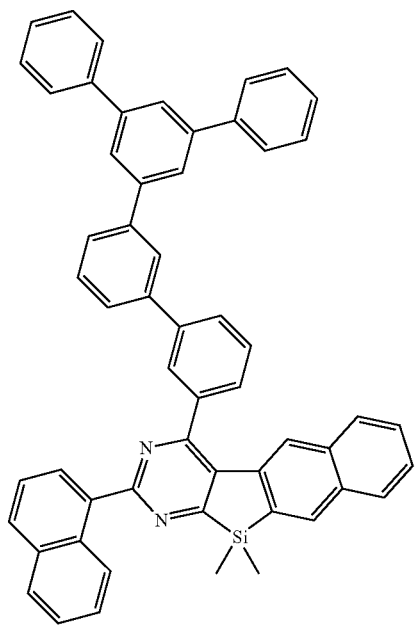

-continued
I-99
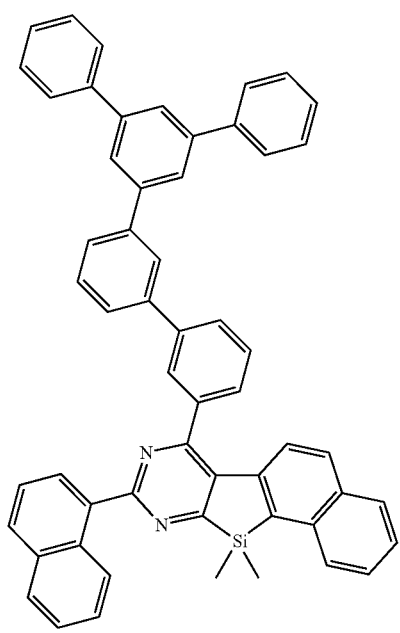
I-100
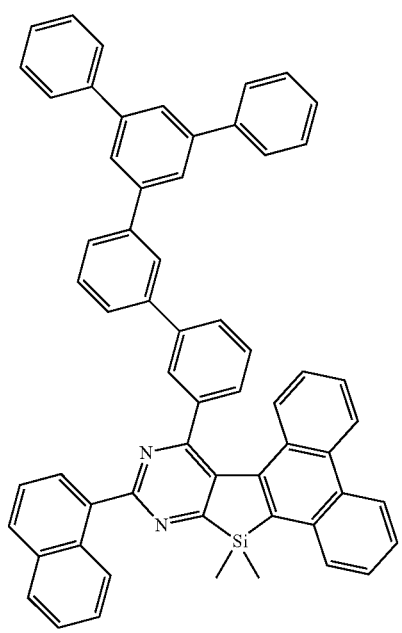
I-101
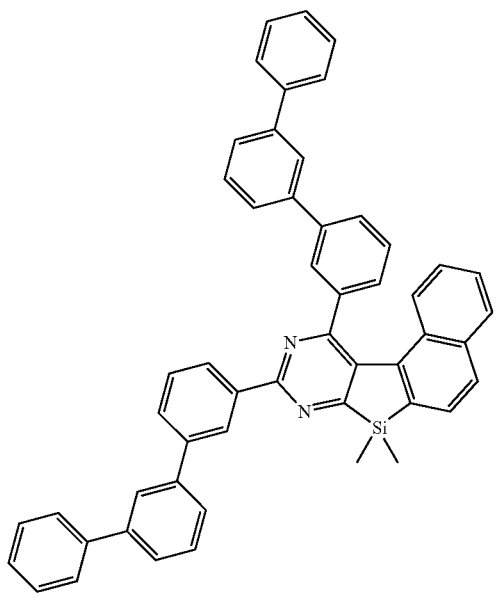
I-102
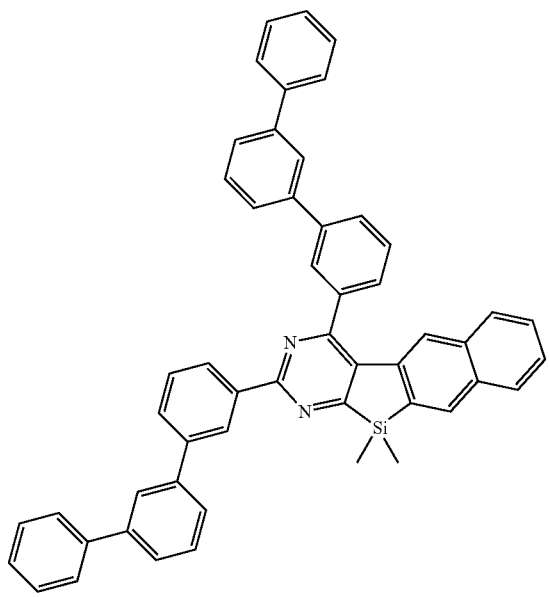

-continued
I-103
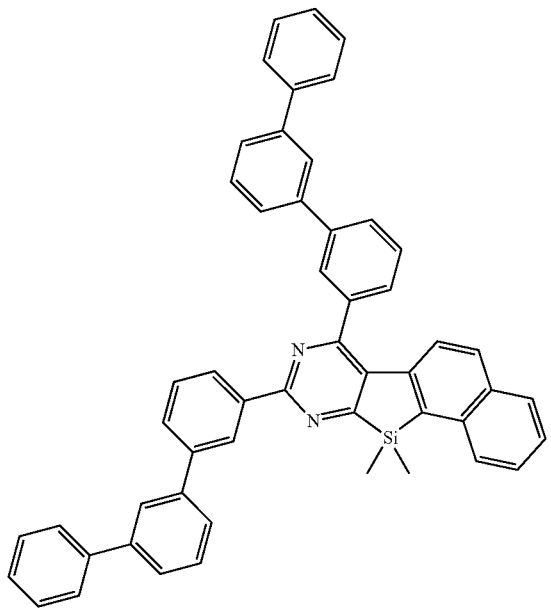
I-104
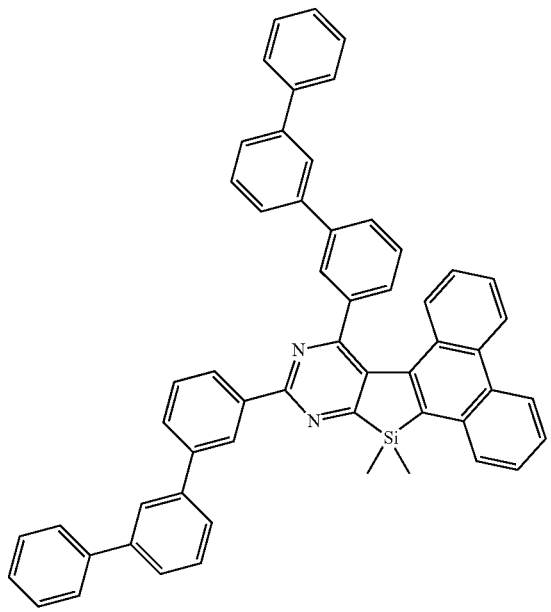
I-105
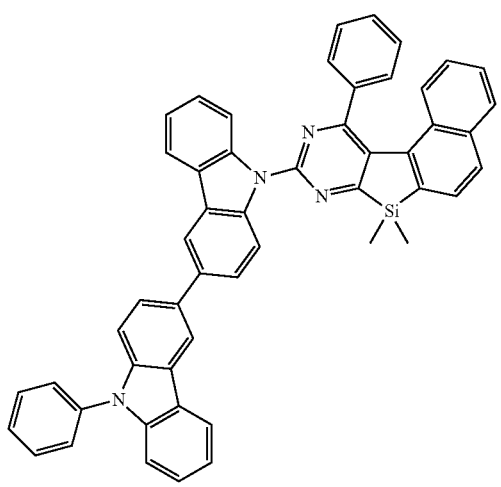
I-106
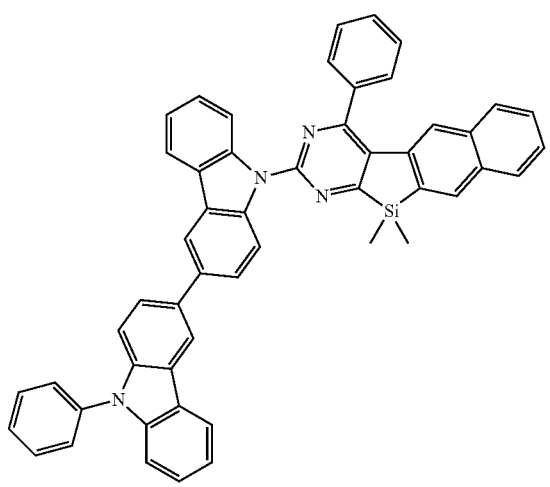
I-107
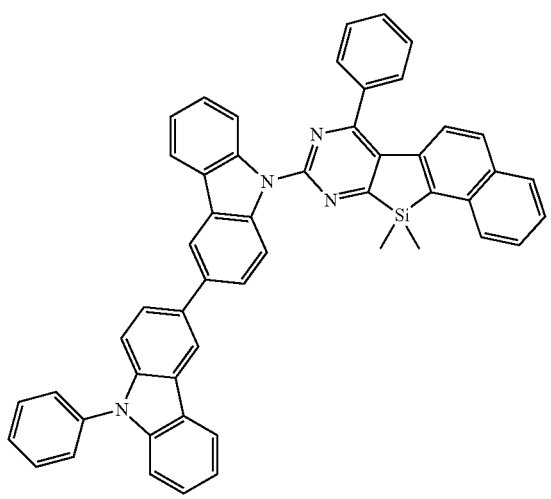
I-108
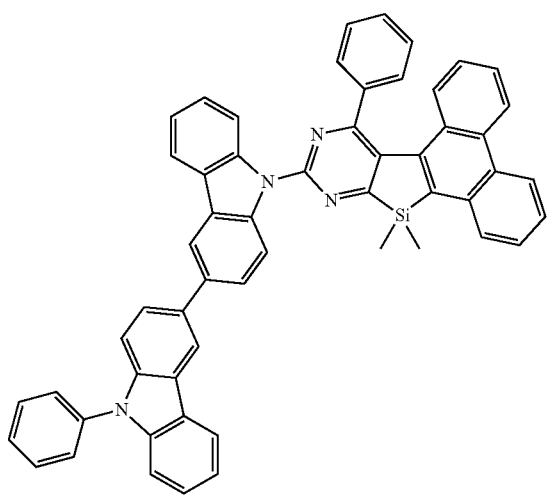

The organic compound may be used for an organic optoelectric device.

Hereinafter, an organic optoelectric device to which the organic compound is applied is described.

The organic optoelectric device may be any device to convert electrical energy into photoenergy and vice versa without particular limitation, and may be, for example an organic photoelectric device, an organic light emitting diode, an organic solar cell, and an organic photo-conductor drum.

The organic optoelectric device includes an anode and a cathode facing each other, and at least one organic layer interposed between the anode and the cathode, wherein the organic layer includes the organic compound.

Herein, an organic light emitting diode as one example of an organic optoelectric device is described referring to drawings.

FIGS. 1 and 2 are cross-sectional views of each organic light emitting diode according to one embodiment.

Referring to FIG. 1, an organic light emitting diode 100 according to one embodiment includes an anode 120 and a cathode 110 facing each other and an organic layer 105 interposed between the anode 120 and cathode 110.

The anode 120 may be made of a conductor having a high work function to help hole injection, and may be for example metal, metal oxide and/or a conductive The anode 120 may be, for example a metal nickel, platinum, vanadium, chromium, copper, zinc, gold, and the like or an alloy thereof; metal oxide such as zinc oxide, indium oxide, indium tin oxide (ITO), indium zinc oxide (IZO), and the like; a combination of metal and oxide such as ZnO and Al or $SnO_2$ and Sb; a conductive polymer such as poly(3-methylthiophene), poly(3,4-(ethylene-1,2-dioxy)thiophene) (PEDOT), polypyrrole, and polyaniline, but is not limited thereto.

The cathode 110 may be made of a conductor having a low work function to help electron injection, and may be for example metal, metal oxide and/or a conductive polymer. The cathode 110 may be for example a metal or an alloy thereof such as magnesium, calcium, sodium, potassium, titanium, indium, yttrium, lithium, gadolinium, aluminum, silver, tin, lead, cesium, barium, and the like; a multi-layer structure material such as LiF/Al, LiO2/Al, LiF/Ca, LiF/Al and $BaF_2$/Ca, but is not limited thereto.

The organic layer 105 includes an emission layer 130.

The emission layer 130 may include, for example the organic compound at alone, a mixture of at least two kinds of the organic compound.

The organic compound may be included as a host of the emission layer 130, for example a phosphorescent host.

The emission layer 130 may further include a dopant. The dopant may be a red, green, or blue dopant, for example a phosphorescent dopant.

The dopant is mixed with the host in a small amount to cause light emission, and may be generally a material such as a metal complex that emits light by multiple excitation into a triplet or more. The dopant may be, for example an inorganic, organic, or organic/inorganic compound, and one or more kinds thereof may be used.

The phosphorescent dopant may be an organic metal compound including Ir, Pt, Os, Ti, Zr, Hf, Eu, Tb, Tm, Fe, Co, Ni, Ru, Rh, Pd or a combination thereof. The phosphorescent dopant may be, for example a compound represented by the following Chemical Formula Z, but is not limited thereto.

$L_2MX$ [Chemical Formula Z]

In the Chemical Formula Z, M is a metal, and L and X are the same or different, and are a ligand to form a complex compound with M.

The M may be, for example Ir, Pt, Os, Ti, Zr, Hf, Eu, Tb, Tm, Fe, Co, Ni, Ru, Rh, Pd or a combination thereof, and the L and X may be, for example a bidendate ligand.

Referring to FIG. 2, the organic light emitting diode 200 further include a hole auxiliary layer 140 as well as an emission layer 130. The hole auxiliary layer 140 may increase hole injection and/or hole mobility between the anode 120 and the emission layer 230, and block electrons. The hole auxiliary layer 140 may be, for example a hole transport layer (HTL), a hole injection layer (HIL) and/or an electron blocking layer (EBL), and may include at least one layer.

In addition, in one embodiment of the present invention, in FIG. 1 or FIG. 2, the organic light emitting diode may further include an electron transport layer (ETL), an electron injection layer (EIL), a hole injection layer (HIL), and the like, in the organic layer 105.

The organic compound may be included in at least one of the electron transport layer (ETL) and the electron injection layer (EIL) besides the emission layer 130.

The organic light emitting diodes 100 and 200 may be manufactured by forming an anode or a cathode on a substrate, forming an organic layer in accordance with a dry coating method such as evaporation, sputtering, plasma plating, and ion plating, and forming a cathode or an anode thereon.

The organic light emitting diode may be applied to an organic light emitting diode display.

[Mode for Invention]

Hereinafter, the embodiments are illustrated in more detail with reference to examples. These examples, however, are not in any sense to be interpreted as limiting the scope of the invention.

Synthesis Example of Organic Compound

Example 1: Synthesis of Intermediate M-6

An intermediate M-6 was synthesized as specific examples of a compound according to the present invention through six steps in the following Reaction Scheme 1.

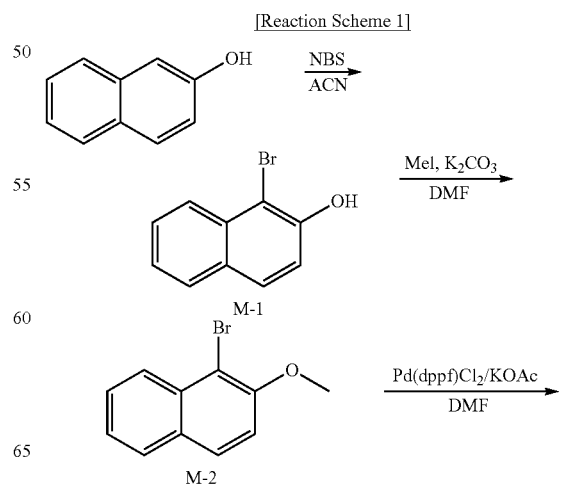

[Reaction Scheme 1]

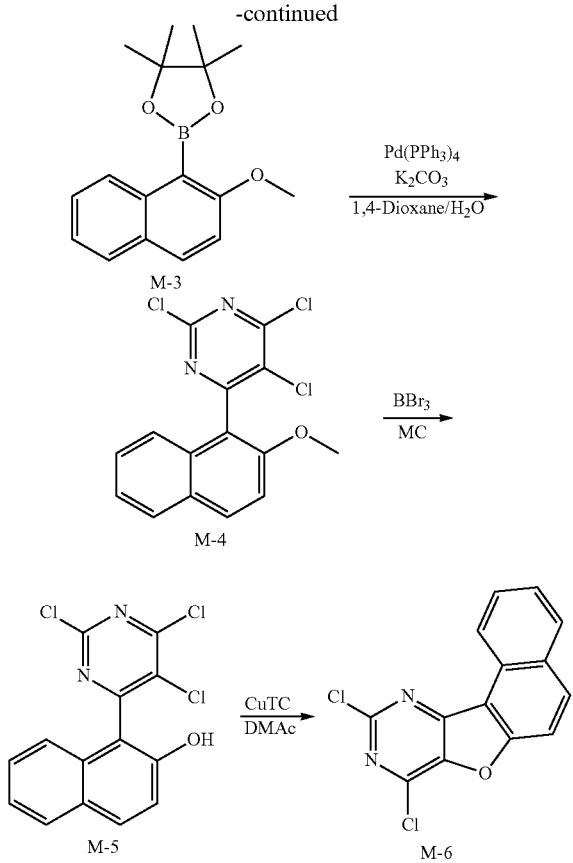

First Step: Synthesis of Intermediate Product (M-1)

50.0 g (437.9 mmol) of naphthalene-2-ol and 77.9 g (437.9 mmol) of N-bromosuccinimide (NBS) were added to 600 ml of acetonitrile in a 1000 mL flask, and the mixture was agitated for 12 hours at room temperature under a nitrogen stream. The obtained mixture was added to 3000 mL of distilled water, and a solid crystallized therein was dissolved in 1,2-dichloromethane, filtered with silica gel/Celite, and then, recrystallized with methanol after removing an organic solvent in an appropriate amount therefrom, obtaining an intermediate M-1 (87.1 g, a yield of 89%).

calcd. C10H7BrO: C, 53.84; H, 3.16; Br, 35.82; O, 7.17. found: C, 53.82; H, 3.11; Br, 35.63; O, 7.11.

Second Step: Synthesis of Intermediate Product (M-2)

77.0 g (345.2 mmol) of the intermediate M-1 and 95.4 g (690.4 mmol) of potassium carbonate were added to 1000 mL of N,N-dimethyl formamide in a 2000 mL flask, and 32.2 ml (517.7 mmol) of methyliodide (MeI) were slowly in a dropwise fashion at 0° C. Then, the mixture was agitated at room temperature for 12 hours under a nitrogen stream. The obtained mixture was added to 3000 mL of distilled water, and a solid crystallized therein was filtered, obtaining an intermediate M-2 (101.1 g, a yield of 83%).

calcd. C11H9BrO: C, 55.72; H, 3.83; Br, 33.70; O, 6.75. found: C, 55.36; H, 3.71; Br, 33.29; O, 6.46.

Third Step: Synthesis of Intermediate Product (M-3)

80.0 g (337.4 mmol) of the intermediate M-2, 102.8 g (404.9 mmol) of 4,4,4',4',5,5,5',5'-octamethyl-2,2'-bi-1,3,2-dioxaborolane, 16.57 g (20.3 mmol) of [1,1'-bis(diphenylphosphino)ferrocene]dichloropalladium (II) (Pd(dppf)Cl₂), and 99.4 g (1012.3 mmol) of potassium acetate (KOAc) were added to 1000 mL of toluene in a 2000 mL flask, and the mixture was heated at 110° C. for 12 hours under a nitrogen stream. The obtained mixture was added to 2000 mL of methanol, and a solid crystallized therein was filtered, obtaining an intermediate M-3 through column chromatography (38.0 g, a yield of 40%).

calcd. C17H21BO3: C, 71.86; H, 7.45; B, 3.80; O, 16.89. found: C, 71.36; H, 7.18; B, 3.53; O, 16.27.

Fourth Step: Synthesis of Intermediate Product (M-4)

38.0 g (174.4 mmol) of the intermediate M-3, 52.0 g (183.1 mmol) of 2,4,5,6-tetrachloropyrimidine, 60.2 g (436.0 mmol) of potassium carbonate, and 10.1 g (8.7 mmol) of tetrakis (triphenylphosphine)palladium (Pd(PPh₃)₄) were added to 600 mL of 1,4-dioxane and 300 mL of water in a 2000 mL flask, and the mixture was heated at 65° C. for 12 hours under a nitrogen stream. The obtained mixture was added to 1000 1000 mL of methanol, and a solid crystallized therein was filtered, dissolved in monochlorobenzene, filtered with silica gel/Celite, and then, recrystallized with methanol after removing an organic solvent in an appropriate amount, obtaining an intermediate M-4 (46.6 g, a yield of 75%).

calcd. C15H9Cl3N2O: C, 53.05; H, 2.67; Cl, 31.32; N, 8.25; O, 4.71. found: C, 52.95; H, 2.34; Cl, 31.15; N, 8.20; O, 4.64.

Fifth Step: Synthesis of Intermediate Product (M-5)

46.0 g (135.5 mmol) of the intermediate M-4 was dissolved in 500 mL of dichloromethane (MC) in a 2000 mL flask, and 270 mL (270.0 mmol) of boranetribromide (BBr₃) was slowly added thereto in a dropwise fashion while the solution was maintained at 0° C. When the reaction was complete, the mixture was washed with a sodium thiosulfate aqueous solution, and an organic solvent was removed therefrom, obtaining an intermediate M-5 (32.3 g, a yield of 80%).

calcd. C14H7Cl3N2O: C, 51.65; H, 2.17; Cl, 32.67; N, 8.60; O, 4.91. found: C, 51.46; H, 2.05; Cl, 32.53; N, 8.41; O, 4.38.

Sixth Step: Synthesis of Intermediate Product (M-6)

32.0 g (98.3 mmol) of the intermediate M-5 and 24.4 g (127.8 mmol) of copper (I) thiophene-2-carboxylate (CuTC) were added to 500 mL of N,N-dimethylacetamide (DMAc) in a 1000 mL flask, and the mixture was refluxed at 190° C. for 48 hours. After After removing an organic solvent from the mixture, an intermediate M-6 (24.7 g, a yield of 87%) was obtained through column chromatography.

calcd. C14H6Cl2N2O: C, 58.16; H, 2.09; Cl, 24.53; N, 9.69; O, 5.53. found: C, 58.06; H, 2.01; Cl, 24.49; N, 9.53; O, 5.42.

Example 2: Synthesis of Intermediates N-6, O-6, P-6, Q-6, R-6

Intermediates N-6, O-6, P-6, Q-6, and R-6 as specific examples of a compound according to the present invention were synthesized through the same six steps of [Reaction Scheme2] as Example 1. Herein, N-5, O-5 P-5, Q-5, and R-5 were prepared by respectively using naphthalene-2-thiol, naphthalen-1-ol, naphthalene-1-thiol, phenanthren-9-ol, phenanthren-9-thiol instead of the naphthalen-2-ol as a starting material in the synthesis step 1 of the [Reaction Scheme 1] according to a [Reaction Scheme 1] method.

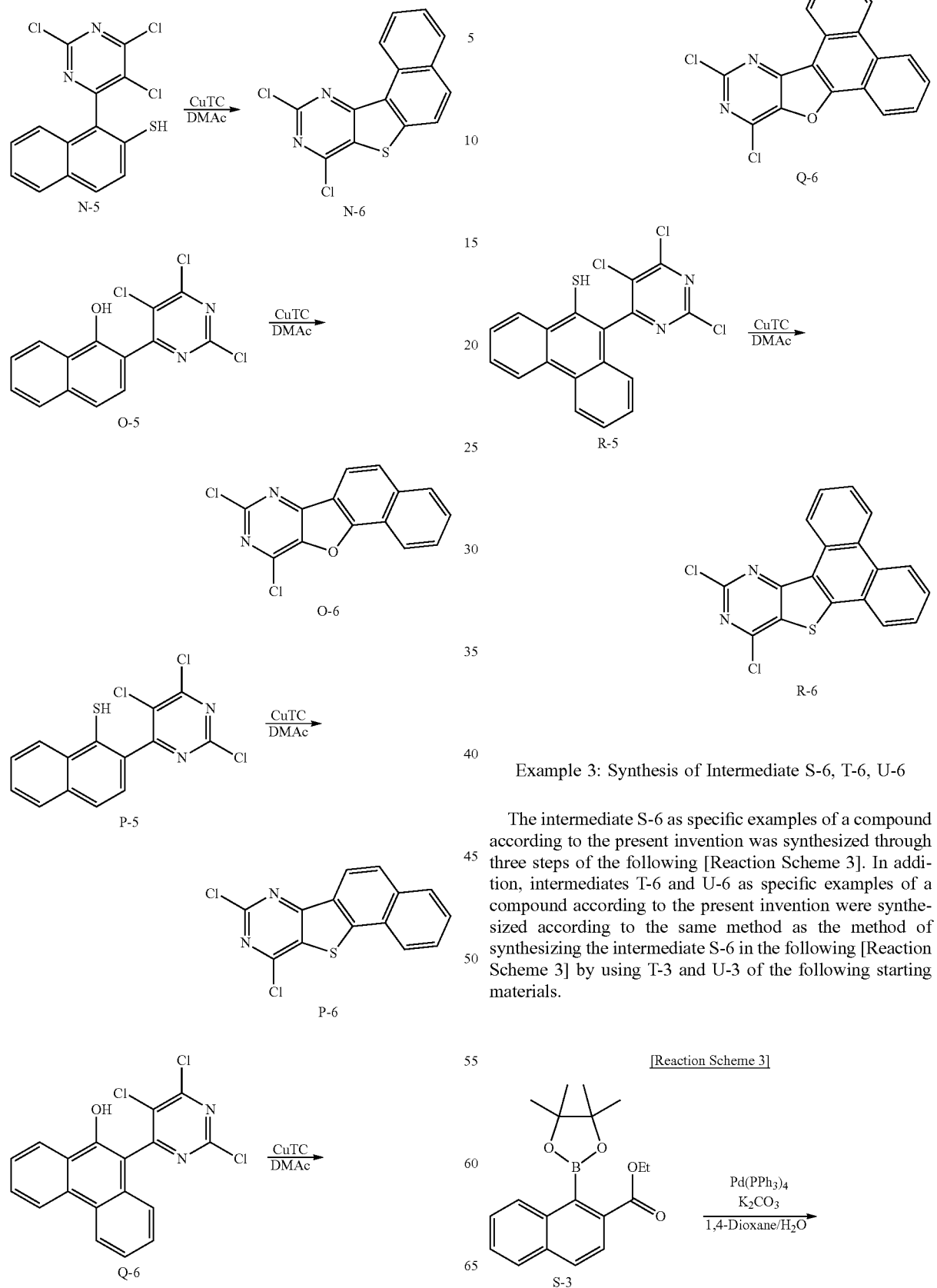

Example 3: Synthesis of Intermediate S-6, T-6, U-6

The intermediate S-6 as specific examples of a compound according to the present invention was synthesized through three steps of the following [Reaction Scheme 3]. In addition, intermediates T-6 and U-6 as specific examples of a compound according to the present invention were synthesized according to the same method as the method of synthesizing the intermediate S-6 in the following [Reaction Scheme 3] by using T-3 and U-3 of the following starting materials.

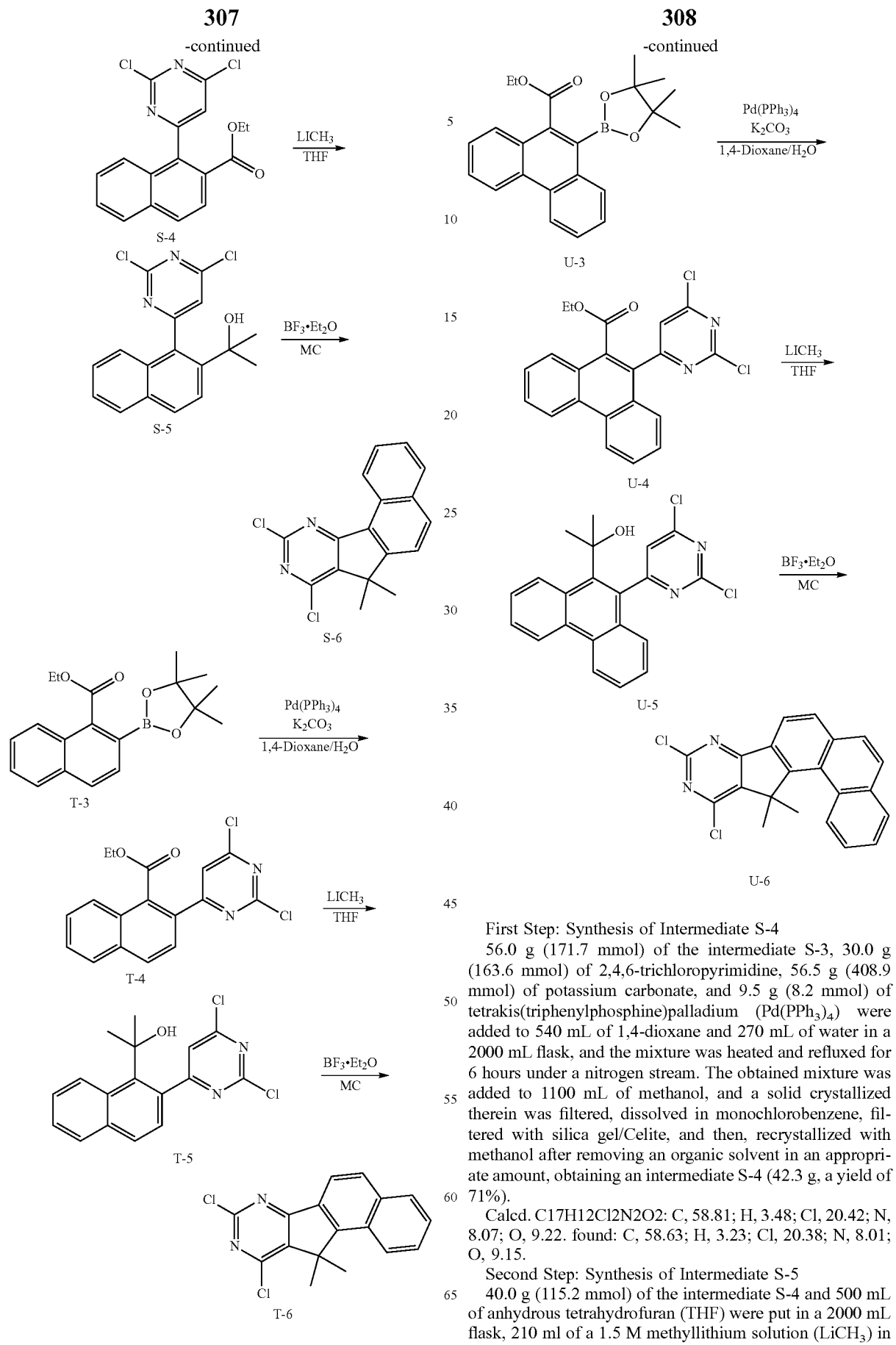

First Step: Synthesis of Intermediate S-4

56.0 g (171.7 mmol) of the intermediate S-3, 30.0 g (163.6 mmol) of 2,4,6-trichloropyrimidine, 56.5 g (408.9 mmol) of potassium carbonate, and 9.5 g (8.2 mmol) of tetrakis(triphenylphosphine)palladium ($Pd(PPh_3)_4$) were added to 540 mL of 1,4-dioxane and 270 mL of water in a 2000 mL flask, and the mixture was heated and refluxed for 6 hours under a nitrogen stream. The obtained mixture was added to 1100 mL of methanol, and a solid crystallized therein was filtered, dissolved in monochlorobenzene, filtered with silica gel/Celite, and then, recrystallized with methanol after removing an organic solvent in an appropriate amount, obtaining an intermediate S-4 (42.3 g, a yield of 71%).

Calcd. C17H12Cl2N2O2: C, 58.81; H, 3.48; Cl, 20.42; N, 8.07; O, 9.22. found: C, 58.63; H, 3.23; Cl, 20.38; N, 8.01; O, 9.15.

Second Step: Synthesis of Intermediate S-5

40.0 g (115.2 mmol) of the intermediate S-4 and 500 mL of anhydrous tetrahydrofuran (THF) were put in a 2000 mL flask, 210 ml of a 1.5 M methyllithium solution ($LiCH_3$) in diethylether was added thereto in a dropwise fashion at −70° C., and the mixture was agitated at the temperature for 2 hours. When the reaction was complete, 100 ml of ice water and then, 300 ml of 50% acetic acid were added thereto. Next, an organic layer was separated therefrom, twice washed with distilled water, dried, and evaporated under vacuum. Then, a colorless solid remaining there was recrystallized with heptane/toluene, obtaining an intermediate S-5 (32.7 g, a yield of 81%).

calcd. C17H14Cl2N2O: C, 61.28; H, 4.23; Cl, 21.28; N, 8.41; O, 4.80. found: C, 61.11; H, 4.03; Cl, 21.24; N, 8.40; O, 4.78.

Third Step: Synthesis of Intermediate S-6

30.0 g (90.0 mmol) of the intermediate S-5 was dissolved in 450 mL of anhydrous 1,2-dichloromethane (MC) in a 1000 mL flask, and 15.0 g (94.5 mmol) of boron trifluoride-diethyletherate (BF$_3$.Et$_2$O) was slowly added thereto in a dropwise fashion for 10 minutes. The mixture was heated up to 50° C. and agitated for 2 hours. The resultant was cooled down to room temperature, distilled water was added thereto, and the mixture was three times extracted with diethylether. Then, an organic layer obtained therefrom was dried with anhydrous magnesium sulfate. After removing a solvent therefrom, a concentrated residue was separated and purified through silica gel chromatography, obtaining an intermediate S-6 (16.7 g, a yield of 55%). calcd. C17H12Cl2N2: C, 64.78; H, 3.84; Cl, 22.50; N, 8.89. found: C, 64.71; H, 3.78; Cl, 22.35; N, 8.62.

Example 4: Synthesis of Intermediates V-6, W-6, X-6

An intermediate V-6 as specific examples of a compound according to the present invention was synthesized through the two steps of the following [Reaction Scheme 4]. In addition, intermediates W-6 and X-6 as specific examples of a compound according to the present invention were synthesized according to the same method as the method of synthesizing the intermediate V-6 of the following [Reaction Scheme 4] by using the W-4 and X-4 as a starting material.

[Reaction Scheme 4]

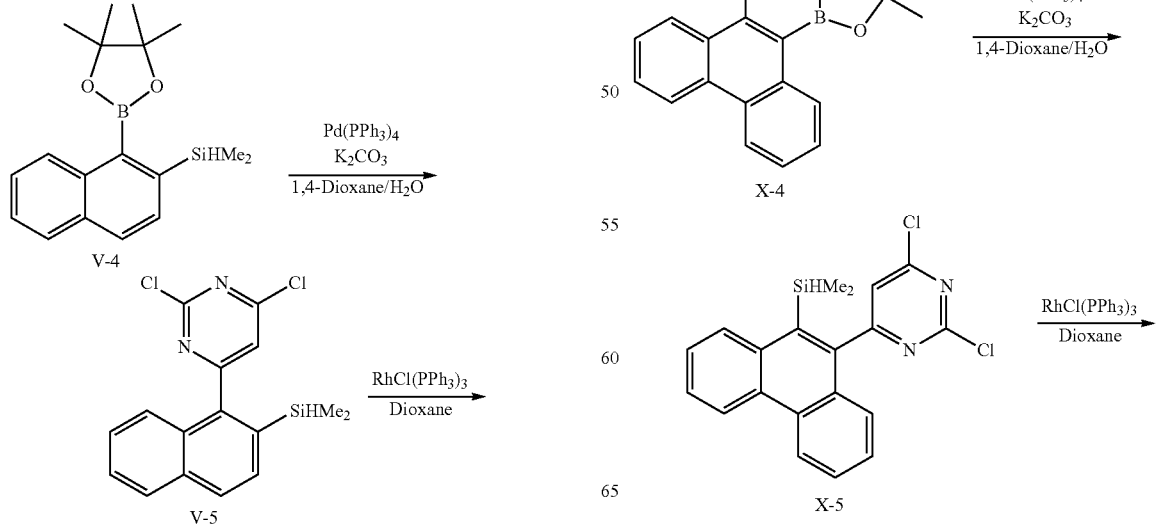

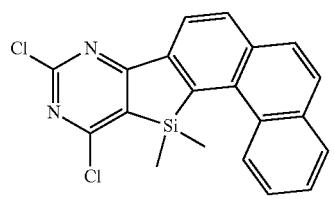

X-6

First Step: Synthesis of Intermediate V-5

53.6 g (171.7 mmol) of the intermediate V-4, 30.0 g (163.6 mmol) of 2,4,6-trichloropyrimidine, 56.5 g (408.9 mmol) of potassium carbonate, and 9.5 g (8.2 mmol) of tetrakis (triphenylphosphine)palladium (Pd(PPh$_3$)$_4$) were added to 540 mL of 1,4-dioxane and 270 mL of water in a 2000 mL flask, and the mixture was heated and refluxed for 8 hours under a nitrogen stream. The obtained mixture was added to 1100 mL of methanol, and a solid crystallized therein was filtered, dissolved in monochlorobenzene, filtered with silica gel/Celite, and then, recrystallized with methanol after removing an organic solvent in an appropriate amount therefrom, obtaining an intermediate V-5 (43.5 g, a yield of 76%).

Calcd. C16H14Cl2N2Si: C, 57.66; H, 4.23; Cl, 21.27; N, 8.41; Si, 8.43. found: C, 57.60; H, 4.21; Cl, 21.19; N, 8.35; Si, 8.39.

Second Step: Synthesis of Intermediate V-6

40.0 g (120.2 mmol) of the intermediate V-5 and 2.2 g (2.4 mmol) of chlorotris(triphenylphosphine)rhodium (I) (RhCl(PPh$_3$)$_3$) were put in a 1000 mL flask, 600 ml of 1,4-dioxane was added thereto in a dropwise fashion, and the mixture was heated and refluxed for 8 hours under a nitrogen stream. When the reaction was complete, the resultant was treated through column chromatography after removing an organic layer therefrom, obtaining an intermediate V-6 (21.87 g, a yield of 55%).

calcd. C16H12Cl2N2Si: C, 58.01; H, 3.65; Cl, 21.40; N, 8.46; Si, 8.48. found: C, 57.89; H, 3.58; Cl, 21.36; N, 8.41; Si, 8.41.

Example 5: Synthesis of Compound A-13

A compound A-13 as specific examples of a compound according to the present invention was synthesized through the following two steps.

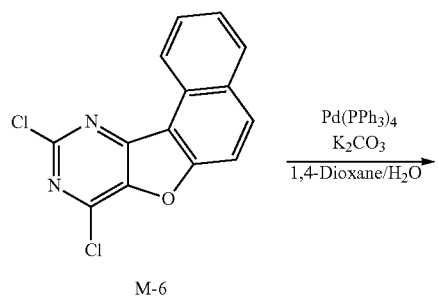

M-6

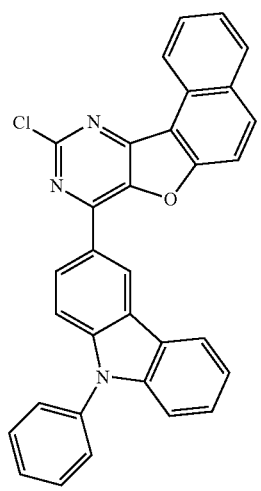

M-6-13

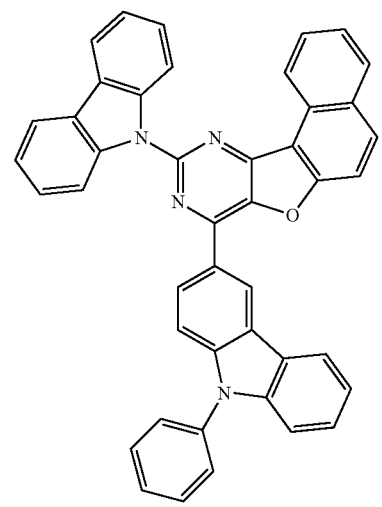

A-13

First Step: Synthesis of Intermediate M-6-13

4.0 g (13.8 mmol) of the intermediate M-6, 5.4 g (14.5 mmol) of phenyl-3-boronic ester-carbazole, 4.8 g (34.6 mmol) of potassium carbonate, and 0.8 g (0.7 mmol) of tetrakis (triphenylphosphine)palladium were added to 50 mL of 1,4-dioxane and 25 Ml of water in a 250 mL flask, and the mixture was heated and refluxed for 6 hours under a nitrogen stream. The obtained mixture was added to 100 mL of methanol, and a solid crystallized therein, dissolved in monochlorobenzene, filtered with silica gel/Celite, and then, recrystallized with methanol after removing an organic solvent in an appropriate amount therefrom, obtaining an intermediate M-6-13 (5.62 g, a yield of 78%).

Calcd. C32H18ClN3O: C, 77.49; H, 3.66; Cl, 7.15; N, 8.47; O, 3.23. found: C, 77.25; H, 3.46; Cl, 7.12; N, 8.45; O, 3.34.

Second Step: Synthesis of Intermediate A-13

5.5 g (11.2 mmol) of the intermediate M-6-13, 1.9 g (11.7 mmol) of carbazole, 2.1 g (22.4 mmol) of sodium t-butoxide, 1.1 g (0.6 mmol) of tris(dibenzylideneacetone) dipalladium (0), and 0.9 mL of tri t-butylphosphine (50% in toluene) were added to 75 mL of xylene in a 250 mL round flask, and the mixture is heated and refluxed for 15 hours under a nitrogen stream. The obtained mixture was added to 200 mL of methanol, and a solid crystallized therein was filtered, dissolved in dichlorobenzene, filtered with silica gel/Celite, and then, recrystallized with methanol after removing an organic solvent in an appropriate amount, obtaining a compound A-13 (5.3 g, a yield of 76%).

calcd. C44H26N4O: C, 84.33; H, 4.18; N, 8.94; O, 2.55.
found: C, 84.32; H, 4.11; N, 8.85; O, 2.49.

Example 6: Synthesis of Compound A-17

A compound A-17 as specific examples of a compound according to the present invention was synthesized through the following first step.

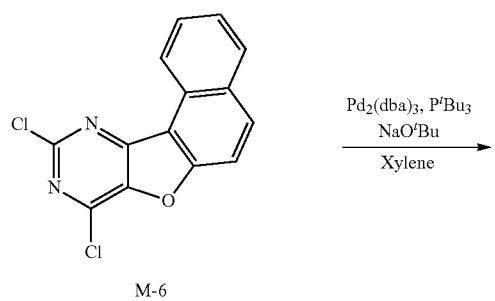

M-6

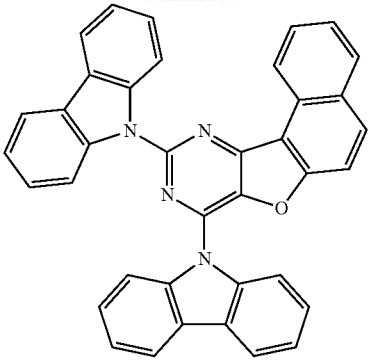

A-17

First Step: Synthesis of Compound A-17

2.3 g (8.0 mmol) of the intermediate M-6, 2.8 g (16.8 mmol) of carbazole, 1.5 g (16.0 mmol) of sodium t-butoxide, 0.5 g (0.8 mmol) of tris(dibenzylideneacetone) dipalladium (0), and 0.6 mL of tri t-butylphosphine (50% in toluene) were added to 50 mL of xylene in a 100 mL round flask, and the mixture was heated and refluxed for 15 hours under a nitrogen stream. The obtained mixture was added to 100 mL of methanol, and a solid crystallized therein was filtered, dissolved in dichlorobenzene, filtered with silica gel/Celite, and then, recrystallized with methanol after removing an organic solvent in an appropriate amount, obtaining a compound A-17 (3.5 g, a yield of 70%).

calcd. C38H22N4O: C, 82.89; H, 4.03; N, 10.18; O, 2.91.
found: C, 82.79; H, 4.01; N, 10.11; O, 2.89.

Example 7: Synthesis of Compound A-33

A compound A-33 as specific examples of a compound according to the present invention was synthesized through the following two steps.

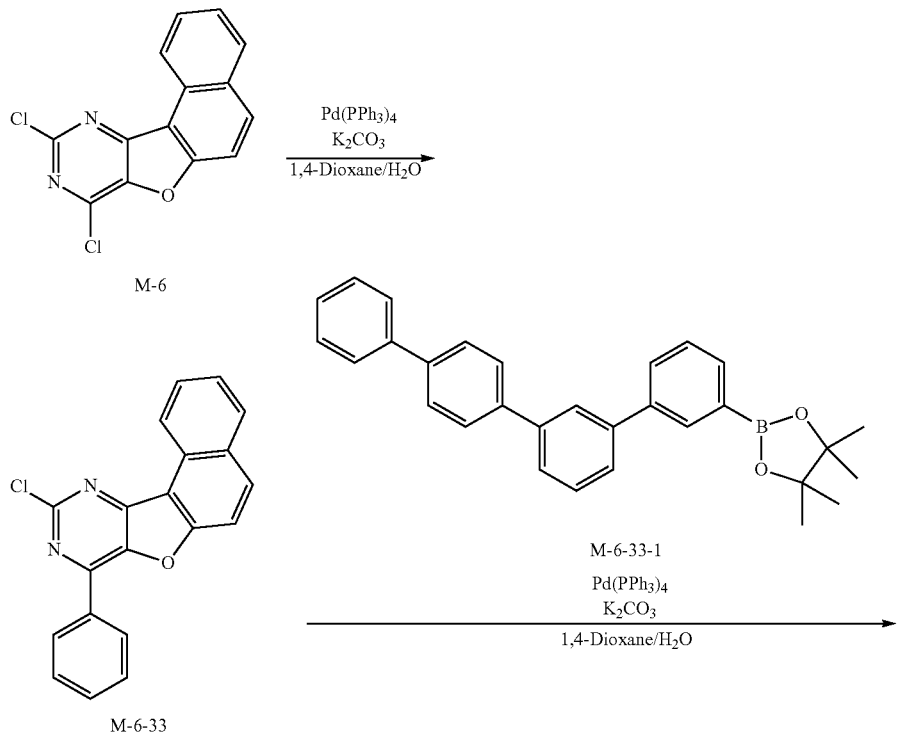

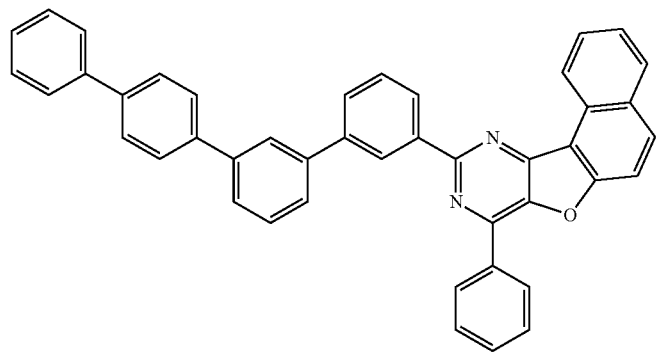

A-33

First Step: Synthesis of Intermediate M-6-33

20.0 g (69.18 mmol) of the intermediate M-6, 8.9 g (72.63 mmol) of phenylboronic acid, 23.9 g (172.9 mmol) of potassium carbonate, and 4.0 g (3.5 mmol) of tetrakis (triphenylphosphine) palladium were added to 200 mL of 1,4-dioxane and 100 mL of water in a 500 mL flask, and the mixture was heated and refluxed for 8 hours under a nitrogen stream. The obtained mixture was added to 400 mL of methanol, and a solid crystallized therein was filtered, dissolved in monochlorobenzene, filtered with silica gel/Celite and then, recrystallized with methanol after removing an organic solvent in an appropriate amount, obtaining an intermediate M-6-33 (18.7 g, a yield of 78%).

Calcd. C20H11ClN2O: C, 72.62; H, 3.35; Cl, 10.72; N, 8.47; O, 4.84. found: C, 72.60; H, 3.32; Cl, 10.52; N, 8.37; O, 4.80.

Second Step: Synthesis of Compound A-33

4.0 g (12.1 mmol) of the intermediate M-6-33, 5.5 g (12.7 mmol) of the M-6-33-1, 4.2 g (30.2 mmol) of potassium carbonate, and 0.7 g (0.6 mmol) of tetrakis (triphenylphosphine)palladium were added to 40 mL of 1,4-dioxane and 20 mL of water in a 100 mL flask, and the mixture was heated and refluxed for 8 hours under a nitrogen stream. The obtained mixture was added to 100 mL of methanol, and a solid crystallized therein was filtered, dissolved in monochlorobenzene, filtered with silica gel/Celite, and then, recrystallized with methanol after removing an organic solvent in an appropriate amount, obtaining a compound A-33 (5.4 g, a yield of 71%).

Calcd. C44H28N2O: C, 87.97; H, 4.70; N, 4.66; O, 2.66. found: C, 87.64; H, 4.62; N, 4.60; O, 2.47.

Example 8: Synthesis of Compound A-37

A compound A-37 as specific examples of a compound according to the present invention was synthesized through the following one step.

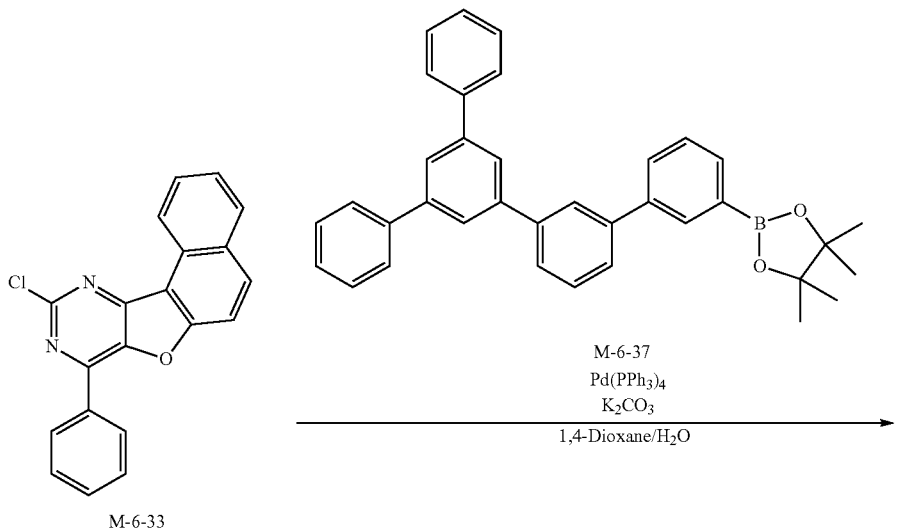

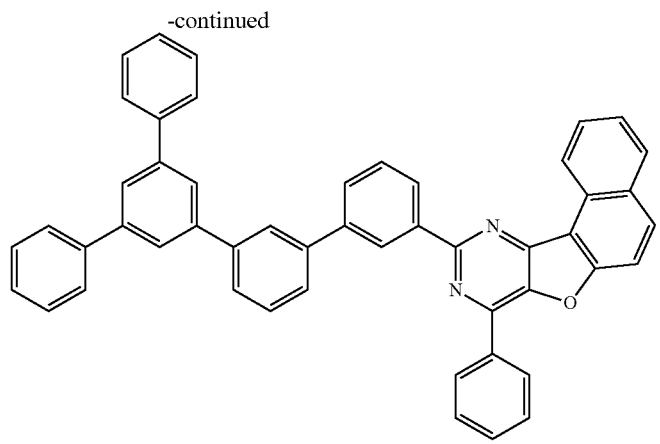

A-37

First Step: Synthesis of Compound A-37

4.0 g (12.1 mmol) of the intermediate M-6-33, 6.5 g (12.7 mmol) of the M-6-37, 4.2 g (30.2 mmol) of potassium carbonate, and 0.7 g (0.6 mmol) of tetrakis (triphenylphosphine)palladium were added to 40 mL of 1,4-dioxane and 20 mL of water in a 100 mL flask, and the mixture was heated and refluxed for 10 hours under a nitrogen stream. The obtained mixture was added to 100 mL of methanol, and a solid crystallized therein was filtered, dissolved in monochlorobenzene, filtered with silica gel/Celite and then, recrystallized with methanol after removing an organic solvent in an appropriate amount, obtaining a compound A-37 (6.36 g, a yield of 74%).

Calcd. C50H32N2O: C, 88.73; H, 4.77; N, 4.14; O, 2.36. found: C, 88.15; H, 4.29; N, 4.11; O, 2.26.

Example 9: Synthesis of Compound A-41

A compound A-41 as specific examples of a compound according to the present invention was synthesized through the following one step.

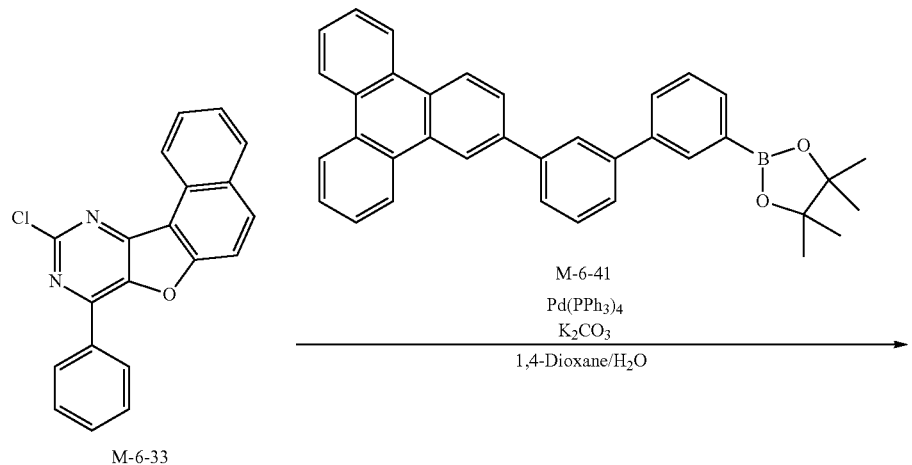

A-41

First Step: Synthesis of Compound A-41

4.0 g (12.1 mmol) of the intermediate M-6-33, 6.4 g (12.7 mmol) of the M-6-41, 4.2 g (30.2 mmol) of potassium carbonate, and 0.7 g (0.6 mmol) of tetrakis (triphenylphosphine)palladium were added to 40 mL of 1,4-dioxane and 20 mL of water in a 100 mL flask, and the mixture was heated and refluxed for 10 hours under a nitrogen stream. The obtained mixture was added to 100 mL of methanol, and a solid crystallized therein was filtered, dissolved in monochlorobenzene, filtered with silica gel/Celite, and then, recrystallized with methanol after removing an organic solvent in an appropriate amount, obtaining a compound A-41(5.48 g, a yield of 64%).

Calcd. C50H30N2O: C, 89.00; H, 4.48; N, 4.15; O, 2.37. found: C, 88.59; H, 4.33; N, 4.07; O, 2.21.

Example 10: Synthesis of Compound A-113

A compound A-113 as specific examples of a compound according to the present invention was synthesized through the following one step.

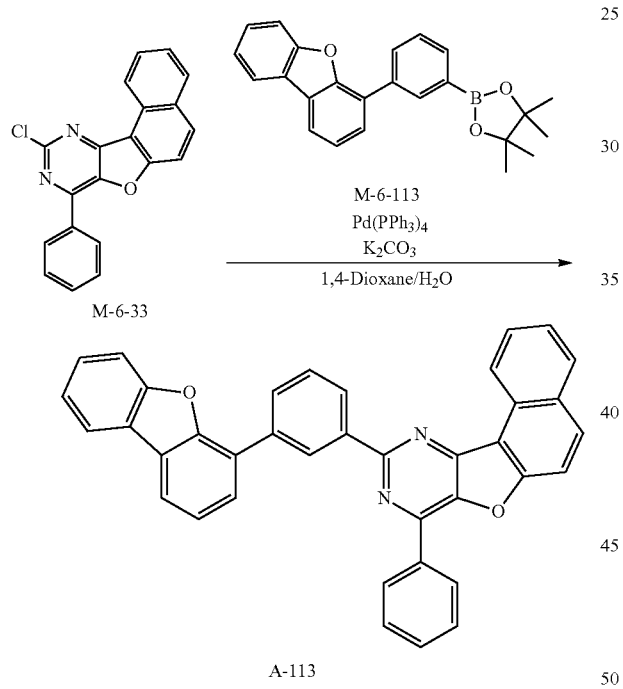

First Step: Synthesis of Compound A-113

4.0 g (12.1 mmol) of the intermediate M-6-33, 4.7 g (12.7 mmol) of the M-6-113, 4.2 g (30.2 mmol) of potassium carbonate, and 0.7 g (0.6 mmol) of tetrakis (triphenylphosphine)palladium were added to 40 mL of 1,4-dioxane and 20 mL of water in a 100 mL flask, and the mixture was heated and refluxed for 8 hours under a nitrogen stream. The obtained mixture was added to 100 mL of methanol, and a solid crystallized therein was filtered, dissolved in monochlorobenzene, filtered with silica gel/Celite and then, recrystallized with methanol after removing an organic solvent in an appropriate amount, obtaining a compound A-113 (4.65 g, a yield of 68%).

Calcd. C38H22N2O2: C, 84.74; H, 4.12; N, 5.20; O, 5.94. found: C, 84.37; H, 4.03; N, 5.10; O, 5.84.

Example 11: Synthesis of Compound A-117

A compound A-117 as specific examples of a compound according to the present invention was synthesized through the following one step.

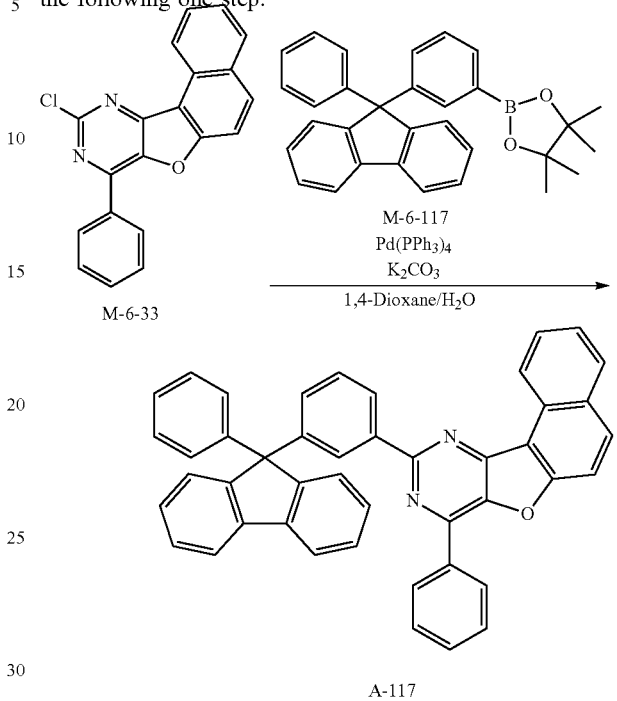

First Step: Synthesis of Compound A-41

4.0 g (12.1 mmol) of the intermediate M-6-33, 5.6 g (12.7 mmol) of M-6-117, 4.2 g (30.2 mmol) of potassium carbonate, and 0.7 g (0.6 mmol) of tetrakis (triphenylphosphine) palladium were added to 40 mL of 1,4-dioxane and 20 mL of water in a 100 mL flask, and the mixture was heated and refluxed for 10 hours under a nitrogen stream. The obtained mixture was added to 100 mL of methanol, and a solid crystallized therein was filtered, dissolved in monochlorobenzene, filtered with silica gel/Celite and then, recrystallized with methanol after removing an organic solvent in an appropriate amount, obtaining a compound A-117 (5.5 g, a yield of 71%). Calcd. C45H28N2O: C, 88.21; H, 4.61; N, 4.57; O, 2.61. found: C, 88.17; H, 4.54; N, 4.43; O, 2.43.

Example 12: Synthesis of Compound A-109

A compound A-109 as specific examples of a compound according to the present invention was synthesized through the following one step.

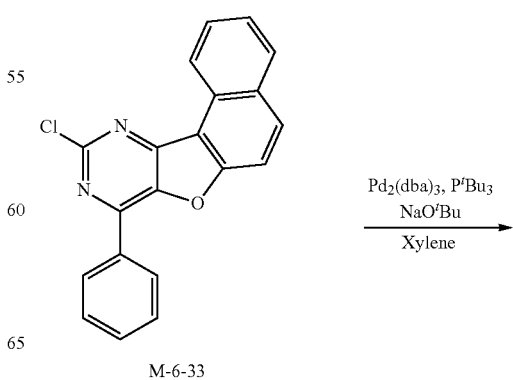

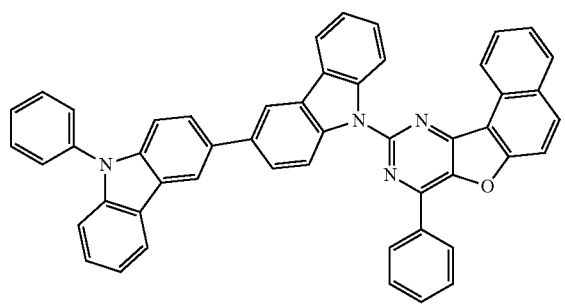

A-109

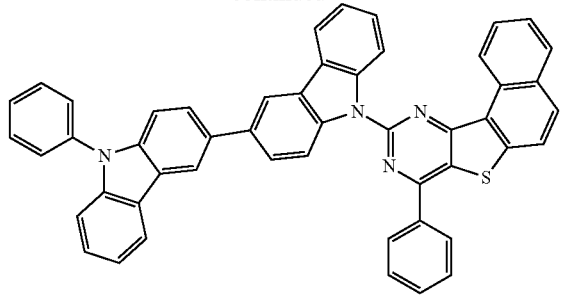

B-109

First Step: Synthesis of Compound A-109

4.0 g (7.1 mmol) of the intermediate M-6-33, 3.1 g (7.5 mmol) of phenyl-3,3-bicarbazole, 1.4 g (14.2 mmol) of sodium t-butoxide, 0.4 g (0.7 mmol) of tris(dibenzylideneacetone) dipalladium (0), and 0.6 mL of tri t-butylphosphine (50% in toluene) were added to 50 mL of xylene in a 100 mL round flask, and the mixture was heated and refluxed for 15 hours under a nitrogen stream. The obtained mixture was added to 100 mL of methanol, a solid crystallized therein was filtered, dissolved in dichlorobenzene, filtered with silica gel/Celite and then, recrystallized with methanol after removing an organic solvent in an appropriate amount, obtaining a compound A-109 (3.6 g, a yield of 72%).

calcd. $C_{50}H_{30}N_4O$: C, 85.45; H, 4.30; N, 7.97; O, 2.28. found: C, 85.33; H, 4.24; N, 7.89; O, 2.15.

Example 13: Synthesis of Compound B-109

A compound B-109 as specific examples of a compound according to the present invention was synthesized through the following two steps.

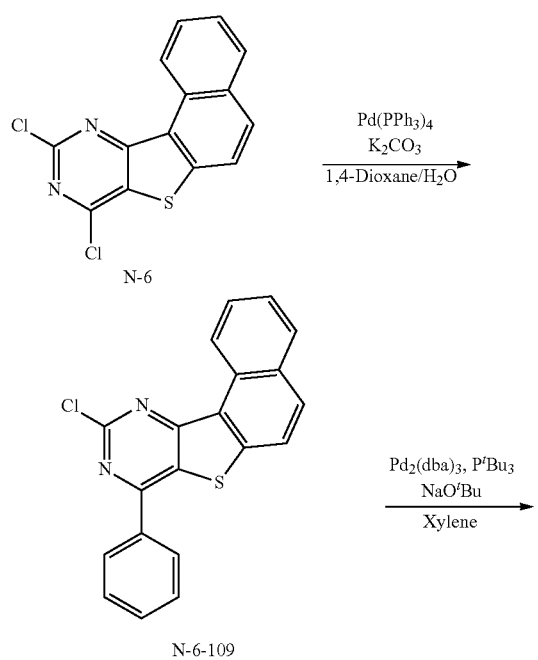

First Step: Synthesis of Intermediate N-6-109

10.0 g (32.8 mmol) of the intermediate N-6, 4.2 g (34.4 mmol) of phenylboronic acid, 11.3 g (81.9 mmol) of potassium carbonate, and 1.9 g (1.6 mmol) of tetrakis(triphenylphosphine) palladium were added to 100 mL of 1,4-dioxane and 50 mL of water in a 250 mL flask, and the mixture was heated and refluxed for 10 hours under a nitrogen stream. The obtained mixture was added to 200 mL of methanol, and a solid crystallized therein was filtered, dissolved in monochlorobenzene, filtered with silica gel/Celite and then, recrystallized with methanol after removing a solvent in an appropriate amount, obtaining an intermediate N-6-109 (7.6 g, a yield of 64%).

Calcd. $C_{20}H_{11}ClN_2S$: C, 69.26; H, 3.20; Cl, 10.22; N, 8.08; S, 9.25. found: C, 69.19; H, 3.07; Cl, 10.17; N, 8.01; S, 9.09.

Second Step: Synthesis of Compound B-109

4.0 g (6.9 mmol) of the intermediate N-6-109, 3.0 g (7.3 mmol) of phenyl-3,3-bicarbazole, 1.3 g (13.9 mmol) of sodium t-butoxide, 0.4 g (0.7 mmol) of tris(dibenzylideneacetone) dipalladium (0), and 0.6 mL of tri t-butylphosphine (50% in toluene) were added to 50 mL of xylene in a 100 mL flask, and the mixture was heated and refluxed for 15 hours under a nitrogen stream. The obtained mixture was added to 100 mL of methanol, and a solid crystallized therein was filtered, dissolved in monochlorobenzene, filtered with silica gel/Celite and then, recrystallized with methanol after removing an organic solvent in an appropriate amount, obtaining a compound B-109 (3.2 g, a yield of 64%).

Calcd. $C_{50}H_{30}N_4S$: C, 83.54; H, 4.21; N, 7.79; S, 4.46. found: C, 83.39; H, 4.11; N, 7.68; S, 4.39.

Example 14: Synthesis of Compound A-111

A compound A-111 as specific examples of a compound according to the present invention was synthesized according to the following two steps.

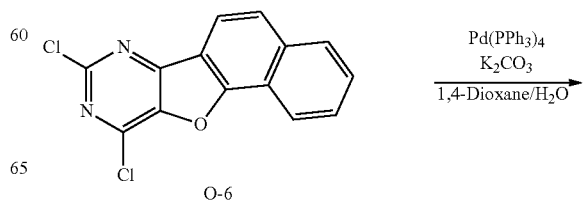

O-6

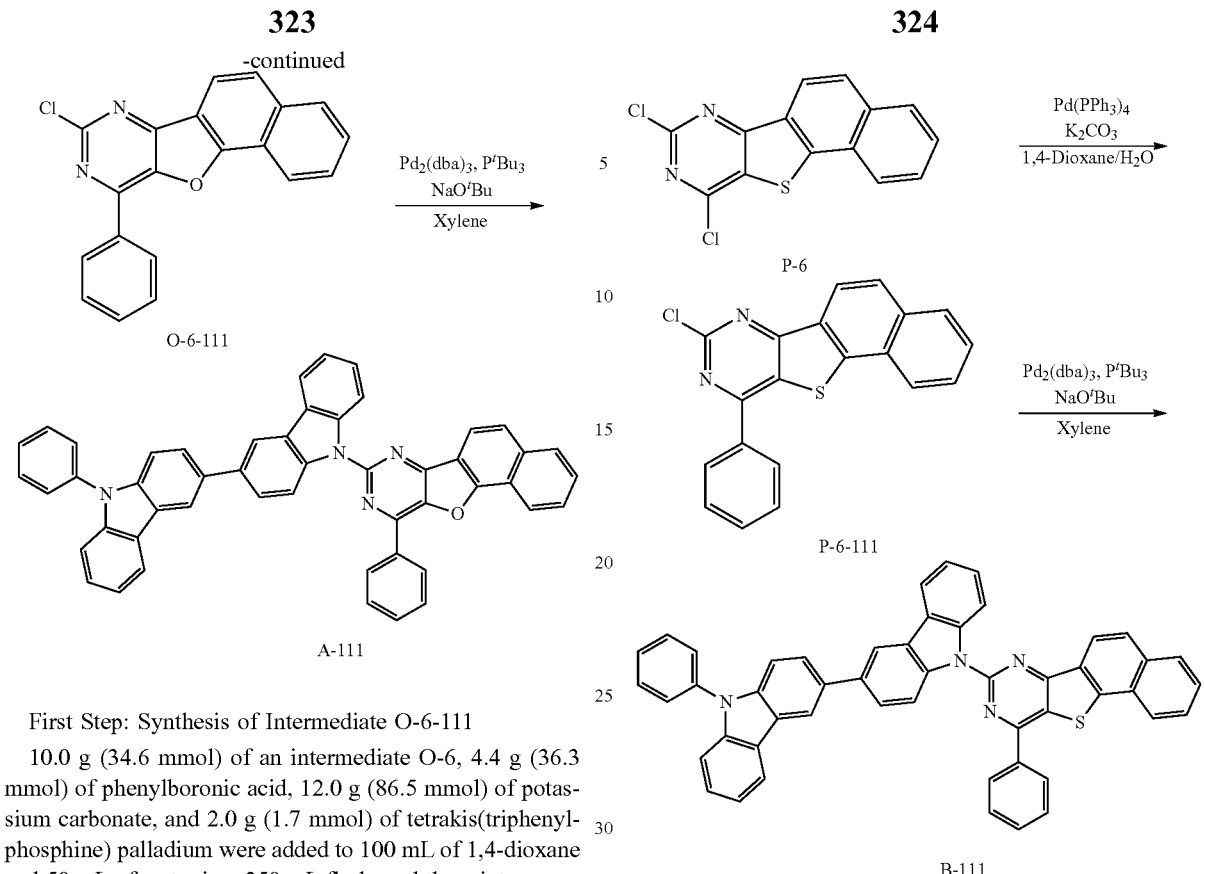

First Step: Synthesis of Intermediate O-6-111

10.0 g (34.6 mmol) of an intermediate O-6, 4.4 g (36.3 mmol) of phenylboronic acid, 12.0 g (86.5 mmol) of potassium carbonate, and 2.0 g (1.7 mmol) of tetrakis(triphenylphosphine) palladium were added to 100 mL of 1,4-dioxane and 50 mL of water in a 250 mL flask, and the mixture was heated and refluxed for 6 hours under a nitrogen stream. The obtained mixture was added to 200 mL of methanol, and a solid crystallized therein was filtered, dissolved in monochlorobenzene, filtered with silica gel/Celite and recrystallized with methanol after removing an organic solvent in an appropriate amount, obtaining an intermediate O-6-111 (8.9 g, a yield of 74%).

Calcd. C20H11ClN2O: C, 72.62; H, 3.35; Cl, 10.72; N, 8.47; O, 4.84. found: C, 72.36; H, 3.11; Cl, 10.53; N, 8.29; O, 4.65.

Second Step: Synthesis of Compound A-111

4.0 g (7.1 mmol) of the intermediate O-6-111, 3.1 g (7.5 mmol) of phenyl-3,3-bicarbazole, 1.4 g (14.2 mmol) of sodium t-butoxide, 0.4 g (0.7 mmol) of tris(dibenzylideneacetone) dipalladium (0), 0.6 mL of tri t-butylphosphine (50% in toluene) were added to 50 mL of xylene in a 100 mL round flask, and the mixture was heated and refluxed for 15 hours under a nitrogen stream. The obtained mixture was added to 100 mL of methanol, and a solid crystallized therein was filtered, dissolved in dichlorobenzene, filtered with silica gel/Celite and then, recrystallized with methanol after removing an organic solvent in an appropriate amount, obtaining a compound A-111 (3.3 g, a yield of 66%).

calcd. C50H30N4O: C, 85.45; H, 4.30; N, 7.97; O, 2.28. found: C, 85.17; H, 4.20; N, 7.77; O, 2.19.

Example 15: Synthesis of Compound B-111

A compound B-111 as specific examples of a compound according to the present invention was synthesized through the following two steps.

10.0 g (32.8 mmol) of the intermediate P-6, 4.2 g (34.4 mmol) of phenylboronic acid, 11.3 g (81.9 mmol) of potassium carbonate, and 1.9 g (1.6 mmol) of tetrakis(triphenylphosphine) palladium were added to 100 mL of 1,4-dioxane and 50 mL of water in a 250 mL flask, and the mixture was heated and refluxed for 10 hours under a nitrogen stream. The obtained mixture was added to 200 mL of methanol, and a solid crystallized therein was filtered, dissolved in monochlorobenzene, filtered with silica gel/Celite and then, recrystallized with methanol after removing an organic solvent in an appropriate amount, obtaining an intermediate P-6-111 (8.0 g, a yield of 67%).

Calcd. C20H11ClN2S: C, 69.26; H, 3.20; Cl, 10.22; N, 8.08; S, 9.25. found: C, 69.08; H, 3.04; Cl, 10.12; N, 7.89; S, 9.16.

Second Step: Synthesis of Compound B-111

4.0 g (6.9 mmol) of the intermediate P-6-111, 3.0 g (7.3 mmol) of phenyl-3,3-bicarbazole, 1.3 g (13.9 mmol) of sodium t-butoxide, 0.4 g (0.7 mmol) of tris(dibenzylideneacetone) dipalladium (0), and 0.6 mL of tri t-butylphosphine (50% in toluene) were added to 50 mL of xylene in a 100 mL flask, and the mixture was heated and refluxed for 15 hours under a nitrogen stream. The obtained mixture was added to 100 mL of methanol, and a solid crystallized therein was filtered, dissolved in monochlorobenzene, filtered with silica gel/Celite and then, recrystallized with methanol after removing an organic solvent in an appropriate amount, obtaining a compound B-111 (3.5 g, a yield of 70%).

Calcd. C50H30N4S: C, 83.54; H, 4.21; N, 7.79; S, 4.46. found: C, 83.32; H, 4.05; N, 7.71; S, 4.44.

Comparative Example 1: Synthesis of CBP

A compound represented by the following Chemical Formula a was synthesized in the same method as disclosed in International Publication WO 2013032035.

Chemical Formula a

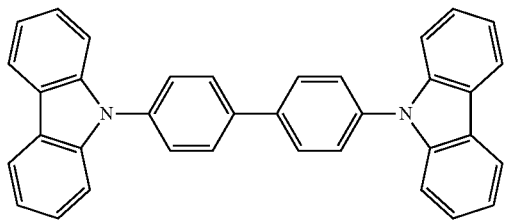

Evaluation 1: Simulation Characteristics Comparison of Organic Compounds

Energy level of each compound was measured by using a Super computer GAIA (IBM power 6) in a Gaussian 09 method, and the results are provided in the following Table 1.

TABLE 1

| compound | HOMO (eV) | LUMO (eV) | T1 (eV) | S1 (eV) |
|---|---|---|---|---|
| CBP (Comparative Example1) | −5.319 | −1.231 | 2.971 | 3.560 |
| A-13 (Example5) | −5.299 | −1.945 | 2.497 | 2.860 |
| A-16 | −5.302 | −1.907 | 2.565 | 2.896 |
| A-17 (Example6) | −5.492 | −2.014 | 2.561 | 2.981 |
| A-33 (Example7) | −5.711 | −2.005 | 2.576 | 3.381 |
| A-36 | −5.709 | −1.966 | 2.632 | 3.417 |
| A-37 (Example8) | −5.871 | −1.978 | 2.578 | 3.473 |
| A-41 (Example9) | −5.647 | −1.980 | 2.579 | 3.369 |
| A-113 (Example10) | −5.763 | −1.986 | 2.576 | 3.379 |
| A-117 (Example11) | −5.719 | −1.954 | 2.578 | 3.428 |
| A-109 (Example12) | −5.019 | −2.032 | 2.431 | 2.594 |
| B-16 | −5.317 | −1.9 | 2.591 | 2.911 |
| B-36 | −5.707 | −1.943 | 2.581 | 3.397 |
| B-109 (Example13) | −5.000 | −2.092 | 2.363 | 2.525 |
| A-111 (Example14) | −5.017 | −1.961 | 2.485 | 2.668 |
| B-111 (Example15) | −4.995 | −2.004 | 2.435 | 2.607 |
| C-16 | −5.317 | −1.731 | 2.441 | 3.09 |
| C-36 | −5.699 | −1.711 | 2.455 | 3.605 |
| D-16 | −5.358 | −1.808 | 2.332 | 3.046 |
| D-36 | −5.696 | −1.853 | 2.33 | 3.396 |
| C-13 | −5.316 | −1.731 | 2.425 | 3.079 |
| C-15 | −5.33 | −1.607 | 2.558 | 3.222 |
| C-16 | −5.319 | −1.728 | 2.441 | 3.096 |
| C-33 | −5.697 | −1.7 | 2.44 | 3.633 |
| C-35 | −5.693 | −1.612 | 2.563 | 3.744 |
| C-36 | −5.699 | −1.711 | 2.455 | 3.605 |
| D-13 | −5.367 | −1.775 | 2.34 | 3.074 |
| D-15 | −5.361 | −1.706 | 2.459 | 3.146 |
| D-16 | −5.358 | −1.808 | 2.332 | 3.046 |
| D-33 | −5.711 | −1.806 | 2.341 | 3.461 |
| D-35 | −5.712 | −1.778 | 2.454 | 3.584 |
| D-36 | −5.696 | −1.863 | 2.329 | 3.393 |

Referring to the Table 1, since excellent electron transport characteristics were expected in a range of a HOMO level of about −4.9 to −5.9 eV and a LUMO level of about −1.6 to −2.1 eV in a simulation, the organic compound of Comparative Example 1 satisfied the HOMO level but not the LUMO level and thus, showed an unbalance between holes and electrons compared with the organic compounds of Examples 5 to 15. The organic compounds of Examples 5 to 15 had an appropriate energy level and thus, were expected to have an excellent efficiency and life-span compared with the organic compound of Comparative Example 1.

Manufacture of Organic Light Emitting Diode

Example 16

An organic light emitting diode was manufactured by using the compound A-13 of Example 5 as a host, and (piq)$_2$Ir(acac) as a dopant.

As for an anode, 1000 Å-thick ITO was used, and as for a cathode, 1000 Å-thick aluminum (Al) was used. Specifically, illustrating a method of manufacturing the organic light emitting diode, the anode is manufactured by cutting an ITO glass substrate having 15 Ω/cm$^2$ of sheet resistance into a size of 50 mm×50 mm×0.7 mm, ultrasonic wave-cleaning them in acetone, isopropylalcohol, and pure water for 15 minutes respectively, and UV ozone cleaning them for 30 minutes.

On the substrate, an 800 Å-thick hole transport layer (HTL) was formed by depositing N4,N4'-di(naphthalen-1-yl)-N4,N4'-diphenylbiphenyl-4,4'-diamine (NPB) under a vacuum degree 650×10$^{-7}$ Pa at a deposition rate of 0.1 to 0.3 nm/s. Subsequently, A 300 Å-thick emission layer was formed by using the compound A-13 of Example 5 under the same vacuum deposition condition, and herein, a phosphorescent dopant of (piq)$_2$Ir(acac) was simultaneously deposited. Herein, the phosphorescent dopant was deposited to be 3 wt % based on 100 wt % of the entire weight of the emission layer by adjusting the deposition rate.

On the emission layer, a 50 Å-thick hole blocking layer was formed by depositing bis(2-methyl-8-quinolinolate)-4-(phenylphenolato)aluminium (BAlq) under the same vacuum deposition condition. Subsequently, a 200 Å-thick electron transport layer (ETL) was formed by depositing Alq3 under the same vacuum deposition condition. On the electron transport layer (ETL), a cathode is formed by sequentially depositing LiF and Al, manufacturing an organic optoelectric device.

The organic optoelectric device has a structure of ITO/NPB (80 nm)/EML (A-13 (97 wt %)+(piq)$_2$Ir(acac) (3 wt %), 30 nm)/Balq (5 nm)/Alq3 20 nm/LiF (1 nm)/Al (100 nm).

Example 17

An organic light emitting diode was manufactured according to the same method as Example 16 except for using the compound A-17 of Example 6 instead of the compound A-13 of Example 5.

Example 18

An organic light emitting diode was manufactured according to the same method as Example 16 except for using the compound A-33 of Example 7 instead of the compound A-13 of Example 5.

Example 19

An organic light emitting diode was manufactured according to the same method as Example 16 except for using the compound A-37 of Example 8 instead of the compound A-13 of Example 5.

Example 20

An organic light emitting diode was manufactured according to the same method as Example 16 except for using the compound A-41 of Example 9 instead of the compound A-13 of Example 5.

Example 21

An organic light emitting diode was manufactured according to the same method as Example 16 except for using the compound A-113 of Example 10 instead of the compound A-13 of Example 5.

Example 22

An organic light emitting diode was manufactured according to the same method as Example 16 except for using the compound A-117 of Example 11 instead of the compound A-13 of Example 5.

Example 23

An organic light emitting diode was manufactured according to the same method as Example 16 except for using the compound A-109 of Example 12 instead of the compound A-13 of Example 5.

Example 24

An organic light emitting diode was manufactured according to the same method as Example 16 except for using the compound B-109 of Example 13 instead of the compound A-13 of Example 5.

Example 25

An organic light emitting diode was manufactured according to the same method as Example 16 except for using the compound A-111 of Example 14 instead of the compound A-13 of Example 5.

Example 26

An organic light emitting diode was manufactured according to the same method as Example 16 except for using the compound B-111 of Example 15 instead of the compound A-13 of Example 5.

Comparative Example 2

An organic light emitting diode was manufactured according to the same method as Example 4 except for using CBP of the following structure instead of the compound A-13 of Example 5.

The structures of NPB, BAlq, CBP and (piq)$_2$Ir(acac) used to manufacture the organic light emitting diodes are as follows.

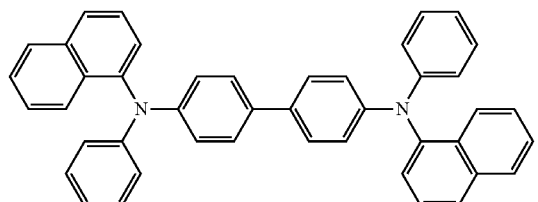

[NPB]

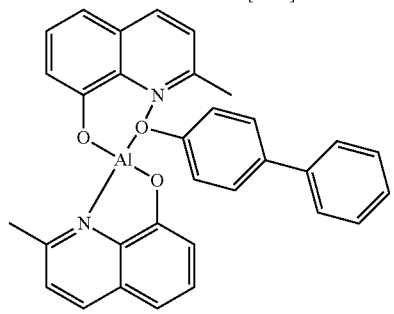

[BAlq]

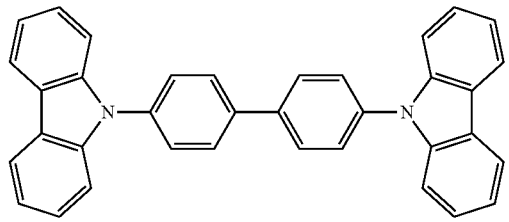 [SMILES: c1ccc2c(c1)c1ccccc1n2-c1ccc(-c2ccc(-n3c4ccccc4c4ccccc43)cc2)cc1]

[CBP]

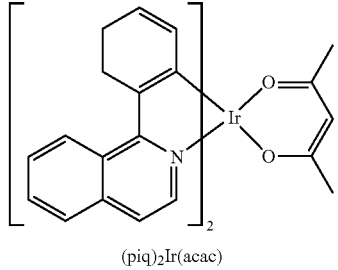

(piq)$_2$Ir(acac)

Evaluation: 2: Performance Measurement of Orrganic Light Emitting Diode

Current density and luminance changes depending on a voltage and luminous efficiency of each organic light emitting diode according to Examples 16 to 26 and Comparative Example 2 were measured.

The measurements were specifically performed in the following method, and the results were provided in the following Table 2.

(1) Measurement of Current Density Change Depending on Voltage Change

Current values flowing in the unit device of the manufactured organic light emitting diodes were measured for, while increasing the voltage from 0V to 10V using a current-voltage meter (Keithley 2400), and the measured current values were divided by an area to provide the results.

(2) Measurement of Luminance Change Depending on Voltage Change

Luminance of the manufactured organic light emitting diodes was measured for luminance, while increasing the voltage from 0 V to 10 V using a luminance meter (Minolta Cs-1000A).

(3) Measurement of Luminous Efficiency

Current efficiency (cd/A) at the same current density (10 mA/cm2) were calculated by using the luminance, current density, and voltages (V) from the items (1) and (2).

(4) Measurement of Life-Span

Life-span was obtained by measuring time taken until current efficiency (cd/A) decreased down to 90% while luminance (cd/m$^2$) was maintained at 5000 cd/m$^2$.

TABLE 2

| Nos. | Emission layer | Driving voltage (V) | Color (EL color) | Efficiency (cd/A) | 90% life-span (h) at 5000 cd/m$^2$ |
|---|---|---|---|---|---|
| Comparative Example2 | CBP | 6.5 | red | 5.8 | 20 |
| Example16 | A-13 | 5.8 | red | 13.2 | 89 |
| Example17 | A-17 | 5.9 | red | 12.1 | 64 |
| Example18 | A-33 | 5.3 | red | 14.6 | 112 |
| Example19 | A-37 | 5.6 | red | 14.7 | 105 |
| Example20 | A-41 | 5.6 | red | 13.5 | 91 |
| Example21 | A-113 | 5.9 | red | 10.4 | 78 |
| Example22 | A-117 | 6.1 | red | 9.3 | 71 |
| Example23 | A-109 | 5.4 | red | 15.2 | 120 |
| Example24 | B-109 | 5.3 | red | 14.9 | 102 |
| Example25 | A-111 | 5.6 | red | 14.6 | 105 |
| Example26 | B-111 | 5.7 | red | 14.9 | 93 |

Referring to Table 2, the organic light emitting diodes according to Examples 16 to 26 showed remarkably improved driving voltage, luminous efficiency, power efficiency and life-span compared with Comparative Example 2.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

DESCRIPTION OF SYMBOLS

100, 200: organic light emitting diode
105: organic layer
110: cathode
120: anode
130: emission layer 230: emission layer
140: hole auxiliary layer

The invention claimed is:

1. An organic compound

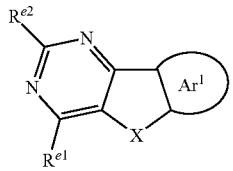

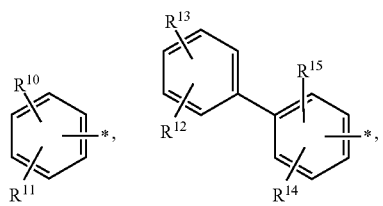

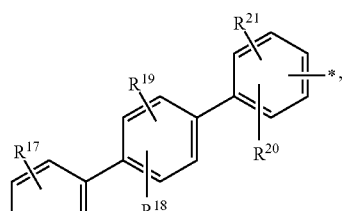

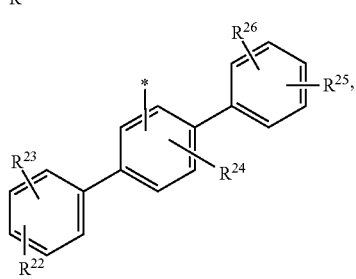

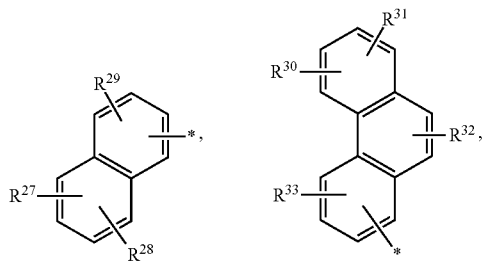

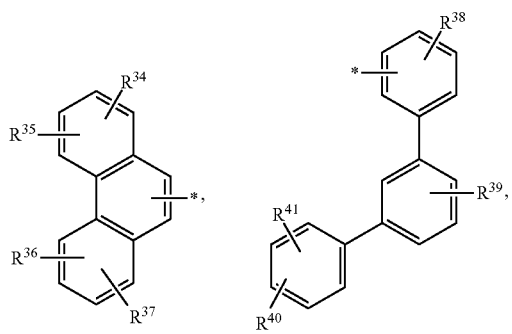

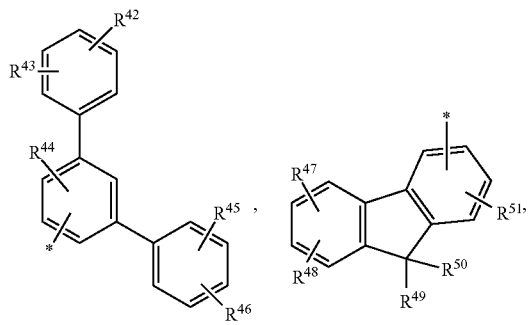

-continued
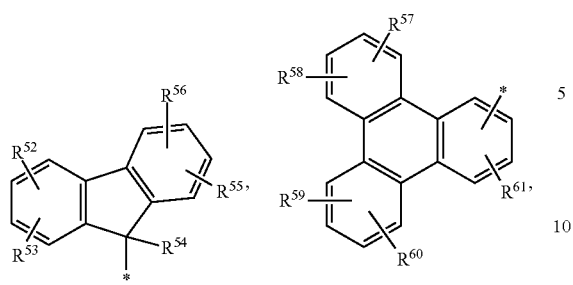
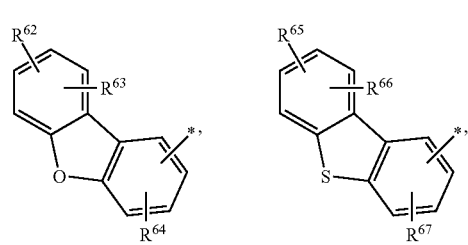
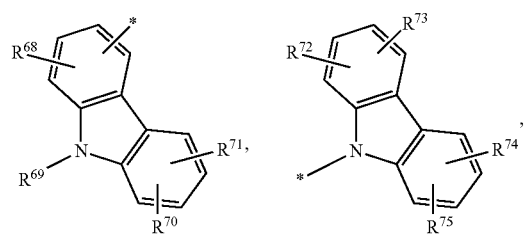
wherein the organic compound is one of the following:
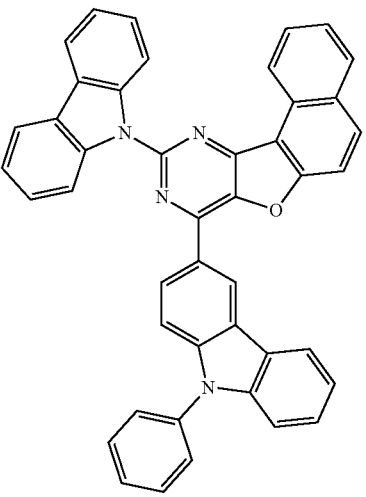
A-13
-continued
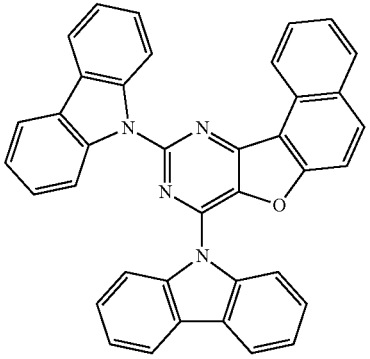
A-17
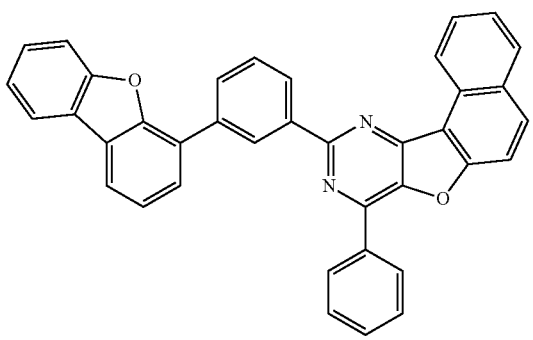
A-113
A-109
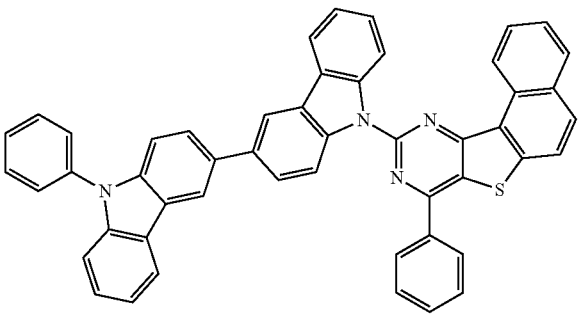
B-109

A-111

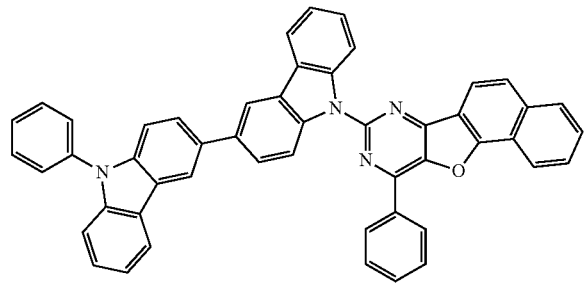

B-111

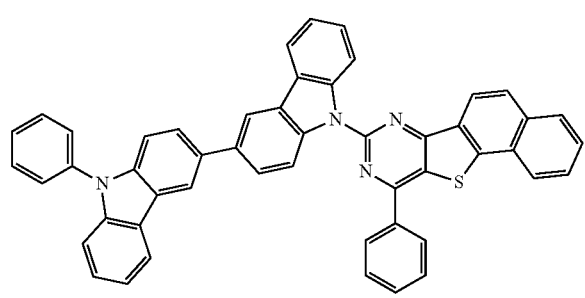

A-33

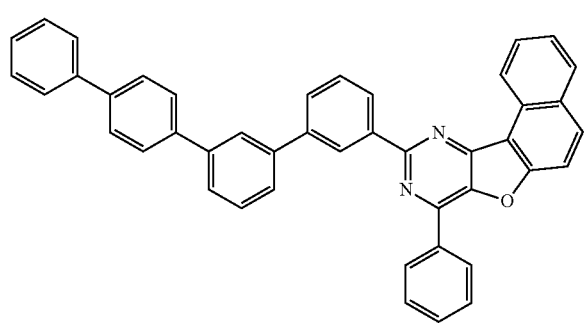

A-37

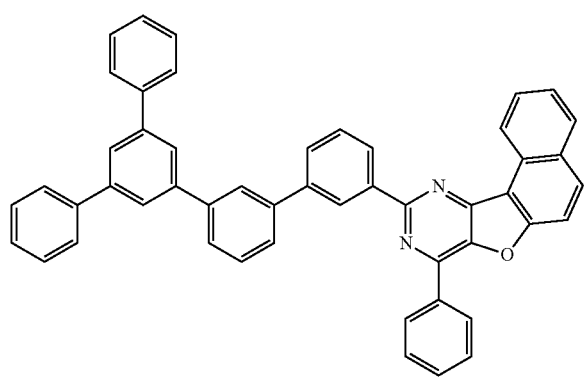

A-41

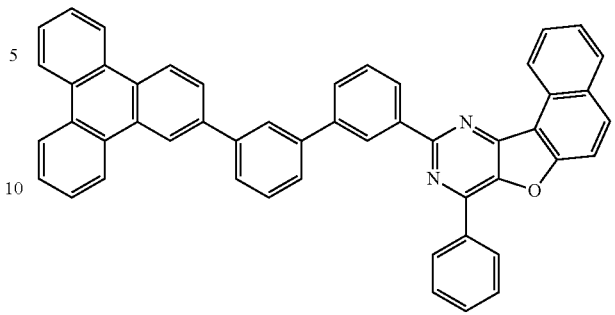

A-117

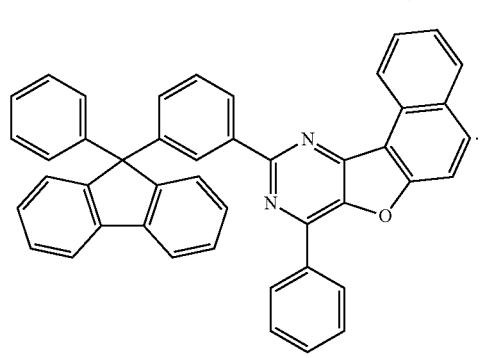

2. The organic compound of claim 1, wherein the organic compound is a red light emitting material.

3. An organic optoelectric device comprising
an anode and a cathode facing each other, and
at least one organic layer positioned between the anode and the cathode
wherein, the organic layer comprises the compound of claim 1.

4. The organic optoelectric device of claim 3, wherein the organic layer comprises an emission layer,
wherein the organic compound is included in the emission layer.

5. The organic optoelectric device of claim 4, wherein the organic compound is included as a host of the emission layer.

6. The organic optoelectric device of claim 3, wherein the organic layer comprises at least one of an electron injection layer (EIL) and an electron transport layer (ETL), and
the organic compound is included in at least one of the electron injection layer (EIL) and the electron transport layer (ETL).

7. A display device comprising the organic optoelectric device of claim 3.

* * * * *